US008876802B2

(12) United States Patent
Grigorov

(10) Patent No.: US 8,876,802 B2
(45) Date of Patent: Nov. 4, 2014

(54) METHODS AND DEVICES FOR PROGRAMMABLE DELIVERY OF MICRODOSES OF LIQUID DRUGS

(76) Inventor: Leonid Grigorov, Redwood City, CA (US)

(*) Notice: Subject to any disclaimer, the term of this patent is extended or adjusted under 35 U.S.C. 154(b) by 618 days.

(21) Appl. No.: 13/119,018

(22) PCT Filed: Sep. 14, 2009

(86) PCT No.: PCT/US2009/005136
§ 371 (c)(1),
(2), (4) Date: May 18, 2011

(87) PCT Pub. No.: WO2010/030390
PCT Pub. Date: Mar. 18, 2010

(65) Prior Publication Data
US 2011/0218516 A1    Sep. 8, 2011

Related U.S. Application Data

(60) Provisional application No. 61/192,056, filed on Sep. 15, 2008.

(51) Int. Cl.
*A61K 9/22*     (2006.01)
*A61M 5/168*    (2006.01)
*A61M 5/145*    (2006.01)
*A61M 5/142*    (2006.01)
*A61M 5/14*     (2006.01)

(52) U.S. Cl.
CPC ... *A61M 5/14248* (2013.01); *A61M 2205/3355* (2013.01); *A61M 5/16854* (2013.01); *A61M 5/16881* (2013.01); *A61M 5/1456* (2013.01); *A61M 5/1413* (2013.01); *A61M 2005/14268* (2013.01)
USPC ......... 604/890.1; 604/891.1; 604/65; 604/66; 604/67; 604/131; 604/132

(58) Field of Classification Search
USPC ............... 604/65–67, 890.1, 891.1, 131–132
See application file for complete search history.

(56) References Cited

U.S. PATENT DOCUMENTS

| | | | | |
|---|---|---|---|---|
| 5,709,225 A | * | 1/1998 | Budgifvars et al. | ............ 128/899 |
| 5,803,917 A | * | 9/1998 | Butterfield et al. | ............. 604/67 |
| 6,592,519 B1 | * | 7/2003 | Martinez | ....................... 600/309 |
| 6,613,280 B2 | | 9/2003 | Myrick et al. | |
| 6,736,796 B2 | | 5/2004 | Shekalim | |
| 7,569,050 B2 | | 8/2009 | Moberg et al. | |
| 2002/0169439 A1 | | 11/2002 | Flaherty | |
| 2004/0064088 A1 | * | 4/2004 | Gorman et al. | ............ 604/93.01 |
| 2006/0184093 A1 | | 8/2006 | Phipps et al. | |
| 2008/0164275 A1 | | 7/2008 | Poutiatine et al. | |

FOREIGN PATENT DOCUMENTS

WO    PCT/US09/05136    11/2009

\* cited by examiner

*Primary Examiner* — Edelmira Bosques
(74) *Attorney, Agent, or Firm* — D. Benjamin Borson; Borson Law Group, PC

(57) ABSTRACT

Devices of this invention include replaceable cartridges for delivery of doses of fluids. Cartridges having a fluid supply reservoir comprising an expandable element are designed to be connected with non-disposable actuating module supplied with a sensor, a mechanism to apply a force to the fluid, thereby forcing a predetermined dose out of the reservoir, and a processor providing control outputs from a sensor system according to preprogrammed instructions. Methods of this invention include delivery of microdoses of fluids using devices of this invention.

35 Claims, 31 Drawing Sheets

METHODS AND DEVICES FOR PROGRAMMABLE DELIVERY OF MICRODOSES OF LIQUID DRUGS

CLAIM OF PRIORITY

This application is filed under 35 U.S.C. 371 as a National Phase application of PCT/US2009/005136, filed 14 Sep. 2009, which claims priority to U.S. Provisional Patent Application No. 61/192,056 entitled: "Methods and Devices for Programmable Delivery of Microdoses of Liquid Drugs and Other Fluids," filed 15 Sep. 2008, Leonid Grigorov inventor, herein incorporated fully by reference.

FIELD OF THE INVENTION

The present invention relates to methods and devices for fluid delivery to patients. More particularly it relates to methods and compact programmable devices for the high precision delivery of low doses of fluids, and even more particularly it relates to methods and compact autonomous devices having replaceable cartridge and capable of introducing small and super small quantities of liquid drugs into a human body accordingly to a programmed regime, supported by the delivery system over a prolonged period of the time.

BACKGROUND

Devices for delivering drugs to patients have become an important aspect of modern pharmaceutical therapy. Known autonomous devices for delivery of medicines can be divided into two basic classes, passive and active systems.

SUMMARY

Notwithstanding the forgoing, none of the prior art devices is capable of self-analyzing directed to detecting potential internal changes occurring with long-term use, and of self-correcting these changes so that the user should not take care of the technical state of the device supporting his or her life.

The inventor has discovered new problems in the art of devices for long-term delivery of drugs to patients. These problems are discussed in details below, but generally relate to the requirements that prior art devices must be precision made, and that with long-term use, the devices function degrades and doses can be poorly controlled, with consequent health problems. Inventor has also discovered simple devices that fulfill requirements of long-term accurate and reproducible drug delivery, with low costs of manufacturing, low maintenance requirements, and other features that make it easier for patients to maintain their therapy.

Certain aspects of invention provide such new methods and new highly reliable compact programmable devices of the intravenous and/or hypodermic delivery of small and super small medicinal doses to a patient which combine simple construction having low manufacturing cost with an ability of delivering of small and super small doses of liquid drugs or other fluids with exceptionally high volume resolution exceeding that of existing devices at least one order of magnitude, and more desirable at least two orders of magnitude.

Other aspects of the invention provide delivery devices capable of fast exchanging of ready-to-use factory pre-filled replaceable sterile cartridges. Such pre-filled cartridges may be easily exchanged by any unskillful user, including children and adults with decreased mental or physical abilities, and can reduce the dangers occurring in connection with periodic necessity to refill the reservoir with additional drug, namely the dangers of both compromised sterility and non authorized introducing of air bubbles and dust contaminations by unskillful users. The invention discloses several designs of low cost disposable cartridges which contain neither electronics nor high precision parts, and are practically fully made of non-expensive plastic materials in order to reduce long-term exploitation cost.

Additional aspects of the invention fully eliminate potential risks of the leak and uncontrollable overdose of liquid medicine. Devices of the invention are capable of alarming in the case of the insurmountable occlusions with the only sensor detecting occlusions.

Further aspects of the invention provide fast and reliable detection of accidental changes of several critically important parameters occurring from time-to-time either outside or inside of any hydraulic part of the device. Devices and methods of the invention further provide automatic compensation of multiple changes, including the compensation of partial occlusion of the flow passage, to maintain the desired dosing regime even in the cases of the high level of incomplete occlusion or non-fatal internal damages of the device. Certain devices of the invention further provide the patient with an unlimited ability of high precision manual operation in rare emergency cases when automatic functioning of the device is interrupted for any reason.

Yet further aspects of the invention include devices of simple construction of the entire device, which can eliminate the need of using the expensive high-precision components, reduces the cost of production, and substantially increases long-term reliability of the whole device. Also new simple construction allows making so small and thin devices that they may be deployed directly on patient's skin and easily hidden under clothes in order to make them practically invisible.

Devices of the present invention comprise few major functional blocks which in certain embodiments are desirably located in at least two different housings. A first separate housing represents a replaceable cartridge containing a full hydraulic system "a" which has at least one exit opening and comprises a reservoir destined to be filled with a fluid. A second separate housing represents an actuating module comprising: a driving force system "d" which is capable of changing over time a force applied to the fluid in the reservoir when both housings are connected, at least part of a sensor system "b" producing output signals, and at least part of a controlling system "c" comprising a programmable processor capable of both: (i) acquiring the output signals produced by the sensor system "b", and (ii) controlling the driving force system "d".

Devices of the invention become fully ready to work when these two housings are tightly connected. That is why the devices are desirably supplied with means destined to provide well fixed temporary connections of the actuating module with pre-filled replaceable cartridge. Accordingly to "plug-n-play" principle, said connecting means are made so simple that the connection of pre-filled cartridge before the work and further disconnection of empty replaceable cartridge can be easily performed by any unskillful user.

In certain embodiments, providing most convenient operation, the devices may also comprise a remote control module located in a third housing comprising a display, certain parts of the system "c", and a system providing remote signal exchange between the third housing and the actuating module. Some elements of the system "b" may also be deployed in the third housing when it makes the use of the device more convenient for users.

The reservoir being a part of the hydraulic system "a" fully located in the replaceable cartridge has at least two spatially separated sections connected so that hydraulic resistance between them is not less than non-zero $R_1$. The system "a" also comprises specific hydraulic means connecting the exit opening with the reservoir. This specific means comprises at least one such component, which has a predetermined non-zero hydraulic resistance $R_2$ so that output hydraulic resistance of the device $R_{exit}$ cannot be less than $R_2$. The reservoir is supplied with at least one expandable element made of resilient material so that elastic deformation of at least part of this expandable element reflects the current status of the entire process of the fluid delivery.

The sensor system "b" comprises at least one sensing element located in the actuating module. Fixed position of the replaceable cartridge relatively the actuating module in ready to work device fixes also relative positions of both said sensing element located in the actuating module and at least part of said expandable element located in the cartridge. Because both the sensing element and said part of expandable element are destined to be directly involved in producing analog input signals of the system "b", it is important that after connection of both housings said expandable element takes such position within the housing of replaceable cartridge which provides said at least one sensing element of the system "b" with an ability of producing input signals associated with the geometry of said expandable element changing due to elastic deformation. That is why both input and output signals of the sensor system "b" become associated with at least one geometric parameter of said expandable element. It is desirable that the actuating module comprises also at least a primary part of a transducer transforming input signals into output signals, and most preferably into digital output signals.

The processor being an inevitable part of the controlling system "c" is capable of acquiring said output signals produced by the system "b" and treating them accordingly to predetermined mathematical algorithm in order to produce another signals controlling the system "d". Few versions of preferred embodiments are described, which are different in regard of details, technical abilities, and algorithms controlling their performance. However, main features listed above are common for all versions of the invention, and each particular example of the disclosed embodiments is just a member of the same family of liquid drug delivery devices covered by the same general scope of the invention.

The fluid delivery process is a programmatically controlled sequence of cycles. Every cycle of the drug delivery is limited in time so that it provides predetermined micro-dose $D_0$ of the fluid related only to this particular cycle, whereas desirable average speed of the drug delivery depends on the adjustable rate of cycle's repetition controlled by the system "c". In order to begin each next cycle the processor initiates a driving force system "d" by a starting electric signal produced at programmatically predetermined moment $t_{st}$.

Before this moment the force applied to the fluid in the reservoir is kept about the zero, and the fluid in the reservoir is subjected to as low pressure as may be necessary to prevent the fluid to flow out of said exit opening. Actually, the initial low pressure in the reservoir is very close to an external pressure $P_{ext}$ which is typically equal external atmospheric pressure $P_{atm}$ applied to the fluid in the exit opening. That is a major reason why the fluid is stopped completely for a while preceding the cycle, and neither leakage nor overdosing can happen during said while.

Another common feature of embodiments of the invention is that in the beginning of each cycle the driving force system "d" applies to the fluid continuous compressing force destined to squeeze the fluid out of the reservoir. In order to stop said squeezing-out of the fluid in the end of the cycle the system "d" terminates said continuous compressing force. However, in certain embodiments a time-dependent decompressing force may be also applied to the fluid after termination of said compressing force.

Driving force system "d" providing zero squeezing-out force before the cycle is allowed to satisfy extremely simple technical conditions. It must only be capable of fast producing the compressing force squeezing the fluid continuously out of the reservoir after $t_{st}$, and then fast terminating said squeezing-out force after receiving an ending electric signal. That means that the desirable time-diagram of the compressing force looks like quasi-rectangular pulse. One more reason why the design of the system "d" may be very simple is that its executive mechanism doesn't need to include high precision parts, and it doesn't matter what particular mechanism fulfills these requirements. For example, one can either use a mechanism based on an electric motor capable of moving a piston of a syringe forth and back, or compress an elastic wall of the reservoir with the use of simple latch-type mechanism based on controllable interaction between at least one permanent magnet and at least one electromagnet. The latch-type system "d" comprising said two magnets is capable of fast switching between two stable states so that the continuous compressing force is created in one state, and, if desirable, time-dependent decompressing force can be created shortly in another state. It does not matter also if the amplitude of such pulse-like changing compressing force varies significantly in different cycles because the method of the invention is capable of keeping the same high precision dosing in wide range of variations of said amplitude.

One more advantage of the latch-type driving force system is that it is capable of preventing significant overdosing even in such rare emergency cases when the system "d" cannot terminate said continuous compressing force and be returned to said another state because after producing start signal either system "c" or system "d" or both become either fully or partially disabled.

Because said peculiarities of very simple system "d" mentioned in previous paragraph the devices of the invention posses uniquely high reliability. However, there is additional possibility to make this reliability even higher when the device of the invention is further supplied with additional emergency means providing a patient with an ability of manual control of a force applied to the fluid in the reservoir. Manual application of said force may be used temporarily in certain emergency cases if controlling system "c" detects substantial malfunctioning of the system "d" for any reason. In such cases the patient should act under supervision of either acoustic, or visual, or mechanical signals of the system "c" for as long period of the time as may be necessary to restore normal automatic functioning of the device.

Major novelties of the invention result from mutually correlated constructive features of both the hydraulic system "a" located in the replaceable cartridge and the sensor system "b" located in the actuating module, said constructive features specifically combined with features of the method of the device operation. The reservoir comprising said expandable element has two hydraulically connected sections: (i) the first, called the compression section, wherein the compressing force of the system "d" may be directly applied to limited surface area of the fluid, and (ii) the second, called the indicator section, wherein certain part of the expandable element is contacting with another limited surface area of the fluid filling the reservoir. Because these two hydraulically connected sections are spatially separated, the direct action of pulse-like compressing force in the compression section can only initiate the squeezing of certain volume of the fluid in the direction of the indicator section. The arrival of additional volume $\Delta V_{ind}(t)$ of the fluid causes a resilient expansion of such part of the expandable element which relates to the indicator section of the reservoir and is involved in producing the analog input signals of the system "b". Volume expansion $\Delta V_{ind}(t)$ of the indicator section causes simultaneously both resilient deformation of said element and an appearance of time-dependent excessive pressure $\Delta P_{ind}(t)=P_{ind}(t)-P_{ext}$ in indicator section.

The deformation of the expandable element means that at least one geometric parameter of this element changes. It was previously mentioned that, when the replaceable cartridge and the actuating module are connected, said expandable element takes such position relatively of at least one sensing element of the sensor system "b" that the analog input signals of the system "b" become associated with said variable geometric parameter reflecting both the change $\Delta V_{ind}(t)$ and the excessive pressure $\Delta P_{ind}(t)$. The point is that the information contained in these signals relates directly to the intensity of the fluid flow reaching the exit opening and, therefore, these signals represent the only real source of an information which can be used by the processor to control the fluid flow while each delivery cycle. Thus, the expandability of the indicator section is critically important for functioning of whole device.

There are many different choices of sensors producing analog input signals. Sensors may comprise either a piezoelectric element mechanically contacting with the expandable part of the indicator section, or non contact sensors represented by either a variable capacitor, or a magnetic sensor, or few optic sensors of different types. The transducer treating the analog input signals and transferring output signals to the processor may comprise standard auxiliary electronic means such as amplifiers, differential amplifiers, analog-to-digit converters, means capable of either transmitting or/and receiving any signals associated with analog input signals, including but not limited to wireless transmitting means or/and wireless receiving means if necessary or desirable.

Wireless information exchange between electronic parts of the device, for example such as the processor and its control panel, may be very convenient when a patient with small actuating module deployed on his or her skin and hidden under clothes needs to change processor's program. In this case the remote control panel may be located anywhere, especially if a patient is a little child and parental control is required. In addition, a long-distance wireless information exchange may be also used when necessary, for example, for urgent automatic communication between the programmable processor accumulating the information related to a patient and the personnel of medical center taking care of him or her.

However, wireless control module may be accidentally disabled from time-to-time for any reason. In order to overcome such emergency situation it is desirable that the actuating module is further supplied with at least such minimum number of control elements which provide the patient with an ability to operate at least most necessary drug delivery programs even without remote control module.

General method of the invention is applicable to all devices of the invention comprising at least such major features as: (i) the actuating module connected with the replaceable cartridge having the reservoir containing the fluid, (ii) said actuating module capable of changing over time a force applied to the fluid located in the compression section of said reservoir, said compression section hydraulically connected with such spatially separated indicator section of the reservoir which comprises at least one resilient element contacting with said fluid, (ii) hydraulic means connecting said indicator section with at least one exit opening, said connecting means comprise a static hydraulic resistor having predetermined resistance $R_2$. The general method comprises following steps of every cycle: (a) initiating a non-zero force squeezing the fluid out of said compression section of the reservoir; (b) acquiring at least one signal associated with at least one geometric parameter of said resilient element; (c) determining a moment $t_{end}$, said determining comprises treating said at least one acquired signal by either analog or digital processor capable of performing predetermined mathematical algorithm; (d) terminating said force at a moment $t_{end}$ determined by said processor. Steps (a, b, c, d) constitute one delivery cycle which can be repeated as prescribed by a delivery instructions.

Before the step (a) there is no substantial squeezing-out force and the fluid in whole reservoir is subjected to as low pressure as may be necessary to prevent the fluid to flow out of the exit opening. The step (a) begins when the driving force system "d" is initiated by at least one starting electric signal produced at predetermined moment $t_{st}$ detected by the processor accordingly to delivery instructions. In response the system "d" creates non-zero compression force quickly and applies it to limited surface area of the fluid in the compression section of the reservoir. Because after $t_{st}$ the fluid is squeezed out of the compression section and arrives into the indicator section of the reservoir, the resilient element related to the indicator section is continuously subjected to depending on time pressure $P_{ind}(t)$ exceeding external pressure $P_{ext}$ within predetermined brackets $P_{max}+P_{ext}>P_{ind}(t)>P_{min}+P_{ext}$. The result is that the same continuous non-zero pressure difference $[P_{ind}(t)-P_{ext}]=\Delta P_{ind}(t)$ forces the fluid to flow out of the indicator section of the reservoir and causes certain geometric change of said resilient element which is reflected in signals of the sensor system. Steps (b) and (c) begin immediately after $t_{st}$ in order the processor could acquire and treat said signals as quickly as possible. This treatment determines quantitatively both pressure difference $\Delta P_{ind}(t)$ and a period $T_c=t_{end}-t_{st}$, wherein $T_c$ is such duration of the compressing force which provides an equality of the predetermined dose $D_0$ and an actual dose delivered. The actual dose is represented quantitatively by an integral found by integrating over time since the moment $t_{st}$ of a ratio, wherein a numerator is said pressure difference $\Delta P_{ind}(t)$, whereas a denominator is a parameter expressing hydraulic resistance $R_{exit}$ of said means connecting the exit opening with the reservoir. The step (d) comprises producing at least one ending electric signal at the moment of the real time coinciding with $t_{end}=t_c+t_{st}$ determined while step (c). This ending signal results in terminating the compressing force so that the pressure of the fluid in the reservoir can relax up to about its initial value which existed before the step (a). At certain point of said relaxation the outgoing flow stops and current cycle of the fluid delivery ends so that the actual dose delivered to the exit opening is equal or very close to desirable dose $D_0$.

In certain embodiments of the invention the step (d) may comprise an initiation of short-term decompressing force which may be also applied to the fluid in the compression section of the reservoir immediately after termination of the compressing force. Said decompressing force helps to restore proper initial state of the reservoir before the next cycle of drug delivery, especially in the case of such construction in which the reservoir is further supplied with an additional section hydraulically communicating with the compression section. Once being applied said decompressing force relaxes shortly automatically without special control operations.

The advantage of both methods and devices of the invention is that the signals treated by the processor contain the information reflecting instant state of the entire hydraulic system "a" while each delivery cycle, including real time-dependence of the pressure squeezing the fluid out of the reservoir. In advanced devices of the invention these signals also reflect actual resistances of hydraulic elements involved in the delivery process. That means that all current variations of major parameters and variables of the device, causing variations of the intensity of outgoing fluid flow, are immediately taken by the processor into account accordingly to actual state of the device. That is why the duration of each cycle $T_c = t_{end} - t_{st}$ is always determined so that the actual dose delivered remains equal or very close to predetermined dose $D_0$ independently on variations of both external conditions and/or current performance of the device.

The excessive pressure created by simplified system "d" after $t_{st}$ is allowed to vary in different cycles in rather wide brackets $P_{max}/P_{min}$ up to about 20. This circumstance is taken into account by all mathematic algorithms determining the moment $t_{end}$ accordingly to constructive specificity of each particular device of the invention. For example, in most simple devices both sections of the reservoir are connected by means having very low hydraulic resistance $R_1$. In this case the actual dose is represented by the integral of the ratio wherein the numerator is proportional to a sum of all signals acquired by the processor since the moment $t_{st}$, and the denominator is equal predetermined $R_2$ which is considered as the parameter expressing output resistance $R_{exit}$. If the $\Delta P_{ind}(t)$ is relatively stable during $T_c$ then even one signal acquired after $t_{st}$ may be enough for high precision determining $t_{end}$. In the case of unstable $\Delta P_{ind}(t)$ more signals should be acquired in order to keep high precision of fluid's dosing. Thus, even most simple devices of the invention are capable of complete eliminating fluctuations inherent for simple system "d" but their precision may drop in the case of an occlusion which increases output resistance significantly.

In advanced devices the communication between two spatially separated sections of the reservoir has a hydraulic resistance $R_1$ which may not be less than 0.05 $R_2$. More precisely the ratio $R_1/R_2$ exceeds 0.05 and is less than 200, more desirably it is in between 0.25 and 40, and most desirably it is in between 1 and 10. Because $R_1/R_2$ exceeds 0.05 the kinetics of the excessive pressure $\Delta P_{ind}(t)$ in the indicator section becomes substantially slowed-down relatively sharp increase of the pressure in the compression section. The discovery of the invention is that slowed-down kinetics $\Delta P_{ind}(t)$ contains quantitative information about actual output resistance $R_{exit}$ related to means connecting the exit opening with the reservoir. In advanced devices actual $R_{exit}$ is determined by the specific algorithm which needs to treat at least two signals acquired while $T_c$. In this case the actual dose of the fluid is represented by analytic expression of the integral wherein the actual $R_{exit}$ determined is substituted to the denominator of said ratio. Because actual parameters and variables of each cycle are determined, such as the excessive pressure $\Delta P_{ind}(t)$ and $R_{exit}$, advanced devices of the invention provide automatic adjustment of $T_c$ which leads to self-compensating both strong fluctuations of simple system "d" and potentially possible increase of the actual $R_{exit}$ occurring in the case of partial occlusion. The method of advanced devices further comprises producing an alarm signal if determined actual $R_{exit}$ exceeds predetermined level corresponding to an insurmountable occlusion. The said means that advanced devices of the invention do not require additional occlusion detector. Such devices need to be calibrated only one time before the work, and then they save calibrated parameters in processor's memory.

The most advanced devices satisfy all requirements considered in previous paragraph, but in addition their hydraulic means connecting the exit opening with the reservoir are further supplied with an element switching hydraulic resistance at predetermined pressure drop $P_{op}$. For example, this element may be a passive valve capable of switching its hydraulic resistance $R_{val}$ so that $R_2$ exceeds $R_{val}$, and more preferably $R_2$ exceeds $R_{val}$ at least by the order of magnitude when a pressure drop applied to this valve exceeds $P_{op}$. When the pressure drops below $P_{op}$ or below $P_{cl}$ which is either less or equal $P_{op}$, the resistance $R_{val}$ exceeds $R_2$, more desirably $R_{val}$ exceeds $R_2$ at least by the order of magnitude, and most desirable $R_{val}$ exceeds $R_2$ more than two orders of magnitude. In the presence of the self-switching valve the kinetics $\Delta P_{ind}(t)$ is combined of two different branches joining at calibrated pressure point $P_{op}$ which is used as an internal etalon. In order to analyze both branches and to obtain as high precision of determined $t_{end}$ as possible, the specific algorithm of most advanced devices of the invention requires acquiring and treating at least five, and most desirably significantly more than five signals while $T_c$. In addition to all self-compensating abilities mentioned above, this algorithm comprises self-calibrating whole system delivering the fluid, checking current performance of major components of this system, checking an amount of the fluid remaining in the reservoir. Also the method of most advanced devices further comprises producing a prompt report and/or alarm signal to inform a user if said amount of remaining fluid is too low, or any malfunctioning of the device is detected which cannot be self-compensated by said algorithm determining $t_{end}$. One more advantage is that after the moment $t_{end}$ the pressure drops below $P_{op}$ and the valve becomes closed. This eliminates entirely any risk of the fluid leakage and potential overdosing even in unlikely event of low residual pressure remaining in the reservoir after the end of the cycle. Because potential residual pressure is very low, the construction of said locking valve can be simple and absolutely free of costly parts requiring high precision.

Because all quantitative parameters and variables defining the actual delivery are always known to the processor while each cycle, devices of the invention posses exceptional ability of immediate self-compensating of many unpredictable external and/or internal events occurring from time-to-time. One can imagine, for example, that typical delivery of desirable dose $D_0$ takes 6 s between $t_{st}$ and $t_{end}$. If simple system "d" is allowed of producing excessive pressure $\Delta P_{ind}(t)$ within brackets $P_{max}/P_{min}$ about 7, and in given cycle $\Delta P_{ind}(t)$ jumps accidentally three times above average value, then the processor detects this event and shortens the $T_c$ also three times. Namely, instead of normal 6 s it sends the ending signal after 2 s, thus keeping constant value of the actual output dose. In other example at normal $\Delta P_{ind}(t)$ the actual output resistance may spontaneously increase from normal $R_{exit}=R_2$ to very high $R_{exit}=20\ R_2$ because of strong partial occlusion. In response the processor delays the ending signal as necessary (roughly about 30 s) to keep the actual output dose with no change. If the device of the invention is used for diabetes treatment of children under ten years, typical average rate of the insulin delivery is close to 10 $mm^3$/hour or less. If the delivery of the single dose $D_0$ about 1 $mm^3$/cycle takes 6 s in normal situation, the average rate requires only 10 cycles/hour. However, if medical situation requires the duration of the cycle to be as short as possible, the minimum dose of the same device can be as low as 0.02 $mm^3$/cycle with precision better than 0.001 $mm^3$. In the case of opposite medical emergency the same device can provide as high rate of the insulin delivery as 200 mm³/hour. These parameters are about two orders of magnitude better than that of currently known devices of the insulin delivery. Also the ability of self-compensating makes devices of the invention exceptionally reliable because they are capable of withstanding either changes of such external parameters as air pressure and a temperature, or accidental partial (but not fatal) internal damages of the device because of mechanical shocks, and so on.

The preferred embodiment of the invention discloses a very simple, replaceable cartridge located in a separate housing and destined to be disposable part of a fluid delivery device comprising another separate housing which contains a driving force system (d) capable of transferring a force into said housing of the cartridge under control of a programmable processor (c) connected with a sensor system (b). The device becomes finally ready to work only after mechanical connection of the cartridge with said another housing. The cartridge comprises: (i) a reservoir destined to be filled with the fluid and having at least two spatially separated sections connected so that hydraulic resistance between them is not less than non-zero $R_1$; (ii) means connecting at least one exit opening with such one section of said two which comprises at least one expandable element made of resilient material, said connecting means having a hydraulic resistance not less than predetermined non-zero value $R_2$ wherein in certain embodiments the ratio $R_1/R_2$ exceeds about 0.05 and is less than about 200, more desirably said ratio is in between about 0.25 and about 40, and most desirably said ratio is in between about 1 and about 10; and (iii) means capable of participating in temporary connection of said housings. After both said housings are connected, the system (d) and system (b) get such positions relatively said two sections of the reservoir that the force produced by the system (d) is transferred to at least one either movable or flexible element of one section of the reservoir and the system (b) becomes capable of producing input signals associated with at least one geometric parameter of the resilient element located in another section of the reservoir. Replaceable cartridges of certain preferred embodiments can be practically fully made of low cost plastic materials. They do not require active mechanisms, electronics, batteries, and/or high precision parts. Ready-to-use, factory pre-filled disposable cartridges can eliminate risks of compromised sterility and accidental introducing of either air bubbles or dust-like external contaminations, and can be easily replaced by any unskillful user.

Top and bottom views show directions of a light beam correspondingly at low and high pressure within the indicator.

Figure 19:
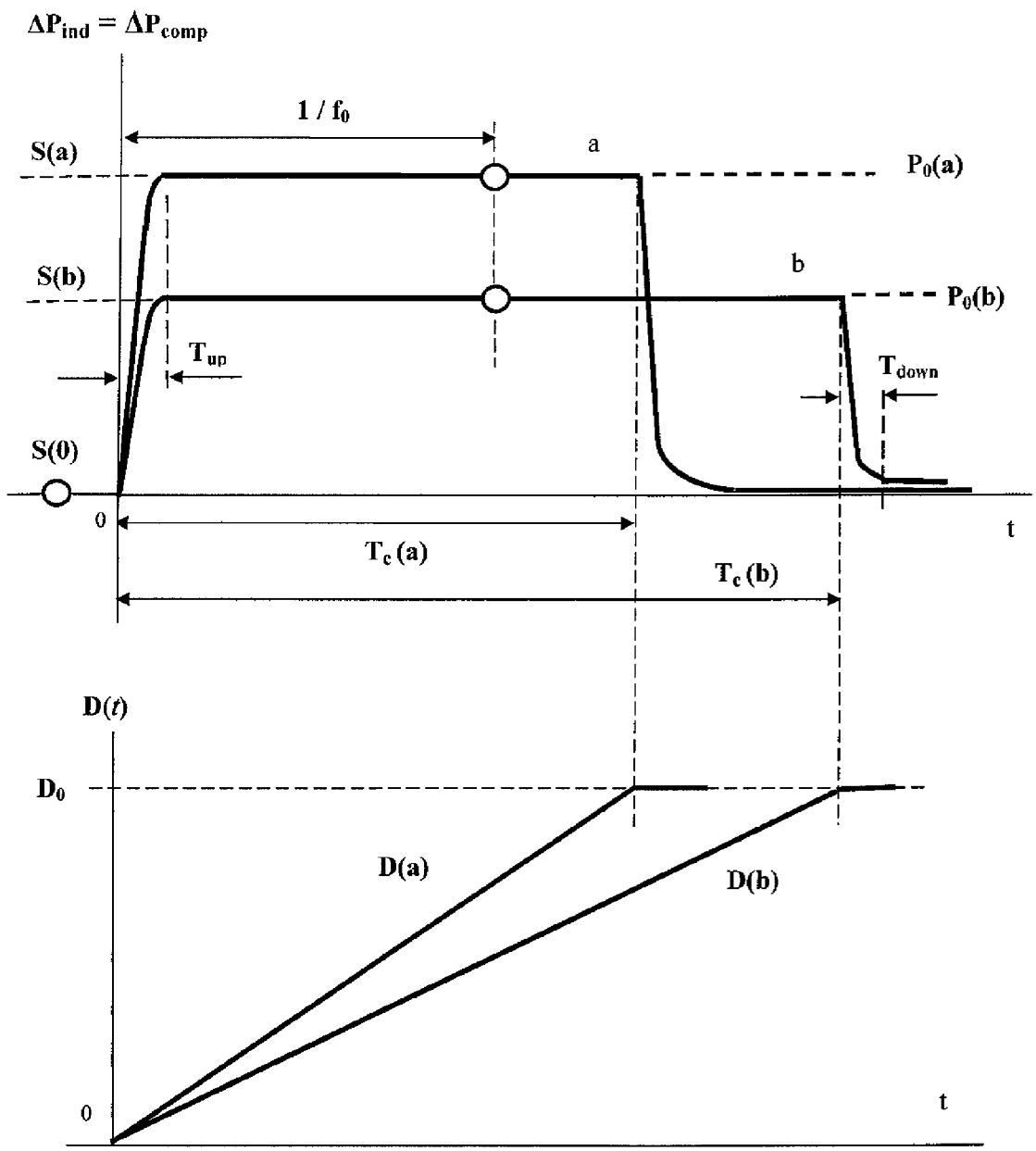

FIG. 19 depicts examples of two different quasi-rectangular time-diagrams of pressure pulses produced in the compression section of the reservoir of an embodiment of this invention having low hydraulic resistance $R_1$ (top view). Bottom view shows corresponding time-diagrams of the fluid doses delivered to the device's exit opening. White circles correspond to the readings of output signals of the sensor system. For simplicity, these signals are shown as if their scale coincides with the pressure scale of the indicator section.

Figure 20:
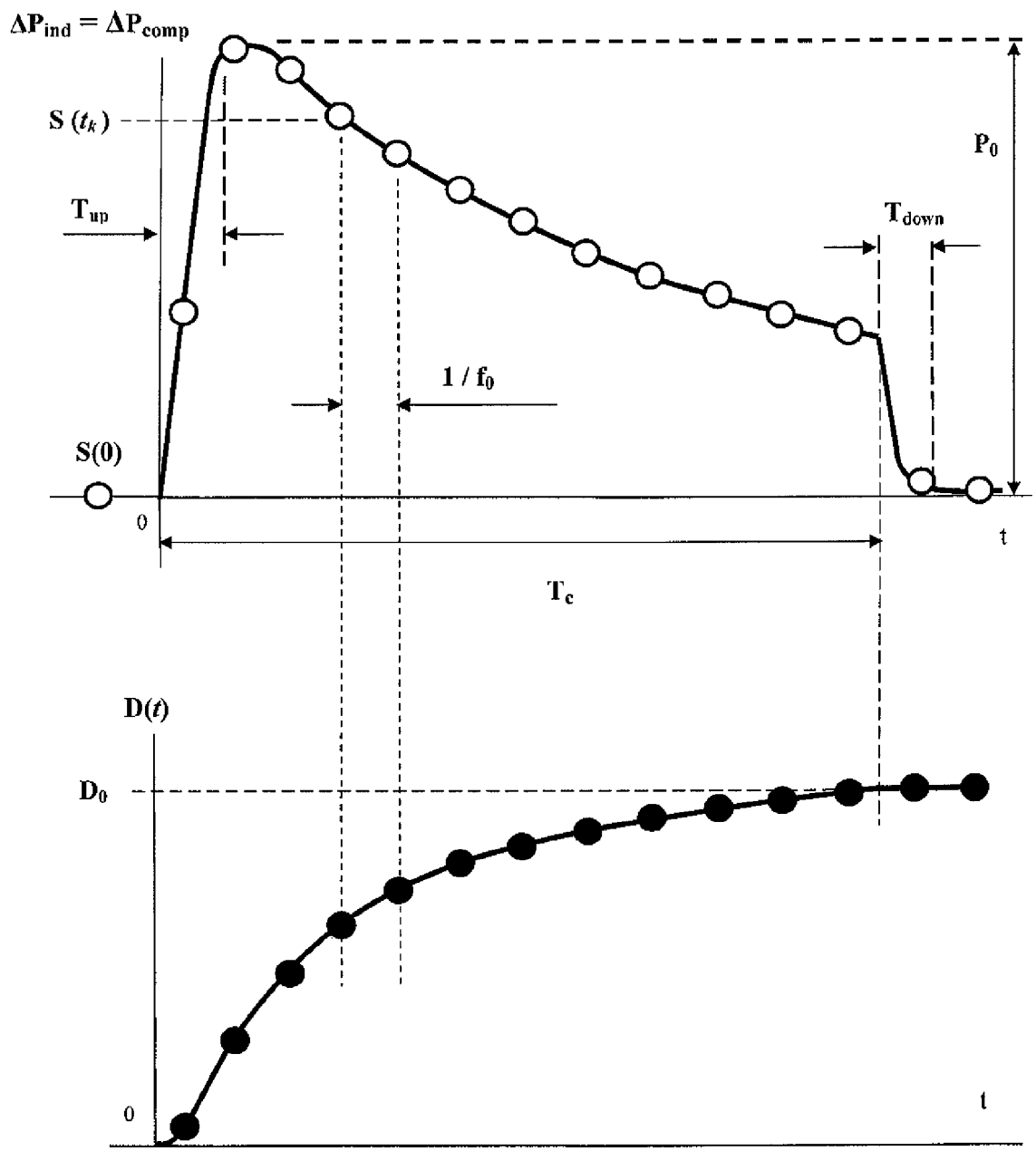

FIG. 20 depicts an example of a rather unstable plateau of a pressure pulse occurring in the compression section of the reservoir of an embodiment of the invention having low hydraulic resistance $R_1$ (top view). Bottom view shows the corresponding time-dependence of the fluid dose delivered to the exit opening. White circles correspond to the readings of output signals produced by the sensor system (for simplicity, signals are shown so as if their scale coincides with the pressure scale of the indicator section). Black circles show result of integrating the sensor's signals to urge the fluid dose delivered to the exit opening.

Figure 21:
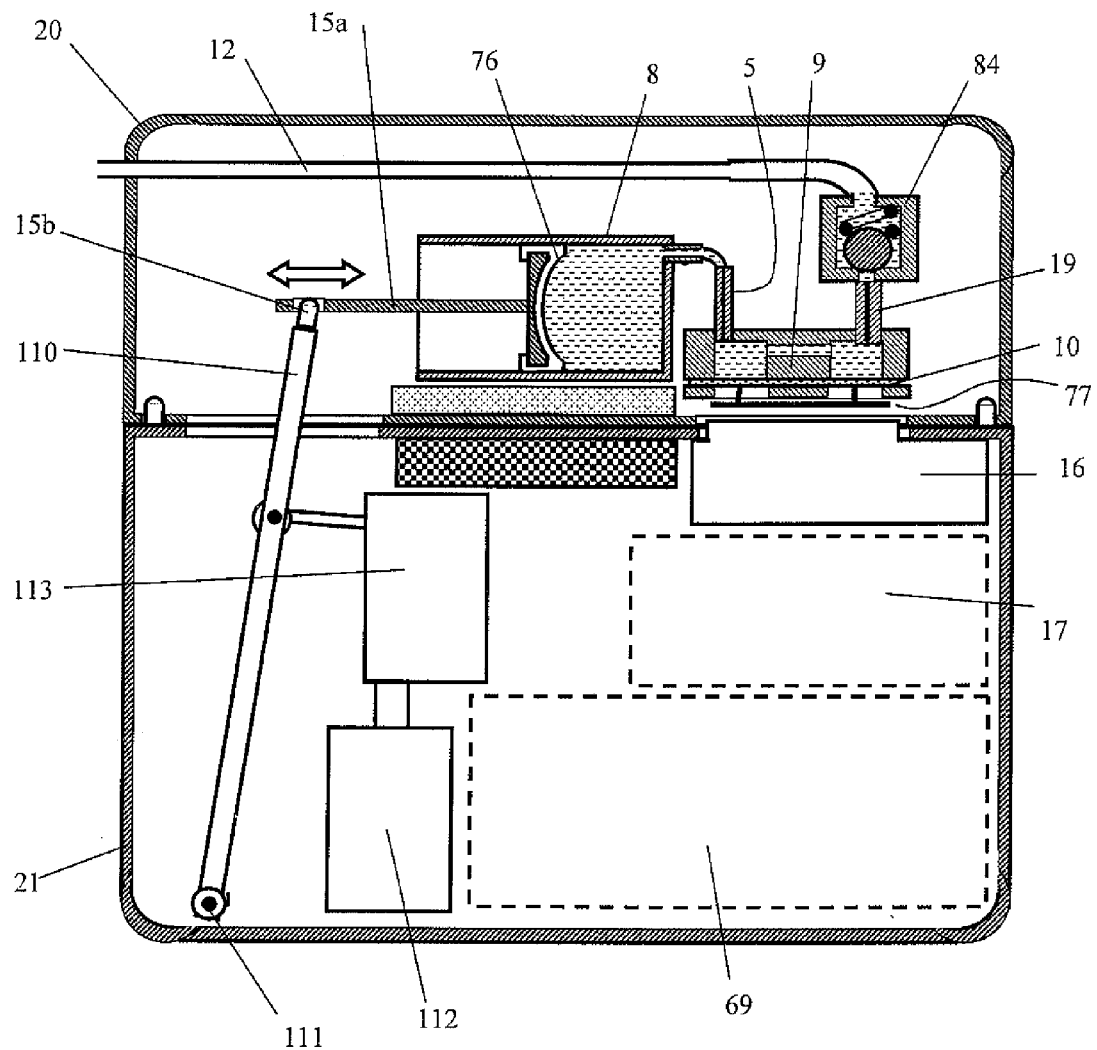

FIG. 21 depicts schematically an example of the invention in which a driving force system is driven by an electromotor in order to perform a drug delivery when the device of the invention comprises the replaceable cartridge having a syringe-like reservoir.

Figure 22:
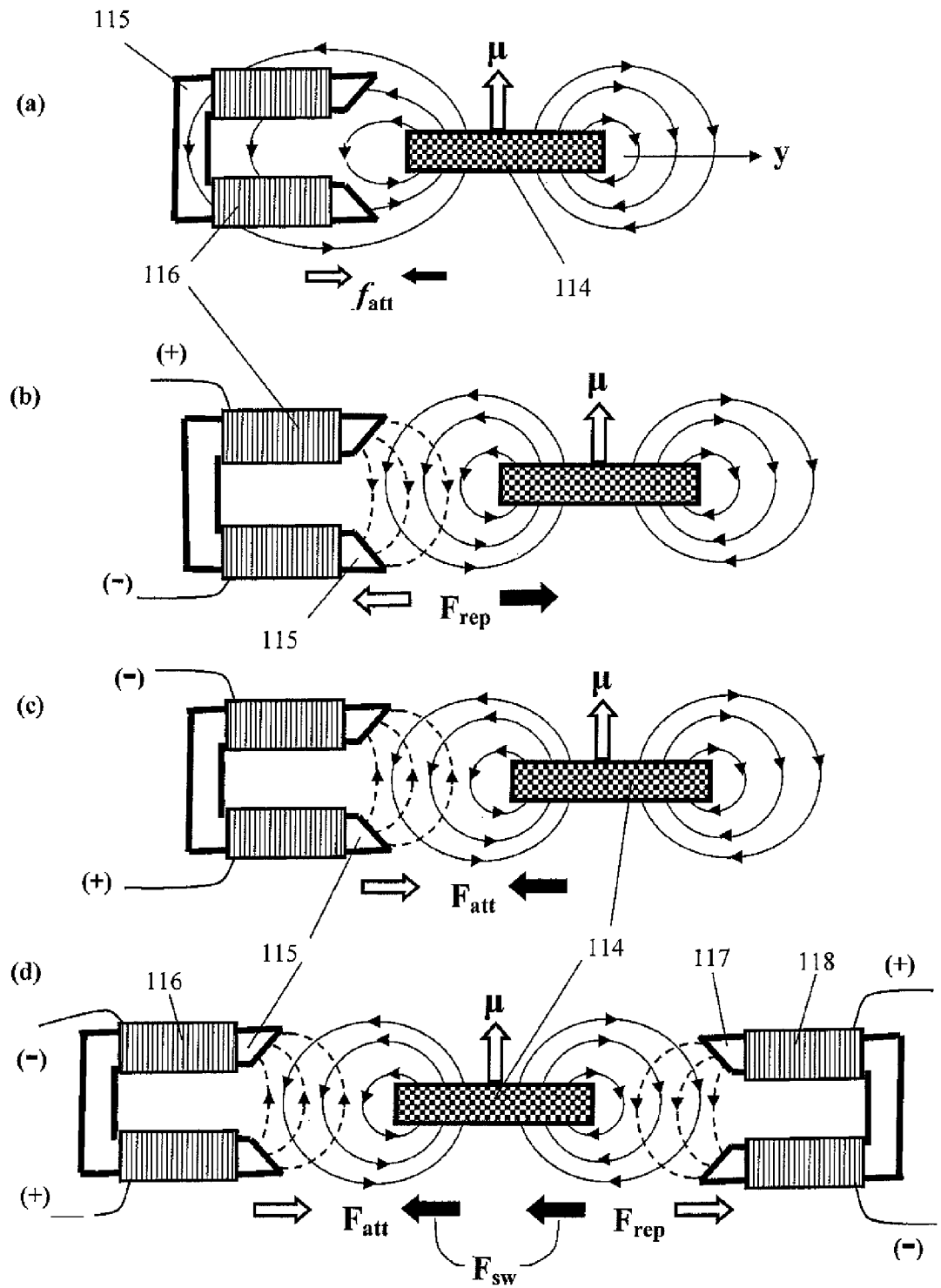

FIG. 22 depicts schematically examples of different forces produced by interaction of oriented permanent magnet with electromagnet(s): (a) passive, relatively weak attracting force with no current in an electromagnet coil; (b) strong repulsion when the current in the coil has specific direction; (c) strong attractive force when the current has another direction; and (d) push-pull design in which two electromagnets create even stronger switching force.

Figure 23:
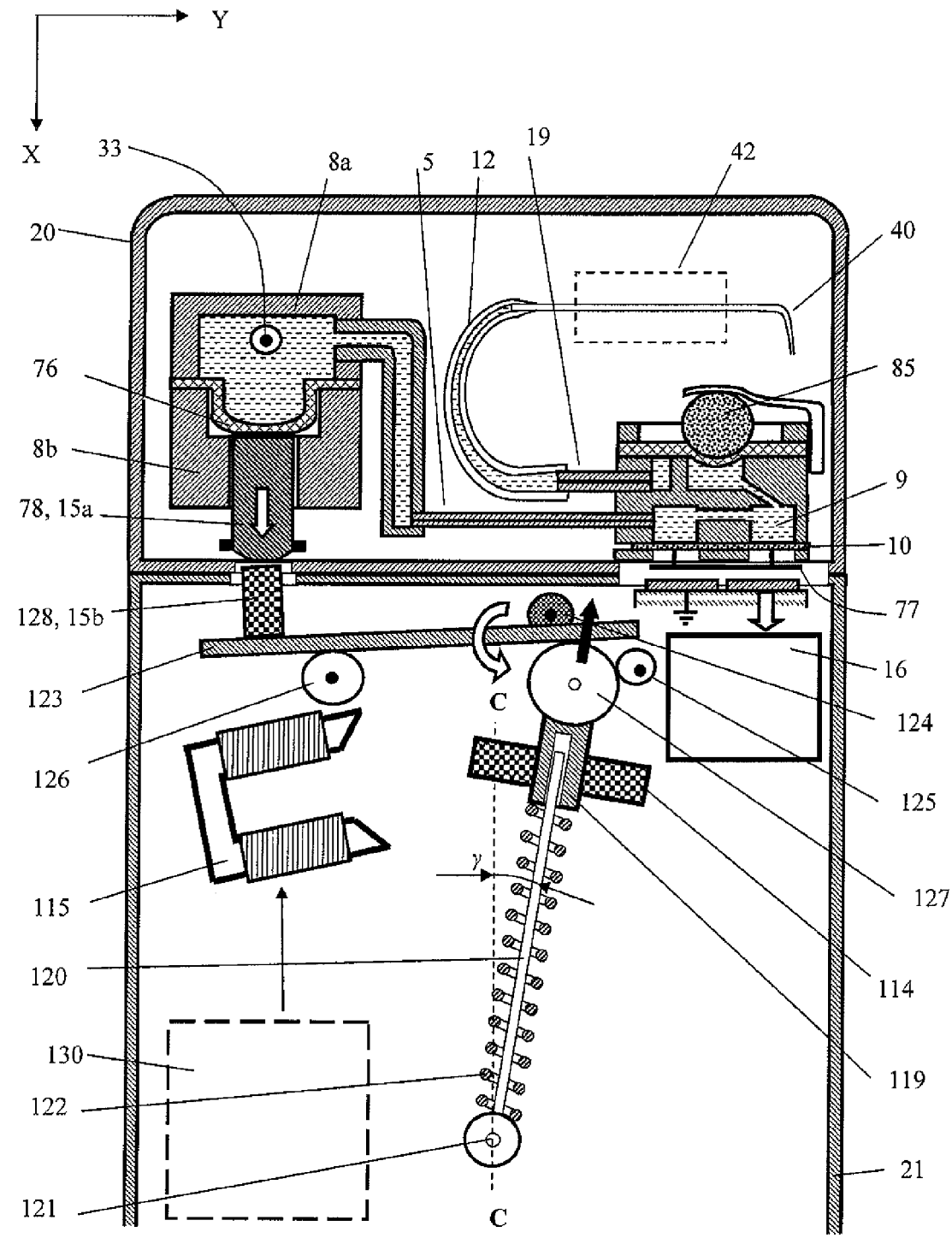

FIG. 23 depicts an example of the embodiment of the invention in which a motorless latch-type driving force system comprising a pushing compressed spring and switching system comprising one electromagnet and one permanent magnet capable of creating a tangential switching force. Latch-type system, shown in its inactive waiting stable state, is compatible with replaceable cartridge comprising the hydraulic system shown in FIG. 12.

Figure 24:
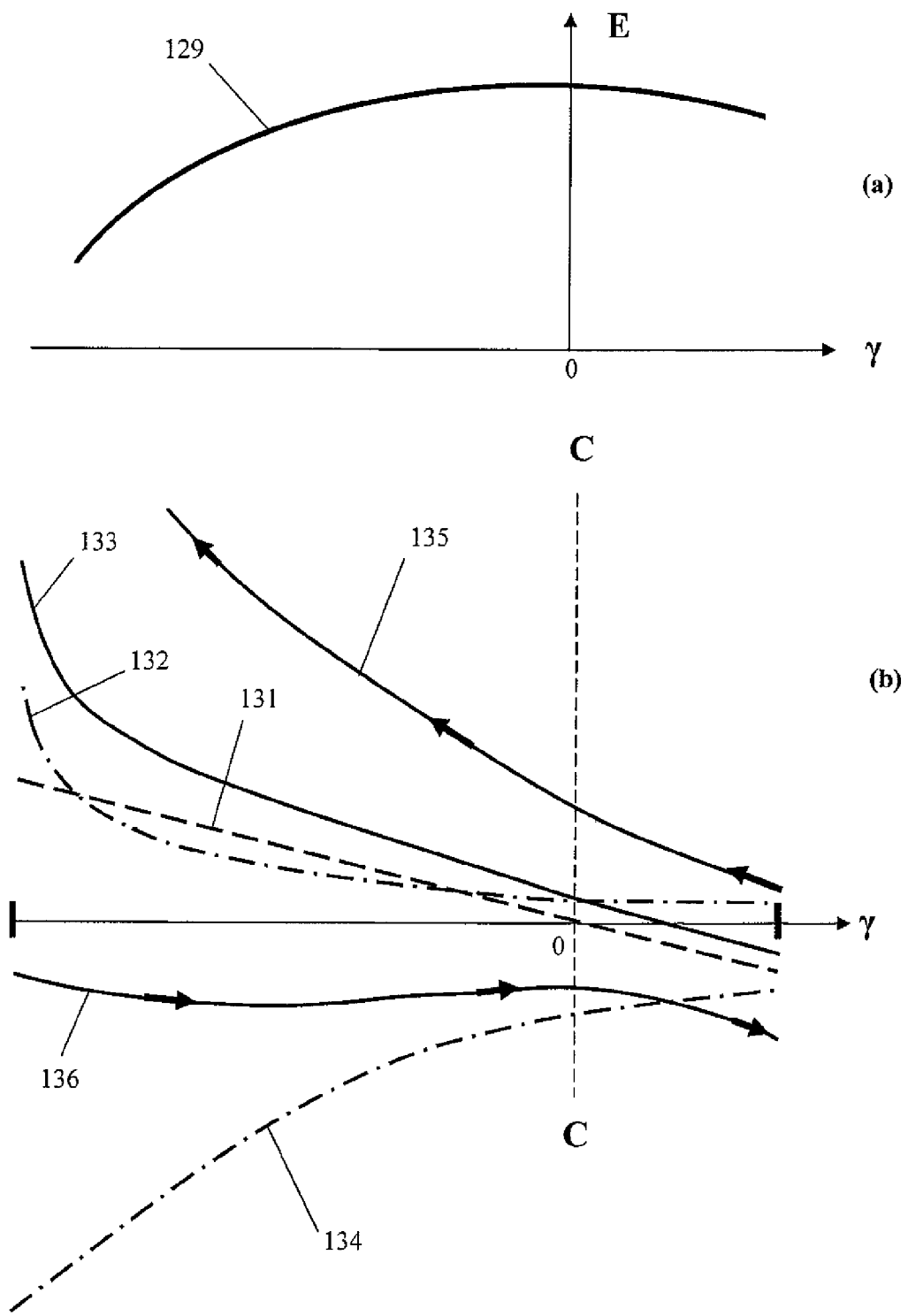

FIG. 24 depicts (a) an energy of compressed spring, and (b) asymmetric tangential forces of latch-type system as a function of an angular position of the permanent magnet shown in FIG. 23 when (i) the electromagnet is off, and (ii) in both active switching processes from left to right and from right to left.

Figure 25:
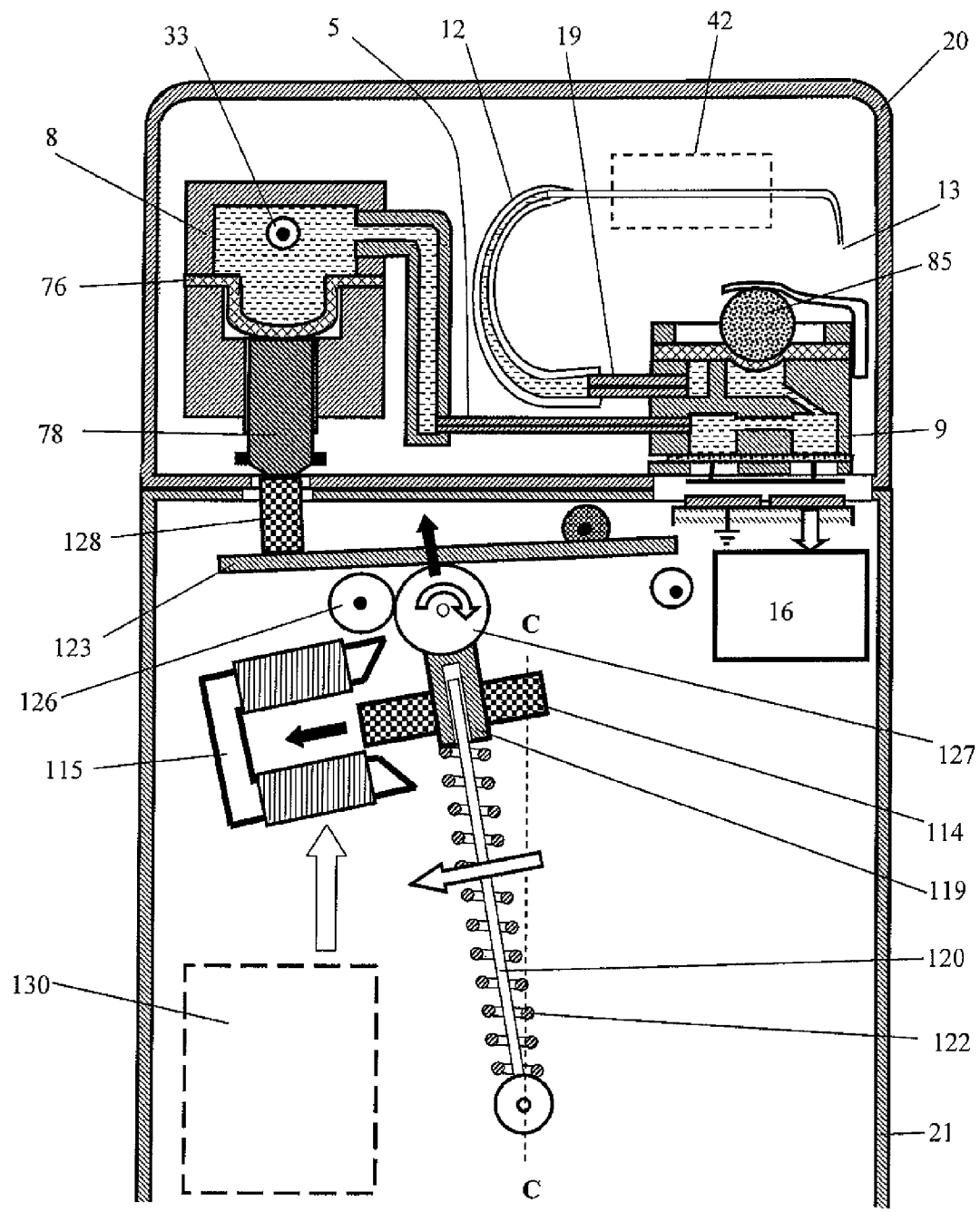

FIG. 25 depicts fast switching of latch-type system from its waiting stable state shown in FIG. 23 to the beginning of active compressing state when the electromagnet is on shortly.

Figure 26:
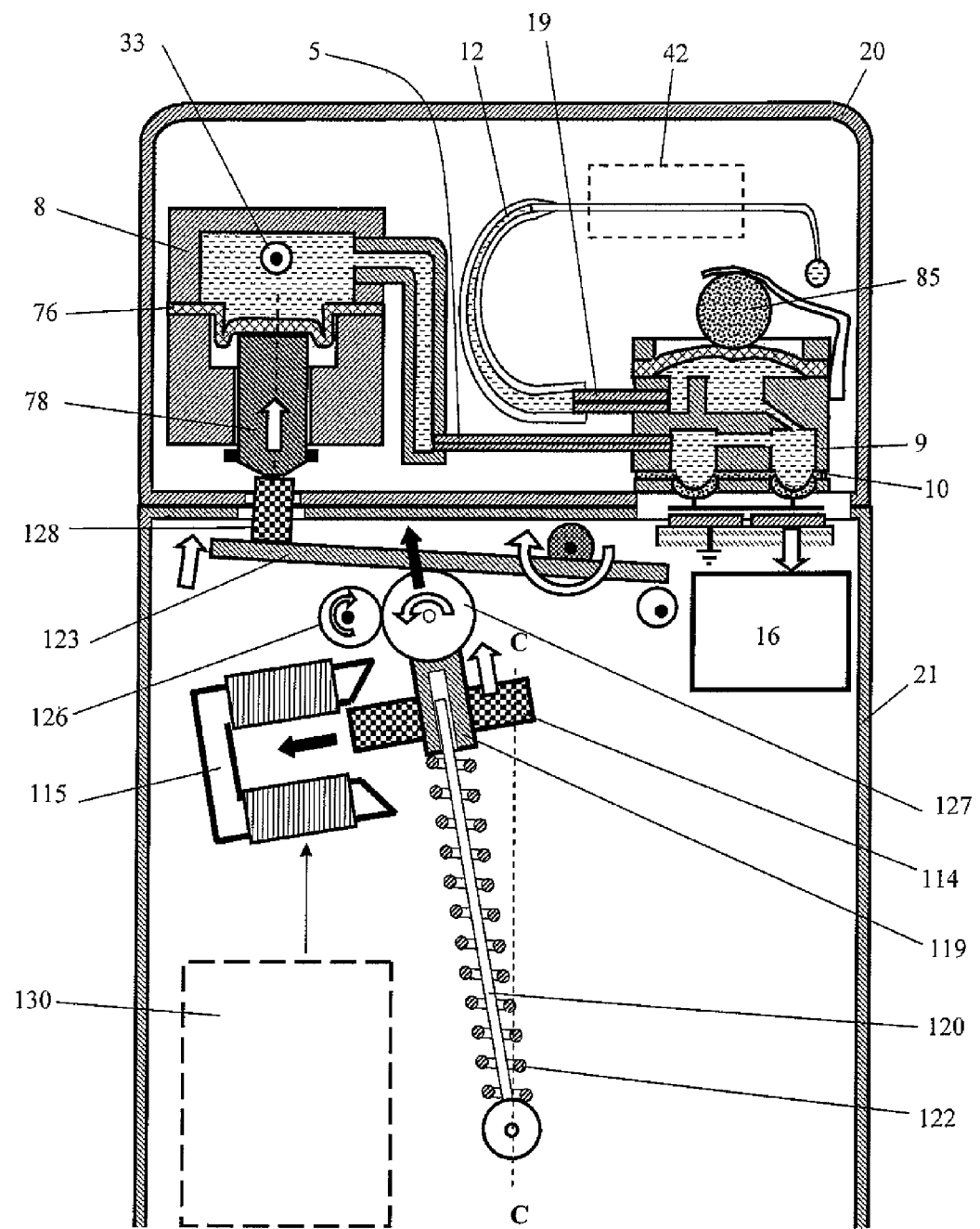

FIG. 26 depicts the process of continuous application of compressing radial force to the fluid in the reservoir provided by the same latch-type system after its quick switching into active state shown in FIG. 25. During the process depicted the electromagnet is off but the latch-type driving force system remains continuously in its stable compressing state.

Figure 27:
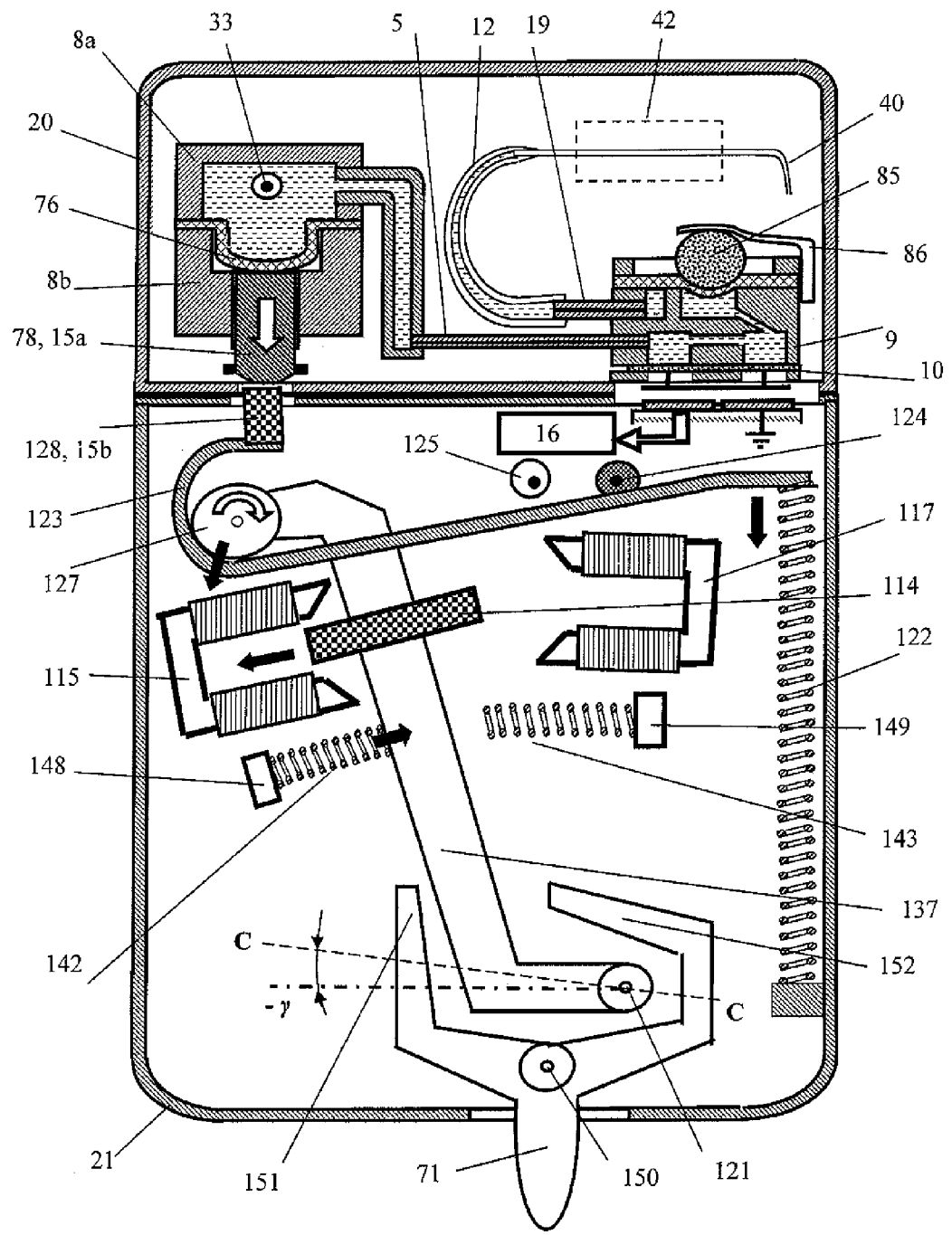

FIG. 27 depicts the embodiment of the invention with another motorless latch-type driving force system comprising a main stretched spring, one permanent magnet and two electromagnets. This latch-type system is shown in its inactive waiting stable state. Two optional springs help to accelerate switching and decrease an energy consumption.

Figure 28:
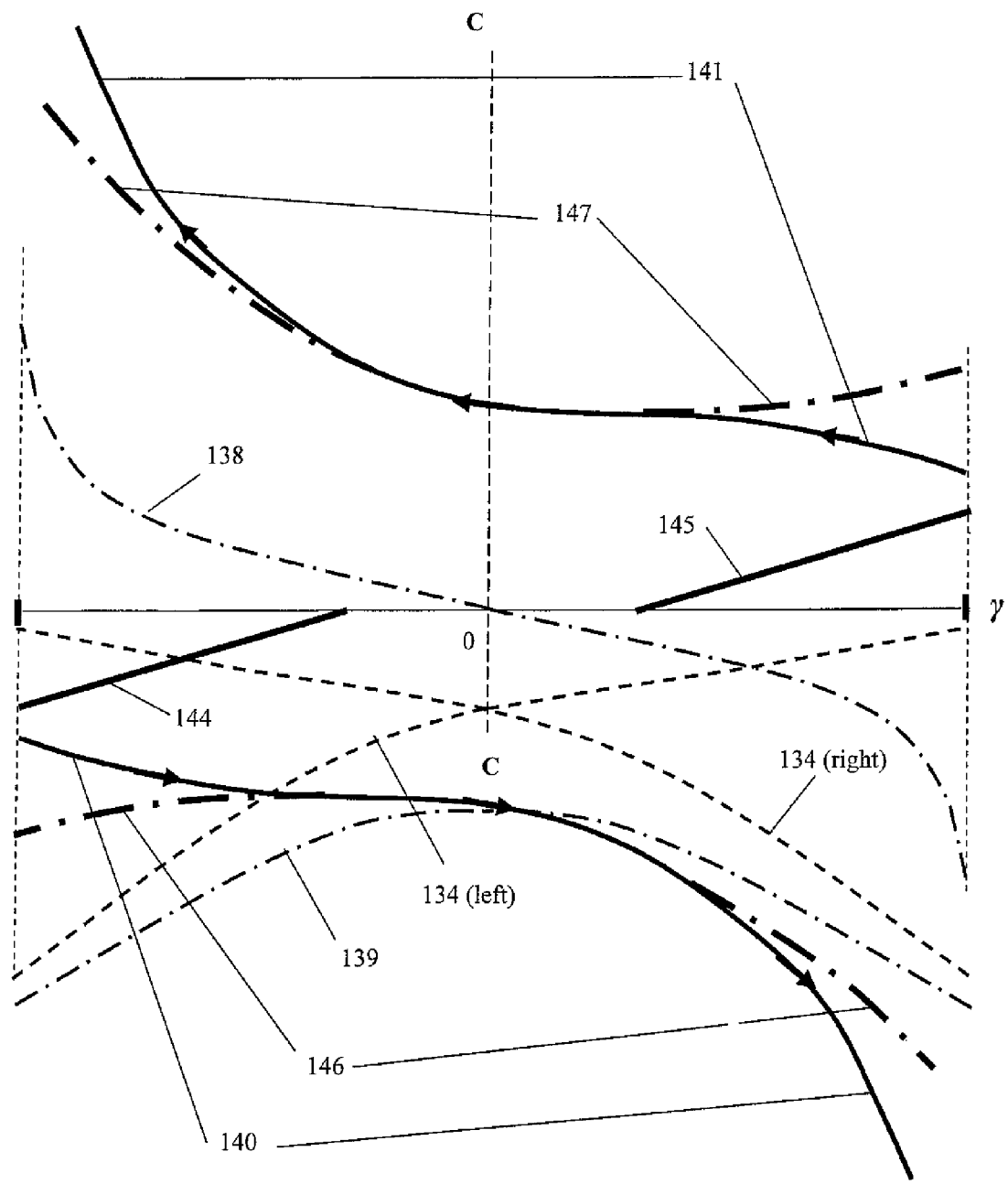

FIG. 28 depicts asymmetric tangential forces of latch-type system as a function of an angular position of the permanent magnet shown in FIG. 27 when (i) both electromagnets are off, and (ii) in both active switching processes from left to right and from right to left.

Figure 29:
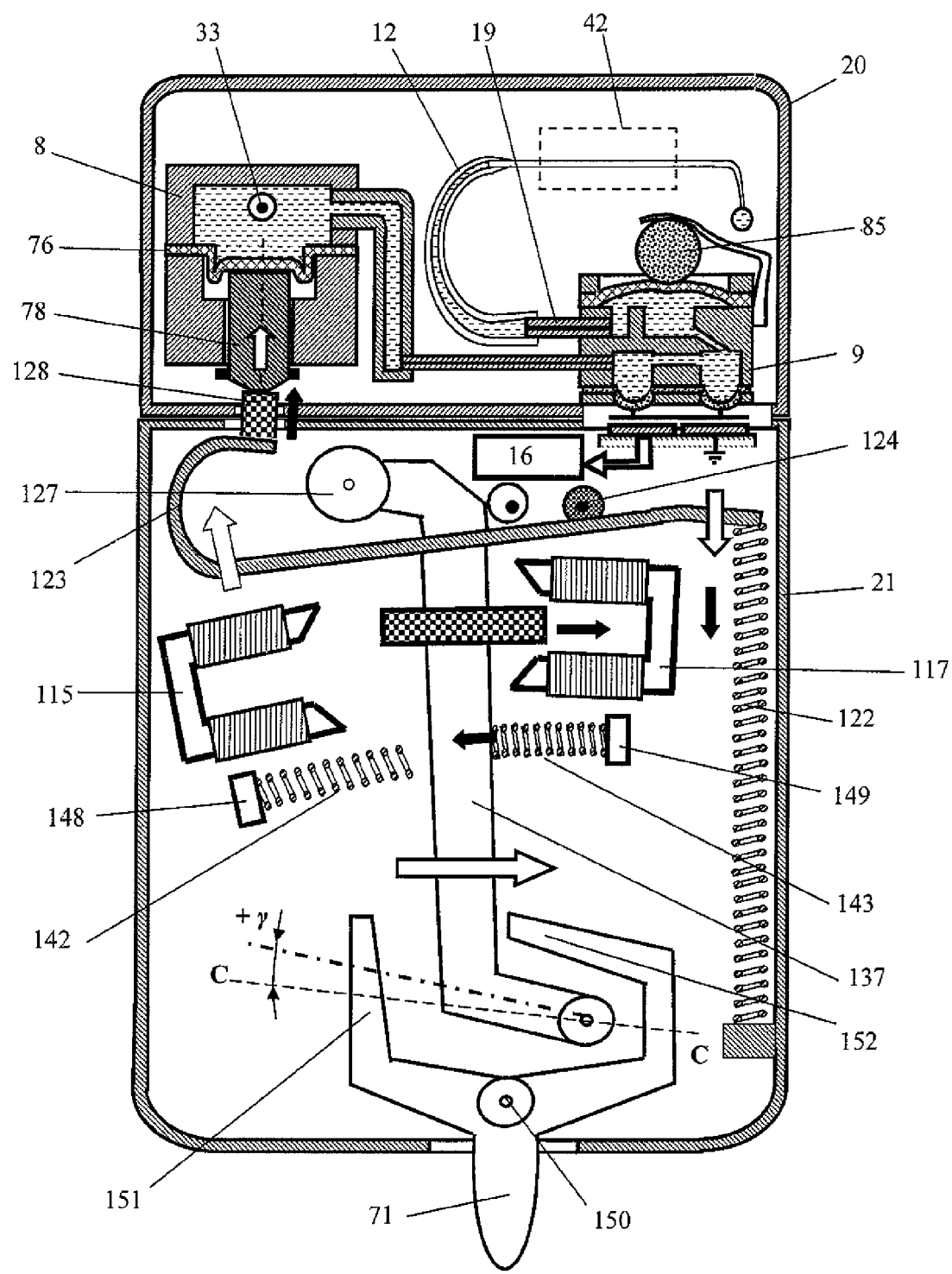

FIG. 29 depicts fast switching of the latch-type driving force system shown in FIG. 27 from its inactive waiting stable state to active compressing stable state, the switching provided by short activation of both electromagnets.

Figure 30:
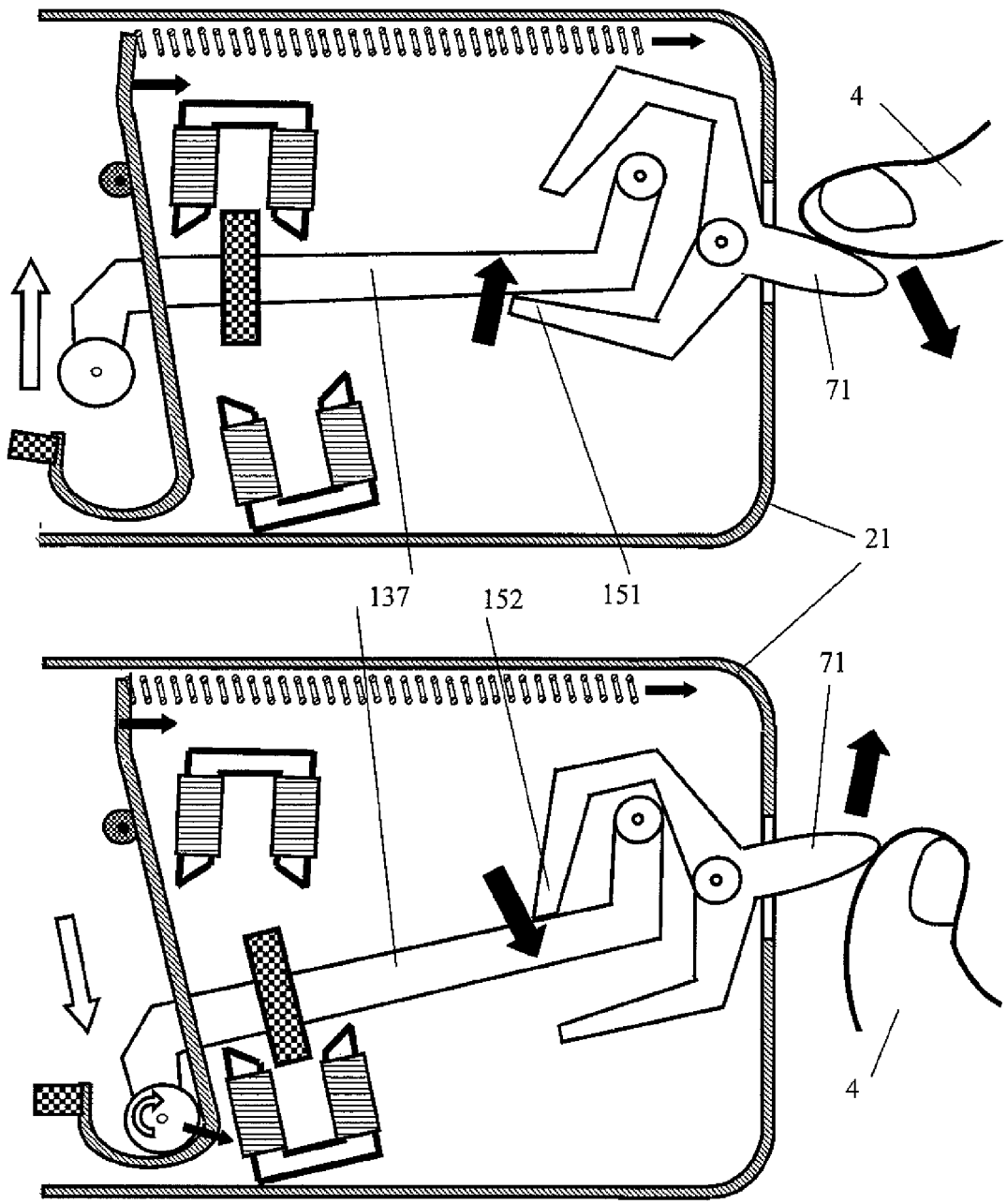

FIG. 30 depicts schematically an example of an emergency case in which a patient switches the latch-type driving force system shown in FIG. 27 manually from its waiting state to compressing state (top view) and back (bottom view).

Figure 7:
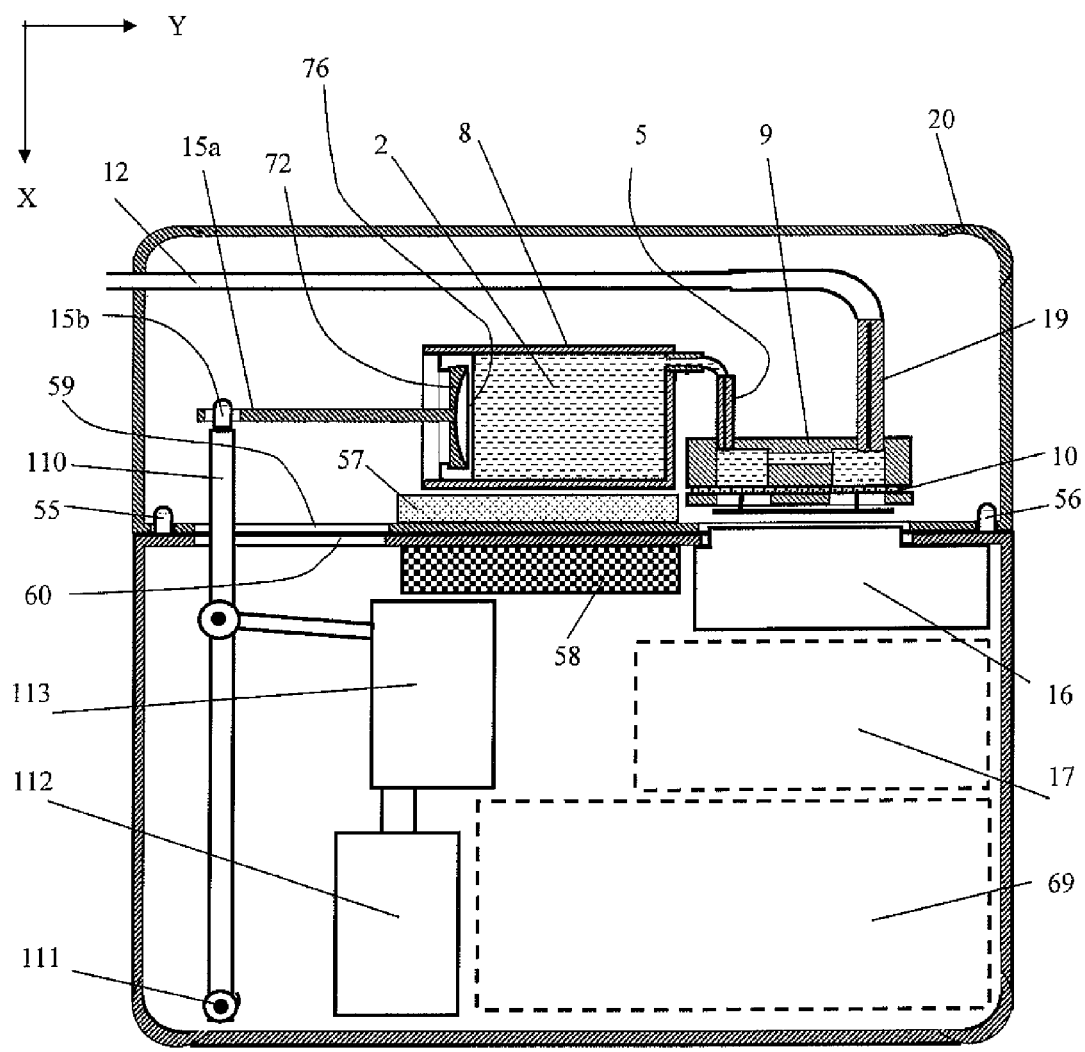
FIG. 7 depicts how the connecting means of the invention can provide temporary connection of both the cartridge and the actuating module shown in FIG. 6.
Figure 31:
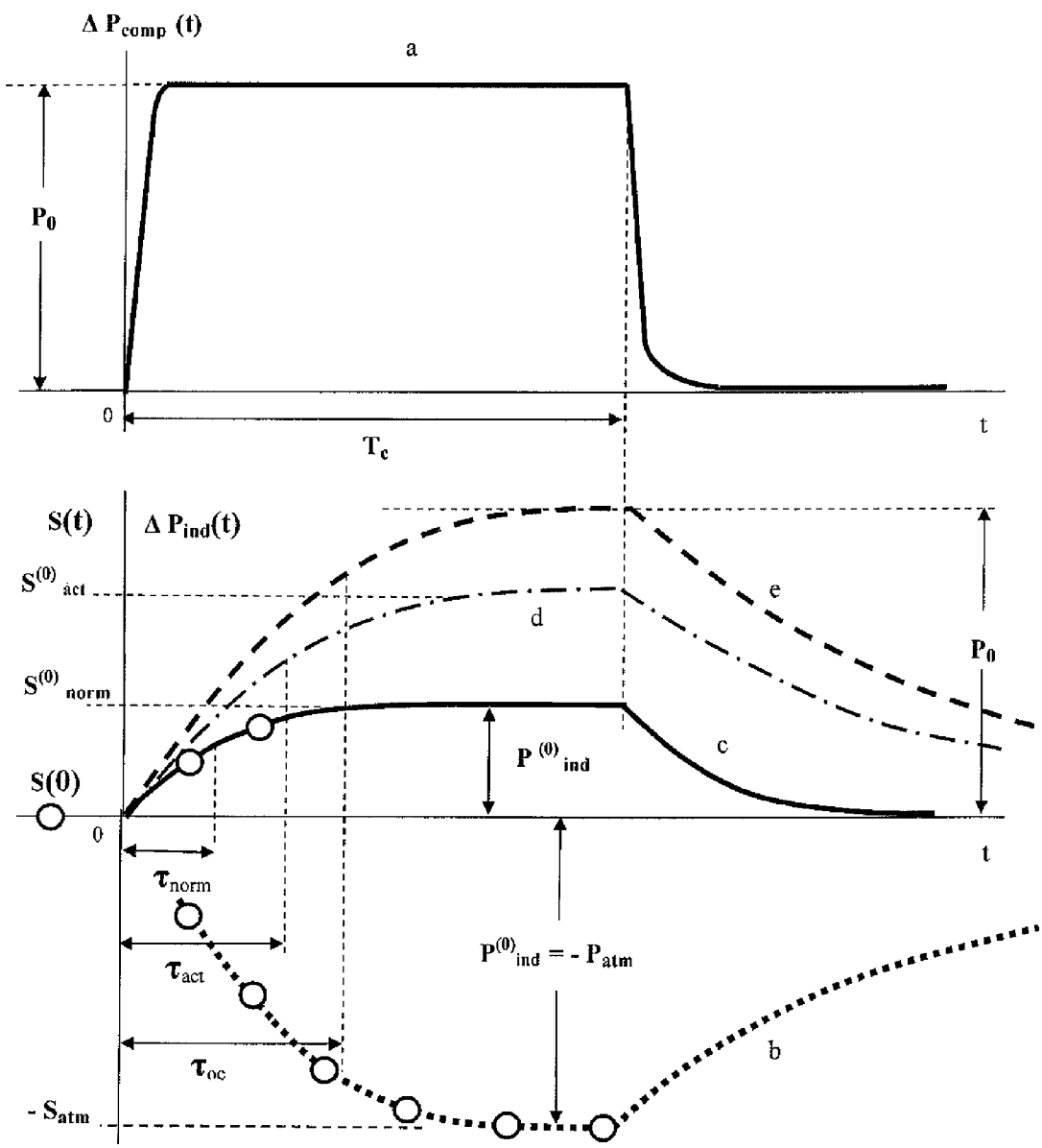

FIG. 31 depicts typical diagrams of all embodiments of the invention in which ratio $R_1/R_2$ exceeds 0.05 and is less than 200, and the hydraulic system of the replaceable cartridge shown in FIG. 7 doesn't comprise locking valve. The top view shows the shape of pulses of the pressure inside the compression section of the reservoir. The bottom view depicts shapes of pressure pulses in the indicator section of the reservoir and corresponding output signals of the sensor system related to different output hydraulic resistances of the entire fluid delivery device. For simplicity, output signals of the sensor system are shown as if their scale coincides with the pressure scale of the indicator section of the reservoir.

Figure 32:
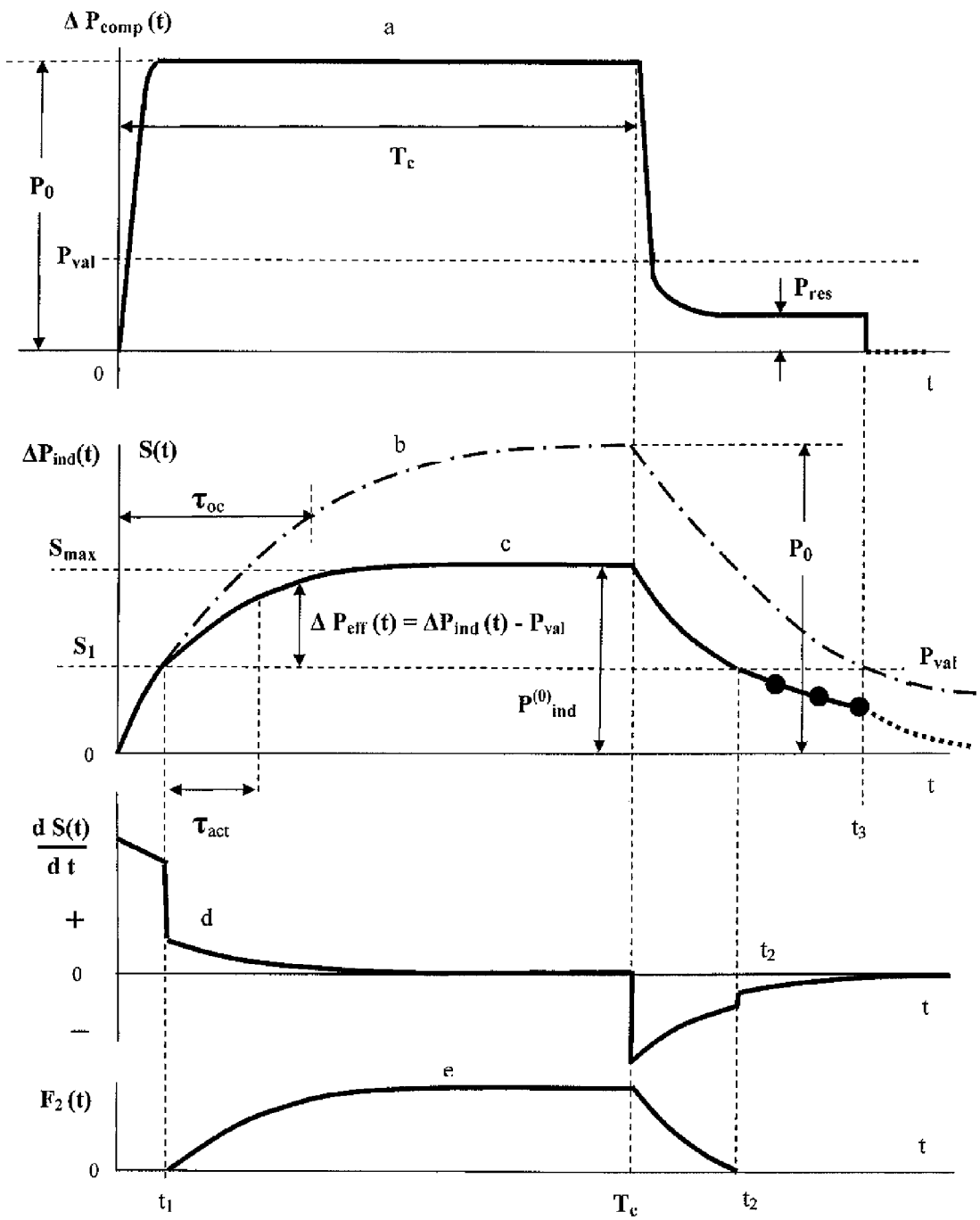

FIG. 32 depicts typical diagrams of an embodiment shown in FIG. 21 and comprising syringe-like compression section of the reservoir and the locking valve in the flow passage: (a) squeezing-out pressure during $T_c$ and low level residual pressure after $T_c$ in the syringe; (b, c) two merging branches of the pressure pulse in the indicator section of the reservoir and corresponding output signal of the sensor system in the case of either insurmountable occlusion (b) or normal work (c) which includes potential cases of partial occlusion. The diagram (d) shows a derivative of the sensor signal corresponding to curve (c). The diagram (e) represents the intensity of the fluid flow leaving the exit opening of the fluid delivery device. For simplicity output signals of the sensor system are shown so as if their scale coincides with the pressure scale of the indicator section of the reservoir.

Figure 12:
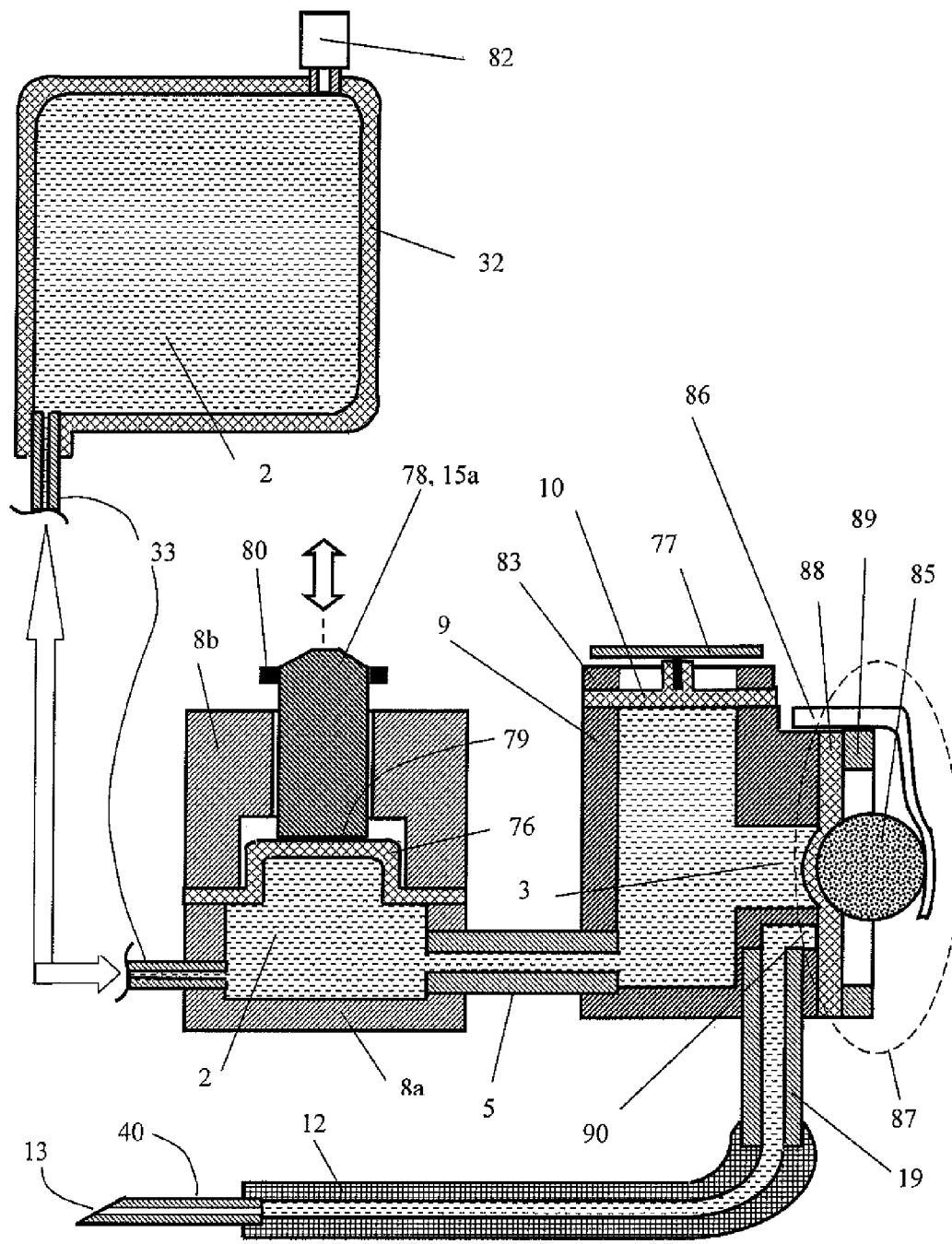
FIG. 12 depicts schematically the initial state and a cross-section of hydraulic system of the replaceable cartridge shown in FIG. 8 when no compressing force is applied to the fluid.
Figure 33:
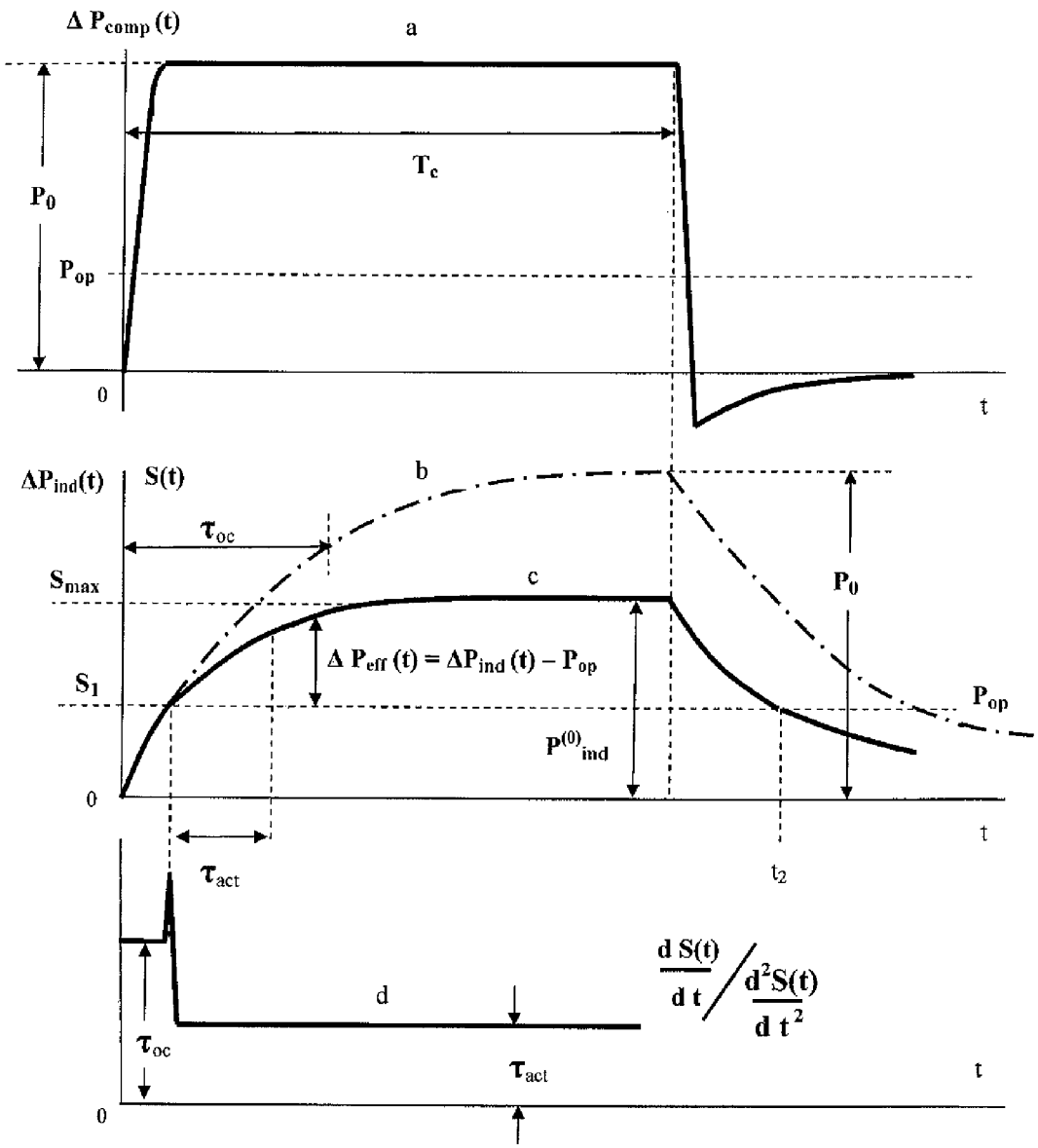

FIG. 33 depicts diagrams related to further improvement of the method applicable to most advanced embodiments of the invention shown in both FIG. 12, FIG. 23, and FIG. 27.

Figure 34:
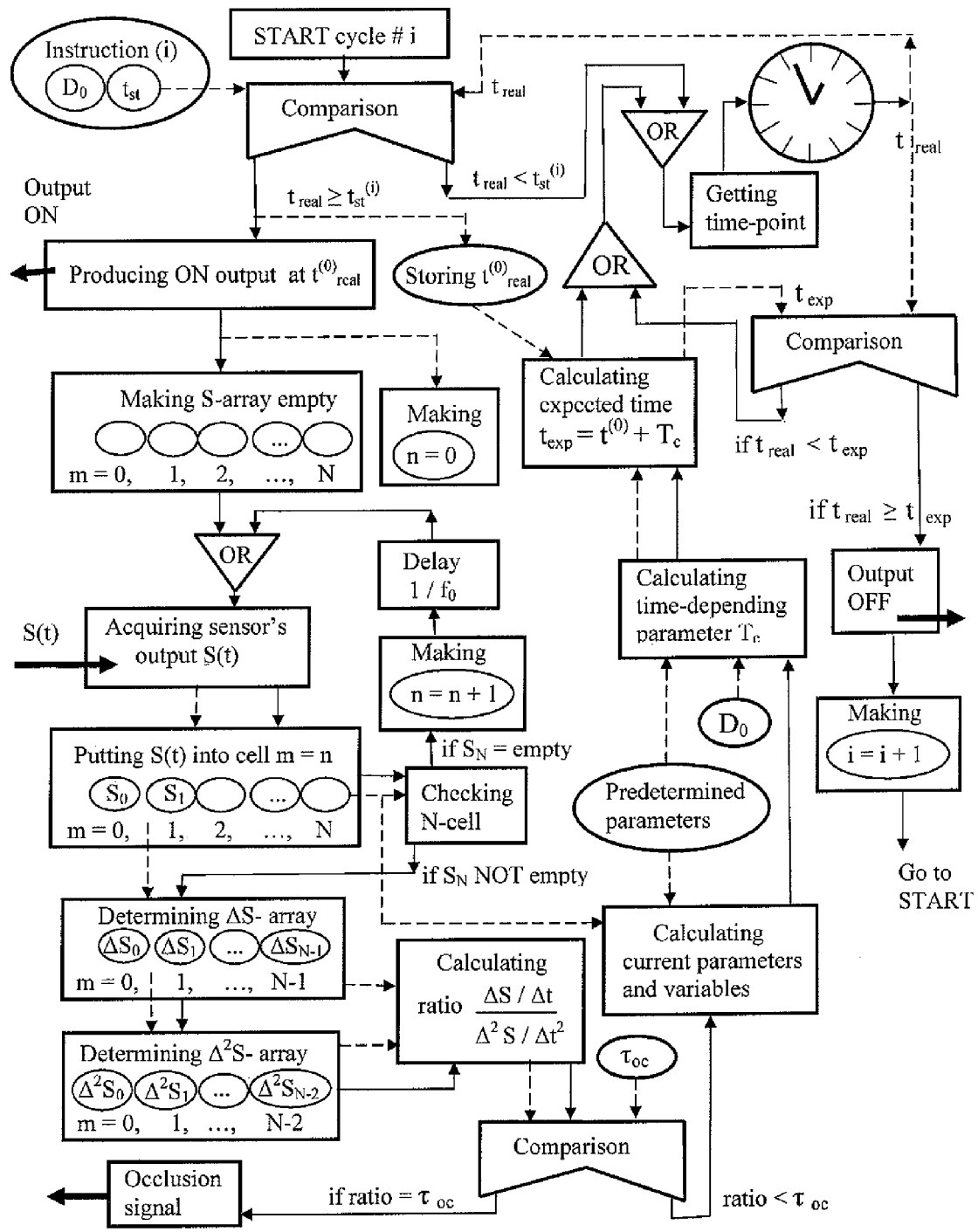

FIG. 34 depicts major algorithmic steps of one fluid delivery cycle used by a processor related to more advanced and most advanced embodiments of the invention.

DETAILED DESCRIPTION

Terminology

It may be relevant to begin detailed descriptions of embodiments of the present invention with a discussion to eliminate potential terminological ambiguity related to hydraulic systems of liquid drug delivery devices. It can be desirable that a whole device is described as such static combination of all critically important parts where functional role of each particular part is brought in unambiguous correspondence with part's name expressed in commonly understood terms.

In that regard rather specific problem of hydraulic devices arises because a fluid placed inside a device becomes its inevitable liquid part widely distributed along full hydraulic path. This specific part is capable of changing its own shape and functioning in the process of dynamic interaction with many other details made of solid materials. In order to obtain the desirable fluid dose at final destination point the fluid must pass through multiple hydraulic elements intended to fulfill different functions. In complicated dynamic hydraulic systems actual functioning of each element may strongly depend on many features including but not limited to geometric shape and sizes of each selected element, peculiarities of a material which this element is made of, specific connection with other parts, the speed and viscosity of fluid flow, the shape of instant distribution of a pressure along full fluid path, and so on. A functional complexity becomes even stronger if some parameters (for example, a pressure distribution and/or speed of the flow) may change in time. The result may be that under variable circumstances some hydraulic parts begin to play more than one functional role. In this case a terminological ambiguity becomes inevitable if one uses conventional term related to that part which can reflect only one function and ignores other ones.

The said above can be easily demonstrated with simple example of potential ambiguity of such conventionally used terms as "a fluid supply reservoir" and "a flow passage" which are intended to express a relationship between what each selected part does and how this part is called.

Figure 1:
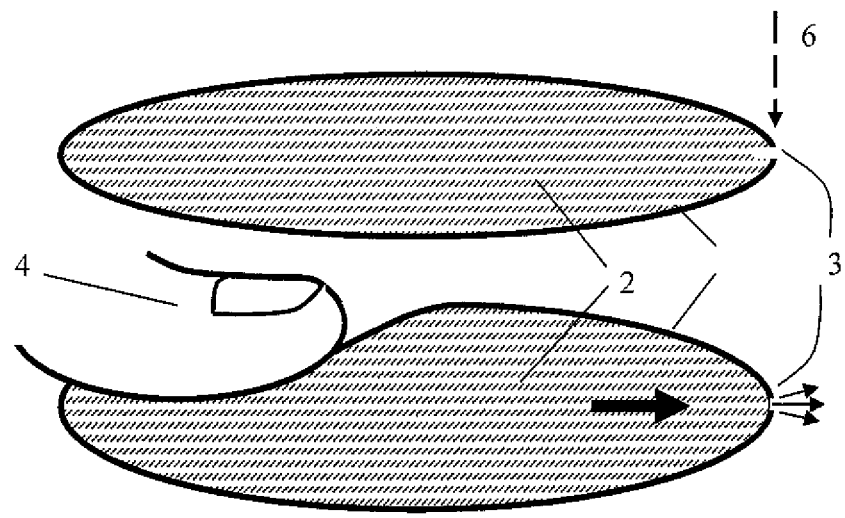
FIG. 1 depicts a method of the invention for fluid delivery by means of time-dependent compression of a reservoir made of resilient material and having one exit opening.

In order to demonstrate the idea, let first consider FIG. 1, having elastic reservoir 1 fully filled with the fluid 2 and having the shape of horizontally oriented ellipsoid supplied with one small exit opening 3 located directly on thin right wall as it is shown in upper portion of FIG. 1. Initially there is no output fluid flow because the pressure inside the reservoir coincides with outside pressure. If one applies, for example, the finger 4 to pressurize the fluid by elastic deformation of the left part of the reservoir 1 then the fluid begins to flow inside the reservoir in right direction as shown with thick arrow in bottom portion of FIG. 1, and then goes out through opening 3 (three thin arrows). A "fluid supply reservoir" is unambiguously present in such simple delivery device, and a probability is about 100% that there is no such another part of this device which could be called "a flow passage".

If the initial shape of the reservoir 1 has been slightly changed near its center (upper portion of FIG. 2) so that finally the reservoir filled with the fluid 2 consists of two connected ellipsoid-like cavities—designated as L (left) and R (right)—where a fluid communication occurs through narrowed neck 5 connecting two cavities. As before the only exit opening 3 exists on right wall of the cavity R. Now difficult questions arise in regard of modified delivery device of FIG. 2: Defining a functional role of each cavity, and how these cavities are characterized with the use of conventional terms follows.

Again, if finger 4 produces the force compressing the elastic wall of left cavity L (see the middle of FIG. 2) the pressure increases in left cavity L first. This makes the fluid to move to the right cavity, thus causing both the increase of the pressure in the cavity R and its elastic expansion. The result is that the fluid begins to flow out through the opening 3 of the cavity R. Now anyone has the right to say formally that the cavity L is "a fluid supply reservoir" whereas the cavity R serves as "a flow passage" because the fluid arrives to R from left cavity L through the neck 5 and leaves through the opening 3. At the same time another expert has also the right to conclude that, as before, there is no "a flow passage" at all in hydraulic system shown in FIG. 2, but both cavities L and R constitute two parts of the same fluid supply reservoir 1, especially if connecting neck 5 is not too narrow. However, the question remains without an answer what reliable criteria are to distinguish "too narrow" neck from "not too narrow" one. The problem becomes even worse at the moment when forcing finger 4 is removed (see bottom of FIG. 2). Because fast relaxation of elastic wall of the cavity L the pressure there drops quickly. At the same time the pressure in expanded elastic cavity R decreases with some kinetic delay in regard of fast pressure drop in the cavity L. The result is that some part of fluid flow is reversed to move from right to left because for a short while the pressure in the elastically expanded cavity R exceeds the pressure in the cavity L. During this short while the cavity L supplies nothing and must be considered formally as "a flow passage". Moreover, during the same while the cavity R is serving as "a fluid supply reservoir" because the non-zero pressure remaining in the cavity R forces the fluid to escape through the opening 3. So, this example shows that just conventional terminology is not enough in some specific circumstances in which so-called "common sense" cannot be a good advisor.

Complicated dynamic behavior, considered above as a simple example only, reflects certain important features of embodiments of the invention. Definitions help to prevent any further terminological ambiguity. Such definitions applicable to whole description of preferred embodiments of the invention are provided below.

For the purpose of universally applicable definitions it is suggested to combine conventional terms reflecting functional roles of different parts with additional criteria based on either hydrodynamic properties of selected parts or certain geometric characteristics of fluid's body filling every part of a hydraulic system. In that regard it may be mentioned that hydraulic parts of a delivery device may be either connected inseparably in some cases or made separable in other cases providing more convenience for a customer. The point is that independently of both particular constructions of separate parts and chosen types of their connections, such definitions become applicable only if a hydraulic system of a delivery device is thought to be entirely assembled and filled with the fluid to be in normal working state. When the system is fully assembled, the fluid placed inside represents a liquid continuum, which is contained within internal cavities of said parts. At least one cavity must have the exit opening or, in some embodiments, more than one exit openings to deliver the fluid to the area where liquid continuum ends and the fluid is to be subjected to an external pressure, which is an atmospheric pressure in certain cases. It may be desirable in some cases that entire hydraulic system comprises also at least one special cavity in which the surface of said liquid continuum is subjected to certain pressure of predetermined gas phase, said pressure is either normal atmospheric pressure or any different one.

The definitions provided below may contain the term "hydraulic element" or "selected hydraulic element" of the hydraulic system. Any of these terms must be understood as such part of whole hydraulic system of the device which has at least one cavity containing the fluid, said cavity limited by internal surfaces of walls made of non liquid material and having at least one such opening which can transfer the fluid either in or out of said cavity, or both in and out.

Definition No. 1. Preliminary comments: The usage of hydrodynamic criteria is always based on quantitative hydrodynamic parameters (such as, for example, an intensity of fluid flow or a value of hydraulic resistance of a selected element). They assume that selected local volume of the liquid continuum placed into the cavity of the selected element is moving with certain velocity through at least one given cross-section of the fluid path. For the purpose of present invention we provide the following definition No. 1: "The intensity $F$ of the fluid flow related to chosen cross-section of the fluid path is understood as a fluid's volume passing through said cross-section in one time unit, preferably in one second." Hereinafter all parameters and variables characterized by their quantitative values are set off in bold italic or Greek characters in order to make them better visible and distinguishable in the text of the description.

Figure 11:
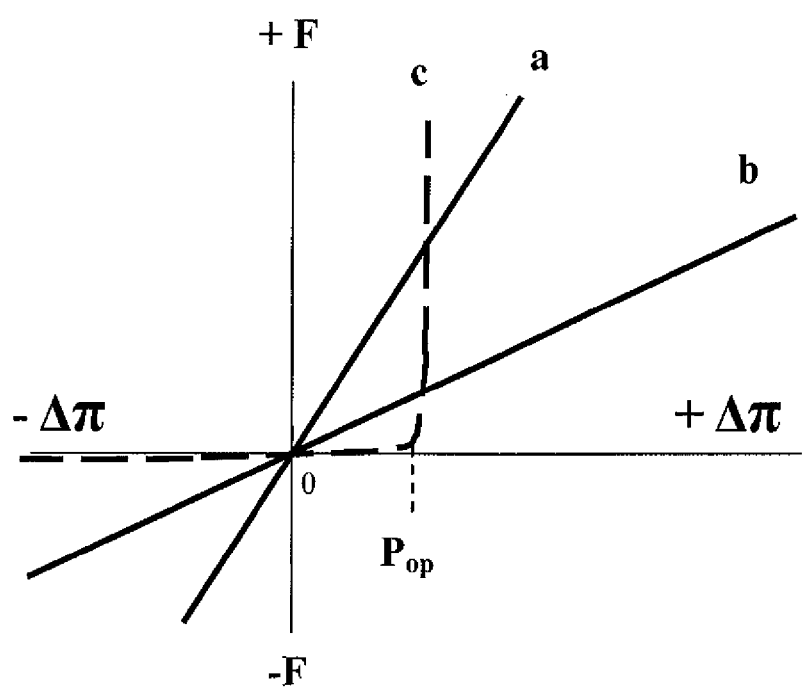
FIG. 11 depicts characteristics of certain hydraulic elements of the invention, namely the dependencies of the intensity of fluid flow on the pressure drop, related to both linear and non linear passive elements of hydraulic system shown in FIG. 9 and FIG. 10.
Figure 14:
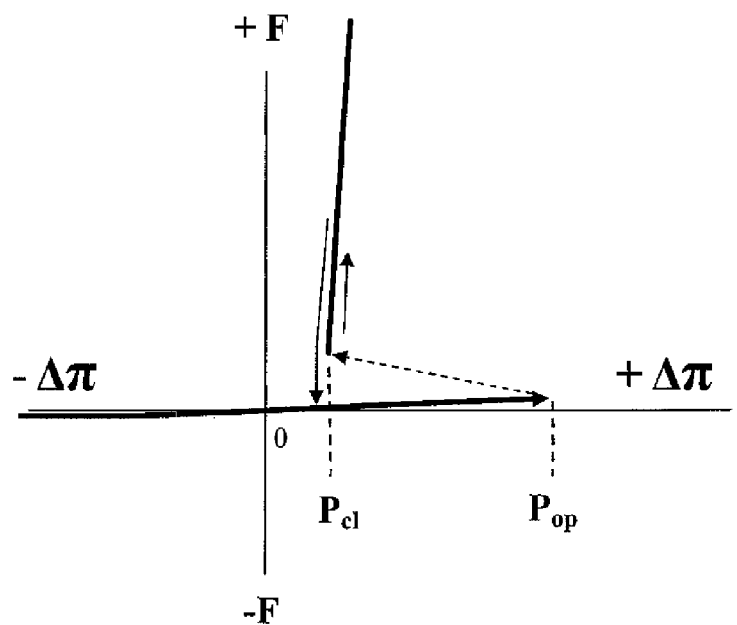
FIG. 14 depicts hydraulic characteristics of passive non linear static resistor, namely the passive valve 87, incorporated in the hydraulic system shown in FIG. 13.

Definition No. 2. Preliminary comments: Both the concept "a static hydraulic resistor" and corresponding quantitative concept "a static hydraulic resistance R" are applicable to any selected element of a hydraulic system if the element satisfies the following conditions: (a) the element is not "a reservoir" determined by the definition No. 4 below; (b) two such spatially separated cross-sections of element's cavity can be chosen that the fluid arrives to said cavity through one cross-section and departs through another one; (c) the intensity F of fluid flow is the same in both said cross-sections; (d) the movement of the fluid through said element is controlled only by a difference of hydraulic pressures applied to said cross-sections. A quantitative definition No. 2 is: "Any selected hydraulic element satisfying all above conditions of present paragraph is a static resistor and may be characterized by a value of its static hydraulic resistance R related to the fluid path between two spatially separated cross-sections of a cavity of said element, where the value R is a factor of following equation (1)

$$RF = \Delta\pi \quad (Eq. 1)$$

where F is the intensity of fluid flow passing from one said cross-section to another one, and $\Delta\pi$ is the pressure difference between both said cross-sections, providing that the pressure distribution along the surface of each said cross-section has approximately constant value." A static hydraulic resistor having at given temperature constant value R may be also called "a linear static hydraulic resistor." In accordance with given definition No. 2 the hydraulic element satisfying all conditions above must be considered as "a static hydraulic resistor" independently on whether its resistance R is a constant or it passively depends on either temperature, or $\Delta\pi$, or direction of fluid flow. In the last case the resistor, having pressure-dependent resistance $R(\Delta\pi)$ or direction-dependent resistance depending on a sign of $\Delta\pi$, may be also called "a non linear static hydraulic resistor". Graphical examples of both linear and non linear static hydraulic resistors are shown in FIG. 11 and FIG. 14.

In a given device any hydraulic element cannot be called "a static resistor" if its resistance R obeying formally the equation (1) may be also controlled by changing any device's parameter or variable other than either direction of fluid flow or a pressure difference $\Delta\pi$ defined above. For example, an externally controlled valve should be called a "dynamic hydraulic resistor" because controlling operations include at least one action other than a change of the pressure difference $\Delta\pi$.

Definition No. 3. Preliminary comments: Because continuity of the liquid continuum distributed over multiple parts of a hydraulic system there may be a difficulty to determine where one part ends and next part begins. That is why the usage of geometric criteria requires explicitly determined concept "a local volume" of the fluid located within selected part. The following definition No. 3 is: "A local volume of the fluid located within the cavity of any selected element of a hydraulic system at any given moment of the time is equal to instantaneous volume of such part of the liquid continuum which is present inside closed surface formed by either entire internal surface of cavity's walls having no openings opened at said moment or both internal surface of cavity's walls having at least one opened opening and as many immovable virtual (or imaginary) surfaces as may be necessary to close cross-sections of all said openings opened at said moment, provided that stable shapes and positions of said virtual surfaces are chosen to obtain as low sum of areas of said cross-sections as possible." Hereinafter the word "imaginary" may be always substituted instead of the word "virtual" providing that both words have equivalent meaning.

As an example, one can use the definition No. 3 to find local volume of the fluid within the reservoir 1 shown in FIG. 1. This reservoir has only one opening, which may be closed with virtual plane oriented perpendicularly and crossing long axis of the ellipsoid 1 in the point shown by dashed arrow 6. Because the reservoir is initially completely filled with the fluid the instant local volume of the fluid corresponding to the top view of FIG. 1 coincides with the volume limited by a combination of internal surface of non deformed reservoir's walls and the surface of virtual small disk closing the opening 3 in its most narrow place. The instant local volume of the fluid contained within the reservoir decreases in the process of the compression because some part of the fluid leaves (see bottom portion of FIG. 1). In accordance with definition No. 3 the local volume of the fluid cannot exceed the instant volume of the cavity but can be less under some circumstances. Such situation happens, for example, when the compression ends and reservoir's elastic wall returns to its initial shape but at this moment the amount of remaining fluid is less than before the compression.

Figure 2:
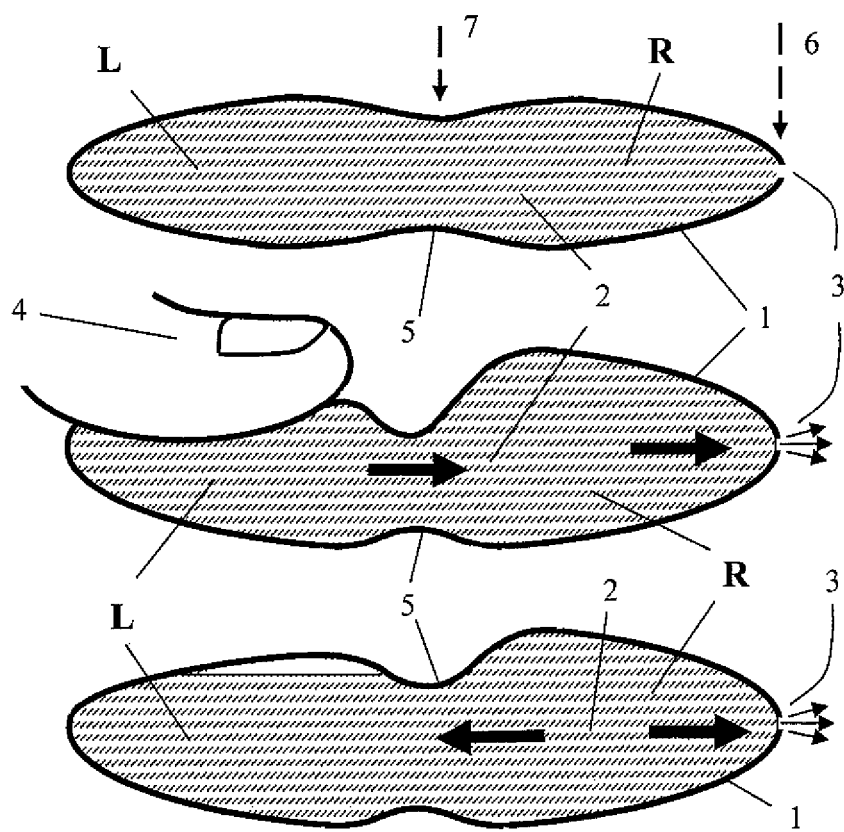
FIG. 2 depicts a method of this invention of the fluid delivery with the use of two communicating reservoirs where the left reservoir undergoes time-dependent compression and the right one provides time-dependent expansion because of resilient behavior of its walls.

A similar approach can be taken to determine the local volume of the fluid in section L of the reservoir 1 depicted in FIG. 2. In this case the cavity L is limited by both the left part of reservoir's wall and one virtual plane shown with dashed arrow 7 which crosses the axis to close most narrow place of the neck 5. At the same time the cavity R of the reservoir 1 depicted in FIG. 2 is limited by the right part of reservoir's wall and two virtual planes situated at positions 6 and 7 correspondingly to close both opening 3 and the neck 5.

Definition No. 4. Preliminary comments: In order to define the term "a reservoir" we take into account that the main feature of any reservoir is its ability to contain different amounts of the fluid at different moments of the time so that the fluid arriving to a reservoir from anywhere may be accumulated, stored inside a reservoir, and supplied to other parts of given hydraulic system at appropriate moments. This approach should be taken in accordance with specific features of each particular device. That is why any selected hydraulic element of given device may be considered as "a reservoir" only if its quantitatively expressed ability to contain different volumes of the fluid is critically required by working process of whole device. These considerations constitute the basis for following definition No. 4: "Independently on how the engineering design is done, any hydraulic element representing a part of a whole device is considered to be a reservoir if intended to perform the normal work of this device, considered as a certain process in the time, comprises such time changes of the local volume of the fluid contained within said element in accordance with the definition No. 3, which are important for proper working process of the whole device. A hydraulic element is not a reservoir if this element does not comply with conditions of previous sentence of this paragraph."

For example, if the proper function of a certain invention does not depend on naturally occurring insignificant thermal expansion of a specific element (for example, a pipe filled with the fluid) the definition No. 4 tells that such element may not be considered as "a reservoir". However, the same pipe incorporated by another invention may be considered as a reservoir if similar thermal expansion is anticipated as an inevitable part of device's functioning, and said change of pipe's volume is high enough quantitatively to be important for proper function of the device.

In that regard, in accordance with definition No. 4, both elastic cavities L and R shown in FIG. 2 correspond to the term "a reservoir" because the decrease of the compressed volume L is required to initiate a delivery of the fluid by means of the expansion of the part R, and even the final dose expelled from the part R in the very end of the process may be compared with full desirable dose. Due to the definition No. 4, the only question is whether cavities L and R are separate reservoirs or they are parts of the same reservoir. For the purpose of present invention an additional definition is provided to resolve this problem unambiguously.

Definition No. 5: "Any two hydraulically communicating reservoirs incorporated into the same device are just sections of the same reservoir if at any moment of device functioning the primary change of the fluid pressure, produced by any means including imaginary ones in any one reservoir of two, causes such immediate movement of a fluid through said hydraulic communication which results in secondary change of fluid volume or pressure inside another reservoir of said two". In this definition the expression "imaginary means" means that an imaginary pressure change may be produced in any one reservoir of two even by certain virtual external appliance which can be imagined in principle but is not present in real device. If such pressure change is imagined in any moment of the functioning of a real device then all virtual consequences should be analyzed from viewpoint of real design of said device.

The definition No. 5 tells, for example, that both elastic reservoirs L and R shown in FIG. 2 are always understood as parts of their common reservoir 1 independently on whether the neck 5 is wide or narrow because this neck is always opened and can provide immediate fluid exchange between reservoirs L and R at any moment of the time. It does not matter whether secondary volume or pressure change is delayed in time or occurs simultaneously with the primary one. It may be important also that the definition No. 5 doesn't depend on whether the communication represented by elastic neck changes its shape in time or not if this communication always remains opened. For better understanding of the definition No. 5 lets consider for a moment an opposite case shown in FIG. 2, wherein communication of reservoirs L and R comprises an externally controlled valve, which may be in either opened or closed states at different moments in the device's operation. If a primary pressure change occurs in one reservoir at a specific moment when the valve is fully closed, then the fluid cannot move through the closed valve. Correspondingly, the primary pressure change in one reservoir causes no secondary pressure change in another reservoir. The definition No. 5 tells that in this case parts L and R must be defined as two independent reservoirs.

On the basis of definition No. 5 one can conclude also that two reservoirs of the same device connected with any static hydraulic resistor obeying definition No. 2 are just sections of the same reservoir if hydraulic resistance R of this connection is not infinitely high and any non-zero pressure difference $\Delta\pi$ initiates a non-zero flow from one section to another one even in the case when an intensity of this non-zero flow is very low.

Definition No. 6: "Any element, providing hydraulic communication of two sections of the same reservoir, said sections being in compliance with the definition No. 5, must be also considered as a part of the same reservoir independently on whether this element taken separately comply with the definition No. 4 of "a reservoir" or not." However, in order to avoid ambiguity, in certain cases it may be desirable that names of elements complying with definition No. 6 are additionally characterized by specific terms. For example, instead of independent name "a pipe providing hydraulic resistance" one could say "a reservoir comprising two sections and a pipe connecting said sections and providing hydraulic resistance."

Additionally, hydrodynamic laws teach that stationary flow of any normal viscous fluid is possible only if a pressure applied to one limited surface area of an entire continuous fluid's body differs from a pressure applied to another limited surface area of the same fluid's body. This principle is exploited by all fluid delivery devices wherein the limited surface area of the fluid contained in the fluid supply reservoir is very different from limited surface area of the same fluid leaving the exit opening of the device. However, in certain devices the excessive pressure applied to the fluid is predetermined directly, for example, by using preliminary compressed gas phase having constant pressure. In other devices the excessive pressure is created indirectly by mechanical means, for example, by syringe-like or peristaltic pumps. Actually, the primary physical action of said mechanical means is to create only a certain force, and only then this force is converted into the fluid's pressure by an appropriate mechanism, for example, the syringe's piston shifted by said force. On the other hand, certain force is also applied to the fluid even if this is a force of direct interaction of limited surface area of the fluid with a gas phase. Taking all these considerations into account the only possible way to keep uniform terminology is to use a universal concept of a primary physical parameter, namely a force squeezing the fluid out of the reservoir. The discussion of specific technical means converting this force into the fluid's pressure is a special matter related to specific features of the invention and considered in appropriate section of present description.

One more ambiguity may be related to such widely used term as "a sensor," especially in regard of a determination of what each particular sensor is for. The term "a sensor" means a transducer transforming one specifically chosen parameter (for example, physical one) to another parameter, typically electric or electronic one, which may be conveniently used to provide an output signal. For example, the electric resistance of properly doped semiconductor plate brought into contact with a certain fluid can depend on the volume concentration of ions contained in this fluid. Thus, primarily this is a sensor of ion concentration. However, if a certain device exploits the diffusion of ions in the fluid, the osmotic pressure may change according to changes of ion concentration. So, such a device may mean "a sensor of ion concentration", but also may mean "a pressure sensor," notwithstanding the fact that just pressure as such does not influence the resistance of said semiconductor. Therefore, terminological ambiguity may be present in this example. It arises only because real technical features are substituted by human's knowledge interpreting known relationship of both an osmotic pressure and an ion concentration in the fluid. In order to avoid this kind of terminological ambiguity the following definition No. 7 is provided.

Definition No. 7: "If an output signal (Sig) of a sensor system may be brought into correspondence with more than one interdependent parameters $(Par)_i$ related to the functioning of a given device, said sensor will be understood and defined as the sensor of such the only primary parameter (whether geometrical, or physical, or any other one), which physically permits said sensor to provide the highest partial sensitivity. In order to choose the only primary parameter the following method can apply: (a) full ranges of all interdependent parameters must be determined accordingly to the full range of normal device's functioning, then (b) a sensor's partial sensitivities $(S_{par})_i$ related to each separate i-parameter must be tested as follows: (i) all interdependent parameters must be fixed except selected one having number i; (ii) partial sensitivity $(S_{par})_i$ in regard of i-parameter having its own full range $(Ran)_i$ is defined as:

$$(S_{par})_i = |\Delta_i(Sig)/\Delta(Par)_i| \qquad \text{(Eq. 2)}$$

where $\Delta_i$ (Sig) is the change of sensor's output signal in response to such chosen change $\Delta(Par)_i$ of selected i-parameter which corresponds to constant ratio $\Delta(Par)_i/(Ran)_i$ for all i-parameters tested independently; and finally (c) the only primary parameter is to be determined which provides highest value of partial sensitivity $(S_{par})_i$ defined by the equation (2) above".

In order to make the definition No. 7 more clear, let return to previous example of the sensor with two interdependent parameters, namely the ion concentration and the pressure. After the full range of each of two parameters is found one must change only ion concentration, for example 10% of its full range, simultaneously keeping the fluid pressure constant by any means. Because this semiconductor is physically sensitive to the change of ion concentration the sensor system produces a certain measurable response. After that only fluid pressure is to be changed the same 10% of pressure's full range by any means which do not involve the change of ion concentration. Only zero or negligibly low sensor's response can be detected in the second test because the pressure as such does not influence physical properties of semiconductor plate. Accordingly to the definition No. 7 the ion concentration complies with a concept of primary parameter, and the sensor may be only called "the sensor of ion concentration."

Yet one more ambiguity may be potentially related to such widely used term as "a processor" which is understood in most cases as specific microelectronic device capable of both acquiring input signals and producing output signals, both types of said signals are low power digital electronic signals characterized by certain predetermined levels of logical "0" and logical "1". However, certain procedures transforming input signals into output ones do not necessarily require digital electronics and may be successfully performed by analog electronics. Because such electric terms as "a low power" and "a digital signal" can be interpreted differently by different experts, in framework of present description "a processor" is always understood as such electronic device which, independently on the power and electric form of both input and output signals, is capable of treating input electric signals so that output signals produced by this processor obey programmatically predetermined mathematical or logical algorithm whether stored in either electronic or any other type of a memory, or directly realized in electronic design of said electronic device.

It can be appreciated by anyone skilled in the art that well defined terminology provides better understanding of the design of certain drug delivery devices. Passive devices of the $1^{st}$ class are rather shortly considered here because this class is represented by relatively simple systems, in which the only predetermined regime of the delivery of medicine is determined by the fixed construction of the device. For example, compact implanted device (U.S. Pat. No. 5,785,681; incorporated herein fully by reference) is intended for the liquid drug delivery with a prescribed constant speed. It includes the reservoir in which the constant excess pressure is applied to liquid medicine. The fixed pressure in the reservoir provides a driving force supporting the constant flow in the delivery line which connects the patient's body with the reservoir and includes a device for flow control. This device divides the delivery line in two consecutively joined sections. The first section contains a flow limiter having high hydraulic resistance. The second section, following after, contains both a second high-resistance limiter and parallel to it, a bypass having low hydraulic resistance. A diaphragm sensor, which reacts to a difference in the atmospheric pressure and the fluid pressure in the sensor station, is installed between the output of the first limiter and the entrance into the second flow limiter. This diaphragm pressure sensor provides mechanical control of the valve, which keeps the low resistance bypass open if the atmospheric pressure is close to the normal. At reduced atmospheric pressure, it shuts the bypass and redirects the fluid's flow into the second limiter having high hydraulic resistance. Thus, the hydraulic impedance of the full line of the delivery reacts to a change in the external pressure, which contributes to the maintenance of the constant velocity of the fluid flow. However, such systems are not flexible, and can support only one prescribed regime of the drug delivery, which cannot be changed during operation even in the case of medical need.

Pump Technology

Advances in pump technology, both mechanical and electrical, have provided patients with new options for having doses of needed drugs administered over prolonged periods of time with concomitant increases in effectiveness of treatment. New options become available only in the second class represented by more complicated and more flexible active systems controlled by a programmable controller. All devices considered below belong to the $2^{nd}$ class. One advantage of devices of this class is that a controller can be reprogrammed to another regime, in accordance with the medical need and the state of the patient. Such systems may be capable of independently reacting to some disturbances in the course of the drug delivery, or of promptly informing user about the serious disturbances for the purpose of the rapid correction of a dangerous situation. They also make it possible for a user to independently replenish stocks of medicine in the device, thus increasing the period of the patient independence.

Accurately supplying patients with the necessary medicines during the prolonged course of treatment is an extremely critical medical task. It can be especially complex technically in the widespread case of chronic outpatient dispensary treatment (from several days to several years), where repeated, cyclic administration of prescribed small quantities of liquid medications are provided automatically by a compact programmed device (e.g., a pump), connected to the patient in such a way as not to interfere with his or her normal means of life. In order to supply further descriptions automatic devices for the delivery of the insulin have been chosen as an example capable of demonstrating quantitatively what reliability and high precision are required in a real life for the successful outpatient treatment of such a serious decease as diabetes. There are also many other diseases requiring at least the same high quality treatment.

At the present time there are many inventions, which relate both to entire systems of a compact devices of the hypodermic or intravenous delivery of liquid medications, and to the separate components of such devices. The use of some systems requires the application of the special methods. Technical requirements for portable automatic instruments for delivery of liquid medications can be high, because their correct and reliable working is required for maintaining the health and the life of the patient. Among many important requirements it is possible to recognize the following features.

(a) A device desirably can be the lightweight and reasonably low volume, and be attached to the patient, ensuring freedom of his or her activities and movements during the course of medical treatment.

(b) Because of standard sterility requirements a fresh portion of a drug has to be reloaded into device every few days. For example, at least 3 $cm^3$ of the insulin solution must be stored within the autonomous delivery device to provide the patient with such freedom for 3 days.

(c) One more important requirement is that after these few days the patient has to dispose of all such parts of the device which are destined to work in direct contact with patient's blood and other tissues located under the skin. Correspondingly, such parts have to be replaced with new ones simultaneously with reloading of next portion of the drug.

(d) In the case of long-term diseases, such as diabetes, the device should possess the prolonged life of an operation up to few years. For the entire long period indicated the device can desirably automatically support the accuracy of the regime of the delivery of small and super small quantities of introduced medicine. In the case of insulin delivery, the desirable precision of a single dose should not exceed 0.1 mm$^3$ for adult patients, and less or about 0.01 mm$^3$ for little children.

(e) A device desirably can maintain precise dosing independent of possible changes of the external atmospheric pressure or other external variables, which frequently can occur during airplane flights or the change by the patient elevation above the sea level. It is desirable that a device keeps predetermined high precision of drug delivery (which is typically about 1-2% of the predetermined dose) even in the case of unpredictable substantial temperature fluctuation, which may be expected within the range ±20° C. near normal room temperature.

(f) It is desirable that a programmable device would be capable of automatic revealing small deviations of the real drug flow from what is prescribed by currently active program, said deviations caused, for example, by small leaks in the hydraulic system or by the partial occlusion of the drug delivery lines. It can also be desirable that the device be capable of mitigating the consequences of such accidental events.

(g) In the case of significant deviations which cannot be compensated by device itself, it should report to a patient about the need for personal attention to correct the deviation. If the patient's health changes suddenly the device in his command must rapidly change the regime of the delivery whether for the introduction of additional drug or for the total cessation of its supply if necessary.

(h) The construction of the device desirably should minimize risks of random overdoses of liquid drug even in the case of total malfunction of the entire device, or individual subsystems or separate parts of the device.

(i) A device desirably should reliably work under conditions of prolonged shaking, impacts and vibrations caused by the displacements of a patient or transportation means. It should also be simple in control and maintenance, ensuring the correct regime of treatment for a patient with lowered mental activity and/or weakened tactile perception.

(j) A device desirably should permit refilling of medicine by a patient, to allow simple and rapid exchanging of an empty cartridge with a new factory pre-filled cartridge, while maintaining sterility and avoiding device damage caused by a user's unskillful handling.

(k) For most patients willing to keep their privacy it is very desirable that the drug delivery device is made so small and flat that it can be directly deployed on the skin and be hidden under clothes in order to be practically invisible for other people.

(l) Taking into account that from time-to-time any automatic device may suddenly stop working and create dangerous situation for patient's life for any reason (for example, if a battery was not charged properly or one of few critically important systems becomes inactive) it may be very desirable that even broken device provides any unskillful patient with an ability of temporary manual operation, which is simple and results in satisfactory precision of a drug delivery, up to a moment when primary technical problem is removed or defective device is replaced with working one.

(m) Assuming that all technical conditions enumerated above are satisfied, it is also desirable to have this simple construction of an entire system so that the cost of the production of both the device itself and replacement cartridges would be limited by the reasonable framework and cost, which offer real financial possibilities for the practical use of a device by a mass user.

None of the known active automatic fluid delivery systems, described in the patent literature, satisfies simultaneously the requirements recited above. Some of the known active compact systems of the liquid drug delivery include a fluid supply reservoir, a mechanism designed to squeeze the fluid out of said reservoir by the application of excess pressure to the liquid in the reservoir, a flow passage connecting the reservoir with the body of a patient, and programmable processor, which is intended to control the dose of the fluid delivered to the exit opening of the system. Active systems may be divided in two groups in regard of the method of an application of the force squeezing the fluid out of the reservoir.

In several systems of the first group, excessive pressure is created in a short interval of time by a pump, which is activated by an electrical motor. For example, this can be a peristaltic pump, which contains elastic tube filled with liquid and being sequentially deformed by compressing force, as it is described in U.S. Pat. No. 5,658,252, and in U.S. Pat. No. 5,772,409, and in the references to other patents being contained in it, which also assume the usage of a peristaltic pump. Other versions of compact active systems are syringe pumps, with a linearly moving piston driven by an electric motor. It is assumed that in these systems the piston stops upon delivering preprogrammed volume of the fluid by activating the proximity switches sending signals to the controller, for instance, described in U.S. Pat. No. 4,731,058, and the later U.S. Pat. No. 5,637,095. Because high demands for reliability and accuracy of dosing, the geometry of both the pump casing and pump mechanism must correlate with design features of syringe's details by rather complex means, as it is described in U.S. Pat. No. 6,652,493. Also high requirements of medical dosing using these prior art devices can be achieved only if all parts of the syringe are made of hard materials treated mechanically with correspondingly high precision.

In prior art systems, the computer controls a short-term activation of the pump motor that makes possible, in the first place, introduction of a desired dose of the liquid drug at the appropriate time, and, in the second place, extend the life of the electrical batteries. The dosing program can be very complex as well. For example, the U.S. Pat. No. 5,181,910 describes the mathematical method of the control of the periods of time between the activations of the injecting pump for guaranteeing the linear change (increase or reduction) in the speed of the drug delivery to a patient.

Some devices of the first group can be made as a combination of two separable parts wherein the first part is destined to be fully disposed of after short period predetermined on the basis of medical considerations whereas another part is destined for long-term usage (see U.S. Pat. No. 7,569,050). Disposable part is a separate housing comprising a traditional syringe which stores full initial volume of liquid medicine. Delivering of each selected small dose, which is much lower than the volume of the drug stored in the syringe, is possible only if rather selective movement of syringe's plunger is provided by a driving mechanism located in second non-disposable housing which comprises also an electric motor and all electric circuits necessary to operate said motor. The operation of the device becomes possible only when both disposable and non-disposable housings are properly connected. In this case a right connection of the motor with syringe's plunger is provided by complex drive linkage which includes gears and other parts capable of moving the plunger selectively with as high precision as necessary to provide desirable low one-time dose. Some parts of high precision drive linkage can belong to non-disposable housing whereas at least some high precision parts of the same linkage must be located in disposable housing. Requirement of high selectivity determines the necessity of high precision parts, low reliability, and high manufacturing cost. However, even in this case the device described in the U.S. Pat. No. 7,569,050 exhibits relatively low precision of a drug delivery typical for all known syringe-based devices.

In all devices of the first group the programmable processor concentrates its main "intellectual" activity on the control of specific mechanism squeezing the fluid out of fluid supply reservoir. A general idea is that proper control of the mechanism can provide predetermined dosage of the fluid. Simplest of such active systems do not contain sensors reflecting whether the exact or correct drug dosage is delivered, or the status of the flow passage, or the external variables, which can potentially influence the dosage. In such simplified cases the rigidly predetermined program of the controller does not permit the production of corrective commands, taking into account the real status of individual parts and the entire system as a whole. That is why the errors of the dosage, caused by, for example, increased friction of the piston of the syringe and/or by its irregular displacement in the housing are very possible. Neither the repair of the delivery system suffering with partial occlusions of the flow passage, nor providing an alarm signal with its complete occlusion is possible without additional sensors.

In other active systems of the first group disclosed in U.S. Pat. No. 4,559,038 the processor governs the dosage not only by starting and cutting off of the pump motor, but also by controlling of the system of valves. Due to the occlusion of delivery lines leading to exceeding a predetermined pressure level, the delivery system of U.S. Pat. No. 4,650,469 produces the occlusion signal with the use of the occlusion detector, which comprises electrical switches located both in the control module and in the flow passage.

In order to detect the occlusions leading to the elevated pressure in both flow passage and fluid supply reservoir, the invention of U.S. Pat. No. 6,485,465 is supplied with the occlusion sensor measuring the mechanical stress or pressure provided by the motor and located in the mechanism moving the piston. Other inventions described in U.S. Pat. No. 6,423,035 and U.S. Pat. No. 6,656,148 comprise both the detector of the effective force applied to piston's mechanism and an additional sensor, which measures the real position of this piston and transfers this information to the controller of the electric motor for achievement of the high dosing accuracy.

U.S. Pat. No. 5,935,106 describes a method of detecting occlusion in a drug delivery system. For this the pressure inside the elastic tube of a peristaltic pump is determined with the use of a pressure sensor brought in direct contact with the elastic tube to compress it slightly. This method comprises the preliminary determination of the stiffness coefficient of the tube together with the compressing sensor, then the first measurement of the force recorded by the sensor before the beginning of the fluid flow, and subsequent second measurement of the same force in the process of the fluid delivery. Finally the pressure of the liquid inside the elastic tube is calculated by subtracting of the first measurement from the second one where preliminarily measured stiffness coefficient is taken into account.

In this method, occlusion detection can be used only as the part of the complete delivery system, since it does not give quantitative information about the intensity of fluid flow, i.e., this one method is not sufficient for the precise dosage control. For the precise occlusion detection the system should have no less than two pressure sensors, located on the entrance of liquid into the pump and on its output respectively. This complicates the entire device and increases its cost.

Complex and expensive construction is a significant disadvantage in the majority of the known active compact systems of the first group which are using short-term pressure change as major method of liquid drug delivery. Typically these systems are represented by complex and costly combinations of high-precision actuators of the pump, mechanically or electro-mechanically operated valves, and also contain the diverse and numerous sensors which control force or pressure developed by pump engine, the position of such elements of the pump which determine the fluid dosage, pressure of the fluid in different sections of flow passage, position of replaceable cartridge in the pump casing, and etc.

However, even very high technical complexity does not eliminate the problem of inevitable gradual decrease of the device's precision during long-term use. This problem originates from low long-term reliability of certain mechanical parts requiring extremely high precision of both the initial manufacturing and further manipulation. For example, it has been mentioned before that typical syringe-like insulin delivery system must contain at least about 3 $cm^3$ of liquid drug and is capable of moving the piston having the area about 1 $cm^2$ so that its full path is as long as about 3 cm. Due to the aforementioned resolution of a typical one time dose of better than 0.1 $mm^3$, and more desirably better than 0.01 $mm^3$, the above means that the piston's position must be controlled with the resolution as high as about at least 1 micron, and more desirably about 0.1 micron. Actually, these numbers correspond to the relative precision of piston's mechanics better than or about 0.001% of the full piston's path. This problem seems to be too complex if one takes into account that notwithstanding the gradual wearing of all mechanical parts and the change of external conditions, the same high precision of the drug delivery must be conserved for at least few years of typical device's exploitation.

One more difficult problem of all syringe-like devices relates to potentially possible unpredictable temperature changes in the range ±20° C. Due to high temperature expansion coefficient about $3 \cdot 10^{-4}$, which is typical for all plastic materials, the length of 3 cm polymer housing of the syringe may fluctuate up to ±180 micron, whereas the length of piston's rod made of a metal fluctuates up to ±15 micron. That is why desirable mechanical precision in between 0.1-1 micron becomes practically impossible under such circumstances.

Due to necessity to keep a mechanical precision of existing syringe-based devices in micron and sub-micron range, the patient cannot be provided with discussed above desirable ability of manual operation in emergency cases when the device becomes inactive. Another common difficulty of all devices storing at least 3 $cm^3$ of the insulin within the syringe casing having about 3 cm length is that diameters of their pistons must be about or exceed 12 mm. Correspondingly, it is practically impossible to hide such a device under clothes because its housing cannot be made thinner than 15-17 mm.

One more common problem of all devices of the first group driven by shortly activated electric motor relates to a potential danger of significant overdosing if the motor starts at proper moment but the control system doesn't produce its stop signal. In this case the motor may continue drug delivering until the reservoir becomes empty. Even if a probability of such event is relatively low it may result in lethal overdosing for diabetic patient, especially if the event occurs in the night time and the patient cannot stop broken device immediately.

The second group of compact active systems providing liquid drug delivery consists of the devices in which the fluid filling the reservoir is constantly exposed at predetermined elevated pressure. In this case the main activity of the programmable processor is mostly concentrated on proper manipulation with hydraulic conductivity of such elements of the flow passage, which can be actively controlled by said processor.

As far as systems of the second group are considered, U.S. Pat. No. 6,736,796 B2 describes devices wherein a pump does not have an electric motor at all, and the liquid drug filling the reservoir is subjected to constant excess pressure. The design of the device includes a special port, which allows multiple refilling of the empty reservoir with new portions of liquid drugs. The pre-pressurized reservoir is connected with an exit opening of the delivery system by the flow passage which comprises two consecutively connected elements: (a) the elongated spiral capillary-like hydraulic resistor, and (b) externally controlled output valve which is constantly closed with the locking spring. At least two different points of the resistor, located upstream and downstream correspondingly, must be hydraulically connected with the opposite sides of the diaphragm of the differential pressure sensor so that the sensor is capable of measuring the pressure drop between these two separated points. The idea is that the signal produced by such a sensor is proportional to the intensity of the fluid flow at each given moment of the time and may be used by the processor controlling the dosage. This processor communicates with piezoelectric actuator which can overcome the action of the locking spring. That is why the instant state of the output valve obeys controlling signals of the processor.

Due to the fact that the output valve must be normally closed, it is assumed that the fluid cannot flow before the beginning of the dosing because valve's hydraulic resistance is very high. At a preprogrammed start time the processor orders the actuator to open the valve. Its resistance drops sharply and the fluid, forced by constant excessive pressure in the reservoir, starts to flow through consecutively connected valve and capillary-like resistor. Due to the fact that the valve is now opened, the intensity of the fluid flow is limited only by the hydraulic resistance of the elongated capillary. The processor acquires sensor's signals and calculates this intensity. Then, using the calculated intensity of the fluid flow, the processor determines a specific moment when the dose delivered to the exit opening should coincide with the dose predetermined by the program. At this moment the processor makes the actuator close the valve and terminates the current cycle of fluid delivery. Taking into account that a typical single dose is very low and the fluid is subjected to rather high constant excessive pressure, the valve must be typically open for few milliseconds only.

Accordingly to this patent the device consists of two separate modules: (i) a base unit comprising the processor, batteries, and piezoelectric actuator, and (ii) removable cartridge filled with the fluid permanently subjected to predetermined high pressure, the cartridge comprising the valve destined to be controlled by said actuator, the capillary, the pressure sensor interconnected with at least two points of this capillary, and the port destined to be used only while refilling of the cartridge.

At the first glance the technical idea disclosed above looks very attractive. However, this idea inherently contains a few mechanical and medical drawbacks. First of all, the open valve controlled by a piezoelectric actuator cannot have open clearance of more than few tens of microns. At the same time, high excessive pressure requires this valve to be closed very tightly before the dosing cycle. That is why the mechanical quality and corresponding cost of the actively controlled valve should be extremely high because all valve's parts must be made with at least sub-micron precision by the order of magnitude.

The requirement for such high precision raises substantial problems of reliability of the whole device. Such precisely made valves can easily become fully disabled if any hard sub-micron or micron-size contaminating particle is brought by the drug flow and lodges in the valve. In the case of improper use of the device, such contaminations (for example, ordinary dust) can be introduced by non-experienced users during reservoir refilling. Such unpredictable events can lead to very dangerous, uncontrollable drug leakage. Moreover, an installation of a new cartridge requires preliminary adjustment of said valve relatively position of said actuator before the device can be used. This adjustment must be manually done by a user with same high precision in micron range. Such complicated procedure can be very difficult for unskillful users, and high probability of serious mistakes always exists.

Another serious problem is that the precision of the dosing may change in time unpredictably. In accordance with the general idea, the processor uses the signals of a differential pressure sensor in order to calculate the magnitude of fluid flow. This involves calculation of the hydraulic resistance of an elongated capillary as given variable related to the fluid path between two points of the indicated capillary. However, due to the device not being capable of measuring this resistance, the processor's algorithm assumes this parameter to be factory pre-set constant. Evidently, it may be right in the beginning of the device's life cycle, but in long-term exploitation this resistance may change significantly if contaminating particles are brought into the device from outside, or even small air bubbles accumulate in the capillary's cavity during refilling. One more potential reason for substantial unpredictable fluctuation of capillary resistance is strong temperature dependence of fluid's viscosity. For example, the viscosity of a drug dissolved in a water changes from +73% to −52% in the range ±20° C. At different temperatures this leads to actual poor precision of drug dosing about 50-70% by the order of magnitude instead of required high numbers about 1-2%. Neither patient nor the device itself has any ability to control both gradual and unpredictable fast changes of capillary resistance, which directly influence the precision of the drug delivery.

Additionally, the reservoir of the above-described devices are under constant pressure, the sensor is a pressure sensor, there is no resilient expandable element and the system is not designed to perform self-diagnosis of the internal state of the device components. Thus, the actuator controls only the opening and closing of the valve and the processor only controls the timing of opening and closing of the valve.

One more serious problem relates to the medical requirement to dispose of frequently all parts brought into direct contact with patient's blood. In present case such replaceable part is represented by whole removable cartridge. It may be very costly for the patient to fulfill this requirement every few days because the cartridge contains expensive valve made with sub-micron precision, and precise pressure sensor which is important part of the sensor system.

Another technical design was disclosed in U.S. Pat. No. 6,740,059. This drug delivery system includes a separate remote control device, which is operated by the user in accordance with his medical needs, and can wirelessly communicate flow instructions to programmed local processors located in a separate housing together with two active valves obeying external controlling signals. This housing comprises full hydraulic system filled with the fluid, and is destined to be deployed directly on patient's skin. The hydraulic system of this device is represented by the line of consecutively connected pre-pressurized fluid supply reservoir having high volume, changing in time gradually and capable of being refilled by the user. The first inlet valve is constantly closed, then the expandable bolus accumulator having low volume, and finally the second outlet valve is also constantly closed. The flow passage following after the outlet valve comprises the exit opening made in the form of sharp hard needle contacting directly with patient's body. Also the local processor may be connected to multiple different sensors, situated in different locations and including at least one of an occlusion detector, a fluid supply reservoir volume transducer, a leak detector, a reservoir empty detector, a pressure transducer, and many other detectors, or any combination of said multiple detectors. The abundance of detectors makes this system very complex and costly.

The dosing procedure consists of several operations determined by the program and the flow instructions received from remote control device. As it was mentioned above both valves are closed initially and there is no fluid flow before the delivery cycle. First of all the local processor opens the inlet valve at appropriate start moment. After that pre-pressurized fluid flows from the fluid supply reservoir to low volume accumulator until it gets predetermined low dose of liquid drug at elevated pressure. Then the local processor closes the inlet valve and thus cuts hydraulic communication between the accumulator and the fluid supply reservoir. Then the local processor opens the outlet valve and waits for some time until a rather small dose, accumulated in the accumulator's volume at elevated pressure, is transferred to the exit opening of the flow passage so that the pressure inside the accumulator gets reduced to the same low value as external atmospheric pressure. Then the local processor closes the outlet valve and thus returns the whole system in its initial state ready for the next delivery cycle.

Due to the requirement that the driving force of this device is based on constantly pressurized fluid supply reservoir, the system suffers from the same disadvantages as the previous ones. To be more specific, both externally controlled valves are inevitably rather costly because of the necessity of extremely high precision of their manufacturing. A high-precision mechanical valve increases cost of the production of the entire system and reduces the reliability of its operation. At the same time the performance of such valves is extremely sensitive to the presence of any hard microscopic contaminations in the fluid. Accidental appearance of hard impurities or even invisible dust in valve's mechanism leads to the problem of unexpected drug leakage, which may cause dangerous overdosing. This can occur even during the insignificant pollution of valve clearance, introduced by unskillful user in the course of operating the system. The unresolved problem of non-controllable leakage has been unintentionally stressed in U.S. Pat. No. 6,740,059.

Accordingly to what is claimed in this patent, the fluid delivery part of the device cannot be manually operated even in potentially possible emergency cases because any control operations are allowed to be performed through remote control device only whereas the part of the device destined to be deployed on patient's skin contains no control elements which may be directly reached by the patient.

There is another device disclosed in U.S. Patent application No. 20060027523 (Feb. 9, 2006). The general idea of this application appears similar to some extent to the idea of the device discussed in four previous paragraphs (U.S. Pat. No. 6,740,059). In this application low doses of the fluid are transferred from a big fluid supply reservoir to a next smaller reservoir, which is intended to provide the user with programmatically controlled cycles of well measured micro-doses of the fluid. In order to fix a very low volume of each dose to about 0.2 mm$^3$, the small reservoir is hydraulically separated from the big one by an inlet valve, whereas the outlet valve separates this reservoir from the exit opening. The valves are self-controlled by their own pressure drop so that the fluid can move downstream only. What makes the major difference between the U.S. Pat. No. 6,740,059 and the application No. 20060027523 is: (a) a big reservoir of the application is not required to be subjected to predetermined excessive pressure; (b) both inlet and outlet valves are unavoidable parts of the pumping mechanism, wherein the small reservoir is supplied with a piezoelectric actuator capable of direct applying a force squeezing the fluid out; (d) the pumping mechanism and small reservoir are fully made of hard materials like a silicon or sapphire as used in semiconductor industry; (e) the hydraulic system of the device and pumping mechanism are made inseparable because they are built on the basis of solid state technology.

In 2007 the assignee Debiotech S.A. has announced that due to unavoidable sterility requirements both entire hydraulic system and pumping mechanism of the diabetes therapy device, based on said application, are intended to be disposable weekly. Such devices would be extremely costly for long-term users because one week is a very short life-time of the complex and expensive parts of the device, requiring high degrees of precision in solid state fabrication. Because the fixed dose of one cycle is very low (it is about 1-2% of typical hourly dose for adult patients) a high repetition rate is required. This leads to increased power consumption, shortens the life of batteries, and increases both the weight and the size of portable device. Also the device described in this application does not permit manual operation in emergency cases of serious malfunctioning of the device.

Taking into account that contemporary compact drug delivery devices are intended to be used by inexperienced patients, including children, teenagers, and seniors having decreased mental and technical levels, the potential dangers of both compromised sterility and the introducing of air bubbles were, before this invention, additional unresolved problems of existing devices, which result mainly from periodical patient's necessity to refill the device manually with fresh portion of the liquid drug. Serious medical consequences of all undesirable events listed above are often unpredictable.

The present description is supplied with several quantitative examples emphasizing advantages of the invention. For that purpose estimations have been chosen which relate to a portable automatic device delivering insulin for treatment of the diabetes. However, the invention can be also used for the delivery of many other liquid drugs requiring different quantitative approach. That is a reason why insulin's delivery should be considered as just one example given for better understanding of the invention only, because it represents may be most impressive but only one of many potential fields of an application of the invention.

General Outline of Devices of the Invention and Methods of their Functioning

Different versions of fluid delivery devices are to be considered in the general scope of the present invention. Any particular member of this family is a programmable device comprising several major systems which, in general, are desirably located in at least two or more separate modules wherein at least one module represents a replaceable cartridge which, at least in certain embodiments, is desirably destined to be a fully disposable part of the device.

Another general aspect of this invention includes actuators that are independent of a replaceable cartridge. Actuators generally contain a device for applying a force to a cartridge containing a reservoir for holding the fluid to be delivered and made at least partially of a resilient material, a sensor to detect a parameter of at least part of said resilient portion of the reservoir, and a processor programmed to control the actuator based on a variables including: (1) the desired volume (dose) of fluid to be delivered, (2) the internal state of the device, (3) information obtained about the amount of fluid delivered.

Accordingly, certain aspects of this invention include fluid delivery devices, comprising:

(a) a replaceable cartridge located in a first housing, wherein the replaceable cartridge comprises:
    a reservoir comprising at least one expandable element made of resilient material, said reservoir having at least two spatially separated sections connected so that hydraulic resistance between said two sections is not less than non-zero $R_1$; and
    a flow passage connecting an internal volume of said reservoir with at least one exit opening so that under conditions of fluid flow, hydraulic resistance to flow of said flow passage is not less than predetermined non-zero $R_2$;

(b) an actuating module located in a second housing, said module comprising:
    a driving force system; and
    at least part of a sensor system, wherein said part of the sensor system is capable of producing an output associated with at least one geometric parameter of said expandable element;

(c) a connector to provide a temporary connection of said replaceable cartridge and said actuating module; and (d) a programmable processor with fluid delivery instructions stored therein, said processor capable of acquiring said output of the sensor system and capable of producing an other output, said other output controlling the driving force system; whereas when both housings are connected to each other, the driving force system is capable of applying a force changing over time to the fluid in the reservoir.

Other aspects include devices wherein at least part of said processor is located in a third housing comprising:
    a display; and
    a system providing a exchange of data between said actuating module and said third housing.

Further aspects include devices wherein the driving force system capable of producing a driving force changing over time comprises at least one a mediatory element which, when said first and second housings are connected, said mediatory element operably transmits said driving force to a force receiving element of said reservoir in said replaceable cartridge.

Additional aspects include devices wherein both said mediatory element and said force receiving element are at least partially made of a ferromagnetic material.

Still further aspects include devices wherein both said mediatory element and said force receiving element each comprises a permanent magnet.

Even further aspects include devices wherein said magnets have an orientation such that the mediatory element transmits said driving force remotely to said force receiving element.

Other aspects include devices wherein said driving force system comprises a latch capable of switching between two stable states;

whereas in a first stable state the driving force transmitted to said force receiving element results in a continuous compressive force applied to the fluid in said reservoir to urge said fluid out of said reservoir; and whereas in a second stable state the driving force transmitted to said force receiving element results in a decompressive force applied to said fluid in the reservoir.

Certain of these aspects include devices having a latch, wherein said latch comprises:
    a permanently stressed spring to create said continuous compressive force;
    at least one permanent magnet;
    at least one electromagnet; and
    a mechanism capable of switching a distance between two said magnets so that one stable state occurs at greater distance between said magnets, and
    whereas said second stable state occurs at shorter distance between said magnets.

Other aspects of devices include an actuating module, wherein the actuating module further comprises a manual switch between said two stable states of said latch; and wherein said processor is programmed to initiate at least one signal to a patient.

Other aspects of this invention include devices that provide a warning signal to a user, wherein said signal is at least one of visual, mechanical, and auditory.

Additional aspects include devices wherein said reservoir further comprises an additional section connected to said other two sections of said reservoir by a hydraulic element providing a resistance $R_0$ so that $R_0$ exceeds $R_1$ when a compressive force is applied to a fluid in said reservoir, and more preferably $R_0$ exceeds $R_1$ at least one order of magnitude, and most preferably more than two orders of magnitude.

Yet further aspects include devices wherein said hydraulic element is a pressure-dependent static hydraulic resistor capable of switching its resistance $R_0$ so that $R_0$ does not exceed $R_1$ when a decompressive force is applied to the fluid.

Additional aspects include devices wherein said reservoir comprises an additional element made of resilient material, said element separating a movable piston from the internal volume of said reservoir, wherein said movable piston is adapted to transmit said driving force to said fluid.

In certain of these aspects, devices include said additional element which is capable of expanding into a cavity made in said movable piston when fluid in said reservoir is subjected to an internal pressure exceeding external pressure.

In further of these aspects, devices include said additional element which is adapted to eliminate direct correspondence between displacement of said movable piston and a dose of the fluid delivered to said exit opening.

In other aspects, elements of both said reservoir and said flow passage are characterized in having a ratio of $R_1/R_2$ so that said ratio is greater than about 0.05 and less than about 200, more desirably said ratio is in between about 0.25 and about 40, and most desirably said ratio is in between about 1 and about 10.

In certain embodiments, said flow passage connecting said internal volume of said reservoir with at least one exit opening further comprises a pressure-dependent valve capable of switching to an open state under conditions of fluid flow so that hydraulic resistance of said open valve is less than $R_2$ at least by one order of magnitude when a pressure drop applied to said valve is equal or exceeds a predetermined value $P_{op}$, and wherein said pressure-dependent valve is capable of switching into a closed state when said pressure drop is below such $P_{cl}$ which is either equal or less than said $P_{op}$, whereas the hydraulic resistance of said closed valve exceeds $R_2$ by at least one order of magnitude, and most desirable it exceeds $R_2$ by more than two orders of magnitude.

In certain aspects, at least one element of said sensor system comprises a piezoelectric sensor, and when said first and said second housings are connected, the device further comprises a direct or an indirect mechanical connection of said piezoelectric sensor with an external surface of said reservoir.

In devices combining a replaceable cartridge and an actuator contained in separate housing, the sensor system comprises at least one such electrically conducting area which is capable of forming a non-contact capacitor sensor so that said electrically conducting area is located in proximity to at least one other electrically conducting area which is attached to said reservoir and capable of relocating in response to deformation of said expandable element.

Other sensor systems comprise a magnetic detector adapted to form a non-contact magnetic sensor when said first and said second housings are connected, so that said magnetic detector is located in proximity to either a magnetic substance or a magnetized substance attached to said reservoir and capable of relocating in response to deformation of said expandable element.

In certain of these sensor systems, at least one element of said sensor system is housed in said actuating module, said one element of said sensor system comprising a non-contact optical sensor comprising:

a light emitter directed onto said replaceable cartridge when said first and said second housings are connected together, and at least one detector adapted to receive light emitted by said light emitter, either reflected by said replaceable cartridge or transmitted through said reservoir.

Other aspects of this invention include replaceable cartridges for a fluid delivery device, comprising:

(a) a reservoir adapted to be filled with a fluid, said reservoir having at least two spatially separated sections, a first section of said two sections comprising at least one expandable element made of resilient material, said two sections connected to each other so that under conditions of fluid flow, hydraulic resistance between them is not less than non-zero $R_1$;

(b) a flow passage connecting at least one exit opening with an internal volume of said first section which comprises said at least one expandable element made of resilient material so that under conditions of fluid flow, hydraulic resistance of said flow passage is not less than predetermined non-zero $R_2$; and (c) at least a portion of a connector to at least temporarily operably connect said cartridge with a housing containing an actuator;

wherein said connector provides that relative locations of said reservoir and said housing containing said actuator to permit transfer a force from said actuator to internal surface of a second section of said two sections of said reservoir.

In other replaceable cartridges, under flow conditions, the ratio $R_1/R_2$ exceeds about 0.05 and is less than about 200, more desirably said ratio is in between about 0.25 and about 40, and most desirably said ratio is in between about 1 and about 10.

Additional aspects of this invention include actuator modules for a fluid delivery device, comprising:

(a) a housing having:
a driving force system; and
at least part of a sensor system, wherein said part of the sensor system is capable of producing an output associated with at least one geometric parameter of an expandable element of a replaceable cartridge having a reservoir;

(b) at least a portion of a connector to provide a temporary operable connection to a replaceable cartridge having a reservoir adapted to hold said fluid; and (c) a programmable processor with fluid delivery instructions stored therein, said processor capable of acquiring said output of the sensor system and capable of producing an other output, said other output controlling said driving force system; wherein when said actuator and said replaceable cartridge are connected to each other, said driving force system is capable of applying a force changing over time to a fluid in the reservoir.

Certain actuators of this invention include a sensor system comprising at least one such electrically conducting area which is capable of forming a non-contact capacitor sensor when said actuator and a replaceable cartridge comprising a reservoir having an expandable element made of resilient material are connected, so that said electrically conducting area is located in proximity to at least one other electrically conducting area which is attached to said reservoir and capable of relocating in response to deformation of said expandable element.

Other actuators of this invention include a sensor system comprising a magnetic detector adapted to form a non-contact magnetic sensor when said actuator and a replaceable cartridge comprising a reservoir having an expandable element made of resilient material are connected, so that said magnetic detector is located in proximity to either a magnetic substance or a magnetized substance attached to said reservoir and capable of relocating in response to deformation of said expandable element.

In additional aspects, an actuator has a sensor system, wherein at least one element of said sensor system is housed in said actuating module, said one element of said sensor system comprising a non-contact optical sensor comprising:

a light emitter directed onto said replaceable cartridge when said actuator and said replaceable cartridge are connected together, and at least one detector, wherein said detector is adapted to receive light emitted by said light emitter, either reflected by said replaceable cartridge or transmitted through said reservoir.

In certain embodiments, a processor has instructions stored therein to calculate a dose of fluid delivered according to the following formula:

$$D(t) = \int_0^t F(t)\,dt = \int_0^t \frac{\Delta P_{ind}(t)}{R_{exit}}\,dt.$$

In other embodiments, a processor has instructions stored therein to calculate a dose of fluid delivered according to the following formula:

$$D(t) = \frac{1}{R_{exit}}\int_0^t \Delta P_{ind}(t)\,dt = \frac{\alpha\beta}{R_2}\int_0^t S(t)\,dt.$$

In still other embodiments, a processor has instructions stored therein to calculate a dose of fluid delivered according to the following formula:

$$D(t) = \frac{P_0}{R_2}\left(t - \frac{T_{up}}{2}\right) = \frac{\alpha\beta S}{R_2}\left(t - \frac{T_{up}}{2}\right).$$

In even further embodiments, a processor has instructions stored therein to calculate a dose of fluid delivered according to the following formula:

$$D(t) = \frac{\alpha\beta}{R_2}\int_0^t dt\, S(t) \cong \frac{\alpha\beta}{f_0 R_2}\sum_{k=1}^{L(t)} S(t_k) = D(t_L).$$

In additional embodiments, a processor has instructions stored therein to calculate a time needed to deliver a dose of fluid according to the following formula:

$$D_0 = \frac{R_2}{\alpha\beta S} + \left(\frac{T_{up} - T_{down}}{2}\right) = T_c.$$

In further embodiments, a processor has instructions stored therein to calculate the time needed to deliver a dose of fluid according to the following formula:

$$T_c = \frac{\tau_{act} D_0 R_1 S_{atm}}{(\tau_{oc} - \tau_{act}) P_{atm} S^{(0)}} = t_{end} - t_{st}.$$

In still further embodiments, a processor has instructions stored therein to calculate a time needed to deliver a dose of fluid according to the following formula:

$$T_c + \frac{\tau_{act} S_1}{S_{max}}\exp\left\{\frac{t_1 - T_c}{\tau_{act}}\right\} = t_1 + \frac{\tau_{act} S_1}{S_{max}} + \frac{\alpha_{ini}\tau_{act} D_0}{P_{val}\left(1 - \frac{\tau_{act}}{\tau_{oc}}\right)\left(\frac{S_{max}}{S_1} - 1\right)}.$$

Other aspects of this invention include methods for a delivering of a dose of a fluid, comprising the steps:

(a) providing a device of any of the above described aspects;

(b) introducing said fluid into said reservoir;

(c) initiating a non-zero force urging said fluid out of said reservoir;

(d) acquiring at least one output from said sensor system associated with at least one geometric parameter of said resilient element;

(e) calculating a time $t_{end}$, comprising treating said acquired output by a processor executing commands based upon instructions stored in said processor; and (f) terminating said force at $t_{end}$.

In other aspects, methods further comprise the steps:

(i) before step (c) above, subjecting said fluid in the reservoir to a sufficiently low pressure to prevent said fluid from flowing out of said exit opening, said pressure in the reservoir close to an external pressure $P_{ext}$;

(ii) the step (c) further comprising producing at least one starting electric output at a predetermined moment $t_{st}$, said starting output resulting in producing:

said force urging said fluid out of said reservoir; and subjecting said expandable element to a pressure $P_{ind}(t)$ within the range defined by the expression: $P_{max}+P_{ext} > P_{ind}(t) > P_{min}+P_{ext}$, wherein $25 > P_{max}/P_{min} > 1$;

(iii) treating said output of said sensor, comprising determining a pressure difference $P_{ind}(t)-P_{ext}$, and further comprising determining a period $T_c$ satisfying the condition $T_c = t_{end}-t_{st}$, wherein $T_c$ is of such duration of said force urging said fluid out of said reservoir to provide an equality of said predetermined dose and an actual dose delivered, said actual dose being an integral found by integrating over time from time $t_{st}$ of a ratio having a numerator being said pressure difference, and a denominator being a parameter expressing hydraulic resistance $R_{exit}$ of said flow passage connecting the reservoir with said exit opening;

(v) the step (f) comprises producing at least one ending electric output at $t_{end}=T_c+t_{st}$, wherein said ending output results in either decreasing the force or changing a direction of the force or both so that the pressure of the fluid in said first section can relax in time up to about its initial value before step (c).

In additional aspects, methods include steps wherein under flow conditions, hydraulic communication between said two spatially separated sections of the reservoir has a resistance $R_1 \geq 0.05\, R_2$;

wherein step (d) above comprises acquiring at least two outputs from said sensor system;

wherein said step (e) above further comprises:

determining an actual hydraulic resistance $R_{exit}$ of said flow passage connecting the reservoir with said exit opening;

setting said denominator equal said actual $R_{exit}$;

producing an alarm signal if said actual $R_{exit}$ exceeds a predetermined level; or substituting said actual $R_{exit}$ into an analytic expression of said integral if said actual $R_{exit}$ does not exceed said predetermined level.

In other aspects, methods include steps wherein said flow passage connecting the reservoir with said exit opening is further supplied with an element switching hydraulic resistance at a predetermined pressure drop $P_{op}$;

wherein step (d) above comprises acquiring at least five outputs and desirably more than five outputs from said sensor system;

said treating of step (e) further comprising:

calibrating said device delivering the fluid;

checking current performance of components of said device;

determining the amount of the fluid remaining in the reservoir; and producing one or more of a report and an alarm signal to inform a user if said amount of remaining fluid is below a predetermined amount or a malfunction is detected that cannot be self-compensated by said steps determining of the time $t_{end}$.

In other of these aspects, methods include steps wherein step (c) above further comprises creating a first emergency signal if after said starting electric signal said force urging the fluid out of said reservoir is not produced, said first emergency signal resulting in the at least one of:

(i) prompting a patient to initiate a manual application of said force to said reservoir;

(ii) determining an actual starting time $t_{st}$, when an appearance of manually created non-zero force urging the fluid out of said reservoir is detected by said sensor system;

(iii) said ending electric output of step (e) above results in creating such second emergency signal at the moment $t_{end}$ which recommends the patient to terminate manually said application of said force, whereas both said first and second emergency signals are visual, mechanical or acoustic signals.

In additional aspects methods include steps wherein said predetermined $R_2$ is substituted into said denominator of said ratio in order to fulfill the role of said parameter expressing said $R_{exit}$, and said integral is proportional to a sum of all said outputs of said sensor system acquired since the time $t_{st}$.

Yet in additional aspects, methods include further steps comprising:

transmitting at least one output of at least one bio-medical device analyzing a physiological feature of a patient to a control system, and correcting the predetermined dose delivered by said device according to said transmitted output of said bio-medical device.

Other aspects of this invention include methods for a delivery of a predetermined dose of a fluid, comprising the steps:

(a) providing a device comprising a replaceable cartridge comprising a reservoir filled with the fluid, said reservoir having both at least one element made of resilient material and at least one exit opening, and a separable actuator module connected with said cartridge, said actuator module capable of switching between at least two stable states, wherein only one of two said states results in a continuous compressive force applied to the fluid;

(b) switching said module into a stable state which results in producing of a continuous compressive force applied to the fluid in said reservoir;

(c) acquiring at least one output from a sensor system associated with at least one geometric parameter of said resilient element;

(d) calculating a time $t_{end}$, comprising treating said acquired output by a processor capable of executing commands stored in said processor; and (e) switching said module into said other stable state at $t_{end}$.

DESCRIPTION OF EMBODIMENTS

Figure 3:
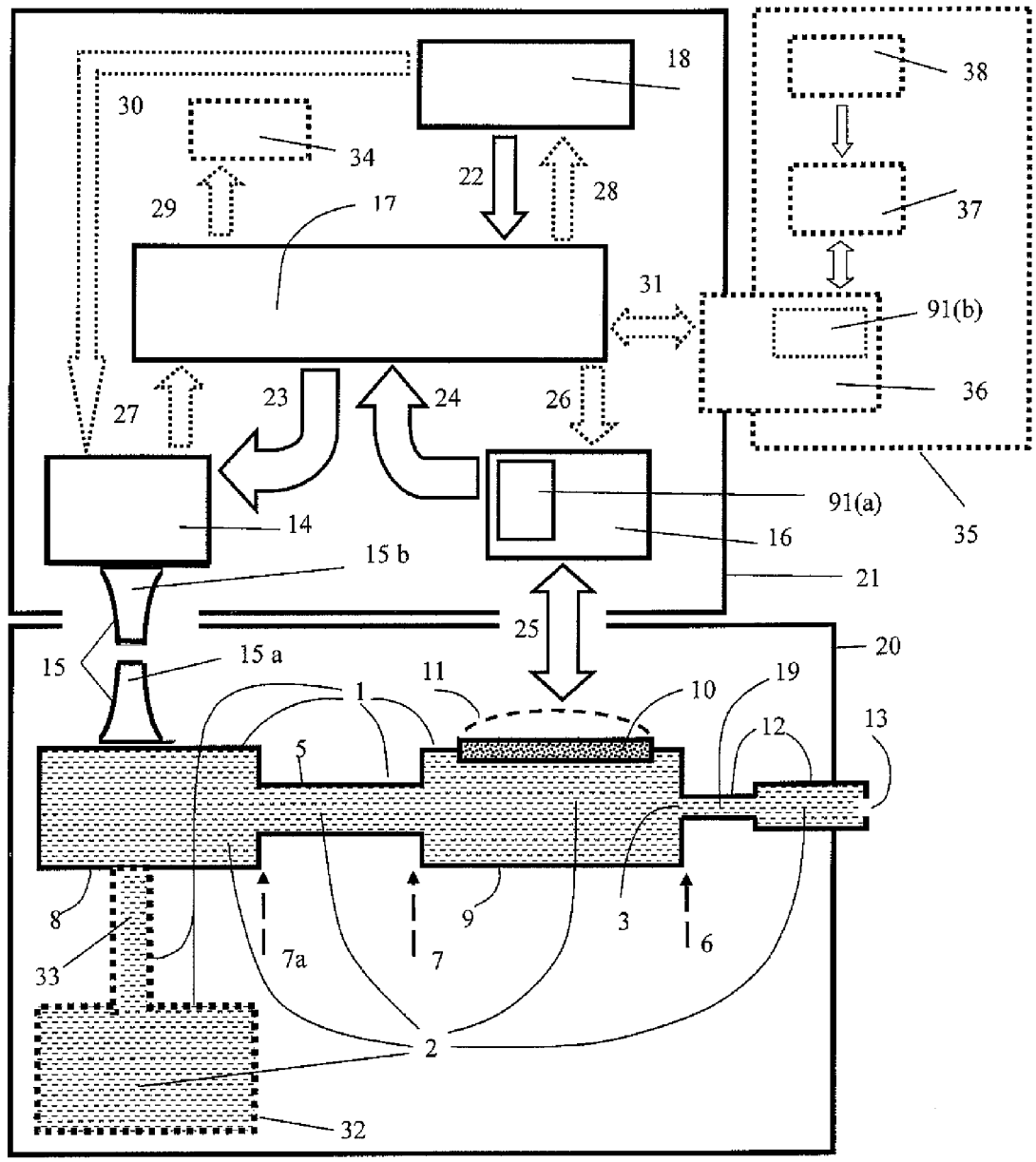
FIG. 3 depicts components and systems of fluid delivery device of the invention as well as some ways and directions of information transfer between all systems.

Advantages of the invention may be achieved if all inevitable systems and their parts, shown schematically in general FIG. 3 with solid lines and numbered from 1 to 25, are involved in the fluid delivery process. Thick frame 20 depicts schematically a separate housing containing all necessary parts of the replaceable cartridge destined to be filled with a fluid 2, whereas thick frame 21 depicts another separate housing related to an actuating module. Independently on peculiarities of any particular embodiment any device of the invention becomes fully ready to work only when both housings 20 and 21, related to the replaceable cartridge and the actuating module correspondingly, are brought into tight connection depicted in FIG. 3 and fixed temporarily with the use of special means discussed later. After both said housings are fixed two sub-elements 15a and 15b, located in the housings 20 and 21 correspondingly, become involved in formation of a specific element 15 which depicts either direct mechanical or remote interaction of a driving force system 14 fully designed within actuating module, with a hydraulic system fully located in the cartridge. Three thick white arrows 22, 23 and 24 depict critically important information transfer, making the systems to work cooperatively whereas double-directed thick white arrow 25 depicts only certain physical interactions of resilient element 10 with a sensor system 16.

All other parts shown in FIG. 3 by dotted lines are either optional elements which are not critical for the device's functioning or elements which may be useful only in certain specific designs of the invention. For example, thick dotted arrows 26, 27, 28, 29, 30, and 31 depict optional directions of controlling signals and information transfer. Another example of optional element is an additional fluid supply elastic section 32 of a reservoir 1, said additional section connected with main sections 8 and 9 of the same reservoir 1 by a static hydraulic resistor 33. It may be desirable that optional alarm system 34 is also included for user's convenience and safety. Certain embodiments can be made even more convenient for users if devices of the invention are further supplied with optional pure electronic parts 36, 37, and 38 located in third separate housing 35 representing a remote control module discussed later in corresponding section of present description.

All devices of present invention are destined to work in programmable cyclic regime wherein each separate cycle should result in delivering of predetermined volume $D_0$ of a single dose which is typically a small fraction of whole volume of fluid stored in the cartridge destined to supply a patient with a drug for at least few days. Exceptionally high precision of every $D_0$, delivered to patient's body through a flow passage 12 supplied with at least one exit opening 13, is reached in present invention only because of special design of a reservoir 1 comprising at least two sections 8 and 9 which are spatially separated by static hydraulic resistor 5 having non-zero resistance $R_1$, wherein the section 9 comprises at least one expandable element 10 made of resilient material (see FIG. 3).

In accordance with teaching of present invention, another feature of the reservoir 1 is that during each delivery cycle the local volume of the fluid contained in each of two said sections 8 and 9 changes so much that the whole process of the fluid delivery can depend on said changes. The comparison of the scheme FIG. 3 with the simple example depicted in FIG. 2 helps to understand functional roles of each section. It can be desirable that typically the section 8 has relatively high volume exceeding the $D_0$ at least few times in certain embodiments and even few orders of magnitude in other ones. In order to raise the pressure in the reservoir 1 one needs to compress the fluid in the section 8 by any driving force system 14 located in external housing 21. That is why the section 8 may be called "compression section of the reservoir 1". When FIG. 2 and FIG. 3 are compared the only serious difference should be mentioned that while normal work the real system 14 must be technical means instead of human's finger 4 shown in FIG. 2. However, in order to get increased reliability of invented devices in certain rare emergency cases even patient's finger 4 can be successfully used as temporary substitute of driving force system if technical means 14 fail due to any reason and control system informs a patient with either visual, or mechanic, or acoustic emergency signal. Such emergency method, incorporated into design of certain embodiments, is separately discussed in present description. Persons of ordinary skill in the art can appreciate that in order to make the fluid flow the compressing force produced by means 14 must affect a part of the surface of fluid's body. In this case the compressing force becomes the squeezing-out force. When such depending on time compressing force is applied to the fluid in the section 8 the pressure $P_{comp}(t)$ in this section exceeds external pressure $P_{ext}$ affecting the fluid in the exit opening 13. Positive value of the expression $[P_{comp}(t) - P_{ext}]$ represents the excessive pressure which forces the fluid to flow out of the section 8 exactly as shown by middle image of FIG. 2. This process decreases the volume of the fluid remaining in the compression section 8. For further aims it may be more convenient if said depending on time t excessive pressure in the compression section 8 is written in shorter form:

$$P_{comp}(t) - P_{ext} = \Delta P_{comp}(t) \quad \text{(Eq. 3)}$$

Section 9 can play two functional roles. In accordance with the teaching of the invention, the first role of the expandable section 9 is to provide substantial change of its local volume in response to application of excessive pressure $\Delta P_{comp}(t)$ produced in the compression section 8 during each delivery cycle. In order to fulfill this function the fluid contained in the reservoir 1 makes contact with at least one elastic element 10 occupying at least some part of internal surface of the section 9. When positive excessive pressure $\Delta P_{comp}(t)$ is created in the fluid located in the compression section 8, this excessive pressure is first of all applied to the opened hydraulic communication, namely the element 5, and causes the transfer of some additional volume $\Delta V$ of the fluid from compression section 8 to the section 9. This transfer is accompanied by a certain increase of the pressure inside the section 9. Because the fluid in section 9 contacts with expandable element 10, the increased pressure deforms the element 10 and makes it to expand so that the increase of the internal volume of the section 9 is equal the additional volume $\Delta V$ of the fluid transferred from the compression section 8. This point is demonstrated by FIG. 3 wherein the non deformed element 10 is shown schematically by shadowed rectangle having the form of flat elastic membrane. Dashed curve 11 is to demonstrate the change of its shape and the increase $\Delta V$ of the volume of the section 9 caused by elevated pressure inside this section. Note that the flat membrane in FIG. 3 is provided as example only because it will be further demonstrated that actual shape of this expandable element 10 depends on chosen design which may vary in different embodiments.

It can be appreciated that resilient expansion of element 10 is accompanied by a corresponding change of at least one geometric parameter related to either the shape or certain characteristic size of this element. The said means that any change of said geometric parameter provides a direct indication of both the increase $\Delta V$ of the local volume of the section 9 and elevated pressure in whole reservoir 1. That is why the section 9 of the reservoir 1 should be further called by its full name "indicator section of the reservoir 1" or, for brevity, simply "the indicator." Moreover, that means that the fluid volume $\Delta V$ transferred from the compression section 8 to the indicator section 9 can be measured if the device is supplied with means, namely the sensor system 16, capable of producing an output associated with said at least one geometric parameter of the expandable element 10. Hereinafter said output can be also called for clarity "signals associated with said at least one geometric parameter of the expandable element 10". The participation in such measurement is a role of the indicator section 9 of the reservoir 1. Because this section is now named "the indicator," its internal volume at a particular time t, is to be further supplied with corresponding index and designated hereinafter as $V_{ind}(t)$. The corresponding change of this volume over time is designated as $\Delta V_{ind}(t)=V_{ind}(t)-V_0$ where $V_0$ is the local volume of non expanded indicator section 9 at initial fluid pressure equal $P_{ext}$.

Roles of the spatial separation of the compression section and the indicator section of the same reservoir can now be appreciated. Measurement of the volume change. $\Delta V_{ind}(t)$ can be carried out correctly in the only case if deformation of the element 10 causing the volume expansion of the whole indicator section is caused only by the fluid. This means that said deformation must not be disturbed by direct involvement of the squeezing-out force provided by element 14. In order to avoid such direct involvement it may be desirable that: (i) means capable of changing over time the force squeezing the fluid out of the reservoir interact directly with only the first limited surface area of the fluid in the reservoir, actually the area located in the compression section, and (ii) said first area of the fluid is spatially separated from another limited surface area of the fluid, actually the limited area of the fluid located in the indicator section and brought into contact with such part of the expandable element 10 which is really involved in the measurement of the change $\Delta V_{ind}(t)$. This complicated sentence takes into account that resilient materials may be present in both the compression and the indicator sections, as shown for example in FIG. 9b and FIG. 12. However, only resilient deformation of this element 10 is related to the indicator section, and in some cases only the deformation of certain part of the resilient elements related to the indicator sections, is capable of reflecting the change $\Delta V_{ind}(t)$. The word "reflecting" means that signals produced by the sensor system 16 in response of the change $\Delta V_{ind}(t)$ must not necessarily be proportional $\Delta V_{ind}(t)$. It may be quite enough if these signals are just associated somehow with at least one geometric parameter of such part of the expandable element 10 which is actually involved in the volume change $\Delta V_{ind}(t)$ of the indicator. It is shown in the next sections of the description that practical types of said involvements and said associations can vary in different embodiments. However, it should be appreciated that correctly done spatial separation of two sections of the reservoir discussed above may be enough to provide proper separation of two said areas of the fluid in the reservoir 1 and, correspondingly, to exclude any possibility of undesirable disturbance caused by direct involvement of means 14 in the formation of signals produced by the sensor system 16. Accordingly to what has been said above the correct spatial separation of two said sections of the reservoir 1 is such their separation, provided by means connecting these two section, that the first limited surface area of the fluid directly interacting with the squeezing-out force is fully located in the first section of the reservoir 1, and another limited surface area of the fluid contacting with said part of the expandable element 10 is fully located in the second section of the reservoir 1. When this condition is fulfilled said signals of the system 16 become capable of reflecting quantitatively actual physical state of the hydraulic system at any time moment independently on how particular means 14 are designed and how they create the squeezing-out force.

The spatial separation of two said sections and corresponding spatial separation of two surface areas of the fluid's body are intentionally stressed in schematic view of FIG. 3 where means 15, destined to transfer the driving force from means 14 to reservoir 1 are shown in close proximity of local cavity of the section 8 whereas the elastic element 10 is shown to belong only to local cavity of the section 9 of the reservoir 1. It will be further demonstrated that certain practical examples of said spatial separation may be sometimes less obvious and need to be analyzed carefully. However, two following considerations must be always taken into account: (i) said part of the expandable element 10 related to the indicator section has a resilient nature, and (ii) this part is deformed only by the difference of the fluid pressure $P_{ind}(t)$ inside the indicator and the external pressure $P_{ext}$ applied to the external surface of the element 10. These facts lead to following local relationship between the volume $V_{ind}(t)$ of the indicator 9 and its internal fluid's pressure $P_{ind}(t)$:

$$\alpha \Delta V_{ind}(t)=\alpha[V_{ind}(t)-V_0]=P_{ind}(t)-P_{ext}=\Delta P_{ind}(t) \qquad \text{(Eq. 4)}$$

where factor $\alpha$ is given stiffness factor which relates only to the indicator 9 in more advanced and most advanced embodiments of the invention, and $\Delta P_{ind}(t)$ is the pressure difference in the indicator section 9 of the reservoir 1. However, it will be shown later that in certain simple embodiments the factor $\alpha$ can relate to whole reservoir 1 if the section 8 is also supplied with another resilient element and a communication between sections 8 and 9 has very low hydraulic resistance. Because the resilient nature of the element 10 the proportionality expressed by the equation (4) is always valid. However, it should be acknowledged by anyone skilled in the art that due to the presence of non-zero hydraulic resistance $R_1$ in the connection of two spatially separated sections of the reservoir 1 the dynamic relationships between excessive pressure $\Delta P_{comp}(t)$ in the compression section 8 and the responding changes of both the local volume $\Delta V_{ind}(t)$ of the indicator section 9 and its local pressure difference $\alpha P_{ind}(t)$ may be rather different in different embodiments. Particular types of these relationships are very important for the operation of whole device and will be thoroughly discussed later in many specific details.

It should be appreciated that in order to simplify the mathematical part of the present description, one can neglect very slight changes of the stiffness factor $\alpha$ while potentially substantial deformation of the resilient element 10 can occur. Similar slight changes are well known for all strongly deformed resilient materials and may require certain small correction of the mathematical algorithm related to the method without any change of the general scope of the invention. This correction can be easily done while factory calibration of the device.

Notwithstanding potential multiplicity of possible designs, devices of present invention exploit the same general method of cyclic fluid delivery. This method comprises the following major steps of every delivery cycle: (a) initiating at programmatically predetermined moment $t_{st}$ a non-zero force squeezing a fluid out of a reservoir 1 having an expandable element 10; (b) acquiring signals associated with a geometry of said expandable element; (c) treating acquired signals by a processor 17 capable of performing predetermined mathematical calculations using an algorithm, which results in determining a moment $t_{end}$; (d) terminating the squeezing-out force at $t_{end}$ determined while the step (c). This is just general outline of the method provided only for better understanding of the content of few next sections describing technical details of systems of the invention. Specific cooperative interactions of said systems are disclosed below as well. More precise definitions of major steps and specific details of most important sub-steps of the general method are provided in final sections of the description. Special attention is focused on detailed description of mathematical algorithms that relate to different embodiments and lead to highly "intellectual" decisions made by the processor in accordance with variations of both external and internal circumstances.

The central and most important feature of the invention is that in some embodiments developed specifically for ambulatory drug delivery, the entire hydraulic system can be made in the form of very simple, low cost factory pre-filled replaceable cartridge practically fully manufactured of cheap plastic materials. In some preferred embodiments, it can be fully disposable, which eliminates the necessity of manual refilling by unskillful users. Being filled with the liquid drug by a manufacturer, such cartridges can be made free of air bubbles and potential contaminants, and can satisfy sterility requirements. It can be desirable that in order to be as simple and cheap as possible the replaceable cartridge does not contain high precision parts either hydraulic or mechanical ones. It should be also designed so that the cartridge is free of batteries, electronics, processors, parts of driving force system 14, and complicated or high precision parts of the sensor system 16. It is anticipated that, in order to activate the replaceable cartridge of the invention, the user should only bring the cartridge into contact with corresponding place of the actuating module of the device. After that the device is fully ready to: (i) be deployed at appropriate place of patient's body, and (ii) start drug delivery when the power switch is moved in ON position.

It should be appreciated that different designs of replaceable cartridges may be used in different embodiments, and simple particular designs may be particularly desired. However, independently on possible individual constructive variations, any replaceable cartridge of the invention desirably possesses two following features: (i) a fluid pre-filling any hydraulic part of the cartridge is subjected to the same pressure which is close to an external pressure $P_{ext}$. This condition stresses that the fluid placed into the cartridge does not need to be kept under high excessive pressure. However, initial pressure inside the cartridge may exceed external one a little bit which is only intended to avoid the formation of air bubble while connecting the exit opening of the cartridge with patient's body; (ii) the location of both sections 8 and 9 of the reservoir 1 inside the housing 20 must be designed so that, after the cartridge is connected with the housing 21 comprising the sensor system 16 and the system 14 destined to transfer time-dependent driving force into the housing 20 (see FIG. 3), sections 8 and 9 of the reservoir 1 in the housing 20 should get such position relative the housing 21 that the system 14 becomes capable of transferring said force to at least one either movable or flexible element related to the section 8 of the reservoir, and more precisely to internal surface of the section 8, and the sensor system 16 becomes capable of producing input signals associated with at least one geometric parameter of expandable element 10 of the indicator 9.

It should be specifically stressed and appreciated by anyone skilled in the art that in certain embodiments of the invention the force applied to the fluid in section 8 of the reservoir 1 is not necessarily equal the primary driving force transferred from the system 14 to the cartridge 20 because quantitative correspondence between two said forces may depend on specific design of each particular cartridge which can include rather different mechanical and non mechanical means transforming primary driving force into the secondary force applied to the fluid. The only correct approach is to say that said primary driving force is to be transformed somehow into said secondary force applied to the fluid. Examples of different transformations will be provided later. However, neither general scope nor performance of devices of the invention can depend on particular mechanism of said transformation.

Special Features of Replaceable Cartridges, Housings, and Connecting Means

Embodiments of the present invention is intended to make drug delivery devices more precise, smaller, cheaper, safer, and as simple and convenient for any kind of potential users as possible. Matters related to these aims and discussed in this section are: (i) special features of a flow passage 12 defining how replaceable cartridges have to be designed in order to provide right delivery of a liquid drug to patient's body, and (ii) mutual complementary features of two housings related to both the replaceable cartridge 20 and the actuating module 21.

Due to usual sterility requirements at least certain parts of any drug delivery device used for long period of time must be disposed of every few days. More precisely, disposable parts are such parts which have to be brought in direct contact with patient's blood or other his or her internal tissues for limited time. In that regard the devices of present invention provide two different choices of how an inevitable part of hydraulic system of the device located in the replaceable cartridge, namely the flow passage 12, can be designed. The first version of a design relates to a first sub-family of devices destined to be suspended on patient's belt because either the device cannot be made very small due to some technical reasons discussed later or external location is just more convenient for certain categories of users. Cartridges of the first sub-family are to be connected with patient's body with relatively long tubing shown in FIG. 4a. In principle, even cartridges of this type may be fully disposable part of the device but too frequent replacement of whole cartridge may be too costly for certain users. However, another option avoiding increased cost is that cartridges of this type comprise the only small and relatively simple disposable part, for example, a disposable part of a separable infusion set 39 connected with the end of said tubing, said infusion set comprising hollow needle 40 having at least one exit opening 13. Many different designs of a separable set 39 can be created by anyone skilled in the art, whereas similar separable set 39 is already described in U.S. Pat. No. 6,572,586 fully incorporated herein by reference as an example only. If a patient chooses this option it provides him or her with an ability of periodic refilling of the same cartridge in which only disposable part of the infusion set 39 is to be frequently replaced.

Figure 4:
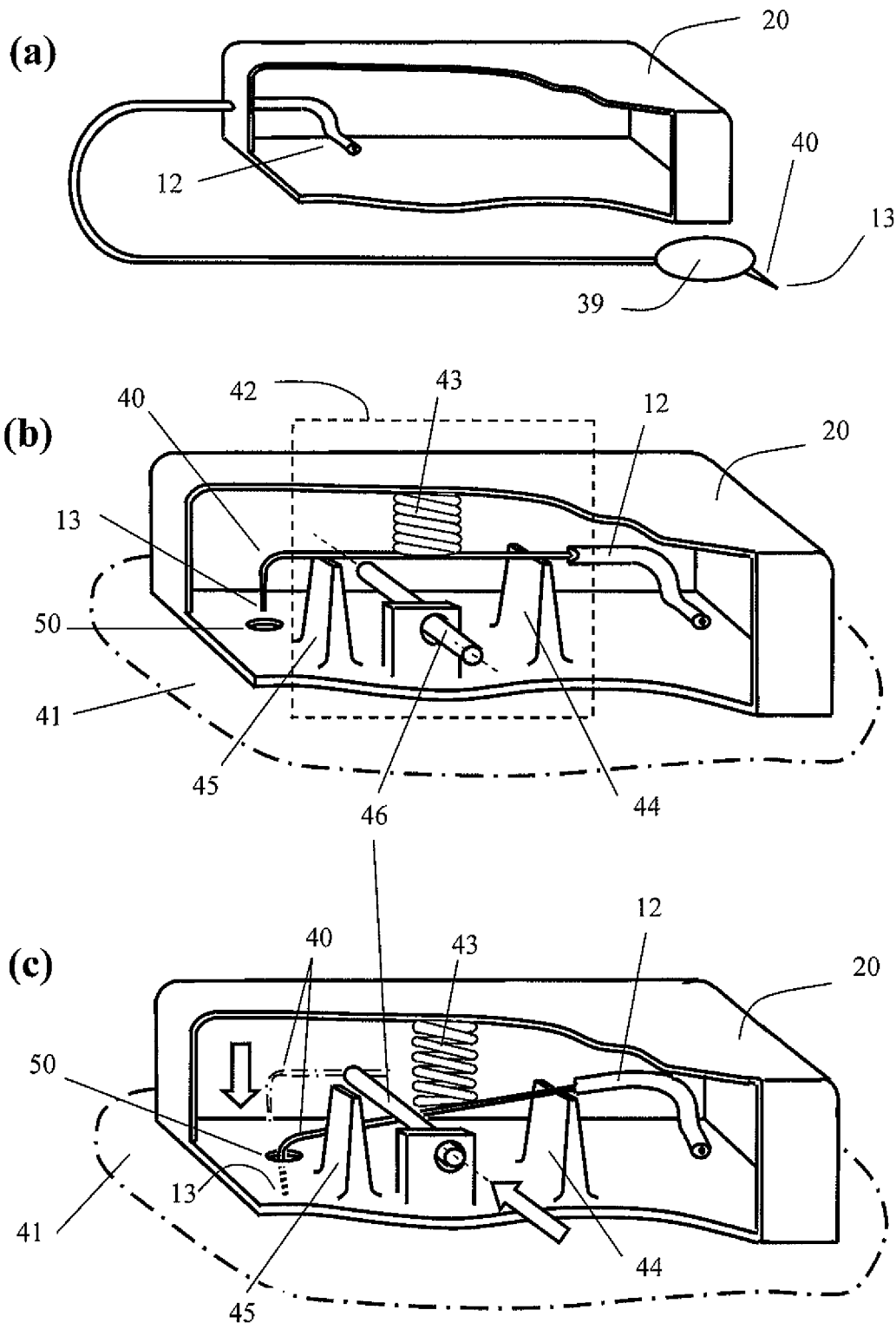
FIG. 4 depicts exploded view of the housing of replaceable cartridge and constructive details of flow passages which may be used in two different embodiments of the invention destined for drug delivery devices either: (a) suspended on the patient's belt or (b, c) directly deployed on patient's skin. For simplicity, other details of the cartridges are not shown here.

Another version of a design relates to a second sub-family of most desirable small and super small devices of the invention destined to be deployed directly on patient's skin 41 shown in FIG. 4b and FIG. 4c with dash-dotted line. It can be desirable that replaceable cartridges of the second type, destined to be fully disposable part of the device, are factory pre-filled with a liquid drug in order to avoid both air bubbles and potential contaminations, then sterilized and packed so that all openings of uninstalled cartridge 20 are protected and said sterility is preserved for a long-term storing period. It can be also very desirable that, in order to simplify an installation procedure and avoid any probability of incorrect installation done by unskillful user, the cartridges of the second type comprise special starting mechanism 42 emphasized in FIG. 4b within dashed rectangular. Before installation, which assumes a connection of both housings 20 and 21, this mechanism, described here as an example only, can comprise short internal flow passage 12 made of flexible material, the needle 40 having at least one exit opening 13, and a compressed spring 43 placed between an upper lid of the housing 20 and said needle 40 supported by two ribs 44 and 45 so that fixed needle 40 is fully hidden inside the housing 20. FIG. 4b shows explicitly that before installation a shifting rod 46 located in vicinity of the needle 40 remains in its waiting position in the housing 20.

In order to install the replaceable cartridge of most desirable embodiments of the invention any user, including rather unskillful one, has merely to take the new cartridge out of said sterile package and to connect the housing 20 with the housing of the actuating module 21 by means discussed below in more details, which are designed so that no mistake can be done (see, for example, FIG. 8). After that the device becomes fully prepared to work and can be deployed on an appropriate place of patient's skin 41. After said deployment is over the last action to start is just to push ahead a main power switch 47 located on the top of the actuating module 21 shown in FIG. 8. This action turns the power ON and activates all systems of the device. The same movement makes pushing end 48 of the switch 47 to penetrate a little bit inside small window 49 of the replaceable cartridge 20 (see FIG. 8) in order to push the shifting rod 46 ahead as shown by thick horizontal arrow in FIG. 4c. That causes the following: (i) releasing only left part of the needle 40 from supporting rib 45, (ii) releasing previously fixed pushing end of compressed spring 43, and (iii) forcing needle's tip 13 to move down and to pass through a hole 50 located on bottom plate of the housing 20 in order to insert tip 13 into a surface layer of patient's skin 41 as shown in FIG. 4c. Thus, starting mechanism 42 disclosed above provides extremely simple procedure of activation of the device. It should be evident that detailed mechanism 42 of present description is just one example only, and other similar simple mechanisms can be easily designed as well by everyone skilled in the art.

Independently on which sub-family of devices of the invention is used, proper work of fully assembled device requires that the housing 20 containing the replaceable cartridge has to be reliably fixed relatively the housing 21 containing the actuating module. In order to reach this aim it is desirable that all devices of the invention are supplied with special means destined to provide fast, easy, and reliable temporary connection of both said housings before the work starts, and further easy disconnection of empty cartridge. It can be appreciated that a cartridge should be supplied with at least a portion of such connector, and an actuator should be supplied with complimentary portion of the same connector in order to at least temporarily operably connect said cartridge with said actuator. Many different approaches can be used to design said connecting means. For example, FIGS. 5, 6, and 7 show how housings 20 and 21 can be connected in a specific case of devices related to certain representatives of said first sub-family which are supplied with a relatively thick syringe-like reservoir 1.

Figure 5:
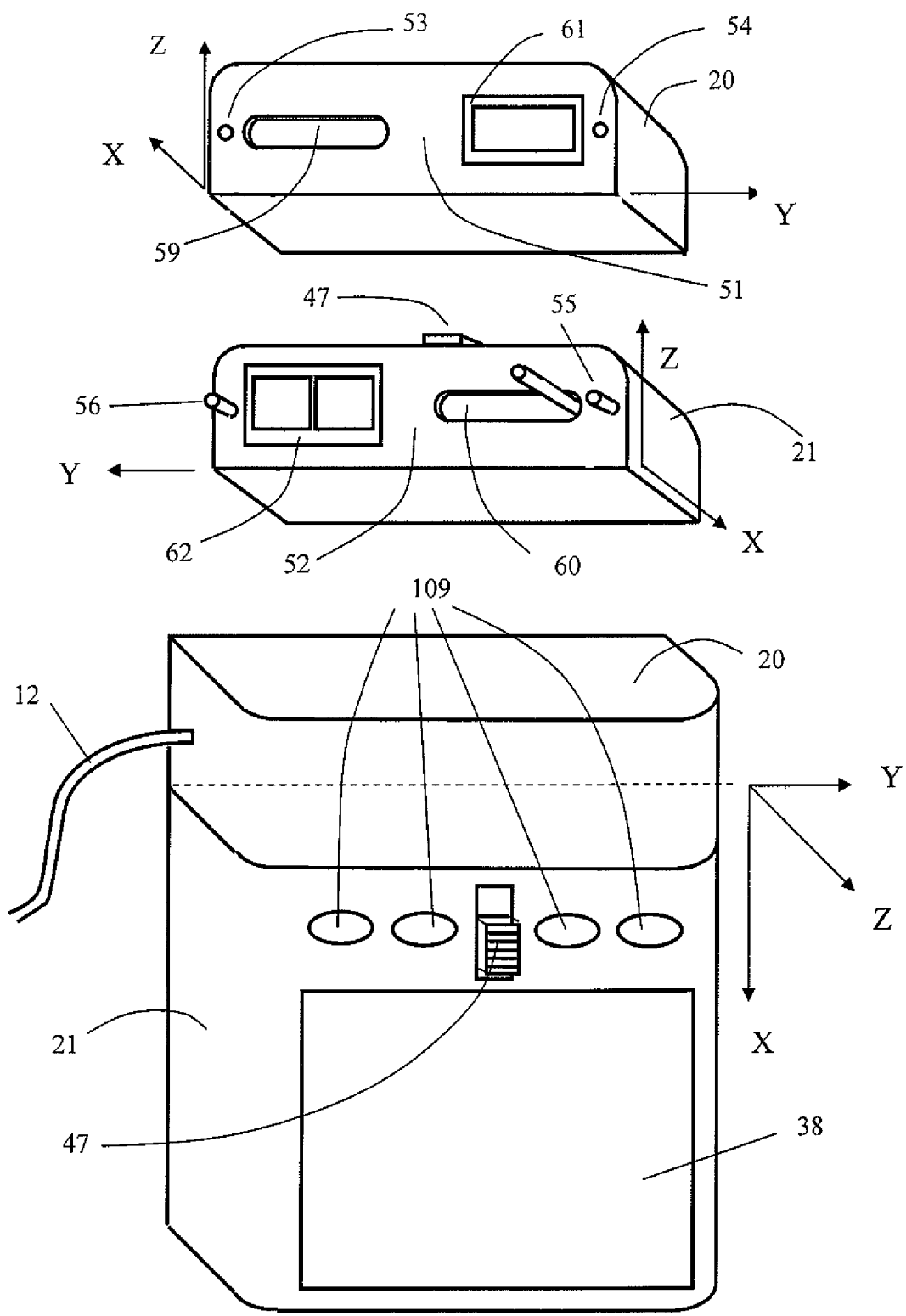
FIG. 5 depicts both separate and assembled general views of the actuating module and the replaceable cartridge having syringe-like reservoir as an example of the first sub-family of embodiments in which devices of the invention are destined to be suspended on patient's belt.
Figure 6:
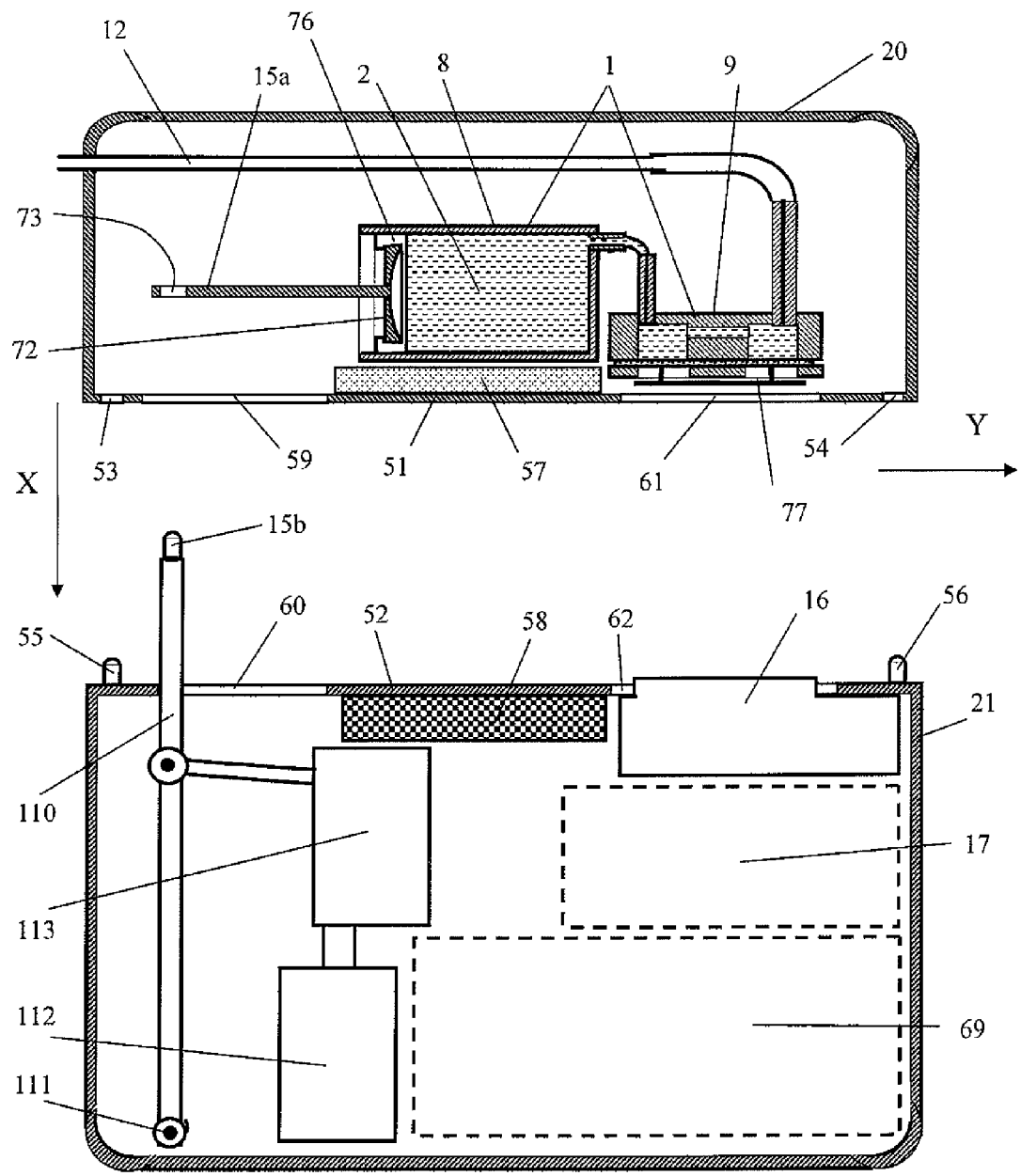
FIG. 6 depicts separate cross-sections of the cartridge (top view) and the actuating module (bottom view) of the invention shown in FIG. 5 in order to demonstrate details of means destined to provide their temporary connection and further disconnection.

In order to provide easiest connection it may be more convenient for users if both the housing 20 and the housing 21 have flat side walls numbered 51 and 52 correspondingly which coincide with the plane YZ when both housings are connected (bottom view in FIG. 5). In first sub-family of embodiments it can be desirable that connecting means located on the wall 51 are two holes 53 and 54, whereas the wall 52 is supplied with two pins 55 and 56 (see FIG. 6 and upper views of FIG. 5). Right installation of such cartridge requires only bringing both flat walls 51 and 52 into contact so that the pin 55 penetrates into the hole 53, and the pin 56—into the hole 54 (see FIGS. 6 and 7). Any accidental mistake of the connection can be avoided if a diameter of coupled pin 55 and hole 53 differs from a diameter of another couple 56 and 54. There are many different ways known to anyone skilled in the art which allow such separable connection to be fixed reliably. For the aim of a simple example only the devices of the invention can be supplied with a magnetic lock which comprises two ferromagnetic elements 57 and 58 located in housings 20 and 21 correspondingly as shown in FIG. 6. At least one of these two elements comprises a strong permanent magnet so that magnetic attraction of said elements provides high locking force when said connection of walls 51 and 52 makes a distance between elements 57 and 58 low enough (see FIG. 7). A simple magnetic lock shown in FIG. 7 can be used only if both walls 51 and 52 are made of materials transparent for magnetic field, for example, plastic materials. Using traditional engineering methods one can always choose such modestly high locking magnetic force which provides, on the one hand, reliable fixation of both housings, and, on the other hand, easy disconnection when necessary.

For further description it may be relevant to mention here that certain embodiments of present invention should desirably have open windows 59 and 60 located on walls 51 and 52 correspondingly in order to provide the device with proper either mechanical or non-mechanical interaction 15 between complementary elements 15a and 15b. For example, FIG. 6 demonstrates that the driving force system 14 located in separate housing 21 comprises an output element 15b connected to nothing. However, after both housings 20 and 21 are connected (see FIG. 7) the same element 15b becomes actually a mediatory element capable of direct transferring a driving force created by the actuating module to a driving shaft 15a connected to a movable piston 72 of syringe 8, said syringe is a part of the reservoir 1 located in the replaceable cartridge. Thus, in this example the driving shaft 15a serves as a force receiving element mechanically involved in a transformation of said external driving force into the force applied to the liquid in the reservoir. Other examples of how mediatory element 15a and receiving element 15b can be designed will be discussed later in more details, including an example of non mechanical remote interaction of elements 15a and 15b. It should be also mentioned that windows 59 and 60, as well as additional windows 61 and 62 which may be present in certain embodiments, should be better considered as optional elements due to a necessity of windows depends on particular design of elements 15a and 15b as well as on specific type of sensors, whereas devices supplied with other sensors and elements 15a and 15b may not need windows at all.

Figure 8:
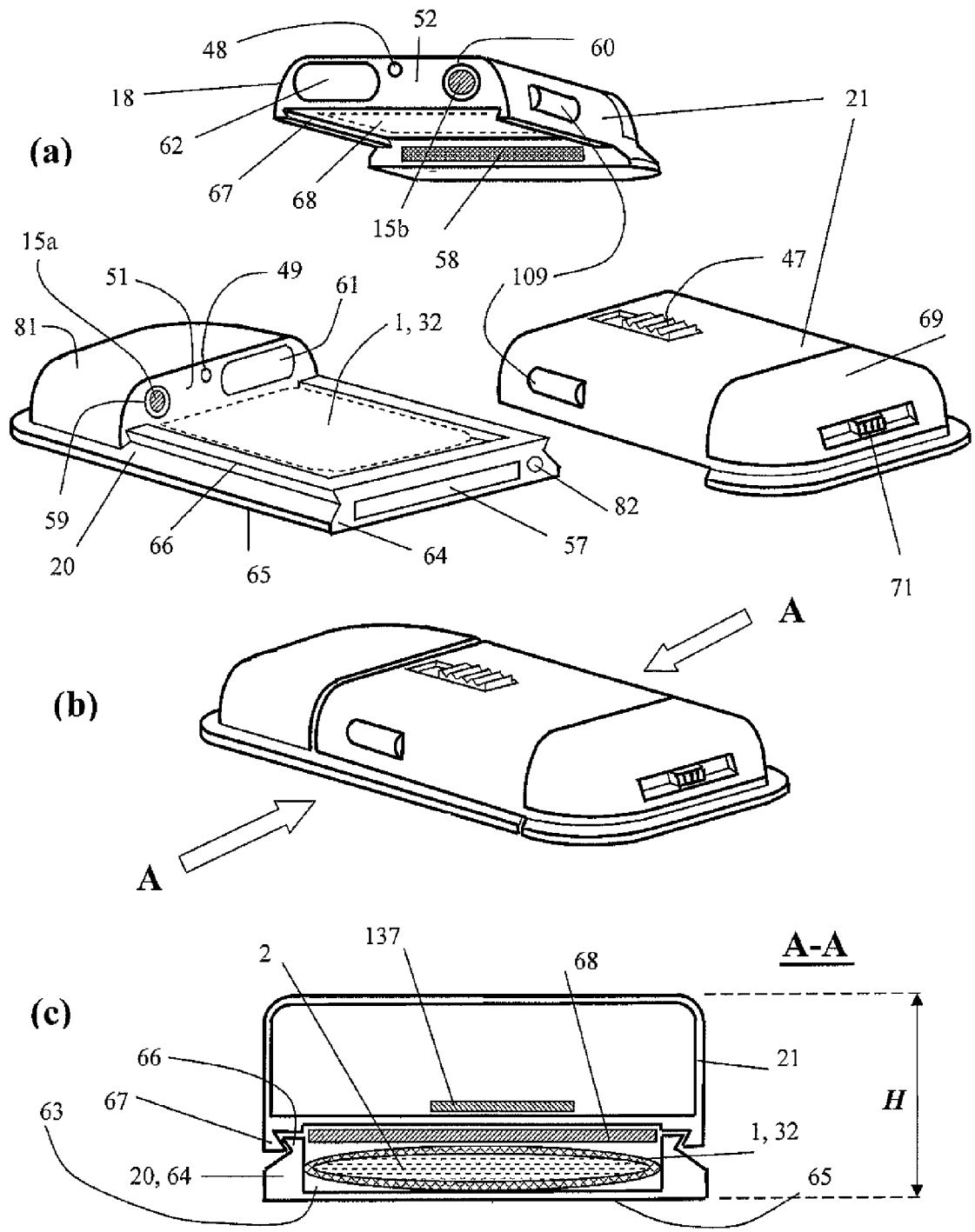
FIG. 8 depicts both separate (a) and assembled (b) general views of the actuating module and the replaceable cartridge having flat bag-like elastic reservoir as an example of the embodiment in which the device of the invention is destined to be deployed directly on patient's skin. Bottom view (c) depicts cross-section A-A of fully assembled device wherein parts located inside the actuating module are intentionally not shown (except flat lever 137).

A different example of connecting means relates preferably to the most desirable second sub-family of embodiments of the invention shown in FIG. 8 and destined to be deployed directly on patient's skin. Corresponding separate views of the replaceable cartridge 20 and the actuating module 21, as well as fully assembled device, are shown in upper and middle sections of FIG. 8. There are two major reasons why devices of the second sub-family can be made so thin that they can be hidden and practically invisible under patient's clothes. The first reason is that these devices do not use relatively thick traditional syringe-like fluid supply reservoir 1 considered in previous paragraph. Instead, the main volume of the fluid stored in reservoirs 1 of this sub-family can be kept in a flat bag 32 made of soft plastic material similar to, for example, a silicon rubber or alike. Correspondingly, this bag, depicted by dashed line in FIG. 8a, is desirably located in a wide and shallow cavity 63 made in elongated flat plate 64 of the housing 20 shown in both general view FIG. 8a and cross-section FIG. 8c. Said elongation provides high area of bottom surface 65 of the housing 20 which can be covered with thin adhesive layer destined to hold whole device firmly on a patient's skin. As a quantitative example only, one can note that, in order to keep 3 $cm^3$ of the insulin solution required to supply diabetic patient for 3-5 days, initial thickness of liquid layer in the flat bag 32 doesn't exceed about 1 mm even when the bottom area of the replaceable cartridge 20 has as low dimensions as about 55×60 mm. The second reason is that, due to discussed later specific features of a driving force system 14 of preferred embodiments, the housing 21 of the actuating module can also be made very thin so that fully assembled device shown in FIG. 8b and FIG. 8c has, for example, as low thickness H as about 7 mm. Replaceable cartridge and the actuating module depicted on FIG. 8 can be desirably fast and easy connected with the help of specific relief made on both housings, said relief forming complementary rails 66 and 67. In order to install new cartridge a patient has only to move an actuating module along these rails until flat walls 51 and 52 contact each other. At that moment magnetic elements 57 and 58 also take close position providing locking magnetic force discussed above. It should be clear for everyone skilled in the art that after said connection all optional windows 48, 49, 59, 60, 61, and 62 (if they are present) are automatically brought in right relative positions. In order to complete this section it may be noted that desirably the housing 21 of the actuating module of preferred embodiments can be supplied with thin movable plate 68 capable of very gentle compressing the flexible bag 32 (for example, with a pressure below 0.1% of external atmospheric pressure) in order to eliminate a free volume appearing in flexible bag 32 in long-term process of liquid drug consumption. For user's convenience and improved safety the housing 21 shown in FIG. 8 is desirably equipped with a removable lid of a battery compartment 69, and both certain means 71 and at least one button 109 used for manual operation as discussed later.

A. Hydraulic System

A hydraulic system of all devices of the invention relates desirably only to the replaceable cartridge 20 as shown in FIG. 3 schematically. The reservoir 1 of this system is destined to be filled with the fluid 2 and has at least one opening 3 which is an output opening of said reservoir considered separately and, at the same time, an intermediate opening when whole hydraulic system is considered. In accordance with the definition No. 4 the entire cavity of the reservoir 1 is limited by all its walls and an imaginary plane located in the narrow cross-section of the intermediate opening 3 shown in FIG. 3 by dashed arrow 6. Reservoir 1 of embodiments of the present invention possesses several features discussed below. In order to simplify present description the general schematic view of FIG. 3 omits less important details, which can be made differently in different embodiments. However, one can find more technical details in FIGS. 7, 8, 9, 10, 11, 12, and 13 related to different examples of the reservoir 1 which will be considered later at appropriate places of present description.

Important feature of the reservoir 1 is that its entire cavity comprises at least two spatially separated sections 8 and 9, said sections hydraulically communicating so that hydraulic resistance between them is not less than non-zero $R_1$. It may be clear for anyone ordinary skilled in the art that said resistance $R_1$ can be provided by different hydraulic elements 5 such, for example, as either a capillary, or at least one (or more) diaphragm(s), or just narrow neck similar to the one depicted in FIG. 2, and so on, because the performance of the invention does not depend on particular construction of the element 5 located between imaginary planes 7 and 7a shown in FIG. 3 by dashed arrows. In certain embodiments the resistor 5 can be present in indirect or hidden form. For example, in the case of thin diaphragm the distance between virtual surfaces 7 and 7a may be so low that both surfaces practically coincide. However, any appropriate shapes of the resistor 5 can be used if they provide desirable non-zero value $R_1$ of the resistance.

For clarity of present description the section 8 of the reservoir 1 was previously named "a compression section", whereas the section 9 was named "an indicator". Critically important feature of a design of the indicator 9 is that it comprises at least one expandable element 10 made of resilient material so that it is capable of working cooperatively with the sensor system 16 as will be further discussed in more details.

The intermediate opening 3 connects the indicator 9 with the flow passage 12 connecting the reservoir 1 hydraulically with at least one exit opening 13. Said flow passage 12 may be further called also "the connector 12" for brevity. An important feature of the connector 12, filled with the fluid 2, is that it comprises at least one static hydraulic resistor 19 having predetermined non-zero resistance $R_2$ which limits the intensity of the fluid flow through the exit opening 13. Connector 12 may also comprise other hydraulic elements contributing additional resistances. However, in any case, the presence of the resistor 19 makes full hydraulic resistance of means 12 not less than $R_2$.

Some devices may have a relatively long flow passage 12 made, for example, of flexible plastic pipe (FIG. 4a and FIGS.

5, 6, and 7). In contrast to that other devices may have as short flow passage 12 as possible (for example see FIG. 4b and FIG. 8). If the device is destined for a drug delivery, it may be desirable that the end of the flow passage is supplied with a sharp needle 40 intended to be connected with patient's body. In this case the exit opening 13 is located on the tip of the needle. It can be appreciated that instead of the single exit opening 13, multiple exit openings of the flow passage 12 may be quite desirable in certain embodiments in order to provide more convenient consumption of the fluid dose delivered to a customer. A similar multi-needle exit port having many exit openings has been mentioned by Flaherty and Christopher in U.S. Pat. No. 6,740,059 incorporated herein fully by reference. However, independent of how many exit openings are present in each particular embodiment, anyone ordinary skilled in the art should appreciate that the performance of present invention does not depend on the number of said exit openings so long as at least one exit opening is subjected to the same external pressure mentioned above.

Devices of the invention are intended to work in the external environment, and due to fact that exit opening 13 is a final point where the desirable dose of the fluid is to be delivered to, during the work of whole device the cross-section of this exit opening 13 is always subjected to external pressure $P_{ext}$. Most typically this external pressure $P_{ext}$ is equal atmospheric pressure $P_{atm}$ which can change in time unpredictably and should be considered as an external parameter.

There is an important feature which relates to both the methods and the devices of the invention and makes the reservoir 1 quite different from the constantly pressurized reservoirs of devices disclosed in the prior art. The point is that before any delivery cycle the fluid in the reservoir 1 of the invention is mostly kept at low pressure, desirably as close to external pressure $P_{ext}$ as possible, and most desirably is equal to $P_{ext}$. Taking into account that the exit opening 13 is also subjected to the same pressure $P_{ext}$ at any time, before any delivery cycle the intensity of the fluid flow is as close to the zero as it may be desirable, because the external force applied to the fluid in reservoir 1 is kept about zero and the fluid is not forced to flow outside. This initial state corresponds to top images of both FIG. 1 and FIG. 2. In accordance with the general method of the invention, the beginning of the fluid delivery cycle is initiated by an application of external non-zero compressing force to a certain surface area of the fluid in the reservoir 1, and more specifically by an application of a continuous compressing force to a surface area of the fluid in the compression section 8 of the reservoir 1. Direct interaction of this force with said fluid's surface area leads to an appearance of an excessive pressure of the fluid in certain sections of the reservoir 1. This excessive pressure exceeds $P_{ext}$ and results in continuous squeezing the fluid out of the reservoir 1. External compressing force continues up to a certain moment $t_{end}$ when preprogrammed processor produces an ending signal which leads to the termination of said external force and, correspondingly, results in stopping of outgoing fluid flow.

Accordingly to what was previously said, it can be desirable to provide such design of the reservoir 1 that at least a limited surface area of the fluid contained in the section 8 of reservoir 1 can directly interact with some technical means which are capable of changing said external force over the time. The means may be designed rather differently as discussed later, both specific designs of said means and specific designs of each particular reservoir 1 must correspond to each other. However, independently on this specificity the common feature of any reservoir 1 of the invention is that both sections 8 and 9 comply with the definition No. 4 of "a reservoir" if these sections are considered separately. Each section is capable of fulfilling its own functional role described previously in general and discussed below in more details. Another common feature is that hydraulic communication 5 of both said sections is always opened and, in accordance with the definition No. 5, both sections are just parts of the same reservoir 1. Accordingly to the definition No. 6 whole element 5, preferably represented by static hydraulic resistor, is also a part of the reservoir 1. In many cases the resistor $R_1$ is typically represented by specific detail, for example, a capillary (see FIGS. 7, 9a, and 12) providing substantially non-zero ratio $R_1/R_2$. In many embodiments it is desirable that said ratio of resistances $R_1/R_2$ exceeds about 0.05 and is less than about 200, more desirably said ratio is in between about 0.25 and about 40, and most desirably said ratio is in between about 1 and about 10. The explanation of the reason why these quantitative limitations are desirable will be provided later.

Previously mentioned spatial separation of two local volumes of the fluid located in two sections 8 and 9 can be very desirable in certain embodiments, and preferably in more advanced embodiments, due to in this case each section can play its own functional role. It is shown in FIG. 3 that the presence of connecting element 5 causes these sections to be actually separated. In many embodiments this separation occurs very naturally as one can see in FIGS. 7, 9a, and 12. However, in certain simple embodiments discussed later the ratio $R_1/R_2$ is allowed to be less than about 0.05. In this case low resistance of the hydraulic communication 5 does not require any such part which can be definitely identified as a resistor, because low non-zero resistance $R_1$ can be provided by any hydraulic detail, even including but not limited to walls of the reservoir 1 containing the fluid having non-zero viscosity. If this is a case the teaching of present invention tells that sections 8 and 9 are to be considered as spatially separated in any case if certain local surface area of the fluid in reservoir 1, involved in direct interaction with applied external force mentioned above, is spatially separated from another local surface area of the fluid involved in direct interaction with said expandable element 10.

Figure 9:
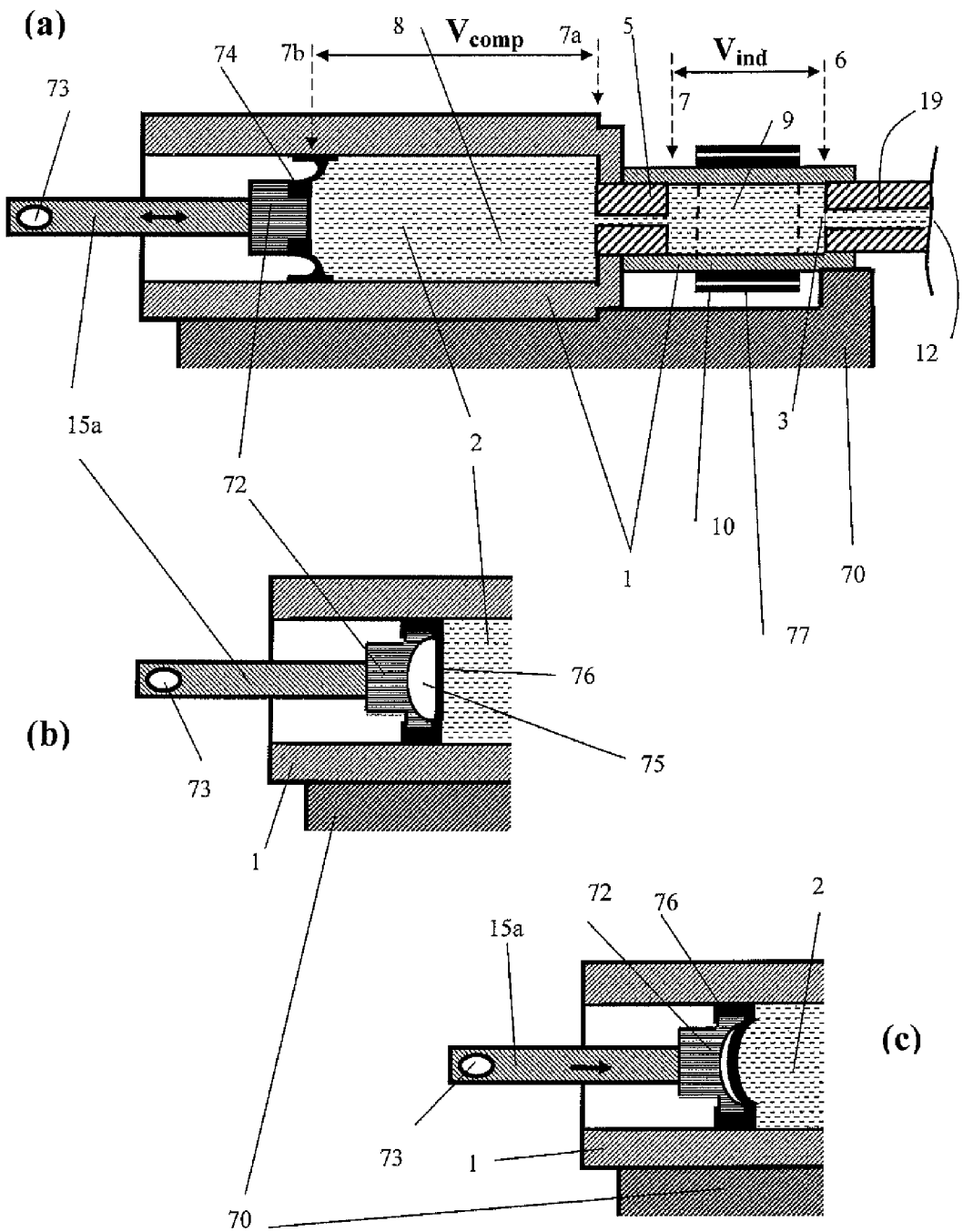
FIG. 9 depicts details of the replaceable cartridge comprising a reservoir made in the form of a syringe having both compression section and expandable indicator section separated by capillary-like static hydraulic resistor (top view). Views (b) and (c) depict the same syringe wherein the modified piston is supplied with a resilient diaphragm.

It can be desirable that reservoirs 1 of the invention have different forms and be made of different materials. The FIG. 9 shows practical examples of reservoir 1 made of a hard material in the form of a syringe firmly connected with the plate 70 situated within a housing 20 of the replaceable cartridge which isn't shown yet in FIG. 9. The section 8 made of hard material contains a piston 72 capable of moving forth and back accordingly to the direction of an external force applied by the driving force system 14 via a driving shaft 15a having the movable piston on one end and the hole 73 on the opposite end, said hole complementary to force transferring mediatory element 15b (see also general FIG. 3 and FIGS. 6 and 7 where cross-sections of both separated modules and fully assembled device are shown). Accordingly to the teaching of present invention it may be also desirable that modestly elastic sealing ring 74 shown schematically in top view of FIG. 9 is a part of the piston 72 to avoid any leak of the fluid. Full area of the piston 72 including the area of the ring 74 limits such surface area of the fluid's body which can directly interact with said external force produced by the system 14. However, the use of relatively narrow sealing ring 74 (FIG. 9a) can result in increased technical requirements applicable to a precision of the system 14, especially in certain embodiments where fast application of the external force is desirable. Because both increased output resistance, which cannot be less than $R_2$, and limited elasticity of narrow ring 74 even small accidental fluctuation of piston's position can cause unpredictable sharp change of the fluid pressure inside the section 8. That is why it is more desirable that hard body of movable piston 72, involved in transformation of the driving force into a force applied to the fluid, is supplied with a cavity 75 having, for example, spherical form. In contrast to narrow ring 74, either main part or full area of movable hard piston 72 is hermetically separated from internal volume of the reservoir by a resilient element 76, for example, disk-like diaphragm made of appropriate polymer material having high elasticity in order to prevent immediate change of fluid's volume in the section 8 (see FIGS. 6, 7 and 9b). The point is that said elastic diaphragm 76 is capable of expanding into the cavity 75 when the fluid in the reservoir is subjected to a pressure exceeding the external pressure. If such design is used the elastic expansion of the diaphragm 76 eliminates selective correspondence between position of the piston 72 and the volume of the fluid remaining in the reservoir. This means that elastic expansion of the diaphragm 76 eliminates direct correspondence between displacement of said movable piston and a dose of the fluid delivered to exit opening. Moreover, in this case the pressure in the section 8 can depend very smoothly on piston's position because even substantial jump-like shift of the piston, for example in right direction, is compensated immediately by elastic deformation of the diaphragm 76 resulting only in moderate pressure change (see FIG. 9c). Another advantage of this design is that substantial decompressing force can be temporarily applied to the fluid when the system 14 shifts the piston 72 in opposite direction. This feature discussed later is useful in certain embodiments for self-calibration of drug delivery devices.

The indicator section 9 of the syringe-like reservoir 1 described in previous paragraph, is (i) spatially separated from the section 8 by the resistor 5, and (ii) comprises, at least one expandable element 10. In particular example shown in FIG. 9a the element 10 is a short piece of a tube made of resilient material, for example, a silicon rubber or alike. An optional element 77 shown in FIG. 9a and FIG. 10 near the expandable tube 10 will be later discussed in the part of the description related to sensors. In certain embodiments this element can be desirably a thin layer covering the surface of the elastic element 10 and capable of either reflecting light, or conducting electric current, or possessing useful magnetic properties, etc. In certain other embodiments the element 77 can be mechanically connected with the elastic element 10 or just located in its vicinity with no direct contact. FIG. 9a shows clearly that inside the section 9 the limited surface area of the fluid brought into a contact with expandable tube 10 is always spatially separated from already mentioned limited surface area of the fluid which undergoes direct interaction with external force transferred from the system 14 and received by driving camshaft 15a capable of moving the piston 72 in the section 8. In this example the spatial separation of two said surface areas of the fluid located in the reservoir 1 is always preserved independently on current position of the piston 72. It should be also appreciated that the presence of at least one resiliently expandable element 10 in the section 9 of the reservoir 1 provides the local internal volume $V_{ind}$ of this section 9 with a feature of expandability too.

An disadvantage of all syringe-like reservoirs storing full amount of the fluid is that the devices based on this approach cannot be made as thin as it may be convenient for certain users including but not limited to little children. For example, internal diameter of the syringe has to be at least 12 mm if its relatively short casing (length about 2.5-3 cm) is destined to store about 3 cm³ of an insulin solution. Correspondingly, the thickness of whole device cannot be made less than 18-20 mm if one takes into account the thickness of syringe's walls, size of holding parts, and a thickness of surrounding material forming the housing 20 of the replaceable cartridge. Said above explains why syringe-based devices of the invention (FIGS. 5, 6, and 7) relate preferably to the first sub-family of devices destined to be suspended on patient's belt rather than be deployed on his or her skin.

Figure 15:
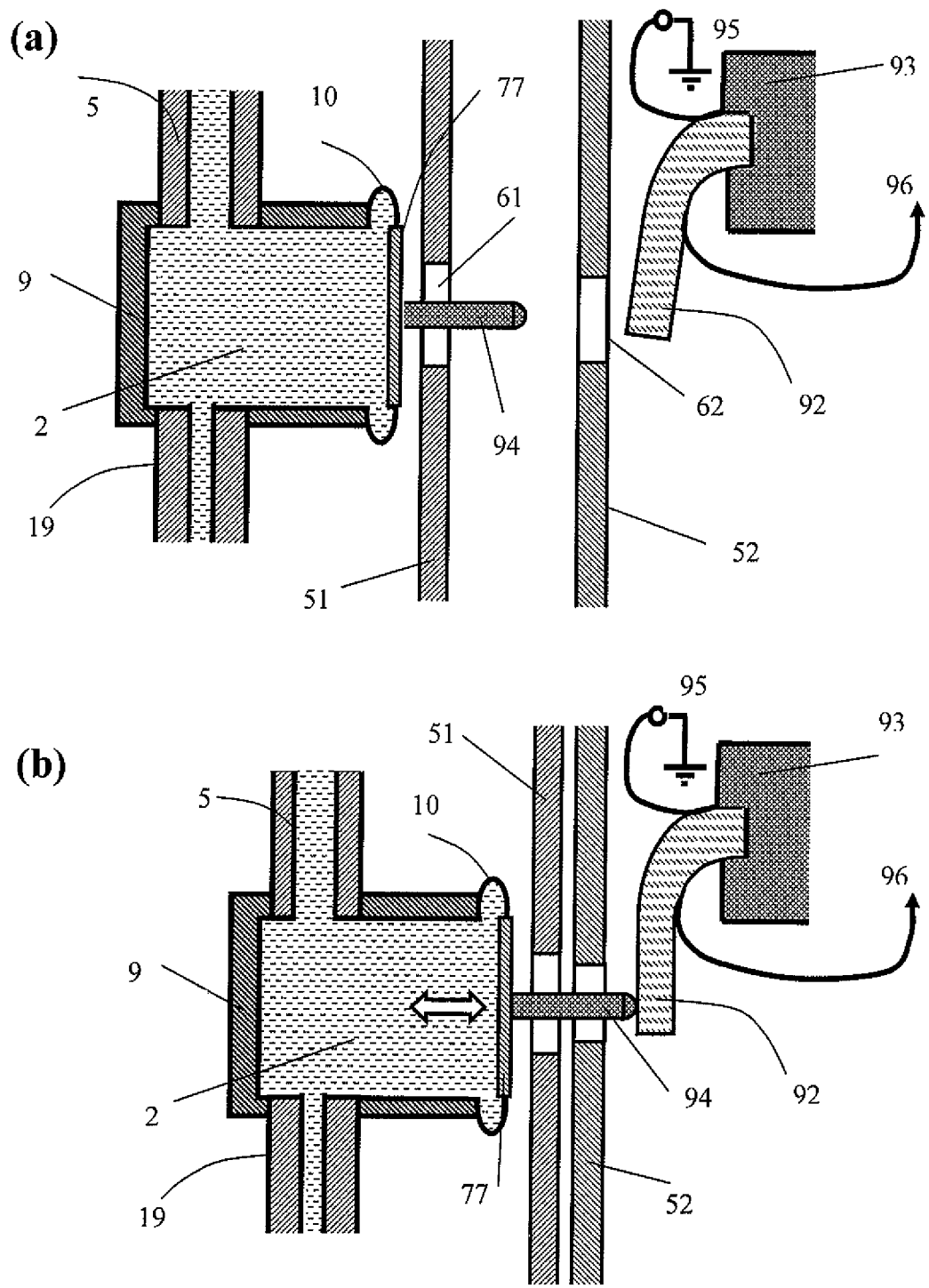
FIG. 15 depicts the example of an embodiment of the invention having a piezoelectric sensor combined with the made of resilient metal expandable element of indicator section of the reservoir located in the replaceable cartridge. Top and bottom views relate to disconnected and connected state of the cartridge correspondingly.
Figure 16:
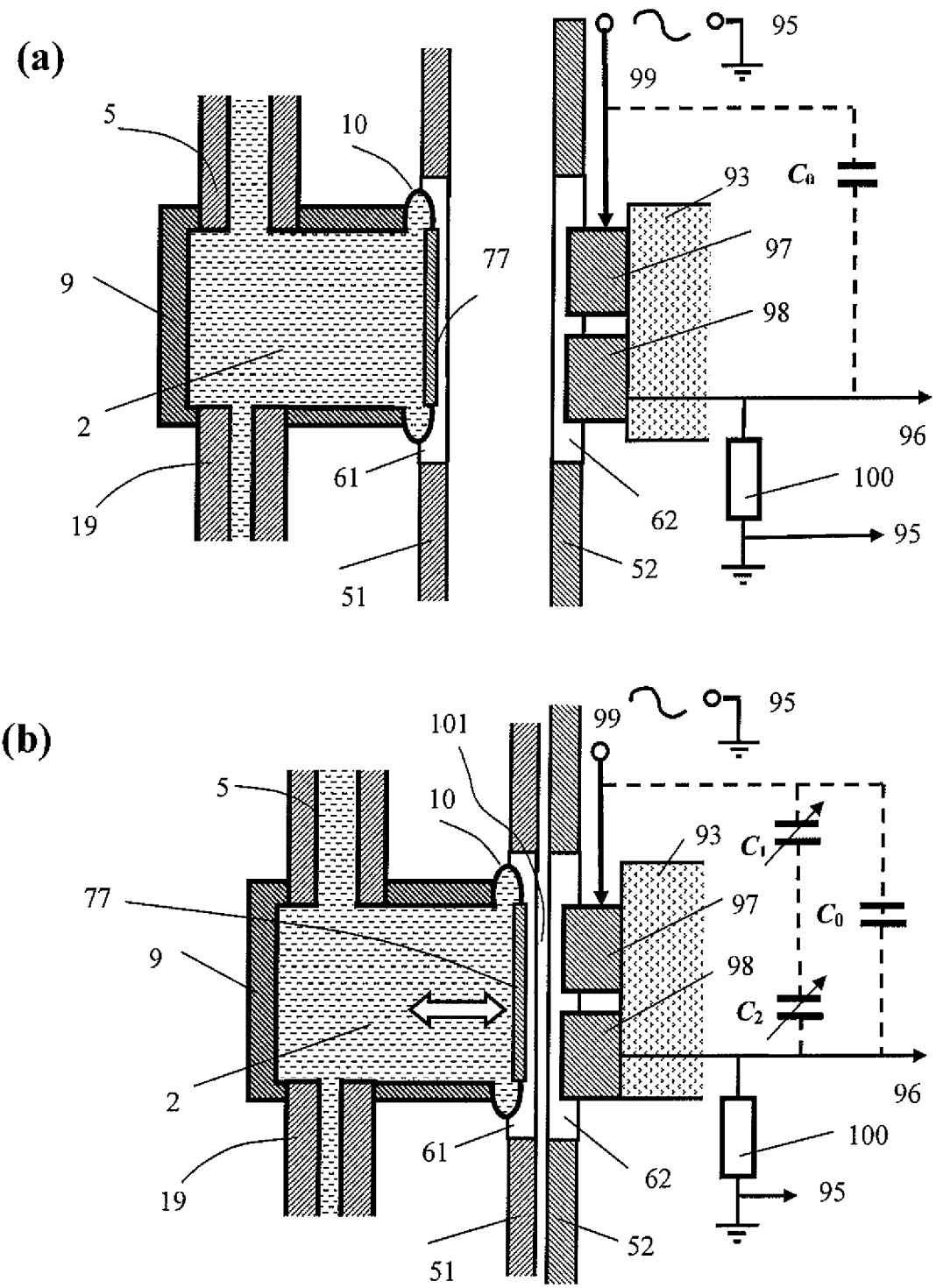
FIG. 16 depicts an embodiment of the invention having a non-contact capacitor sensor combined with the made of resilient metal expandable element of indicator section of the reservoir located in the replaceable cartridge. Top and bottom views relate to disconnected and connected state of the cartridge correspondingly.

However, it should be appreciated by anyone skilled in the art that the spectrum of different designs and different materials of the reservoir 1 located in the replaceable cartridge of the invention is much wider than just traditional syringe-like example shown in FIG. 9. The only inevitable point is that the design of parts of the section 8, including the element 15a receiving the external force, should correlate with the particular design of mediatory element 15b of the driving force system 14, whereas the design of the indicator 9 should correlate with the particular choice and design of the sensor system 16 discussed later. The teaching of the invention tells that one more general point of said correlation is that, independently on specificity of each particular design of the reservoir 1, the section 9 must be expandable because it is always supplied with at least one expandable element 10 made of any appropriate resilient material. The example of the expandable section 9, made entirely of a metal and including a resilient sylphon bellows 10 either welded or soldered with non-deformable metallic walls of the section 9, is shown in FIGS. 15 and 16. Other examples shown in FIGS. 17 and 18 demonstrate that main part of similar sections 9 can be made at least partially of either metal, or glass, or ceramics, or hard plastic materials wherein its expandable part 10 is made at least partially of resilient polymer materials whether transparent in some cases or not in other cases.

Accordingly to what has been said above the invention provides another practical example of the reservoir 1 (FIGS. 12 and 13) related preferably to the second sub-family of devices which are free of intrinsic limitations of syringe-like approach in regard of either thickness or other dimensions of whole device. This particular embodiment is based on the fact that volume $D_0$, which has to be delivered during one cycle, is always much smaller than the volume of the fluid stored in non-used replaceable cartridge. That means that there is no practical necessity to keep whole volume of the fluid in compression section 8. FIG. 12 shows how this idea can be practically realized. In this embodiment the main body of compression section is represented by a casing 8a having low internal volume $V_{comp}$ which desirably exceeds maximum one time dose $D_0$ slightly, for example only few times. For quantitative example only, $V_{comp}$, may be chosen about 50 mm³ by the order of magnitude if one cycle maximum dose $D_0$ of insulin solution is expected to be about 10 mm³. One of few walls of the casing 8a made preferably of any appropriate hard material has an opening having desirably low diameter and closed by the diaphragm 76 made of any appropriate either flexible or elastic polymer material, for example, silicon rubber or alike. It should be appreciated that other elastic materials, for example resilient metal foils, can be used as well if it is dictated by either technical or medical considerations. Lid 8b can be joined firmly with main body 8a so that hermetic connection of all parts of the compression section 8 is provided by the diaphragm 76 which is desirably connected with a piston 78 by any appropriate means, including but not limited to thin layer 79 of an appropriate glue. The lid 8b can be easily made so that the piston 78 is capable of moving forth and back with negligibly low friction. Thus, in this example movable piston 78 is fully separated from internal volume of the reservoir by either flexible or resilient element 76 wherein said movable piston is adapted to transmit said driving force to said fluid. It should be appreciated by anyone ordinary skilled in the art that, accordingly to both FIG. 12 and FIG. 13, any external force making the piston 78 to be shifted a little bit inside the section 8 causes a compressing force applied to the fluid in the compression section 8, said compressing force squeezing the fluid out of section 8 in the direction of indicator 9 through the static resistor 5. Thus, in present example the piston 78 can be considered as force receiving element which is involved into transformation of external driving force produced by the driving force system 14 into the force applied to the fluid. Hard material of said piston is optional one, however in certain embodiments it can be desirable that such force receiving element is at least partially made of ferromagnetic material, for example, an iron or alike. In other embodiments the piston 78 can comprise a permanent magnet for improved non-mechanical remote interaction with a mediatory element of the driving force system 14. If this last option is to be realized it may be useful also that spiral spring surrounding the piston 78 and pushing it slightly out of the lid 8b of compression section 8 is installed between limiting ring 80 and said part 8b (this optional spring is not shown in FIG. 12 and FIG. 13 for simplicity). If such spring is present the external driving force received by the piston 78 is combined with decompressing force of the spring thus transforming primary force received from the system 14 into the secondary force applied to the fluid. Specific design using both said spiral spring and the piston comprising permanent magnet is discussed in more details in the very end of present section.

In the beginning of delivery cycle the external driving force is always transformed into a compressing force which continues up to moment $t_{end}$ so that the fluid is gradually squeezed out of the section 8 and the piston 78 continues its slow sinking into the section 8. However, in order to avoid any accidental overdosing the volume of the liquid squeezed out while one cycle can be desirably limited by an optional limiting ring 80 which can stop squeezing out even in rare emergency case when compressing force is not properly terminated due to any reason. It has to be evident to anyone skilled in the art that an external force produced by properly working device can be further easily converted into a decompressing force applied to the fluid after moment $t_{end}$ when current cycle is over and the system 14 causes the piston 78 to be shifted back in order to return it into initial position before next cycle.

Taking into account said low volume $V_{comp}$ of the section 8, important feature of the embodiment described in previous two paragraphs is that its reservoir 1 comprises additional section 32 destined (i) to store the main volume of the fluid, and (ii) supply this fluid to compression section 8 periodically in order to refill it at appropriate time, preferably after the end of a previous cycle and before the beginning of next one. That is why the fluid supply section 32 is to be hydraulically connected with other sections of the reservoir, and preferably with the section 8, said connection performed by a static hydraulic resistor 33 having a predetermined resistance $R_0$ (see FIGS. 3, 12 and 13). In order to make devices of the invention as thin as possible it can be desirable that additional section 32 has the shape of flat bag made of flexible material, for example, silicon rubber or alike, which can be conveniently deployed in shallow cavity 63 made in elongated plate 64 of the replaceable cartridge shown in FIG. 8. Also it can be desirable to choose such shape of connecting resistor 33 which allows separate location of low volume section 8 in slightly elevated part 81 of thin replaceable cartridge (see FIG. 8). In certain embodiments it can be also desirable that the cartridge is supplied with an optional port 82 destined to be used only while pre-filling of the cartridge with the fluid.

Communication provided by hydraulic resistor 33 between additional section 32 and other sections of the reservoir 1 must not disturb normal fluid delivery occurring before said moment $t_{end}$. Such disturbance can appear in principle due to during delivery cycle said compressing force causes the pressure in the section 8 to exceed the pressure in the section 32, and, correspondingly, can cause back flow from the section 8 to the section 32. In order to fulfill the condition said above it can be desired that during delivery process, namely when said compressing force is applied to the fluid in the section 8, the resistance $R_0$ exceeds $R_1$, more preferably $R_0$ exceeds $R_1$ at least one order of magnitude, and most preferably $R_0$ exceeds $R_1$ more than two orders of magnitude. In this case the normal delivery process is practically not disturbed because said back flow from the section 8 to the section 32 is negligibly low in comparison with a main flow directed from the section 8 to section 9, said main flow controlled by the element 5 having non-zero resistance $R_1$. On the other hand, when the compressing force is over after $t_{end}$ and the system 14 provides said decompressing force, the pressure in the section 8 drops temporarily below the pressure in the flexible bag 32 which is always exposed at the pressure $P_{ext}$ typically coinciding with an atmospheric pressure. This circumstance makes the fluid contained in the bag 32 to flow slowly through the resistor 33 in the direction of the section 8. This refilling flow stops automatically when the section 8 is fully refilled with the fluid and the pressures in both sections become equal.

The refilling function can be rather satisfactory fulfilled by linear static resistor 33 having high $R_0$ in certain embodiments destined to have such working regime that waiting time between delivery cycles are much longer than a duration of each separate delivery cycle. In other embodiments it can be required that effective refilling takes place even if waiting time intervals are comparable by the order of magnitude with said duration of delivery cycle. That is why it can be desirable that hydraulic element 33 is a pressure-dependent non linear static hydraulic resistor capable of switching its resistance so that $R_0$ becomes at least close to $R_1$ by the order of magnitude, and more preferably $R_0$ does not exceed $R_1$ when said decompressing force is applied to the fluid in the compression section of the reservoir. However, it has to be stressed that accordingly to conditions of previous paragraph the communication between additional section 32 and other sections of the reservoir 1 is never closed completely, so all three said sections 8, 9, and 32 are just parts of the same reservoir 1.

Figure 13:
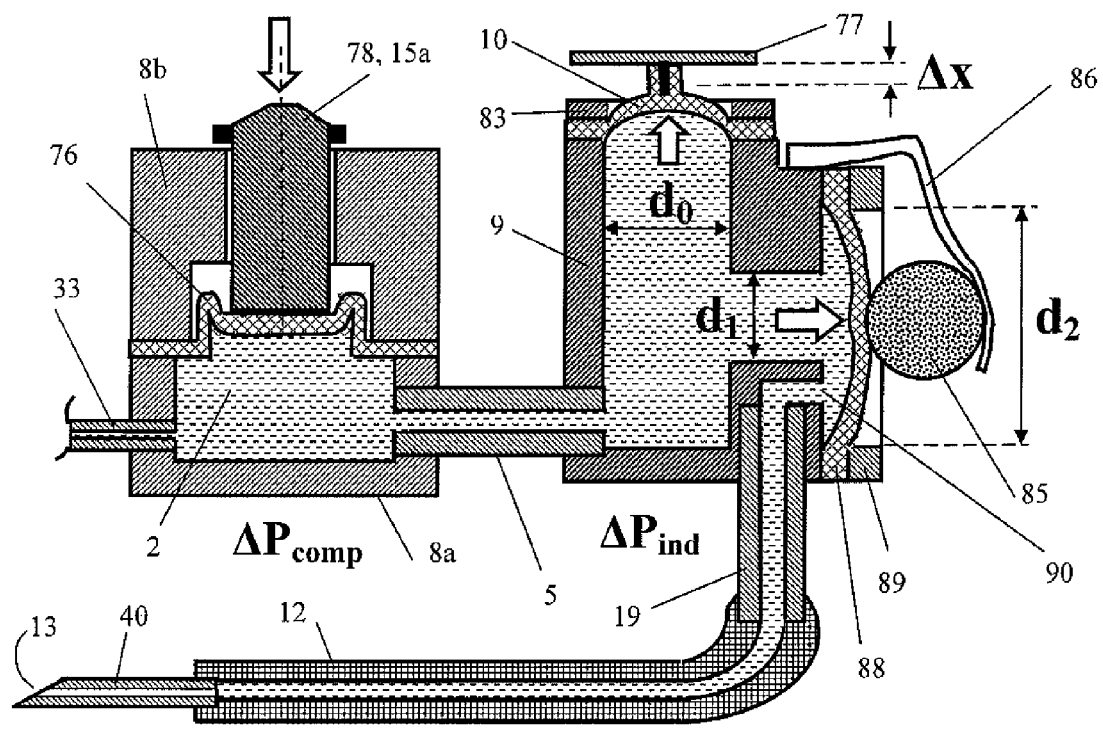
FIG. 13 depicts schematically the state of hydraulic system of the invention shown in FIG. 12 when a compressing force is applied to the fluid in the compression section.

Because devices of said second sub-family are destined to have as low dimensions as possible the size of the indicator 9 can be decreased substantially when contacting with the fluid area of expandable element 10 is represented by flat disk-like resilient film which closes an opening made on the wall of main body 9 made of any appropriate hard material, including but not limited to plastics, metals, ceramics, and so on, said opening having low diameter $d_0$ as depicted in FIG. 13. Hermetic connection of the elastic film 10 with the indicator 9 can be enforced by external ring 83 pressing round border of film 10 firmly to hard body 9 as shown in FIGS. 12 and 13. When excessive volume $\Delta V_{ind}$ of the fluid arrives into the indicator 9, resulting in appearance of excessive pressure $\Delta P_{ind}$, the resilient disk 10 expands and gets spherical form shown in FIG. 13. That change of the geometric shape causes certain shift $\Delta x$ of the element 77 made, in this particular example, in the form of light weight foil connected with the center of resilient element 10. Said shift can be recorded by the system 16 supplied, for example, by either a capacitor sensor if the foil is capable of conducting electric current, or magnetic sensor if the foil comprises magnetic material, or even optical sensor if the element 77 posses light reflecting properties.

These and other embodiments are more specifically considered in sensor section of present description. If necessary or desirable the indicator 9 can be supplied with two or more (see, for example, FIG. 21) disk-like resilient elements, similar to the one shown in FIG. 12, in order to eliminate mechanical instability of the element 77 in the case of vibrations and other mechanical shocks.

Persons of ordinary skill in the art should appreciate a quantitative, example which demonstrates how one can sharply decrease the thickness of devices of most desirable second sub-family and simultaneously avoid the necessity of high precision parts located in the replaceable cartridge. Because typical one time dose $D_0$ is expected to be as low as about 10 mm$^3$ by the order of magnitude it can be quite enough if the piston 78 serving low volume section 8 has low diameter about 3.5 mm with the area about 10 mm$^2$. A desirable dose of the fluid will be squeezed out if during one delivery cycle said compressing force received from the system 14 causes the piston 78 to be sunk into the section 8 approximately 1 mm, whereas in the case of traditional syringe having piston's diameter about 12 mm the shift producing the same dose should be about 80 micron. That is why mechanical precision of devices of the invention can be increased at least about 12 times. It will be shown later that due to invented special method of operation the precision of fluid delivery is so high that required mechanical precision of devices of the invention can be further increased even more than said 12 times. Another consequence of decreased diameter of piston 78 is that the transverse size of whole section 8 located in elevated part 81 of the replaceable cartridge (see FIG. 8) can be as low as about 5-5.5 mm only. Taking into account that (i) thickness of actuating module of the invention can be adjusted in accordance with sizes of the replaceable cartridge, and (ii) bag-like fluid supply section 32 can have low thickness about 1 mm previously mentioned, one can conclude that full thickness H of whole device can be made as low as about 7 mm. Thus, certain devices of the invention can be made 2.5-3 times thinner than any similar traditional portable drug delivery device related to prior art. Yet one more advantage of low diameter piston 78 estimated above is that the driving force system 14 is required to produce only very moderate force about 0.3N resulting in rather substantial excessive pressure $\Delta P_{comp}$ about 0.3 Bar in compression section 8. That allows very simple design of system 14.

Teaching of the present invention tells that characteristics of devices can be improved if the flow passage 12 connecting the reservoir 1 with the exit opening 13 further comprises certain optional element, which, in accordance with the definition No. 2, is considered as a pressure-dependent static hydraulic resistor capable of switching its resistance accordingly to pressure drop applied to this resistor. It may be desirable that this pressure-dependent resistor exhibits non linear dependence of the intensity of the fluid flow F upon the pressure drop $\Delta \pi$ as shown by curve (c) in FIG. 11. Technically this type of the dependence $F(\Delta \pi)$ can be realized by the passive valve 84 shown in FIG. 10 as an optional element of devices belonging to said first sub-family. Similar or modified passive valve 87 shown in FIGS. 12 and 13 can be used as an inevitable element of any most desirable embodiment related to the second sub-family. The difference between characteristics of passive non-linear valve 84 and other linear hydraulic elements, such as static resistors 5 and 19, is easily seen from FIG. 11 where strait line (a) serves as the example of typically desirable characteristics of the resistor 19, line (b) is the example of typically desirable characteristics of the resistor 5, wherein positive values F correspond to a stream directed to exit opening, and negative values—in opposite direction.

Dashed curve (c) in FIG. 11 shows that the valve 84 remains closed if the pressure drop $\Delta \pi$ applied to its ends is negative or less than calibrated value $P_{op}$. At a positive pressure drop equal or a little bit more than $P_{op}$ the valve 84 becomes open and provides rather low hydraulic resistance. Non-linear hydraulic characteristics (c) shown in FIG. 11 can be provided by variety of different passive valves, and particular details of present valve 84, namely the locking ball 85 and calibrated spring 86 (see FIG. 10), should be considered as an example only.

Improved hydraulic characteristics (FIG. 14) can be provided by another example 87 of passive valve shown in its closed state in FIG. 12 and in open state in FIG. 13. For clarity parts of the valve 87 in FIG. 12 are placed in dashed ellipsoid. It comprises the locking ball 85, calibrated flat spring 86, and elastic diaphragm 88 sealed on hard body of the section 9 by a fixing ring 89. Behavior of the valve 87 is different from that of valve 84. When initial pressure drop is less than $P_{op}$ (lower branch in FIG. 14) the diaphragm 88 shown in FIG. 12 closes intermediate opening 3 having diameter $d_1$ because the spring 86 provides predetermined locking force which is high enough to overcome fluid pressure in cross-section of the opening 3. In this state the valve 87 is fully closed and the fluid pressure in its output opening 90 is equal external $P_{ext}$. Said locking force becomes exactly compensated when excessive pressure $\Delta P_{ind}$ in indicator 9 reaches predetermined value $P_{op}$. At this moment the fluid begins to fill the cavity under the diaphragm 88 and elevates the diaphragm even more because said cavity has higher diameter $d_2 > d_1$ (see FIG. 13). This causes a momentary transition of the valve into low resistance open state characterized by upper branch in FIG. 14 where dashed arrow represents said transition. Open valve 87 provides connection of the reservoir 1 with exit opening 13. In contrast to the valve 84, due to condition $d_2 > d_1$ the valve 87 can get its closed state at certain other pressure limit $P_{cl}$ which typically obeys condition $P_{cl} < P_{op}$. Main advantage of the design 87 is that this valve provides both up and down switching transitions much faster than that of the valve 84. However, both diameters $d_2$ and $d_1$ can be chosen so that both pressures $P_{op}$ and $P_{cl}$ are practically equal. In this case valves 84 and 87 have practically the same characteristics (c) shown in FIG. 11.

If any optional valve 84 or 87 is used in embodiments of present invention they are destined to fulfill two different functions which are combined in the same design. First, this valve can prevent even low undesirable leakage of the fluid from the exit opening 13 in unlikely case if after the end of the fluid delivery cycle the reservoir 1 remains subjected to some low residual pressure which does not exceed $P_{op}$ of the valve 84 or $P_{cl}$ of the valve 87. The second function of these valves is to provide highly stable internal etalon of the switching pressure point $P_{op}$ based on high mechanical stability of calibrated spring 86. This internal etalon is used by discussed later most advanced mathematical algorithm of the invention in order to provide automatic self-calibration and self-control of all critically important systems of whole device. Both these functions can be fulfilled successfully if quantitative relationship of the predetermined value $R_2$ and the hydraulic resistance of said valves satisfies at least following requirements: (i) hydraulic resistance of pressure-dependent valve $R_{val}$ is less than $R_2$ at least by one order of magnitude when a pressure drop applied to said valve is equal or exceeds predetermined $P_{op}$, and (ii) the same valve is capable of switching into closed state when said pressure drop is below such $P_{cl}$ which is either equal or less than $P_{op}$ whereas hydraulic resistance $R_{val}$ of said closed valve exceeds $R_2$ by at least one order of magnitude, and most desirable it exceeds $R_2$ by more than two orders of magnitude.

Teaching of the present invention takes into account certain specific peculiarities which can happen unpredictably in the process of practical usage of drug delivery devices. It has been mentioned before that the flow passage 12 comprises hydraulic resistor 19 providing non-zero resistance $R_2$. At the same time it should be appreciated by anyone skilled in the art that due to different reasons the actual output hydraulic resistance $R_{exit}$ of the device may increase accidentally in the process of the work. In the case of drug delivery devices it may happen from time-to-time because of either partial or insurmountable occlusion of the exit opening 13 brought in direct contact with patient's body. The output resistance $R_{exit}$ may also increase if the fluid flow carries hard microscopic contaminations, which may be delayed in certain narrow places of the hydraulic system like capillaries, too precise valves, and so on. The value $R_{exit}$ can increase also in the case of accidental damage of fine parts of the flow passage 12 occurring, for example, because of shaking of the device or any other kind of inaccurate usage. However, the said above means that actual output hydraulic resistance must be expressed as:

$$R_{exit} = R_2 + R_3 \geq R_2 \quad \text{(Eq. 5)}$$

where additional resistance $R_3$ should be considered as an unpredictable external parameter that is either equal to zero (especially just after device manufacturing) or exceeds zero, for example after some aging of the device while its long-term work.

B. Sensor System

A purpose of the sensor system 16 shown in FIG. 3 schematically and located at least partially within the housing 21 of the actuating module is to transform certain appropriate geometric parameter associated with either entire local internal volume $V_{ind}(t)$ of the indicator section 9 of the reservoir 1 or time-dependent change $\Delta V_{ind}(t)$ of the same volume into corresponding output signals which are to be transferred to programmable processor 17 for further treatment (see arrow 24 in FIG. 3). That means that an output produced by any sensor system of the invention has to be designed so that the processor 17 is capable of acquiring said output. It has been already demonstrated that the volume expansion of the indicator section cannot be separated from the deformation of its expandable element 10 and, correspondingly, output signals of the sensor system 16 are always associated somehow with certain geometric parameter of said expandable element 10. Examples of many different sensors provided below show how said appropriate geometric parameter can be chosen and used in each particular case. However, independently on what particular physical principle is exploited by the sensor, there are few features which are common for all sensor systems of the invention. The first common feature is that every sensor system 16 comprises at least one input sensing element which is directly involved in producing analog input of the sensor system 16 (or, in other words, analog input signals of the system 16), said analog input signals are associated with at least one geometric parameter of the expandable element 10 of the indicator 9. The second common feature is that every sensor system 16 comprises a transducer 91 (shown schematically as internal rectangular in FIG. 3) which (i) transforms each said analog input into corresponding output or, in other words, output signal and (ii) transmits said output signal to the processor. Typically such transformation is performed by standard microelectronics which may include either amplifiers or/and differential amplifiers, high frequency generators, analog-to-digit converters, and/or many other standard electronic appliances which do not require special disclosure. The only requirement is that an electronic format of said output produced by the system 16 must correspond to input format of the processor 17.

It should be appreciated that independently on physical form of output signals both analog input signals and said output signals contain the same information related to the primary physical process $\Delta V_{ind}(t)$. The physical form of output signals can be chosen according to the kind of electronic processor 17 treating this information. In principle, certain simple algorithms of mathematical treatment of the information, for example integration of electric signals, can be realized by very traditional analog electronics. Correspondingly, in some embodiments the output signals of the system 16 may be analog ones if they are intended to be treated by corresponding analog processor 17. However, for better precision of whole delivery device it may be desirable that the sensor system 16 produces digital output signals reflecting either $V_{ind}(t)$ or $\Delta V_{ind}(t)$ so that any of these variables, represented by said output signals in digital form, can be treated by more contemporary digital processors. It can also be desirable and can be easily achieved with contemporary analog-to-digit transducers 91 whereby input analog signals of the system 16 are converted to digital output signals with the precision of at least about 0.1% of full range of analog input signals. It may be even more desirable that said analog-to-digit converting occurs with the precision about 0.01% by the order of magnitude.

However, the present invention doesn't depend on the physical form of said output. Also it doesn't depend on what electronic means are used to transform said analog input of the sensor and further deliver the information contained in the output signals to said processor. For example, in some cases it may be convenient to transmit output signals to the processor by wires only, especially if full operating system, comprising both the entire sensor system 16 and the processor 17 together with its controlling means 18, is assembled in the same housing 21 of actuating module. In other embodiments it can be more desirable if said operating system is partially deployed in separate housings 35 containing a remote control module which comprises means 36 for remote communication depicted by the arrow 31 in FIG. 3 and optional additional co-processor 37 also capable of treating signals of the system 16. In the last case it may be more appropriate if the entire sensor system 16 is subdivided in two or more parts. For example, first part 16(a) may comprise input sensing elements and a primary transducer 91(a) delivering its output signals to primary processor 17, whereas a second part 16(b) may comprise a secondary transducer 91(b) located in the housing 35 and connected with co-processor 37 so that each transducer is located in its own separate housing. The primary transducer 91(a) is capable of transforming said analog input signals to certain another signals which (i) are intermediate signals also associated somehow with said analog input signals, and (ii) have electronic format fully acceptable for primary processor 17. A secondary transducer is not required at all if said remote control is not incorporated into a design of whole device. However, simplified diagram in FIG. 3 assumes that, if remote control module is present, both the housing 21 and the housing 35 comprise certain means 36 capable of transmitting signals, including but not limited to said intermediate signals, and receiving said transmitted signals. It should be appreciated that even in this case wires can be sometimes used to transmit signals between housings 21 and 35. In other cases it may be more convenient for customers and/or manufacturer if such transmitting of signals is provided wirelessly by either radio waves or pulses of infrared light.

It may be appreciated by anyone skilled in the art that in certain cases the output signal of properly designed transducer depends linearly on its input signal reflecting changes of both $\Delta V_{ind}$ and $\Delta P_{ind}$. One can express such linear dependence with the use of certain constant factor $\beta$ which reflects the inverse sensitivity:

$$\beta S(t)=\Delta V_{ind}(t)=[V_{ind}(t)-V_0]=[P_{ind}(t)-P_{ext}]/\alpha=\Delta P_{ind}(t)/\alpha \qquad (Eq.\ 6)$$

where the equation (4) has been also used to express the relationship between S(t) and $\Delta P_{ind}$(t). It is desirable that simple linear equation (6) is equally applicable to all examples of the sensor system 16 provided hereinafter. Minor deviation from actual linearity, which may happen in some practical devices, can be further easily corrected by corresponding algorithm of the programmable processor.

Another feature of the invention is how said analog input can be produced. It should be appreciated by anyone skilled in the art that at least one sensing element of the input circuitry of the system 16 must physically interact with such at least one part of the indicator 9 which is capable of changing its at least one geometric parameter simultaneously with physical changes $\Delta V_{ind}$(t). In FIG. 3 double directed arrow 25 depicts such interaction schematically. There are many different physical types of interactions which may be successfully used within the scope of the invention. The examples of such interactions are: (i) mechanical or electro-mechanical interaction of certain parts of the indicator 9 with at least one sensing element providing the analog input signals of the sensor system 16, (ii) interactions involving electric or magnetic fields, (iii) interactions using light beams, and so on. In the present description an attention is focused on specific ways of the formation of analog input electric signals directly produced by sensing input elements of a corresponding sensor system 16. Due to the geometry of the elastic element 10 of the indicator 9 is chosen to be the primary parameter of the sensor (see the definition No. 7) it should be apparent that both the indicator section 9 of the reservoir 1 and said at least one sensing input element of the sensor system 16 are desirably fixed relative to each other so that only changes of the geometry of the element 10 are permitted to cause corresponding changes of the sensor's analog input signals.

Thus, taking into account multiple types of different physical interactions applicable to the sensor system 16, there is no possibility to make the only choice of specific sensor's name based on physical nature of any particular interaction. At the same time it should be further appreciated by anyone skilled in the art that, independently on particular type of said interaction used for the creation of primary analog signals, any such primary analog signal always changes in either direct or indirect association with the change of at least one geometric parameter of expandable resilient element 10 of the reservoir 1, and only this geometric change corresponds directly to time-dependent volume change $\Delta V_{ind}$(t). That is a reason why in accordance with the definition No. 7 an acceptable primary physical parameter of sensor systems of the present invention is a certain geometric parameter related either directly or indirectly to either the size or the shape of at least one expandable resilient element of the reservoir 1. Correspondingly, the full general name of all sensors of the invention should be the following: "Sensor capable of producing output associated with at least one geometric parameter of the expandable resilient element of the reservoir". Wide applicability of this definition to all sensors of the invention follows from examples below. Each of these examples (i) reveals at least one specific element located within the actuating module 21 and directly involved in producing analog input signals of each particular sensor system 16, and also (ii) reveals specific details of physical interaction, appearing after housings 20 and 21 are connected, between each particular sensor and particular element 10, located in the cartridge 20 and compatible with given sensor, in order to explain what type of resilient deformation or relocation of either external or internal surface of said element 10, being a part of the indicator section of the reservoir 1, participates in producing said input signals.

Right side of FIG. 15a depicts an example of a sensor wherein at least one such element of the sensor system 16, which can be directly involved in producing of the analog input signals when housing 20 of the replaceable cartridge is connected with the housing 21 of the actuating module, is a piezoelectric element 92 located in the housing 21 and fixed in said housing on a support 93 in certain proximity of flat wall 52 supplied with open window 62. In this particular example the expandable section 9 of the reservoir 1 is entirely made of metal and fixed in the housing 20 so that metal disk 77 is capable of relocating accordingly to resilient deformation of sylphon bellows 10 which is either soldered or welded. Left side of FIG. 15a shows that the disk 77 is located in certain proximity of flat wall 51 supplied with open window 61. Desirable variability of the indicator's internal volume is provided by short resilient sylphon bellows 10, connecting movable disk 77 hermetically with immovable hard walls of the indicator 9. The disk is supplied with a intermediate tip 94 elongated so that its free end looking through the window 61 takes a position a little bit outside of the wall 51 of housing 20. When both housings 20 and 21 are connected the tip 94 penetrates through the window 62 and provides slight mechanical compression of piezoelectric element 92, thus providing reliable permanent contact between sensing element 92 and external surface of the indicator 9 (see FIG. 15b). FIG. 15 shows that, due to the resilient nature of the sylphon bellows 10, in this particular case the disk 77 together with its extension 94 form the external surface of the indicator 9 capable of relocating in the process of indicator's expansion. Any positive or negative change of the fluid pressure inside the indicator makes the disk 77 to move (it is shown with double directed arrow). This movement results simultaneously in: (i) the change of the shape of elastic bellows 10, (ii) the change $\Delta V_A$(t) of internal volume of the indicator 9 caused by the change $\Delta P_{ind}$(t) of its internal pressure, and (iii) the deformation change of piezoelectric element 92. In response to all these changes the element 92 produces the change $\Delta U$(t) of input voltage which is further transferred by the grounding wire 95 and the signal wire 96 to the primary transducer 91(a) and then, if applicable, to the secondary transducer 91(b). Thus, in this example transducer's output signal S(t) is always associated with certain geometric parameter characterizing the expansion of the sylphon bellows 10 which represents the resilient part of the reservoir entirely made of the metal. In this particular example said geometric parameter associated with output signals S(t) can be either a width of the sylphon bellows, said width defined as linear distance between its opposite ends, or its curvature radius. Both said parameters are mutually correlated so that each of them equally represents the geometry of resilient element.

It can be appreciated that the example shown in FIG. 15 may be desirable for such fluid delivery devices where the expandable indicator 9 of the reservoir 1 and piezoelectric element 92 are fixed within their housings with high precision in order to prevent potential break of relatively fragile element 92 while contact of walls 51 and 52 is being established. The danger of said break can be reduced if devices using this type of sensors can be supplied with resilient suspension of either indicator 9 or piezoelectric element 92 or both.

A second example shown in FIG. 16 does not require so high precision of the fixing of the indicator 9 relatively the position of input sensing elements of the sensor system 16. This example represents non contact capacitor sensor system located in the housing 21. At the same time the metallic indicator 9 is practically the same as in FIG. 15, and its immovable part is fixed in the housing 20. When both housings are connected, non-contact capacitor sensor can be formed by both at least one electrically conducting area represented by metallic disk 77 attached to the section 9 of the reservoir and capable of relocating accordingly to deformation of its resilient element 10, and located in a proximity of the disk 77 at least one another electrically conducting area fixed within the actuating module 21. However, technically it may be more desirable that two electrically conducting metallic plates 97 and 98 are fixed on insulating support 93 of the same housing 21 so that the initial capacitance formed by only plates 97 and 98 is low $C_0$ when housings 20 and 21 are not connected yet (FIG. 16*a*). The wire 99 connects the plate 97 with the AC generator of the transducer 91(*a*) of this particular sensor system. It is desirable that said AC voltage applied to the plate 97 is stable enough in regard of both the frequency and its amplitude. At the same time the plate 98 is the only sensing element which is connected with the main input circuitry of the transducer by the wire 96 grounded by an input resistor 100. Simple equivalent electric diagram of the initial input circuitry before installation of the replaceable cartridge is shown with dashed lines in the top right corner of FIG. 16*a*. Accordingly to this diagram the AC voltage of the plate 98 is low due to the low capacitance $C_0$ existing between the plate 97 and the only sensing plate 98 when capable of relocating metallic disk 77 is far away and cannot make any contribution into this capacitance.

In order to obtain good sensitivity of such sensor system when the replaceable cartridge is already installed and both flat walls 51 and 52 can practically contact each other, the movable part of the indicator 9, namely the metallic disk 77, should be located in proximity to both plates 97 and 98 so that relatively narrow gap 101 is formed between conducting disk 77 and two conducting plates 97 and 98 as shown in FIG. 16*b*. Because the disk 77 is capable of relocating accordingly to the deformation of the sylphon bellows 10, the gap 101 is a variable depending, for example, on the width of the sylphon bellows 10. It should be appreciated by anyone skilled in the art that due to said gap is low and electrically conducting area of movable metallic disk 77 overlaps widely with electrically conducting areas of fixed plates 97 and 98, the variable gap 101 depending on the state of the internal volume of the indicator 9 controls two variable capacitances $C_1$ and $C_2$ shown in equivalent electric diagram in right corner of FIG. 16*b*. One has to take into account that, if the gap 101 is narrow enough, both variable capacitances $C_1$ and $C_2$ are relatively high in comparison with $C_0$. In this case variable capacitances $C_1$ and $C_2$ provide the main contribution in final variable capacitance between fixed plates 97 and 98. Consequently, the change $\Delta V_{ind}(t)$ associated with the change of width of the sylphon bellows 10 provides the change of the gap 101, resulting in corresponding change of final capacitance which leads to substantial amplitude change of AC analog input signal produced by the plate 98. The transducer 91 consisting of either one or two parts mentioned above measures this amplitude and produces corresponding digital output signals. This long chain of dependencies explains why and how the output signals of the sensor system 16 are associated with the variable geometric parameter of the sylphon bellows 10, namely with either its width or its curvature radius.

It can be appreciated that the absence of direct mechanical interactions in the non contact capacitor sensor depicted in FIG. 16 makes this type of sensors well compatible with replaceable cartridges. For example, if the AC frequency is about 1 MHz or more, and the area of the overlapping of the disk 77 with fixed plates 97 and 98 is about 1 cm$^2$ then analog input signals are well measurable even if the gap 101 varies in quite reasonable range between about 0.3 mm and 0.5 mm. Correspondingly, proper work of the sensor of this type is preserved even if housing 20 of the replaceable cartridge is installed and fixed with as low precision as about 0.1 mm. Variation of the gap's width during said installation can influence only the sensitivity but the system 16 as such keeps its ability of producing proper signals. It will be shown later that algorithms of most advanced devices of the invention are capable of self-calibrating the sensitivity so that no additional trouble occurs for unskillful users. In addition it is necessary to stress that shown in FIG. 16 electric diagram of capacitance measurement is provided as simplest example only. Those skilled in the art may know that other measurement schemes can be used as well, for example, a little bit more complex capacitance bridge provides much better precision and higher sensitivity.

It may be desirable in some embodiments that at least one element of the sensor system, which is directly involved in producing of analog input signals, comprises a magnetic detector fixed within the housing 21. Magnetic detector located in the housing 21 is capable of forming non contact magnetic sensor if said detector is fixed in proximity of any either a magnetic substance or a magnetized substance which is attached to any such part of the indicator section 9 of the reservoir 1 which is capable of the relocating accordingly to the deformation of its expandable element 10. For example, any of said substances can be attached to the surface of movable disk 77 considered before, or whole disk can be made of a metal providing desirable magnetic properties. In the case of tube-like shape of the indicator 9 (see FIG. 10) the layer 77 of magnetic powder can be introduced into resilient polymer forming the wall 10 of the indicator. In all these cases high precision measurements associated with at least one geometric parameter of the expandable element 10 can be done with magnetic sensor. Such types of non contact sensors are well known and there is no need to discuss its details here. At the same time it can be relevant to mention here that in order to protect critically important parts of the device in the case of improper usage done by unskillful users certain embodiments of the invention, exploiting non-contact either magnetic or capacitance sensor to produce said analog input signals, can avoid a necessity to make optional windows 61 and/or 62. Said avoiding becomes possible if in certain vicinity of location of said sensor both modules intended to be connected have solid but thin enough walls 51 and 52, said walls made of an appropriate material, preferably plastic material, which is transparent for magnetic field in the case of magnetic sensor, and/or for electric field in the case of capacitance sensor. Actual thickness of such walls having no windows depends only on whether the sensitivity of sensor system 16 is high enough or not. However, for better clarity of the description all further figures depicting devices of the invention contain images of optional windows 61 and 62 independently on whether they are actually required or not.

Further example demonstrates how another input circuit of the system 16 (see FIG. 17) exploiting non-contact capacitance sensor, similar to the one described in previous paragraphs, can be combined with the indicator 9 which has a low diameter opening made in hard main body and sealed by disk-like expandable element 10 made of resilient polymer material as described before and shown in FIG. 13. Practically all previously mentioned features related to location and fixation of both the indicator 9 and main elements of the sensor remain the same as before. In comparison with FIG. 16 the only significant difference related to design of the indicator is that in present example the elastic diaphragm 10 having flat initial form gets spherical shape when excessive pressure $P_{ind}(t)$ causes an expansion of internal volume $V_{ind}(t)$. It may be relevant to stress here without long but simple mathematical calculations, which are rather standard and are well known for anyone ordinary skilled in the art, that spherical deformation of resilient element 10 can provide lowest possible factor β in the equation (6) provided before and, therefore, the highest sensitivity of any sensor of present invention. That is why in present example output signals produced by this sensor system are associated with such variable geometric parameters of resilient element 10 as either curvature radius of said sphere or linear shift Δx of its central point depicted explicitly in FIG. 13.

Figure 17:
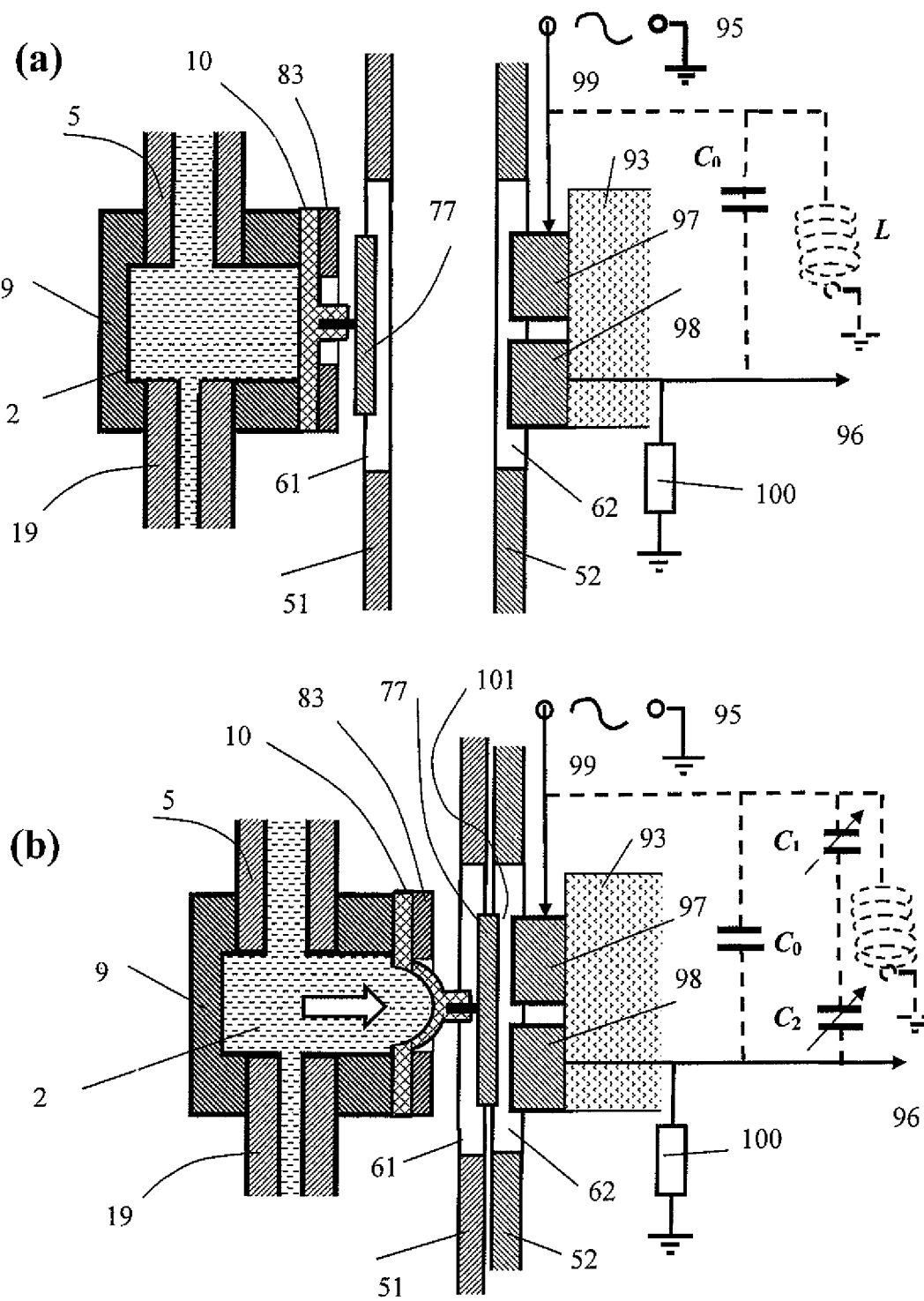
FIG. 17 depicts an example of the invention having a non-contact capacitor sensor combined with an indicator section of the reservoir located in the replaceable cartridge and having an expandable element made of resilient plastic material. Top and bottom views relate to disconnected and connected state of the cartridge correspondingly.

Another important feature of this example is that depicted in FIG. 17 input circuitry of the sensor comprises high frequency coil L having appropriate constant inductance. It should be appreciated by persons ordinary skilled in the art that in the presence of two variable capacitances $C_1$ and $C_2$ discussed before a resonance frequency of this input circuitry changes accordingly to said linear shift Δx of conducting element 77. The point is that analog signals produced with the same variable resonance frequency can be directly detected in the point 96 of the resistor 100 when these signals provide also proper feedback to high frequency AC generator connected with the point 99. In order to measure said resonance frequency the simple transducer 91 is desirably to be supplied only with digital counter which can just periodically count said analog signals whereas resulting information provided by such counter automatically gets proper digital form and can be directly accepted by conventional digital processor 17. Advantages of this approach are: (i) simplicity of analog-to-digit transformation, and (ii) very good precision of measurement of said shift Δx which can be easily as high as about 0.01-0.001% of full range even with very simple AC generator.

Figure 18:
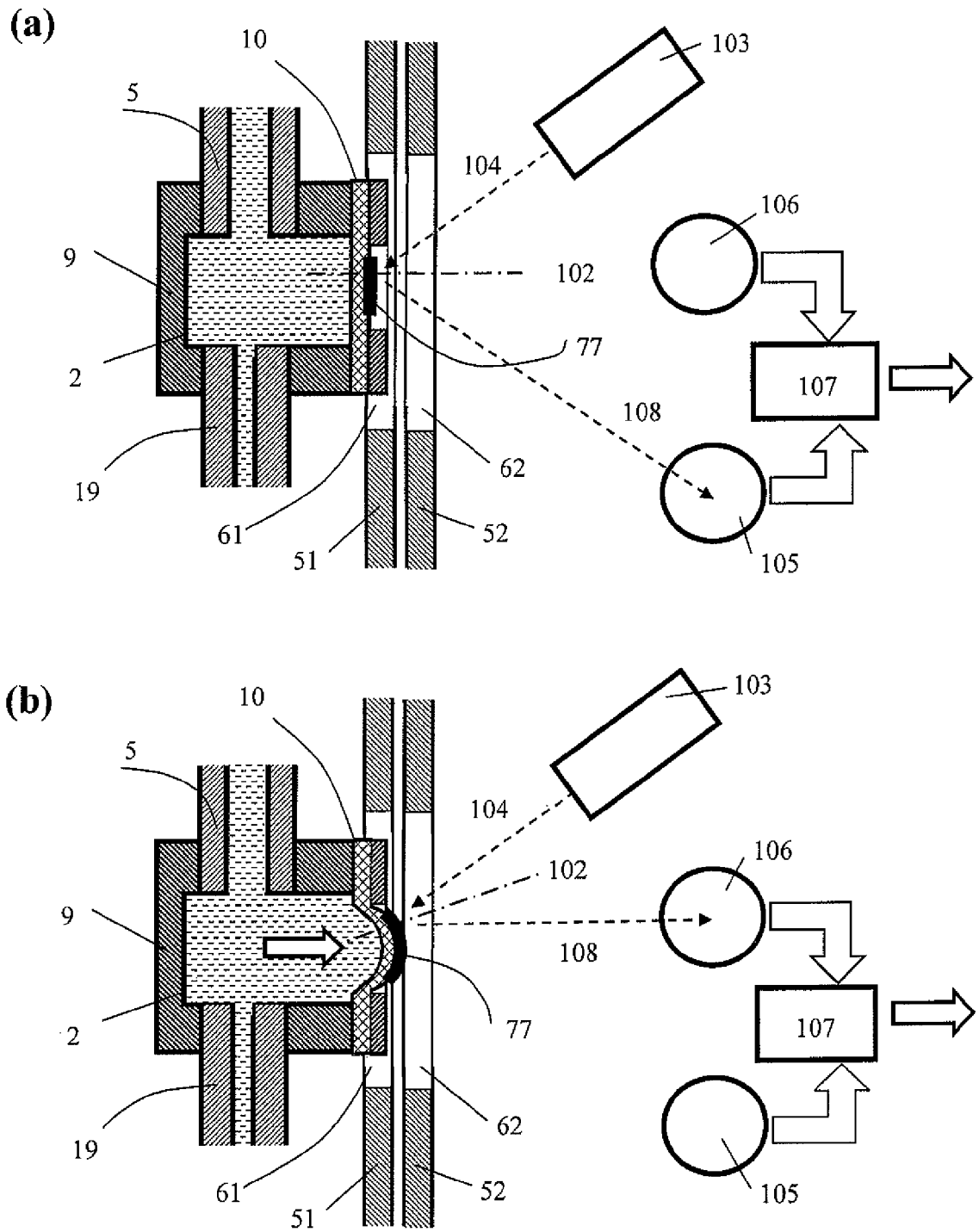
FIG. 18 depicts an example of the invention having a non-contact optical sensor combined with a connected replaceable cartridge wherein freely moving external surface of a resilient element of an indicator section is capable of reflecting light.

Non contact sensors of the invention can also exploit certain optic features of the indicator section of the reservoir 1 located in the replaceable cartridge 20. FIG. 18 represents further example of such parts of non contact optical sensor system located in the actuating module 21, said parts directly involved in producing analog input signals associated with the changes of at least one geometric parameter of disk-like diaphragm 10 made of resilient polymer film which seals the round opening located on hard wall of the indicator 9. In this particular example an external surface of the film 10 is covered with thin layer 77 which doesn't influence elastic properties and is capable of reflecting the light as a mirror. For visual aids dash-dotted lines 102 perpendicular to the surface of film 10 are provided in both FIG. 18a and FIG. 18b whereas ways of light beams are depicted by dashed lines. It is assumed in FIG. 18 that the cartridge is already installed and fixed so that windows 61 and 62 coincide. If desirable from viewpoint of safety considerations, these windows can be also protected by any optically transparent materials preventing an accidental damage of critically important parts in the case of improper usage. This optical sensor comprises a light emitter 103 (for example, a low intensity semiconductor laser) which is a source of primary light beam 104 directed onto said replaceable cartridge, and more precisely directed onto reflecting surface 77 so that the beam 104 is shifted a little bit from the center of disk-like diaphragm 10. Also the sensor comprises at least one photo-detector of reflected light, and more desirably it comprises at lest two such photo-detectors 105 and 106, all fixed in the housing 21. Both said detectors are connected with inputs of differential amplifier 107. It may be also desirable that output signal of the transducer 91 is proportional to the difference of input signals of said detectors.

When a pressure inside the indicator 9 is low the film 10 is practically flat and its radius of curvature is infinitely high. Top view of FIG. 18 shows that in this case the primary beam 104 is reflected by non-disturbed surface 77 so that it becomes the final beam 108, which falls preferably to the detector 105 and can only slightly touch the detector 106 because of inevitable light scattering. At low pressure the analog signal of detector 105 is high whereas the detector 106 produces low analog signal, and their difference produced by amplifier 107 results in positive output signal of the transducer 91. If the internal pressure of the indicator 9 increases the resilient film 10 expands and gets explicit spherical shape having lower radius of curvature (see bottom view of FIG. 18). Change of the shape of the element 10 means relocation of its parts which causes the change of direction of perpendicular 102 resulting in the shift of final beam 108 in the direction of the detector 106 and can even result in negative output signal of the transducer 91 if the change of the volume $V_{ind}(t)$ is high enough. Gradual transition from positive to negative output signals can be recorded during a gradual volume change from its initial zero value up to its highest value allowed by the dynamic range of the transducer. Therefore, this example shows how optical sensor system 16, supplied with light detector directly involved in producing analog input signal, transforms said input signal into the output signal associated with geometric parameters related to the shape of external surface of the expandable element of the reservoir 1.

However, in certain embodiments of the invention it can be desirable to design such optical sensor that output signals of the system 16 are associated with changes of certain internal geometric parameter of resilient element 10. The concept of such optical sensor is desirably based on the fact that all drug containing liquids are capable of absorbing light in specific optical range. Such sensors can be used if there is a necessity to decrease high frequency noise of the sensor system caused by undesirable vibrations of resilient element 10. In order to avoid such vibrations it may be desirable that external surface of resilient element 10 is fixed. If this is a case it can be appreciated by anyone skilled in the art that optical sensor shown in top view of FIG. 18 can be slightly modified so that the sensor needs to be supplied with the only fixed detector 105. In this particular example of modified sensor the previous indicator section 9 having disk-like elastic diaphragm, which can be free to vibrate, is to be substituted by elastic tube 10 having relatively thick transparent wall placed tightly inside short rigid tube 77 fixed reliably in the housing 20 to exclude any vibration (see, for example, FIG. 9 or FIG. 10 wherein said fixing is not depicted for simplicity). The tube 77 is desirably supplied with at least one small window which provides external light with an ability to penetrate into cavity of indicator 9 and then, after traveling inside said cavity, to leave it through the same window due to internal surface of the tube 77 is desirably made in the form of cylindrical mirror. Note that this particular embodiment is simpler because the second detector 106 is not required. All other optical parts and direction of primary beam 104 produced by light emitter 103 remain the same as shown in top view FIG. 18. Such sensor becomes capable of measuring changes $\Delta V_{ind}(t)$ even if external surface of resilient tube 10 cannot expand because it is surrounded tightly by walls of fixed tube 77 made of hard material.

However, due to the fact that the thick wall of the tube 10 is made of highly elastic plastics similar to silicon rubber, the internal surface of the tube 10 remains capable of relocating so that even modest increase of the internal pressure compresses thick plastic wall and increases simultaneously both tube's internal diameter $L(t)=L_0+\Delta L(t)$ and its volume so that both $\Delta V_{ind}(t)$ and $\Delta L(t)$ are proportional to $\Delta P_{ind}(t)$. The light source 103 fixed in the housing 21 produces narrow beam 104 directed to enter into said window on the wall of surrounding tube 77 near its diameter. After that the light crosses the internal volume of transparent elastic tube 10, and falls on reflecting internal surface of the tube 77. This reflection makes the light to: (i) turn in the direction 108, (ii) cross internal volume of the indicator 9 one more time, and then (iii) leave the cavity of indicator 9 through the same entrance window. Therefore, the final beam 108 is a beam transmitted by the expandable internal volume of the indicator section 9. This beam reaches the only photo-detector 105 and creates analog input electric signal.

The result of the process described in previous paragraph is that the path of the light traveling inside the cavity of indicator 9 is always proportional to doubled internal diameter $L(t)$. It is desirable that the wavelength of the light source 103 is chosen in such optical range, which corresponds to both high absorption of the fluid in the reservoir (or its optically active component) and relatively high transparency of the tube's plastic material. It may be appreciated by anyone skilled in the art that in the case related to this particular sensor the intensity $J_{108}(L)$ of the outgoing light beam 108 recorded by the detector 105 obeys well known optic law:

$$J_{108}(L)=J_{104}\exp\{-2\xi L(\Delta P_{ind})\epsilon c\} \quad \text{(Eq. 7)}$$

where $J_{104}$ is the intensity of the light beam 104 produced by the light source 103, the c is molecular concentration of either fluid itself or its optically active component (for example, the drug dissolved in the fluid), and $\epsilon$ is its extinction factor corresponding to specific optical spectrum of given fluid at chosen wavelength of the light. The effective path of the light $2L(\Delta P_{ind})$, multiplied by a constant $\xi \geq 1$ related to chosen direction of the light inside the cavity 9, expresses a dependence of the internal diameter of the indicator's tube on the pressure change $\Delta P_{ind}$. Typically the time-dependent change of variable $L(t)=L_0+\Delta L(t)$ is proportional to $\Delta P_{ind}$.

It can be appreciated that in this example the recorded light beam 108 does not change its direction. Instead, the analog input signal produced by the detector 105 is proportional to only the intensity of the transmitted light which, in contrast to previous examples, depends on internal geometric parameter of the expandable element 10 of the reservoir. Equation (7) shows explicitly that both the intensity of the transmitted light recorded and output signals of this type of non contact optical sensor are exponentially associated with such specific geometric parameter of the resilient volume of the indicator 9 as its internal diameter L depending on the pressure change $\Delta P_{ind}$ and reflecting volume change $\Delta V_{ind}(t)$. Those skilled in the art may note that due to exponential law of the equation (7) is always known in advance, the actually recorded non linear variable $J_{108}$ can be easily transformed to such output signal S(t) which satisfy the linear equation (6). It does not matter whether this logarithmic transformation is done directly by the transducer 91 or said transformation is included into special mathematical algorithm of programmable digital processor 17.

C. Programmable Control System

It can be desirable that the programmable control system comprises programmable processor 17 and control means 18. Most important feature of the invention is that said processor is capable of both acquiring said output of the sensor system 16 and producing an other output which is destined to control the driving force system 14. Said control is physically provided by said other output in the form of short electric signals transmitted to the system 14 at proper moments of the time. Flexible organization of the control system and ways of information exchange between its parts are shown schematically in FIG. 3. The control system may include few optional blocks shown with dotted lines. Actually, the control system plays an important role of preprogrammed "brain," which organizes the work of all the systems of the device in real time. However, devices of the invention are desirably designed so that control system can start its work only after proper installation of replaceable cartridge. It is assumed in present description that said inevitable condition is always fulfilled. That is why it will not be further additionally mentioned. It can be appreciated that time-sensitive actions can be performed by any electronic processor with a given precision in time. This precision is an inherent feature of any preprogrammed action and need not be described in detail herein. In accordance with the method of present invention the "brain" mentioned above is designed to fulfill the following major operations.

(a) Initiating a squeezing of the fluid out of the reservoir at the predetermined start moment when next delivery cycle is to be performed accordingly to programmed instructions. In order to do so the processor, having its internal clock, fulfills consecutively two sub-operations: (i) waiting until running real time coincides with preprogrammed start time-point $t_{st}$ of the next cycle; (ii) when the coincidence of both said times is detected the next operation is sending (see the arrow 23 in FIG. 3) the first, at least one starting signal to the driving force system 14. This action results in producing non-zero force causing such fast increase of the pressure in the compression section 8 which squeezes the fluid continuously out of both the reservoir 1 and exit opening 13. It follows from the properties of the hydraulic system disclosed before that sharp jump of the pressure in the compression section 8 causes certain time-dependent (or, in other words, dynamic) continuous exposure of the expandable indicator 9 to certain pressure difference which relates directly to the fluid delivery process.

(b) The next general task of the processor is analyzing the dynamic response of the expandable indicator section of the reservoir 1. The fulfilling of this task also consists of few sub-steps: (iii) acquiring at least one output of the system 16 containing information S(t) based on physical processes recorded by the sensor of system 16 (see the arrow 24 in FIG. 3), and preferably more than one output; (iv) treating the information received in accordance with predetermined mathematical algorithm in order to analyze this information and evaluate real parameters of current fluid delivery process; (v) determining the expected moment $t_{end}$ when the squeezing-out force must be terminated in order to stop outgoing fluid flow and provide an equality of the predetermined dose of current cycle and an actual dose delivered.

(c) When an expected time-point $t_{end}$ is determined the last task of the processor is terminating the squeezing-out force. It requires two sub-steps: (vi) waiting until running real time coincides with time-point $t_{end}$ determined in sub-step (v); (vii) when the desirable coincidence of both values is detected the processor must produce the second, at least one ending signal to the driving force system 14. In certain relatively simple embodiments this ending signal results in decreasing the squeezing-out force so that the pressure of the fluid in the reservoir can relax up to about its initial value before the cycle. In other, typically more advanced embodiments, the ending signal can cause both a termination of squeezing-out force and also make the system 14 to create time-dependent decompressing force applied to the fluid in the reservoir before the pressure finally relaxes to its initial value before the cycle. Processor can also fulfill some additional operations which are described in details in the part of the description related to methods.

It has been mentioned before that in certain cases the processor may comprise analog circuitry which may be desirable only if the math operation (v) comprises the simplest algorithm of direct integration of electric output signals $S(t)$. However, analog mathematics provides less precision and is now a little bit obsolete. In further discussion of present invention it is always assumed that the contemporary digital processor is used which is capable of using rather complex mathematical programs in order to treat digital output signals.

The controls 18 are designed to activate one or more of several different programs stored in processor's memory and/or change parameters of stored programs in accordance with current needs of a user, or even replace previous program with another one. For example, a special program can be used to calibrate the device automatically after the installation of the new cartridge. Other programs may correspond to different medical regimes of the drug delivery which can be chosen and changed at any moment by a user accordingly to his or her current medical state. It may be desirable in some embodiments that all systems of whole delivery device, depicted in FIG. 3, are assembled in the single housing, namely the housing 21 of the actuating module shown in bottom view of FIG. 5. If this is the case, in order to provide customer's control over whole device the control means 18 should be supplied with control buttons 109 and information LCD display 38. The bottom view of FIG. 5 shows the example of how these control elements may be located on the side wall of the housing 21 wherein the processor, full sensor system, and driving force system are assembled together.

However, it can be appreciated that the invention provides a flexible approach for spatial organization of the control system because of three features of the invention: (i) the hydraulic system uses only passive hydraulic elements and does not contain any material part which needs to be electronically operated while the delivery cycle; (ii) the driving force system 14 also does not need to be continuously operated while the delivery cycle because it produces pulse-like forces, namely main compressing force and, if desirable, optional decompressing force. So, the system 14 needs only to be turned either on or off at $t_{st}$ and at $t_{end}$ correspondingly; (iii) taking the two previous points into account the control system acts like "a supervisor" watching the actual delivery process patiently and providing only start-stop commands when necessary. That is why the control system of the invention is focused mainly on its own "intellectual" activity occurring in time rather than on actual continuous operations with other material objects. That is a reason why the processor of the invention can "think" and operate effectively independently on particular place of its location.

In other embodiments, related preferably to drug delivery devices destined to be deployed on patient's skin, it may be more desirable for customer's convenience that entire control system including the processor 17 together with its control means 18 is distributed between two modules, namely between the actuating module 21 and optional remote control module 35. If this is the case, the part of control means 18 depicted in FIG. 3 inside the housing 21 should be considered as local control means. Two previous sentences mean that each said module located in its separate housing is designed so that it comprises its own processor and at least such part of control means which is necessary to operate said own processor. Taking into account that full control system is destined to operate the same device the previous sentence means that both said own processors must be capable of working cooperatively at least from time to time and, therefore, must be supplied with corresponding means providing proper information exchange between two said housings. Each of said two processors must play its own functional role which doesn't cause improper interference with the role of other processor.

The idea of said distribution is based on the fact that, on the one hand, it may be rather difficult and inconvenient for the user to provide the actuating module with routine everyday delivery instructions because practically invisible housing 21 of actuating module, destined to be hidden under clothes and deployed on patient's skin, has to be very small and possibly can be deployed at such inconvenient place of patient's body where LCD 38 cannot be seen. That is why an additional remote control module located in optional separate housing 35 and capable of providing any kind of delivery instructions to separate actuating module 21 can be very desirable. Separate remote control module has to be portable and, at the same time, be supplied with such relatively big display 38 which can be easily seen even by people having reduced vision. It may be convenient for users if remote control module is supplied with wireless means providing information exchange between said remote control module and the housing of actuating module.

However, on the other hand, certain probability can always exist that separately located remote control module can either become broken by inaccurate users from time to time, or be stolen, or be lost, or just be forgotten anywhere by certain absent mind users. Even if said probability is relatively low, any of few accidental cases listed above can create extremely dangerous situation if only remote control module is a source of drug delivery instructions because a patient may vitally depend on proper drug delivery instructions. His or her life can be at risk if actuating module cannot get the instruction on time. It is shown below how a contradiction between this paragraph and previous one can be satisfactory resolved.

In order to provide highest level of patient's safety, combined simultaneously with as high convenience of usage as possible, the whole processor 17 can desirably consist of two cooperatively working parts located in different housings. Accordingly to the teaching of the invention, in addition to two inevitable housings, namely the housing of replaceable cartridge 20 and the housing of actuating module 21, devices of the invention can desirably comprise the third housing 35, namely the housing of remote control module, said remote control module comprising at least part of means destined to provide the actuating module 21 with delivery instructions, said means comprising at least a display and a system providing a remote signal exchange between the housing 21 and the housing 35. It is well known that certain types of touch-sensitive screens are capable of direct communicating with a processor, so avoiding a necessity of additional buttons or key board. However, additional buttons can be also used in certain embodiments, said additional buttons desirably located on the wall of the housing 35. The rectangular 38 in FIG. 3 depicts the display, including but not limited to touch-sensitive screen, which can be also supplied with said additional buttons if they are necessary or desirable. Thus, located in the housing 35 means 38 represent certain part of controlling means of whole device. The rectangular 37 in FIG. 3 depicts schematically a co-processor playing very important role which will be discussed a little bit later. Being located inside remote control module this co-processor 37 should be capable of both (i) interacting with said part of controlling means and (ii) being involved in providing the actuating module 21 with delivery instructions. The rectangular 36 depicts schematically a system providing a remote signal exchange between the housing 21 and the housing 35, whereas double-directed arrow 31 in FIG. 3 depicts the process of said exchange. Being purely electronic the system 36 can contain certain optional part of the transducer 91, namely the part 91(*b*) previously discussed in the section B of present description. The work of devices of the invention doesn't depend critically on whether said signal exchange is provided by wires or any known wireless means.

However, in any case the first, vitally important part of whole processor 17 is to be located in the actuating module 21. The memory of said first part of the processor must be capable of storing both (i) at least minimum delivery instructions, including but not limited to last delivery instructions received from said co-processor 37, and (ii) at least minimum set of programs, including but not limited to last programs received from said co-processor 37, which are necessary to fulfill the method of the invention previously discussed briefly in present description, because fulfilling of said method is necessary for correct functioning of the device. Words "at least minimum delivery instructions" mean such limited set of delivery instructions which is absolutely necessary to save patient's health and life even in the absence of working remote control module. Words "at least minimum set of programs" mean such limited set of programs which is absolutely necessary to fulfill said minimum delivery instructions. Said above means that an actuating module 21 satisfying the conditions listed in this paragraph can provide at least temporary independent work of vitally important systems of drug delivery device even in certain emergency cases when controlling signals of remote control module 35 cannot be received for any reason. Therefore, the ability of temporary independent work in emergency cases is most important condition preserving patient's life under any circumstances.

It can be appreciated by persons skilled in the art that, in order to initiate and control said independent work in emergency cases, the housing 21 of the actuating module needs to be supplied with at least minimum amount of local controlling means 18 depicted in FIG. 13, wherein the arrow 22 depicts direct interaction of said local means 18 with said first, vitally important part of whole processor 17. Because said exclusive destination of local means 18, used preferably in limited number of specific and/or relatively rare circumstances, said local means do not need to be too sophisticated. Instead, they have desirably to be made as simple as possible so that the patient is capable of activating these means with only one of more simple touches which do not require either to see LCD screen or to enter another program. For example, the actuating module can be supplied only with couple of simple control buttons 109 located on both side walls of actuating module destined to work under patient's clothes (see FIG. 8 where only one button 109 of said two can be seen). Looking at view (b) of FIG. 8 anyone skilled in the art should appreciate that specific relief of these buttons can be made so that, after the device is deployed on a skin, tactile abilities of patient's hand are enough to easily operate buttons hidden under clothes without seeing them. It can be desirable that activation of any emergency function of the device occurs after simultaneous pressing of both buttons located on opposite walls of the housing 21 in order to avoid accidental activation. For example, short simultaneous pressing of both buttons 109 can activate a one-time delivery of standard basal dose to a diabetic patient, whereas quick double pressing (similar to double click of computer's mouse) can activate one-time delivery of standard bolus dose. Long (more 3 sec) pressing can lead to termination of current program stored in the memory or, for example, switching to another program, and so on. Therefore, few simple operations are always available which are necessary for safety.

At the same time the co-processor 37 located in separate housing 35 supplied with LCD display and, if necessary, multiple buttons is destined to provide an advanced operation. Thus, it desirably becomes a master providing the user with an ability of producing any kind of delivery instructions, including but not limited to rather complicated ones, when remote control module is in its normal working state and is present in hands of the user. When the processor located in actuating module 21 receives any new instruction sent by remote control 35 it has to be treated as an order having highest priority over all previous instructions.

However, in any case the general scope of the invention does not depend on how many housings are used to locate different parts of the control system, and what particular means provide their information exchange if it occurs in accordance with the general teaching of the invention. At the same time it should be appreciated that there is one feature characterizing the speed of the control system in its combination with the sensor system. This feature is the maximum frequency $f_0$ reflecting the process of sequential generation of output signals S(t) by the sensor system, their further transfer to programmed processor in the form of the information cluster, and final mathematical treatment of this information in order to fulfill operations (iv, v) disclosed previously in this section. The said above means that the device is spending at least minimum finite time $1/f_0$ in order to produce and treat each single information cluster reflecting, for example, the instant state of the delivery process in one given time-point. Assuming that one cycle of the fluid dosing requires at least the time $T_c$, the number N of such information clusters (or points) produced by the sensor system and treated by the processor in one delivery cycle cannot exceed $N=T_c f_0$.

Minimum N depends on how the device is designed and what mathematical algorithm is used. It will be shown later that in the case of a simple device the minimum N is at least one and desirably it is more than one. However, more advanced devices providing better characteristics may require at least N=2 or more, and most advanced devices of present invention require at least N=5 or more.

There are other options that are not critical for the device functioning but may be rather useful for users. In rare cases of improper functioning of the device the mentioned above analysis (iv) should detect such dangerous events and result in alarm signals produced by optional alarm sub-system 34 which is intended to inform a user that the device itself is not able to work properly. It may be desirable also that a user is provided with the information on reasons of improper work, said information produced by analyzing algorithm and reflected typically on the display 38. One more option can be used if particular fluid delivery device of the invention is intended to be used for vitally important drug delivery. In this case the remote control module may be supplied with additional long-distance wireless transmitters and receivers providing remote communication of the patient's device with medical professionals capable of prompt resolving emergency situations. This external medical help may include personal directions provided to a patient, or remote re-programming of the device if it seems to be necessary from medical viewpoint.

In order to make the device well controllable it may be desirable in some embodiments that the driving force system 14 reports to the processor 17 how its start-stop commands are understood and fulfilled. The arrow 27 in FIG. 3 shows this optional way of the information exchange. It may be desirable also that optional signals 26 are sent by the processor to activate the sensor system 16 while the delivery cycle. These optional signals can help to synchronize the information exchange and conserve batteries in the dead time periods between cycles. Advanced embodiments of the invention can also possess an optional ability to provide mechanical control over the driving force system 14 in certain emergency cases, said specific part of local control means 18 is depicted schematically in FIG. 3 with dotted arrow 30 and will be considered in next section of present descriptions in more details.

D. Driving Force System

The driving force system 14 shown in FIG. 3 schematically is designed to activate the fluid flow by squeezing the fluid out of the reservoir 1. In accordance with the teaching of the invention, during each cycle only a predetermined relatively low dose $D_0$ of the fluid is to be delivered to the exit opening of the device. That is why it is desirable that the system 14 is represented by such technical means which are capable of changing over time the compressing force which leads to squeezing the fluid out of the reservoir 1. It may also be desirable that the compressing force continues only for a limited time $T_c$ corresponding approximately to the duration of one cycle of the fluid dosing. It may be desirable that the system 14 is capable of creating pulse-like compressing force applied only to certain limited surface area of the fluid filling the compression section 8 of the reservoir 1 in order to cause a compression resulting in rapid increases of the pressure in said compression section. As it has been described before, the time-dependent pulse-like change of the excessive pressure in the section 8 is designated as $\Delta P_{comp}(t)$. In accordance with the equation (3) the positive term $\Delta P_{comp}(t)$ expresses a difference of full fluid pressure $P_{comp}$ in the compression section 8 and external pressure $P_{ext}$ which is typically external atmospheric pressure. Because of the fact that the driving force system 14 is capable of causing the compression of the fluid in the reservoir during said time interval $T_c$, it may be also called hereinafter as "the compression system" for brevity. As it has been already mentioned, before each dosing cycle the fluid in the reservoir is subjected to as low pressure as may be necessary to prevent the fluid to flow out of the exit opening. Actually, this low pressure in whole reservoir, including its compression section 8, must be close to an external pressure $P_{ext}$ which is typical atmospheric pressure. However, in certain embodiments it can be also desirable that after the end of delivery cycle the fluid in compression section 8 undergoes relatively short decompressing force which helps both to refill the section 8 and to establish desirable low pressure in this section which is close to an external pressure $P_{ext}$.

Each dosing cycle begins at programmatically predetermined moment $t_{st}$ which is the moment of the real time. However, in order to make the description as simple as possible it is more convenient hereinafter to consider all processes of each given cycle in terms of its local time t which is chosen so that local t=0 at the moment $t_{st}$ of the real time. What is said in previous paragraph means that the cycle starts at local moment t=0, and $\Delta P_{comp}(0)$ is about the zero.

The desirable pulse-like excessive pressure $\Delta P_{comp}(t)$ begins when compression system 14 gets the first starting electric output signal produced by programmable control system. It is desirable that immediately after said starting signal the increase $\Delta P_{comp}$ occurs rapidly until it reaches a certain level $P_0$ corresponding to predetermined bracket condition $P_{max}>P_0>P_{min}$. It also may be desirable that after a short raising period further increase of the pressure is stopped so that the elevated pressure in the section 8 remains close to obtained high value $\Delta P_{comp}=P_0$ during the time $T_c=t_{end}-t_{st}$ of the delivery cycle. In other words this means that the first starting signal activates the system 14 for only rather short time $T_{up}$ which should be enough to cause a pressure increase $\Delta P_{comp}=P_0$. After that the system 14 goes automatically to the waiting mode and does nothing until it receives the next controlling output signal produced by the processor. This process is analogous to what is depicted in the middle image of FIG. 2 where fast increase of the pressure in the elastic reservoir is caused by one quick move of the finger 4, and then excessive pressure remains almost constant for some time even if a position of compressing finger is fixed.

Termination of the delivery cycle is a reverse of the above process. It occurs when the system 14 gets at least one ending electric output signal initiated by control system at local moment $t=T_c$. It is desirable that said ending signal activates the system 14 again and makes it to remove the compressing force over a short time $T_{down}$. After that pressure drop occurs in the section 8 until $\Delta P_{comp}$ either returns back immediately to its initial zero value or, in certain embodiments, even becomes slightly negative for a short while and then relaxes to its initial zero value This process is analogous to some extent to what is depicted in the bottom image of FIG. 2 after the finger 4 is removed and elastic wall of the reservoir relaxes quickly.

Thus, it can be desirable in most cases that the time diagram representing $\Delta P_{comp}(t)$ must look as purely rectangular pulse having the desirable amplitude $P_0$ and algorithmically determined duration $T_c=t_{end}-t_{st}$ which is understood hereinafter as the time interval between said starting and ending output signals of control system. However, it can be appreciated that in real devices the shape of actual diagram $\Delta P_{comp}(t)$ may differ significantly from ideal one. Two diagrams shown in the top of FIG. 19 represent more realistic examples of two independent cycles $\Delta P_{comp}(t)$ having different amplitudes $P_0(a)$ and $P_0(b)$ notwithstanding their quasi-rectangular shape is close to ideal expectations. An advantage of the present invention is that precision of the fluid delivery can be maintained in the face of even substantial variations of real diagrams $\Delta P_{comp}(t)$ related to different cycles. Thus, a mechanism of the compressing system 14 can be made simple without the need for high precision parts. For example, the amplitude $P_0$ produced in different cycles may be up to five times more and/or up to five times less than its average value expected by a preprogrammed processor. In other words, the bracket ratio $P_{max}/P_{min}$ can be as high as about 25. Moreover, some embodiments can work properly even if the elevated plateau of the pressure pulse is not quite stable and can change during $T_c$ up to about 70% of $P_0$ or even more (see top view of FIG. 20 for example). Discussed later "smart" algorithms related to the method of present invention are capable of compensating very strong variations of the shape of $\Delta P_{comp}(t)$.

It can be appreciated that due to "soft" technical requirements the mechanism of the compression system 14 of the invention may be simpler and less precise than complicated high precision mechanisms of known devices of the prior art. However, actual behavior of the system 14 desirably satisfies at least certain minimum requirements related to average $T_c$. It may be desirable that average interval $T_c$ exceeds at least about two times the typical time $T_{up}$ of fast transition from initial level $\Delta P_{comp}(0)=0$ to the highest pressure achieved in the compression section 8 during $T_c$. It can be desirable that average $T_c$ exceeds $T_{up}$ at least about ten times, and it can be more desirable that average $T_c$ exceeds $T_{up}$ by about fifty times or more. For example, if the average duration $T_c$ of the dosing cycle is chosen to be about 20 s then a desirable transition time $T_{up}$ can be not longer than 0.4 s, and alternatively, not exceed 10 s whereas more desirable time $T_{up}$ should not exceed 0.04 s.

It may also be desirable that after the ending output signal is sent by the control system, a rapid pressure drop occurs in the compression section 8 of the reservoir 1 during as short time $T_{down}$ as the first transition time $T_{up}$ discussed above. The examples depicting both transition times $T_{up}$ and $T_{down}$ are provided in FIG. 19 and FIG. 20.

Multiple different executive mechanisms of the system 14 can be used to fulfill simple technical conditions disclosed above. FIG. 7 represents schematically an example of a simple device of the invention wherein the replaceable cartridge 20 exploiting traditional syringe is already connected with the actuating module 21 supplied with motor-driven compressing mechanism of the system 14. For more clarity the same modules 20 and 21 are also shown separately in FIG. 6. This particular example relates preferably to the first subfamily devices destined to be suspended on patient's belt. Replaceable cartridges 20 based on syringe-like approach have been thoroughly discussed in previous sections. That is why the only detail which has to be especially stressed here again is the piston 72 connected with driving shaft 15a supplied with hole 73. This detail is important because the only mechanical output of such particular system 14 is a tip 15b located on one end of a lever 110 whereas its another end is fixed by an axis 111 so that the tip 15b is capable of easy moving forth-and-back along axis Y. Diameter of the tip 15b corresponds to the size of hole 73 so that in the process of joining modules 20 and 21 the tip 15b penetrates through the hole 73 and connects mechanically driving force system 14 with said piston representing part of hydraulic system located in replaceable cartridge (see FIG. 7). In this assembled state any force applied to the tip 15b by the mechanism 14 is automatically transferred to joining element, namely the driving shaft 15a which receives said force. Thus, in this example the function of tip 15b is to be a mediatory element which is capable of operably transmitting a force produced by driving force system to at least one force receiving element located in the replaceable cartridge. In this example it has to be appreciated that the force receiving element, namely shaft 15a, is directly involved in further transformation of driving force received into the force applied to the fluid. It has to be appreciated also that due to inevitable friction between the piston and casing of the syringe the force applied to the fluid can be less than the driving force received by said shaft.

In order to change the force applied to the fluid over time, and first of all to cause the force squeezing the fluid out, this kind of compressing system comprises an electromechanical system capable of moving said piston 72 in either of two opposite directions according to two control signals 23 sent by the processor. Also, this mechanism comprises the electric step-motor 112 combined with the mechanical reducer 113. The motor is connected with standard controller causing the step-motor to make a programmatically determined number of angular steps in any direction, whether clockwise or counterclockwise, according to either starting or ending signals of the processor 17. The internal output eccentric wheel of reducer 113 is combined with the lever 110 in order to transform the rotation of the motor into back-and-forth movement of both the shaft 15a and the piston 72 (see thick double directed arrow in FIG. 21). In this example it is desirable that the syringe's body 8 is made of hard materials, whereas the piston 72 is supplied with both the cavity 75 and elastic diaphragm 76 shown also in FIG. 9b and FIG. 9c. It may be desirable also that simple devices satisfy the condition $R_1 \ll R_2$ so that a ratio $R_1 \ll R_2$ is less than 0.05. Note that the last condition is very optional one. In this particular example it is taken only in order to make later certain quantitative comparison of most simple devices of the invention with known traditional drug delivery devices based on syringe-like approach.

A typical cycle of a syringe-like compressing system 14 shown in FIG. 7 and/or FIG. 21 is described below. A first starting signal sent by the processor 17 causes the step-motor to make programmatically predetermined number $M_{up}$ of steps by rotating in, for example, counterclockwise direction. Correspondingly, this rotation of the step-motor makes the piston 72 to slide predetermined distance $\Delta l$ in the right direction. This first movement takes a short time $T_{up}$, for example about 0.2 s, and then the step-motor stops to conserve the battery. Piston 72 applies the compressing force only to the limited surface area $S_{pist}$ of the fluid 2 located inside the syringe 8. Because the piston has the cavity 75 which is free of liquid and is located behind elastic diaphragm 76 (see FIG. 9b) said force causes sharp increase of fluid's pressure $\Delta P_{comp}(t)$ in the section 8 which deforms the elastic diaphragm 76 immediately and decreases free volume of said cavity by certain value $\Delta V$ (see FIG. 9c). The change of free volume of said cavity is equal a volume deformation of said elastic diaphragm. However, it has to be stressed that during short time $T_{up}$ the amount of the fluid expelled from the exit opening 13 is negligibly low because of high resistance $R_2$. Because of the fact that in condition $R_1 \ll R_2$ the pressure in both sections 9 and 8 practically coincide all the time, the deformation of resilient element 10 recorded by the sensor system 16 reflects the shape of pressure pulse $\Delta P_{comp}(t)$ having amplitude $P_0$. It can be desirable that volume deformation $\Delta V$ caused by the piston's relocation exceeds the preprogrammed fluid dose $D_0$ of current delivery cycle by the order of magnitude, for example about 20 times. It can be appreciated that this volume $\Delta V$ expelled into cavity 75 during the short transition time $T_{up}$ by moving piston can be expressed as: $\Delta V = S_{pist} \Delta l$. In the case of a simple device supplied with the syringe-type system 14, the amplitude $P_0$ of jump-like pressure increase obeys, in accordance with the equation (4), the following equation:

$$P_0 = \alpha S_{pist} \Delta l \qquad \text{(Eq. 8)}$$

Due to low $R_1$ in this particular example the coefficient $\alpha$ relates to whole volume of the reservoir 1 including both the element 10 and elastic diaphragm 76.

Both the resistance $R_2$ and actual pressure $P_0$ measured by the sensor system during each cycle are known to the processor, which calculates both the real magnitude of the fluid flow and right cycle duration $T_c$ corresponding to the desirable dose. When the proper $T_c$ is reached and desirable dose $D_0$ is obtained, the processor sends the ending signal to the system 14, namely to step-motor's controller. After that the step-motor 112 rotates clockwise and makes predetermined number $M_{down}$ of back steps making the piston 72 to slide back in the left direction. This takes short time $T_{down}$ only and results in fast decrease of squeezing-out pressure in the reservoir as shown in top view of FIG. 19. It should be appreciated that typically the numbers of motor's steps are to be chosen in accordance with simple condition $M_{up} > M_{down}$, providing an effective way of controlling the piston's actions.

Equation (8) can be further used in order to compare more specifically the features of the devices of the invention with those of prior art syringe-like drug delivery devices. The quantitative example considered below is based on a few parameters which can be practically used in simple devices of the invention. A device is supplied with the syringe-like system 14 wherein typical syringe, containing about 3 cm$^3$ of insulin solution, has piston area about $S_{pist}$=1 cm$^2$. For a quantitative comparison, consider that typical preprogrammed one-cycle dose of the insulin is $D_0$=12 mm$^3$, and desirable precision of the insulin delivery is selected to be about 0.1 mm$^3$. In order to provide such a dose in one cycle, the piston of prior art devices must be shifted 0.12 mm with the precision better or about 0.001 mm, thus corresponding to about 1 micron.

In contrast, equation (8) tells that in simple devices of the invention the factor α, depending in present example on resilient properties of the elastic element 76, can be easily made equal or about 1 Kgram/cm$^5$. In this case it also follows from equation (8) that the average amplitude of the pressure pulse in both compression and indicator sections of a simple device (for example see the curve (a) in top view of FIG. 19) is about $P_0$=0.2 Kgram/cm$^2$ when the program orders the piston's shift equal Δl=2 mm. So, during the short time $T_{up}$ the piston is pumping up the additional fluid volume about $\Delta V_{ind}$=200 mm$^3$, which is really about 20 times more than requested dose $D_0$=12 mm$^3$. At the same time resistor 19 included in the flow passage can be made in the form of the short needle having typical length of about 2 cm and internal diameter of about 0.07 mm, thus providing high hydraulic resistance about $R_2$=330 (Kgram·s)/cm$^5$. It follows from the equation (1) that rather moderate magnitude of the outgoing flow F=0.6 mm$^3$/s appears in the exit opening 13 when the pressure difference 0.2 Kgram/cm$^2$ is applied to said high resistance $R_2$. Correspondingly, the delivery cycle must continue about $T_c$=20 s in order to obtain the full desired dose $D_0$=12 mm$^3$. It should be apparent that both the processor 17 and executive mechanics of the system 14 can easily control the cycle's duration $T_c$ with the precision at least 0.025 s or better. At given intensity F=0.6 mm$^3$/s this time-precision 0.025 s corresponds to very high dosing precision 0.015 mm$^3$ easily achieved even with the simplest device of the invention. This estimate shows advantages inherent even for the simplest embodiments of the invention. At the same time it can be appreciated that particular numbers are provided above as an example only, which cannot create any limitations for any other embodiments of the invention.

The estimate of previous paragraph contains the assumption that elevated pressure remains constant while whole period $T_c$. Real processes can be close to this assumption because the expandability of the diaphragm 76 is high, and low dose $D_0$ leaving the reservoir for $T_c$ represents only small fraction of elastic volume deformation ΔV of the diaphragm 76. That is why in the process of slow relaxation of resiliently deformed diaphragm 76 during $T_c$ said volume ΔV can change few percent only. At quantitative parameters chosen for this particular example it is easy to see that $\Delta P_{comp}(t)$ changes during $T_c$ not more than about 5%. Because this change is fully predictable the processor's algorithm can take it into account and make necessary correction of calculated $T_c$. Higher stability of $\Delta P_{comp}(t)$ can be easily achieved if one increases the preprogrammed volume change ΔV and/or decreases preprogrammed $D_0$. For example, the stability of the pressure $\Delta P_{comp}(t)$ becomes better than 1% in each $T_c$ if predetermined dose $D_0$ of one cycle is chosen to be 2.4 mm$^3$. Correspondingly, in order to keep the same final dose 12 mm$^3$ one needs only that the high precision cycle of 2.4 mm$^3$ is repeated five times.

In contrast to known syringe-based devices of prior art, similar to disclosed in U.S. Pat. No. 7,569,050) an advantage of the present example of the system 14, which is compatible with a syringe-based hydraulic system of the invention, is that neither high precision parts nor any selectivity of piston's movement are required for getting high precision drug delivery. In order to complete the quantitative comparison of prior art devices and those of the present invention, let make an assumption that due to certain mechanical errors occurring in one embodiment of the invention, the piston 72 has been actually moved only 1.3 mm instead of programmatically expected value Δl=2 mm. It follows from equation (8) that due to such error the real pressure increases only up to $P_0$=0.13 Kgram/cm$^2$ which is much lower than expected (compare, for example, curves (b) and (a) in top view of FIG. 19). Correspondingly, the intensity of the output flow becomes equal low value F=0.39 mm$^3$/s. However, in order to keep the desirable output dose $D_0$=12 mm$^3$ constant, one needs only to increase the duration of the delivery cycle from the previous 20 s to new $T_c$=30.8 s (see bottom view of FIG. 19). This task is the responsibility of processor 17 which calculates the correct $T_c$ on the basis of the information about the real amplitude $P_0$ received from the sensor system 16. This calculation causes proper delay of the ending signal and restores desirable output fluid dose. Therefore, one can see that even a large mechanical error of a piston's shift of about 700 microns, occurring accidentally in the system 14 of the invented device, does not influence the final precision of the fluid delivery because resilient element 76 separating movable piston from an internal volume of the reservoir is adapted to eliminate direct correspondence between displacement of said piston and a dose of the fluid delivered to the exit opening. At the same time prior art devices fail if their similar error exceeds 1 micron. These numbers explain why and how the devices of the invention can achieve better precision and reliability simultaneously with simplification of their executive mechanisms.

However, even well working syringe-based devices of the invention described above have certain disadvantages such as: (i) relatively high thickness of short syringe storing required amount of the fluid, (ii) relatively low energy efficiency inherent for small electric motors, and (iii) complicated controller of step-motor. Those skilled in the art may appreciate that neither the syringe nor the electric motor are required features of the means 14 capable of changing over time the force squeezing the fluid out. Examples provided below demonstrate further improvements of means 14 related preferably to more advanced second sub-family of devices of the invention. These improvements, capable of eliminating all said disadvantages, exploit direct magnetic interactions, and this is a reason why it can be relevant to consider the nature of such interactions before detailed description of said improvements. FIG. 22 represents schematically how permanent magnet 114 having oriented magnetic moment μ can interact with at least one electromagnet 115 having a core which is magnetically soft and made of, for example, an iron or alike. In FIG. 22 solid ellipsoid-like lines demonstrate both the structure and orientation of magnetic field created by permanent magnet. Similar dashed lines represent the field created only by electromagnet when a non-zero voltage is applied between ends of a coil 116. It is well known that direction of magnetic field created by such electromagnet depends on polarity of said voltage. Magnetic interaction always results in certain force applied to both permanent magnet and electromagnet. For better clarity, magnetic forces applied to permanent magnet 114 are shown in FIG. 22 with thick black arrows whereas thick white arrows relate to magnetic force applied to electromagnet. There are few different cases important for practical applications. For example, FIG. 22*a* depicts a first situation when no voltage is applied and there is no current in the coil 116. However, magnetic field of permanent magnet 114 always penetrates partially inside said core of electromagnet 115 having high magnetic permeability. Well known result is that some attraction appears between both magnets 114 and 115. This attraction is characterized quantitatively by a certain force $f_{att}$ which is constant in time and depends strongly on the distance between both magnets. The force $f_{att}$ is further called "passive attracting force" because it is always present even without activation of electromagnet. Situation changes if some voltage is applied to the coil 116 to activate non-zero current J resulting in appearance of own field of electromagnet 115 accordingly to both an intensity and a polarity of the current. In order to find a resulting field both the permanent field of the magnet 114 and newly created field of electromagnet 115 are to be summarized as vectors. In particular example depicted in FIG. 22b a polarity of the current is chosen so that in the space between said magnets the direction of pure electromagnet field coincides with direction of permanent field. Because summarized field located between both magnets has increased intensity they begin to repulse each other with a force $F_{rep}$. The higher J the stronger field between magnets and stronger repulsion force $F_{rep}$. Thus, if the current is high enough and has proper polarity the repulsion force $F_{rep}$ can be much stronger than passive attraction $F_{att}$. Assuming that position of electromagnet is fixed, high repulsion force $F_{rep}$ depicted in FIG. 22b can be used to move in right direction such parts of the system 14 which can be connected with permanent magnet 114. The opposite situation occurs if one changes polarity of the voltage as shown in FIG. 22c. In this case the permanent field and the electromagnet field are oppositely directed so that the summarized field between both magnets has reduced intensity. The result is that magnets begin to attract each other with a substantial force $F_{att}$ which also can exceed passive attraction $f_{att}$ many times. So, the last situation can be used to move parts of the system 14 in left direction. Moreover, effectiveness of usage of permanent magnet 114 can be doubled if it is located between two electromagnets 115 and 117 as shown in FIG. 22d. In this case both left and right sides of the magnet 114 can simultaneously participate in magnetic interactions if the voltage is simultaneously applied to coils 116 and 118 of electromagnets 115 and 117 correspondingly. This example shows that if polarities are chosen right the left electromagnet creates the force $F_{att}$ which pulls magnet 114 whereas pushing force $F_{rep}$ is created by right electromagnet 117. Both said forces are oriented in the same direction and create resulting force $F_{att}+F_{rep}=F_{sw}$ which is called hereinafter "switching force $F_{sw}$". It should be appreciated that direction of switching force $F_{sw}$ changes when polarities of both voltages applied to coils 116 and 118 are changed simultaneously.

Magnetic peculiarities disclosed in previous paragraph provide a basis for quite new type of driving force system 14 of the invention, namely latch-type system 14 having no electric motor at all. FIG. 23 demonstrates the first example of motorless latch-type system 14 specifically designed to be combined with second sub-family replaceable cartridges having thin hydraulic system A supplied with additional flexible bag 32 depicted in FIG. 12. This bag isn't shown in FIG. 23 because it is hidden in the cavity 63 under the module 21 (see FIG. 8c). Main feature of latch-type mechanism 14 is that it has a latch having only two stable positions so that, for example, the first stable position of said latch corresponds to inactive waiting state of the device before the cycle, whereas the second stable position, corresponding to active fluid delivery state of the device, is to be taken in order to start the process of fluid delivery. Therefore, proper fast switching if said latch between its said two stable states allows precise fulfilling of processor's commands controlling time $T_c$ of the delivery cycle.

A latch-type mechanism, depicted in FIG. 23 in its inactive state, is designed as follows. Switching between two said stable states is controlled by magnetic system similar, to the one shown in FIGS. 22a, b and c. It comprises at least one electromagnet 115 fixed in the housing 21 and at least one permanent magnet 114 connected with a shuttle 119 which is capable of moving forth and back along a rod 120 representing the latch mentioned in previous paragraph. The rod 120 is connected with the housing 21 in the only point by an axis 121 providing said rod with an ability of rotation in the plane XY so that an angle γ shown in FIG. 23 can change. The rod 120 holds a stressed elongated cylindrical spring 122 located between the axis 121 and the shuttle 119. In this particular example said stressed spring is permanently compressed with predetermined force which pushes the shuttle 119 ahead all the time as shown in FIG. 23 with thick black arrow. Resilient compression of said spring is to be chosen so that said predetermined force remains approximately the same in whole range of potentially possible relocations of the shuttle 119 along said rod. Because this rod is capable of changing its angle γ relatively central direction C-C shown in FIG. 23 with dashed line, the shuttle 119 is capable of applying said predetermined force, produced by compressed spring 122, to either shoulder of a lever 123 which has its own rotation point provided by an axis 124. Eccentric bolt 125 and a roll 126 capable of free rotating are destined to limit said changes of the angle γ. In order to decrease a friction appearing while relocation of the rod, the shuttle 119 is desirably supplied with freely rotating small wheel 127. Left end of the lever 123 comprises a small cylindrical element 128 desirably made at least partially of ferromagnetic material. It can be even more desirable that the element 128 comprises permanent magnet located near the window 60 of the actuating module 21 (see also FIG. 8a). Destination of magnetic cylinder 128 is to be a mediatory element capable of direct transferring a driving force produced by such latch-type driving force system 14 to hydraulic system located in the replaceable cartridge 20. Therefore, magnetic element 128 of this particular example plays the same role as the element 15b shown in FIG. 3 schematically. Those skilled in the art can appreciate that cylindrical shape of the element 128 is provided as an example only and other shapes can be used as well.

FIGS. 23, 24, 25, and 26 help to understand how this particular latch-type system 14 works and why it has only two stable states. The point is that the energy E of compressed spring depends on how much it is compressed. The less compression the lower said energy. It is well known also that any mechanical system behaves so that its energy becomes as low as possible at given circumstances. Those skilled in the art can appreciate that highest compression of the spring 122, corresponding to highest energy, is reached when position of the rod 120 coincides with line C-C in FIG. 23 which corresponds to zero angle γ. Energetic dependence of mechanical system depicted in FIG. 23 on its angle γ is represented by curve 129 in FIG. 24a. The said above explains why the top point of curve 129 represents maximum energy corresponding to unstable position of the rod 120 whereas one energetic minimum can be reached at highest possible positive γ defined by a position of the bolt 125 (eccentric shape is provided for fine adjustment of this limit), and another energetic minimum can be reached at highest negative γ depending on a position of the roll 126. Because the energy is minimized each limit of said two provides its own mechanically stable state either at maximum positive or maximum negative angle γ. Neither intermediate position between said limits can be stable.

It may be desirable that before any dosing cycle, as well as before installation of new replaceable cartridge 20, the rod 120 takes most right stable position limited by the bolt 125 in order to bring the system 14 in its inactive waiting state shown in FIG. 23. At that time the power supply 130 of electromagnet 115 is in the off state in order to conserve the battery, whereas compressed spring 122 pushes the shuttle 119 ahead so that it applies predetermined radial $F_{rad}$ force to the right shoulder of lever 123 (see thick black arrow in FIG. 23) and causes it to rotate counterclockwise (see rounded white arrow in FIG. 23) in order to bring mediatory magnetic element 128 in its deepest position in the housing 21. However, due to piston 78 of hydraulic system is made at least partially of ferromagnetic material (as it has been mentioned previously in section A of present description) the permanent magnetic field of the element 128 attracts the piston 78 and causes it to be shifted slightly out of the section 8 in the direction shown with thick white arrow. The result of such shift is that elastic diaphragm 76, connected with the piston 78, expands a little bit and, therefore, applies certain decompressing force to the fluid in the section 8 causing the pressure in this section to become a little bit lower than constant atmospheric pressure $P_{atm}$ exposing the fluid in not shown flexible bag 32 (see FIG. 12). Because the replaceable cartridge of the second subfamily, compatible with latch-type system 14, is desirably supplied with the valve locked at this period by the ball 85, the only temporary process can occur that the fluid located in supplying bag 32 flows for some limited time through static resistor 33 into section 8 until the pressure in both the bag 32 and section 8 become equal external atmospheric pressure $P_{atm}$. At this point whole device is ready to start the delivery cycle.

In order to start fluid delivery cycle the rod 120 must be relocated from said right limit to the left one. This relocation requires an application of switching force $F_{sw}$ which, in present design, must be a tangential force applied to the rod 120. Those skilled in the art can appreciate that invented latch-type system can exhibit high energetic advantage when required change of the angle γ is chosen to be Δγ<<1. In this case required tangential force $F_{sw}$ can be only low fraction of radial force $F_{rad}$ created by compressed spring. The only condition required is that $F_{sw}$ overcomes tangential component of radial force $F_{rad}$ equal $\gamma F_{rad}$ (see dashed line 131 in FIG. 24b wherein positive values correspond to left direction of forces whereas negative values correspond to right direction), because said tangential component $\gamma F_{rad}$ provides stability of both said limits and, therefore, resists to relocation of the rod 120 from one limit to another one. One more force, which has to be taken into account, is passive force $f_{att}$ of static attraction between permanent magnet 114 and ferromagnetic core of electromagnet 115. Sharp dependence of passive attracting force $f_{att}$ on the distance and, correspondingly, on said angle γ is demonstrated by dashed-dotted line 132 in FIG. 24b. One can see that in vicinity of the right limit only resisting force 131 plays main role, thus preserving stability of inactive state of the device. However, in vicinity of the left limit said passive attraction can make the main contribution into stability of the left state. Finally, in this example of the system 14 full static tangential force applied permanently to the rod 120 depends on momentary angular position of said rod as a sum of both curves 131 and 132, said sum shown in FIG. 24b by a curve 133.

In accordance with some embodiments, the starting signal sent by processor 17 turns the power supply 130 on so that short voltage pulse is applied to the coil of electromagnet 115. At this moment additional time-dependent tangential switching force $F_{sw}$ appears which pulls primarily permanent magnet 114 and the shuttle 119 in order to cause the rod 120 to relocate in left direction. One can pay attention that the curve 134 in FIG. 24b is negative and relates to angular dependence of repulsing switching force $F_{sw}$. However, it was explained before that simple change of the polarity can transform the repulsion into attraction. That is why there is no need to provide separate curve reflecting a positive force $F_{sw}$ producing attraction of magnets 114 and 115 because positive force $F_{sw}$ differs from the curve 134 by the sign only with no change of the shape. Given that one can easily use the curve 134 to get the sum of short-term positive force $F_{sw}$ and said static tangential force 133 in order to obtain final short-term force acting while said first pulse. Said final force is represented by the curve 135 in FIG. 24b, wherein black arrows show how the rod 120 travels from its right stable position to left one. One can see that the curve 135 is positive in full range of available γ. That means that created shortly by electromagnet 115 additional (for example, positive) magnetic field is capable of temporary converting stable right position of the rod into unstable one.

FIG. 25 demonstrates with white thick arrows where pulse voltage is applied to, and how parts of the system are moving during this fast change of rod's position. For the aim of an example only it should be noted that typical transition time doesn't exceed 0.05 s and can be in certain embodiments as short as about 0.02 s. Image depicted in FIG. 25 corresponds to the state of the device obtained immediately after the left limit is reached. At this moment actual fluid delivery starts and the power supply 130 is turned off as soon as possible in order to conserve the battery. The left part of curve 133 in FIG. 24b shows that the force stabilizing whole system near its left limit is high enough even if electromagnet 115 is deactivated.

Those skilled in the art can appreciate that jump-like transition disclosed in the previous paragraph results in immediate transfer of said substantial radial force $F_{rad}$ from the right shoulder of the lever 123 to its left shoulder as shown in FIG. 25. A certain part (for example, 70% or about) of said radial force is further transmitted to mediatory magnetic element 128 which already contacts with force receiving element, namely piston 78, located in the replaceable cartridge. The piston 78 receives this jump-like force and transforms it to compressing force applied to the fluid in section 8 of the reservoir so that the pressure in section 8 jumps up immediately. However, it has to be stressed here that, due to high non-zero resistance $R_1$ of the element 5 and high resistance $R_0$ of the element 33, said $R_0$ exceeding $R_1$ when said compressing force is applied (see the explanation in the section A), the fluid cannot leave the section 8 too fast. That is why after the system 14 gets its left stable state shown in FIG. 25 the substantial radial force $F_{rad}$ constantly produced by compressed spring 122 can cause only slow movement of the shuttle 119 along the rod 120 so that gradual clockwise rotation of the lever 123 allows to keep practically constant force transmitted from mediatory element 128 to force receiving element 78 during the time of slow sinking of the piston 78 into compression section 8 (see FIG. 26 wherein important forces are shown with thick black arrows and slow movement of parts of system 14 is shown with thick white arrows). That explains why the compressing force applied to the fluid by means of latch-type driving force system 14 (said compressing force resulting in urging the fluid out of the reservoir), is a continuous force capable of holding practically constant increased pressure in the compression section 8 up to the moment $t_{end}$ when the processor sends terminating signal to the system 14. At this moment $t_{end}$ the power supply 130 is turned on again so that the polarity of short-term voltage pulse applied to the coil of electromagnet 115 is opposite to the polarity of the first pulse produced at start moment described above. Correspondingly, now repulsing switching force produced by electromagnet is represented by negative curve 134 in FIG. 24*b*. Final pulse-like force is represented by curve 136 in FIG. 24*b* which is a sum of curves 134 and 133. It shows that now the left position becomes temporary unstable whereas the right position remains stable. It has to be appreciated that now activated electromagnet 115 pushes the rod 120 to make fast transition from unstable left state to the stable right state shown in FIG. 23. Said radial force of compressed spring becomes again applied to the right shoulder of the lever 123 and turns this lever counterclockwise in order to pull the piston 78 out of the section 8 and return it into initial position before the cycle. Thus, the terminating signal of the processor 17 causes whole latch-type system 14 to return into initial state and to be prepared for the next cycle. The only last point should be reminded here that in present example related to the latch-type driving force system combined with advanced hydraulic system of second sub-family the returning of the piston 78 into initial position is always accompanied by certain insignificant expansion of the flexible diaphragm 76 which results in creation of temporary decompressing force applied to the fluid in the section 8. This decompressing force relaxes in time and disappears automatically when the pressure in the reservoir becomes equal external pressure.

One more note can be made related to a latch-type system 14 of the present invention. Because magnetic force is always equally applied to both permanent magnet and electromagnet it doesn't matter which type of the magnet is connected with the latch chosen to be a primary part capable of relocating from one stable state to another one. For example, in particular system considered above the permanent magnet can be fixed in the housing 21 whereas in this case the electromagnet must be connected somehow with either shuttle 119 or directly with the movable rod 120. In that regard any of two said approaches can be taken depending only on which one is more convenient from engineering viewpoint.

It can be appreciated that specific mechanism thoroughly described above is given as an example only. Disclosed general idea of latch-type driving force system 14 can be further improved on the basis of previously discussed design providing more effective usage of a magnetic field (see FIG. 22*d*). The improved and most desirable design of latch-type system 14 is depicted in FIG. 27 and FIG. 29, whereas a graphical explanation of its work is provided in FIG. 28. First of all it may be relevant to emphasize how the design of present example differs from previous one. The first important difference is that the shuttle 119 disclosed in previous embodiment is now removed, and the rod 120 surrounded by compressed spring 122 is replaced in present embodiment by a latch made in the form of flat lever 137 which is supplied with the wheel 127 capable of easy rotating and located on one end of said lever, whereas its another end is connected with the housing 21 by the axis 121 so that in the plane XY the lever 137 can change its angle γ relatively certain central axis C-C (see FIG. 27). Both lever 137 and the permanent magnet 114 are connected so that said magnet cannot move in radial direction but can move in any of two tangential directions either right or left. A disadvantage of previous design was that relatively long rod surrounded by relatively thick spiral spring was destined to move between two spatially separated limits and, therefore, occupied a lot of central space inside the housing of the actuating module. In contrast, said flat lever 137 having neither shuttle nor spring can be made of thin sheet of an appropriate non magnetic material and, correspondingly, conveniently deployed on the very bottom of thin housing 21 (see FIG. 8*c* for example) in order to preserve the space to deploy other systems over this lever.

Another difference is that in present example said permanent magnet is located between two fixed electromagnets, namely 115 and 117, in accordance with an idea shown previously in FIG. 22*d*. This difference provides two advantages: (i) increased efficiency of a usage of permanent magnetic field, and (ii) increased passive attracting force $f_{att}$ in vicinity of both left and right limits (see curve 138 in FIG. 28*a*) which is high enough to stabilize two locations of permanent magnet, namely its location in close vicinity of left electromagnet 115 and symmetric location near the right electromagnet 117. Correspondingly, the lever 137 firmly connected with the magnet 114 also has two stable states which can be switched only when electromagnets become active. Thus, in this particular embodiment there is no need to use compressed spring for creation of two stable states of the system 14. That is why the third important difference is that the stressed spring 122, creating said continuous compressive force transmitted to the force receiving element by the mediatory element 128, can be placed in most convenient location near the wall of the housing 21 as shown in FIG. 27 and FIG. 29. In present embodiment the stressed spring 122 is stretched so that pulling force is permanently applied to the right shoulder of the lever 123, said force depicted in FIG. 27 with thick black arrow. FIG. 27 depicts the system 14 in its stable inactive waiting state wherein the magnet 114 stays near left electromagnet 115. Those skilled in the art can appreciate that in this state of the system 14 the wheel 127 located on the lever 137 applies certain force to the left shoulder of the lever 123 (see thick black arrow in FIG. 27) in order to: (i) bring the mediatory element 128 into start position explained before, and (ii) compensate rotating moment applied to the lever 123 continuously by the stretched spring 122. Thus, FIG. 27 shows waiting state of the device before delivery cycle when both electromagnets are inactive and only decompressing force can be temporarily applied to the fluid in compression section 8.

In order to produce desirable quasi-rectangular change $\Delta P_{comp}(t)$, the starting signal of the processor 17 urges the power supply 130 (not shown in FIG. 27) to apply simultaneously short pulse-like voltages to both electromagnets 115 and 117. As a response left electromagnet produces expelling force 134 (left) whereas the right electromagnet produces pulling in force 134 (right), both said forces are simultaneously applied to permanent magnet 114 as shown in FIG. 28. It can be appreciated that resulting joint force 139 produced by both electromagnets is substantially higher than each said separate force, therefore it can exceed the force of passive attraction 138 which provides both stable states of the lever 137 and tries to prevent its relocation. Curve 140 in FIG. 28 represents the sum of all forces involved during application of voltage pulse. It can be appreciated that resulting curve 140 is negative in whole range of the angle γ and, therefore, the lever 137 jumps to its stable right position (see FIG. 29) because the left position of the lever 137 holding permanent magnet 114 becomes temporary unstable.

FIG. 29 shows that being in its right position the wheel 127 is out of contact with the left shoulder of lever 123 so that immediately after said relocation of the wheel 127 the stretched spring 122, permanently pulling the right shoulder of the lever 123, causes very slow clockwise rotation of said lever as shown in FIG. 29 with thick white arrows. Those skilled in the art can appreciate that certain percentage (for example, about 50% or more) of the force of stretched spring is transmitted to the mediatory element 128 established on the left shoulder of the lever 123. Force receiving piston 78 further transforms this jump-like force into the force continuously applied to the fluid in compression section 8 which results in pulse-like increase of the fluid pressure $\Delta P_{comp}(t)$. This pressure pulse continues up to the moment when the processor 17 sends terminating signal. At this moment the voltage having an opposite polarity is applied shortly to both electromagnets again so that short-term electromagnetic force having an opposite direction (see curve 141 in FIG. 28) appears and causes all parts of the system 14 to return to initial waiting stable state shown in FIG. 27. Correspondingly, after this back transition the cycle is over and the pressure change $\Delta P_{comp}(t)$ can relax to its initial low value.

In this particular example of advanced latch-type driving force system 14 its design can be further improved if the mechanism shown in FIG. 27 and FIG. 29 is also supplied with optional springs 142 and 143. A purpose of these springs is to compensate certain part (for example, at least 40% and not more than 80-90%) of said passive attracting force which can be too high in vicinity of both stable states of the system (see curve 138 in FIG. 28). Being compressed the springs 142 and 143 produce additional repulsing forces 144 and 145 correspondingly shown in FIG. 29. Said additional forces help to: (i) increase effectiveness of both electromagnets in the beginning of relocation of the lever 137 (see resulting curves 146 and 147 in FIG. 29 replacing curves 140 and 141 correspondingly), and (ii) make more soft landing of the lever 137 in the end of its relocation. In order to inform the processor 17 about actual position of the lever 137 (see optional arrow 27 in general FIG. 3), an elements 148 and 149 fixing said optional springs in the housing 21 can be also supplied with appropriate detectors, for example, end switches or alike.

Two embodiments comprising latch-type system 14 considered above provide exceptionally high energetic effectiveness. For quantitative example, compressing driving force produced by permanently stressed spring 122 during the delivery cycle and applied continuously to both said mediatory element 128 and said force receiving element (piston) 78 can be as low as about only 0.03 Kgram in order to create pulse-like pressure increase $\Delta P_{comp}(t)$ about 0.3 Kgram/cm$^2$ if the piston 78 has low diameter about 3.5 mm previously discussed in A-section of present description. In order to squeeze out typical basal dose about 10 mm$^3$ of insulin solution the displacement of the piston during the cycle has to be about 1 mm. On the one hand, this distance is so high that there is no need to manufacture any part of whole system with a precision in either micron or sub-micron range. On the other hand, the same distance is so low that said slow piston's displacement requires as low mechanical energy as only about 0.0003 Joule. At the same time, the minimum switching force $F_{sw}$ required for relocation of latch-type system from its one stable state to another one can be as low as about 20% of said force stressing the spring 122 if the range $\Delta\gamma$ is chosen to be about 0.2 or less. Therefore, magnetic parts of the system 14, including at least one permanent magnet and at least one electromagnet, can be designed so that the passive attracting force $f_{att}$ is only about 3 Grams (which is enough to provide both highly stable states) whereas short-term switching force $F_{sw}$ can be chosen about 10 Grams to overcome reliably both $f_{att}$ and certain friction which is inevitably present in any mechanical system. Taking into account an expectation of rather small size of the actuating module 21 the wheel 127 has to be relocated while switching not more than 4-5 mm so that one switching process requires mechanical energy not more than about 0.0005 Joule, and two consecutive switches constituting one delivery cycle require not more than 0.001 Joule. Now it is time to remind that latch-type driving force systems consume electric energy only while very short switching time as low as in between 0.02 s and 0.05 s. That is why well designed combination of one or two electromagnets with strong permanent magnet can transform electric pulses into said mechanical energy with high efficiency exceeding 1% so that one delivery cycle requires only about 0.1 Joule electric energy or less, whereas one day consumption includes typically 100 cycles and, therefore, requires electric capacity about 10 Joules or less. Taking into account that even rather small coin-like lithium battery (for example, 16×3.2 mm) is typically charged with electric energy about 500 Joule, it can be appreciated that the advanced devices of the invention supplied with both latch-type system 14 and couple of said batteries can work longer than three months before batteries have to be replaced or recharged. Said battery's life-time of present invention is approximately 5-10 times longer in comparison with typical motor-driven devices described in prior art. Another advantage of magnetically driven latch-type system described above is that all its parts need to move in XY plane only and can be made so thin that their Z-thickness doesn't exceed 4-5 mm. Correspondingly the housing 21 comprising such latch-type system can be made as thin as about 7 mm or less. However, it has to be appreciated that all quantitative estimates disclosed in present paragraph are provided for the aim of example only, and even better particular parameters are possible as well.

It can be appreciated that advanced devices of present invention comprising latch-type driving force system 14 can further comprise additional means providing a patient with an ability of manual switching between two previously mentioned stable states of said latch-type system. This feature can be extremely important for patient's safety in certain emergency cases, because there is always certain low probability of critically strong malfunctioning of the system 14 controlled by the processor 17. Said low probability malfunctioning can be caused by either low battery, or broken power supply 130 capable of applying short-term voltage pulses to switching electromagnets, or even pure mechanical reasons including but not limited to internal dirt or damage caused by improper exploitation of the device by unskillful user. External mechanical control over the system 14 can be also desirable from time-to-time even in certain cases of properly working system 14 when a patient decides to correct specific cycle of the fluid delivery without disturbing main program stored within the processor. For example, if patient wishes, one or more extra delivery cycles can be added manually between two other preprogrammed cycles. In other cases even current preprogrammed delivery cycle can be interrupted manually if patient's health requires to do so. In both cases considered above, namely either patient's decision or technical problem, the manual operation allows to supply the patient with at least minimum amount of the drug necessary to save his or her life at least up to the moment when either technical or medical help is provided to this person.

A mechanism providing such mechanical control comprises a manual switch between said two stable states of the latch, said manual switch represented by flat lever 71 having complicated configuration and fixed in the housing 21 with the help of an axis 150. In FIG. 27 and FIG. 29 the manual switch 71 is shown in central neutral position, in which both fingers 151 and 152 of the lever 71 do not disturb automatic relocation of the latch lever 137. It can be desirable that for better safety of a patient the lever 71 is hidden under the lid of battery compartment 69 as shown in FIG. 8 in order to prevent accidental involvement of manual operation mechanism when it is not required. However, when manual operation becomes desirable said lid 69 can be opened to make the lever 71 available for patient's finger 4 as shown in FIG. 30. Top view of FIG. 30 assumes that before manual operation the lever 137 has been in left stable state corresponding to inactive waiting state of driving force system. It shows also that the end of lever 71 can be shifted down from its neutral position by one move of the finger 4. The result of this first shift is that left finger 151 of the manual switch makes the lever 137 to relocate to another stable state corresponding to activation of delivery process. Thus, said first move results in manual starting of an ordinary delivery cycle. Actual moment of said starting is always automatically recorded by the processor 17 due to either sharp changing in time output signals received from sensor system 16, or direct output signal received from end switch 149 (not shown in FIG. 30 for simplicity), or both. Accordingly to main method of the invention, the processor watches delivery process by acquiring output signals of the system 16 and determines the terminating moment $t_{end}$ when actual dose delivered is expected to be at least approximately equal one-time preprogrammed dose. At said terminating moment the processor initiates either visual signal (preferably performed at remote control module if it is in use), or mechanical vibrating signal, or an acoustic signal, or any simultaneous combination of said signals produced by emergency system 34 (see FIG. 3). Any of said signals is destined to be accepted by the patient as a recommendation to terminate current delivery cycle manually. Bottom view of FIG. 30 shows that just after receiving of said recommending signal the second move of patient's finger 4 shifting the switch 71 in opposite direction causes the right finger 152 to return all parts of the system 14 in their initial inactive stable states. Thus, after the second manual action the delivery process is stopped and desirable dose of the drug is received by the patient. Similar manual cyclic operation can be repeated as many times as necessary or desirable. It can be appreciated that in the case of manual operation the precision of dosing may be a little bit less in comparison with automatic operation due to typical human's reaction can be about 0.1-0.2 s instead of automatic time resolution about 0.02-0.05 s mentioned before. However, notwithstanding slightly decreased precision the device in manual operation mode can save patient's life at critical circumstances when there are no other means to help him or her.

Examples of invented latch-type driving force system, provided in present section of the description, show that more advanced devices of the invention supplied with said system can have exceptionally low power consumption. Because of the simplicity of mechanical design these devices can also be extremely reliable in long-term usage, low cost and simple in manufacturing because of the absence of costly high precision parts. One more interesting and useful feature can be achieved in certain embodiments comprising said latch-type system 14 if both the mediatory element 128, related to driving force system. and the piston 78, which is a force receiving element and inseparable part of the hydraulic system (see FIG. 12 for example), comprise strong permanent magnets oriented so that both said magnets repulse each other strongly when the replaceable cartridge 20 is connected with the housing of the actuating module 21. In the case of said orientation of both said permanent magnets a force applied by the driving force system 14 to the mediatory element is further transmitted remotely to said force receiving element. This design excludes completely a necessity to bring the mediatory element 128 in mechanical contact with force receiving elements 78. The idea of remote force transmitting is based on strong dependence of repulsive magnetic force on the distance between properly oriented magnets. When the system 14 is in its inactive waiting state, said distance can be made so high that low repulsive force is fully compensated by previously mentioned spiral spring located between limiting ring 80 and the lid 8b (see FIG. 12 and explanation in the A-section of a hydraulic system). Therefore, no compressing force can be applied to the fluid in said inactive state. When delivery cycle starts the system 14 moves mediatory element 128 ahead as explained before, and makes the distance between magnetized elements 78 and 128 shorter. Correspondingly, the force of magnetic repulsion increases enough to overcome resisting force of said spiral spring. Since this moment the piston 78 can begin its slow movement into the section 8 and apply compressing force to the fluid in the reservoir so that desirable pulse-like pressure increase $\Delta P_{comp}(t)$ is created. However, due to said movement is very slow all parts involved obey laws of static mechanics and, therefore, the open gap between elements 78 and 128 cannot be completely removed because, in accordance with said static laws, magnetic repulsing force is not allowed to exceed constant force created by the lever 137 which holds the element 128. Practically constant compressing force continues for whole cycle because elements 78 and 128, repulsing each other, are slowly moving together in the same direction thus keeping constant open gap between them. When the delivery cycle is over, the system 14 returns magnetized mediatory element 128 into its initial position. The distance between elements 78 and 128 increases sharply and said repulsive force drops so that said spiral spring can expel piston 78 out of the compression section 8, thus creating temporary decompressing force discussed before. It may be relevant to stress one more time that in the case of remote transfer of the force from the housing 21 to the housing 20 described in this paragraph the force applied to the fluid is not equal the driving force applied by the system 14 to mediatory element 128. Actually, the force created by the system 14 is transformed somehow into another force applied to the fluid in the section 8 of the reservoir.

The advantage of this example is that in such particular case neither window 59 nor window 60 are actually required if housings 20 and 21 are made of non magnetic materials transparent for magnetic field. Such design, excluding mechanical interaction of the mediatory element with force receiving element, avoids the window 60 and allows to make the housing 21 of the actuating module fully hermetic in order to avoid penetration of both a dust and a moisture inside. The absence of the window 59 makes the housing 20 more protected against unskillful user. These features improve the safety and provide longer life-time of non-disposable part of the device.

Examples of different driving force systems 14 discussed above provide evidence that the pulse-like pressure change in the fluid, filling the compression section of the reservoir, can be achieved with multiple choices of different mechanisms and materials. Each particular choice may depend first of all on how other parts of the device are designed and what technical demands are to be satisfied in given specific application. However, it should be appreciated that the general teachings of the present invention do not depend on the technical peculiarities of the system 14 if the real shape of the time-dependent pressure pulse $\Delta P_{comp}(t)$ produced by this system is close enough to the ideal shape anticipated by the preprogrammed algorithm of the processor. In the next sections of this description preprogrammed algorithms of certain devices are based preferably on quasi-rectangular shapes of $\Delta P_{comp}(t)$, whereas other devices can be suitable even with relatively unpredictable shapes $\Delta P_{comp}(t)$ which may be very different from quasi-rectangular ones.

E. Methods for Programmable Drug Delivery: General Points

Here, it may be relevant to recapitulate a few points which apply to certain versions of the invention. Hereinafter, any current cycle of the fluid delivery will, in this section, be called simply "the cycle" for brevity. Processor 17 has its internal electronic clock providing real time synchronization of all operations of the current cycle, including measurements, sending and/or receiving all service signals, mathematical operations, and so on. That means that the processor's memory stores a reading of the real time corresponding to preprogrammed moment $t_{st}$ of the beginning of current cycle. Real time $t_{st}$ of the processor's algorithm operates with local time starting at t=0. That is why processes and operations related to this cycle are represented below in terms of local time t≥0, and the preceding period is denoted as t<0. Because the processor remembers the start point $t_{st}$, it can correlate the local time t of the cycle with running readings of the real time when such correlation is necessary.

Also at t<0 driving force system 14 keeps the compressing force, which can cause the fluid to be squeezed out, about the zero so that both the exit opening of the device and the fluid inside the reservoir are subjected to about the external pressure $P_{ext}$. Thus, at t<0 the elastic element 10, involved directly in producing output signals of the sensor system 16, is not stressed and only its non-disturbed geometric parameter (or parameters) are reflected by the output signals during this time. It can be appreciated that due to unpredictable temperature changes, aging of materials, and other similar processes, the physical properties of both the elastic element 10 and sensing elements of the system 16 can slowly drift with time. For better precision it may be desirable that at t<0 the processor automatically acquires signals S(t) from time-to-time, for example, one signal per min, and remembers the last signal received before t=0. This last signal is denoted hereinafter as S(0). Due to drift, processes are very slow and the S(0) represents the actual starting state of both the element 10 and sensing elements of the system 16 at the moment t=0. That means that only the difference [S(t)–S(0)] can correctly reflect change of the indicator's volume caused by the appearance of non-zero squeezing-out force. However, as an approximation, the value S(0)=0 can be used, thus converting the long expression [S(t)–S(0)] to the shorter form S(t).

It can be appreciated by anyone skilled in the art that the fluid delivery of the present invention includes a preliminary step, namely a connection of the pre-filled replaceable cartridge with the housing of the actuating module in order to prepare fully assembled device for the delivery process. Preliminary step has to be performed one time only when a new replaceable cartridge is to be installed. Methods of said connections have been already described in many details so that there is no need to discuss this matter again. At the same time particular details of invented methods of cyclic fluid delivery, following after said preliminary step, must be considered thoroughly. The first step in the delivery process is the initiating non-zero compressing force resulting in squeezing the fluid out of the reservoir. (Hereinafter it is assumed that words "compressing force" and "squeezing out force" have the same meaning in frameworks of the present invention). It occurs at local time t=0 as determined by the processor in accordance with preprogrammed delivery instructions. If desired, for example in the case of an emergency, the moment t=0 may be also defined by personal actions of a patient using either the buttons 109 located at actuating module, or the control panel 38, or emergency lever 71 if it is available in particular device.

At t=0 the processor 17 produces at least one starting signal and transmits it to the system 14, which creates non-zero compressing force for time $T_{up}$, and applies this force directly to a portion of the surface area of the fluid located in the compression section of the reservoir. This leads to an increase of fluid's absolute pressure $P_{comp}$ in the compression section of the reservoir. The increase in pressure $[P_{comp}-P_{ext}]=\Delta P_{comp}(t)$ forces the fluid to flow out of the reservoir and, correspondingly, out of the exit opening at the beginning of the dosing process. Simultaneously the non-zero pressure difference $\Delta P_{ind}(t)$ occurs in the indicator section, which is used to control the entire process of the delivering the dose of drug.

The actual $P_{comp}$ achieved during each particular cycle may differ from the desired value determined by the processor's program. Taking this into account, it may be desirable that the compressing system 14 be capable of subjecting the fluid to excessive pressure within predetermined brackets $P_{max} > \Delta P_{comp}(t) > P_{min}$. The maximum value of the excessive pressure related to given cycle is denoted $P_0$. The actual value of this parameter can fluctuate from one cycle to another one even if the processor orders the same desirable value $P_0$. Because of the hydraulic connection of both compression and indicator sections, the pressure difference $\Delta P_{ind}(t)$ is also limited by pressure brackets similar to ones limiting $\Delta P_{comp}(t)$.

After initiation of $\Delta P_{comp}(t)$ the system 14 goes automatically into passive waiting mode that continues up to local time moment $t=T_c$. At this moment $T_c$ determined by the processor, the compressing system 14 receives the ending signal which orders the system 14 to terminate the compressing force over time $T_{down}$. It can be desirable that this time period be short. That means that between the starting and ending signals, the system 14 is not required to do anything what could change the non-zero compressing force creating both the excessive pressure $\Delta P_{comp}(t)$ and pressure difference $\Delta P_{ind}(t)$. Variations of the general method relate to actions performed by both the sensor system 16 and the processor 17 during period $T_c$ between said starting and ending signals. Actions occurring during $T_c$ comprise the second step of the general method, namely producing at least one, and alternatively more than one, output signal by the sensor system 16, and then acquiring said signals associated with at least one geometric parameter of the resilient element 10 of the reservoir 1 by programmable processor 17. Treating acquired signals by the processor performing a predetermined mathematical algorithm represents the third step of the general method. It results in determining a real time moment $t_{end}$ corresponding to the duration of the cycle $T_c=t_{end}-t_{st}$, which provides the dose actually delivered to the exit opening equal the desirable dose predetermined by delivery instructions. Actions constituting the third step of the general method will be specifically discussed later. The last step of the general method of the invention begins at local moment $T_c$ and instructs the system 14 to terminate the compressing force so that the excessive pressure $\Delta P_{comp}(t)$ either drops to about zero or, in some embodiments, drops temporarily below zero and then automatically relaxes to about zero. In any case, the result of this action is that the pressure of the fluid in the whole reservoir, including $\Delta P_{ind}(t)$, can return to about its initial value. Correspondingly, the last step of the method stops the flow of outgoing fluid flow and terminates the current cycle.

Because the invention incorporates both a motor-driven and a latch-type driving force system 14, methods of the operation can differ a little bit in these two cases. The reason for this difference is that in the case of syringe-based replaceable cartridge the electric motor of the system 14 must be controlled selectively in order to move the piston selectively and provide programmatically predetermined $P_0$. Moreover, the number of motor's steps done in the beginning of the cycle is to be different from the number of steps done in the end of the same cycle. The said assumes that in the case of motor driven system 14 both $t_{end}$ and $t_{st}$ signals must be accompanied by a set of certain secondary signals produced by either processor or motor's controller. In contrast, the latch-type driving force system 14 doesn't provide any selectivity in regard of either position or speed of piston's movements because this type of the system 14 possesses only two discrete stable states as described in section D. No additional signals must be sent to the latch-type system except said $t_{st}$ and $t_{end}$ t signals. That is why the general method of the invention used in combination with any latch-type driving force system must comprise following steps:

(0) preliminary step resulting in fully assembled device, wherein a replaceable cartridge comprising a pre-filled reservoir having both at least one element made of resilient material and at least one exit opening, is connected with a separable module capable of switching between two such stable states that only one of two said states results in a continuous compressing force applied to the fluid;

(1) switching said module at moment $t_{st}$ into such one stable state of two which results in said continuous compressing force;

(2) acquiring at least one signal associated with at least one geometric parameter of said resilient element;

(3) calculating a time $t_{end}$, comprising treating said acquired signal by a processor capable of executing commands based upon a predetermined mathematical algorithm; and (4) switching said module into another stable state of two at $t_{end}$.

The organization of the third step is worth further discussion. Because the fluid flows from the exit opening for time about $T_c$ the actual dose delivered during each cycle depends on both the duration $T_c$ of the squeezing-out force and actual magnitude of outgoing fluid flow F(t) which is also time-dependent. Determining the actual dose delivered to the exit opening is a responsibility of the processor using a predetermined algorithm to treat signals acquired during the cycle. An algorithm of the invention must take into account that in accordance with the equation (6) these signals always reflect time-dependent pressure difference $\Delta P_{ind}(t)$ in the indicator section of the reservoir. That is why the kinetics of the actual dose D(t) expressing its dependence on the time can be represented mathematically as:

$$D(t) = \int_0^t F(t)dt = \int_0^t \frac{\Delta P_{ind}(t)}{R_{exit}} dt \quad \text{(Eq. 9)}$$

where the parameter $R_{exit}$ has been defined before (see Eq. 5). The equation (9) gives a universal mathematical approach applicable to all devices of the invention wherein the flow passage 12 communicates hydraulically with the indicator section 9 as shown in FIG. 3. In other words, a major algorithm of the invention considers the actual dose delivered to the exit opening as a time-dependent integral found by integrating over time since the moment $t_{st}$ of a ratio, wherein the numerator is the pressure difference $\Delta P_{ind}(t)$, and the denominator of the ratio is a certain parameter expressing output hydraulic resistance $R_{exit}$ of hydraulic means 12 connecting the reservoir with the exit opening. In certain simple embodiments having no pressure-dependent elements in the flow passage the constant parameter $R_{exit}$ can be considered as certain time-independent constant. In other cases of some more advanced embodiments, comprising passive valve in the flow passage, the resistance $R_{exit}$ may be time-dependent parameter. For example, it may be very high during certain relatively short time intervals when said valve remains in its closed state. Correspondingly, the algorithm of the invention takes into account that such intervals provide zero contribution into the integral defined in the equation (9).

When the dependence of the actual dose on the time D(t) is determined according to Eq. 9, an algorithm of the invention further compares D(t) with the predetermined dose $D_0$ in order to find proper $T_c$ needed to provide the proper dose delivered. The actions listed above are common for all methods of the invention, and only details of some actions can be performed differently in different devices. In that regard one can note that in some embodiments the kinetic features of the pressure difference $\Delta P_{ind}(t)$ in the indicator section may be different from those of excessive pressure $\Delta P_{comp}(t)$ in the compression section of the reservoir. In order to take this circumstance into account, a few different algorithmic versions are considered below. The specificity of each particular algorithm is focused on two following matters: (i) how the integration procedure is performed, and (ii) what information source is used in order to determine the parameter $R_{exit}$ substituted into the denominator of the Eq. 9.

Devices of the present invention may be subdivided in three groups representing different technical designs, namely simple devices, more advanced devices, and most advanced devices. Correspondingly, the third algorithmic step of the general method of the invention contains specific operational details and additional features related only to each particular group of the three. It may be reasonable to begin the description of these specific features from the method related to simple devices, and then to consider more advanced versions.

F. Methods for The Drug Delivery Executed by Simple Devices

A simple algorithm useful in the operation relates to the group of simple devices built in accordance with previously mentioned condition $0.05\ R_2 > R_1$. In this case the fluid has approximately the same pressure in both sections 8 and 9 of the reservoir 1, and both diagrams of elevated pressure $\Delta P_{comp}(t)$ and $\Delta P_{ind}(t)$ coincide with a precision better than 5%. Before the beginning of the work, the programmable processor of any simple device must contain the value of the resistance $R_2$ which is factory pre-set constant coinciding with the output resistance $R_{exit}$ at least in the beginning of the work of the device. Correspondingly, the processor considers pre-set $R_2$ as output resistance $R_{exit}$ and substitutes this value into the denominator of the Eq. 9. Because preliminary factory calibration any replaceable cartridge is to be supplied with the information regarding constants $R_2$, α, and β related to this particular cartridge only. It is responsibility of a user to use control means 18 or 38 in order to enter these constants into processor's system of the device when new cartridge is to be installed. Simple devices can neglect parameter $R_1$ due to it is very low. In accordance with the equation (1) the knowledge of the resistance $R_{exit}$ provides knowledge of the magnitude of the fluid flow delivered by the simple device to the exit opening at any time moment t during full time $T_c$ of the cycle. This magnitude is expressed as follows:

$$F(t) = \Delta P_{comp}(t)/R_{exit} = \Delta P_{ind}(t)/R_{exit} = \Delta P_{ind}(t)/R_2 \quad \text{(Eq. 10)}$$

where both equalities $\Delta P_{comp}(t) = \Delta P_{ind}(t)$ and $R_2 R = R_{exit}$ are taken into account. Now the right-hand part of the equation (10) can be substituted into general equation (9) and calculated by the processor with the use of an appropriate algorithm providing the integration. Because the processor acquires the signals S(t) reflecting the kinetics of the pressure change $\Delta P_{ind}(t)$ in accordance with the equation (6), one obtains the final expression which shows the relationship between the output signals of the sensor system and the actual dose D(t) of the fluid delivered by any simple device of the first group at any moment t>0 of the cycle:

$$D(t) = \frac{1}{R_{exit}} \int_0^t \Delta P_{ind}(t) dt = \frac{\alpha\beta}{R_2} \int_0^t S(t) dt \quad \text{(Eq. 11)}$$

It does not matter in this particular example whether the section 8 is made in the traditional form of the syringe made completely of hard materials (see FIG. 9*a* for details) or it comprises at least one elastic element similar to resilient diaphragm 76 (FIG. 9*b* and/or FIG. 12) which may be compressed or expanded by any appropriate means. All that is used is the relationship between the stiffness parameter $\alpha$ of the expandable indicator 9 and other parameters of given device. Taking into account that both the amplitudes of the pressure pulses $P_0$ created by the system 14 and the desirable doses of the fluid $D_0$ may vary in different cycles, only average values of $P_0$ and $D_0$ are used to answer quantitatively whether the parameter $\alpha$ is low or high. The parameter $\alpha$ relates to the change of the indicator's volume, which in accordance with the equation (4), can be expressed as: $\Delta V_{ind}(t)=\Delta P_{ind}(t)/\alpha$. The average value $P_{avr}$ substituted into this expression instead of $\Delta P_{ind}(t)$, provides the average volume change $\Delta V_{avr}$ which must be further compared with the average fluid dose $D_{avr}$. Two different cases may exist according to results of this comparison, and, correspondingly, two different approaches are considered below. Note, that due to previously mentioned specific condition of the first group of simple devices $0.05\ R_2 > R_1$, the parameter $\alpha$ relates to full volume of reservoir 1 even in the case if the reservoir is supplied with both the resilient element 10 and another resilient element like, for example, elastic diaphragm 76.

F-1. Method for the Case of Low Stiffness Factor of the Reservoir

It follows from the above that in a simple device of the first group the value of the parameter $\alpha$ is considered to be low when the condition $\Delta V_{avr} \gg D_{avr}$ is fulfilled. This condition means that during cycle time $T_c$ combined volume of the indicator section and the compression section of the reservoir loses only a small part of its expanded volume $\Delta V_{avr}$, and, accordingly, the elevated pressure inside the reservoir remains relatively constant during $T_c$. This situation is reflected in both quasi-rectangular diagrams shown in top view of FIG. 19. Due to the relatively constant $P_0$ of each selected cycle, the equation (11) has a linear solution represented by the equation (12) below and shown in bottom view of FIG. 19, because neither pressure pulse $\Delta P_{ind}(t)=P_0$ in the indicator 9 nor output signals S(t) of sensor system 16 can change in the active period $T_{up} < t < T_c$. This statement is mathematically expressed with following equation representing the relationship between the actually delivered dose D(t) and the relatively constant value $P_0$ related to the pressure in the reservoir during the current cycle:

$$D(t) = \frac{P_0}{R_2}\left(t - \frac{T_{up}}{2}\right) = \frac{\alpha\beta S}{R_2}\left(t - \frac{T_{up}}{2}\right) \quad \text{(Eq. 12)}$$

In most cases of practical calculations the short transition time can be neglected if $T_{up} < t < T_c$. However, one can see that short transition time $T_{up}$ is taken into account in the precise solution represented by the equation (12). It also reflects the fact that even single reading S, provided by the sensor system 16 at any voluntary chosen moment within the interval $T_{up} < t < T_c$, can be enough to determine both the constant excessive pressure $P_0$ created during the current cycle and the function D(t), representing the actual dose delivered.

Equation (12) can be used for obtaining an expression that predicts the final moment $T_c$ corresponding to the equality of the dose actually delivered D(t) and the desirable dose $D_0$ predetermined by the delivery program. A prediction of the final time-point results from the comparison of calculated function D(t) with the desirable dose, as follows:

$$D_0 = \frac{R_2}{\alpha\beta S} + \left(\frac{T_{up} - T_{down}}{2}\right) = T_c \quad \text{(Eq. 13)}$$

Therefore, the conclusion is that, in the case of low stiffness factor $\alpha$ of the expandable elements of the reservoir, the processor is only required to acquire at least one signal from the sensor, and this is enough to accomplish the entire task related to the third step of the general method of the invention. Both the signal acquisition and the following mathematical prediction provided by the equation (13) must be complete at the time $t \le T_c$. The diagrams in FIG. 19 demonstrate that the shortest cycle time $T_c$ cannot be less than minimum time $1/f_0$ required to take one reading of the signal S and to process it. The algorithm based on the equation (13) does not require very high frequency $f_0$. For example the $f_0$ about 1 Hz may be enough.

The calculation of the predicted time $T_c$ means the end of the third step of the method. However, this calculation takes only time $1/f_0$ which is normally shorter than $T_c$. That is why in the case of simple devices having low parameter $\alpha$, the beginning of the last step requires performing additional actions. After the moment $T_c$ is calculated, the processor must wait for the moment of the real time corresponding to the predicted, $T_c$. Only when such moment of the real time is detected the processor sends the terminating signal to the system 14. It may be desirable that the decrease of the pressure in the reservoir occurs in a short time $T_{down} \ll T_c$ so that final relaxation process does not contribute significantly into the precision of the dose delivered. However, the predicting equation (13) shows that this precision can be additionally improved if both transition times $T_{up}$ and $T_{down}$ are known in advance as factory pre-set parameters.

Two dosing diagrams shown in bottom view of FIG. 19 demonstrate how the correct determining of $T_c$, predicted by the equation (13) for simple devices having low parameter $\alpha$, provides stable dosing of the fluid notwithstanding rather high variations of the amplitude $P_0$ of the pressure pulses produced in two different cycles.

F-2. Method for the Case of High Stiffness Factor of the Reservoir

In some embodiments a simple device, considered in the section F-1, may become a device with relatively high stiffness factor $\alpha$ related to expandable elements of the reservoir. For example, this may happen in an emergency situation when a patient needs to increase the dose of the drug many times so that desirable $D_0 \gg D_{avr}$. The result may be that new $D_0$ is comparable with $\Delta V_{avr}$ and previous condition $\Delta V_{avr} \gg D_0$ becomes not valid. In this case the reservoir may lose a substantial part of its expanded volume during the same cycle, and the plateau $\Delta P_{ind}(t)$ of the pressure pulse can become unstable in time as shown in top view of FIG. 20. The quantitative definition given above takes into account this situation where there is a high stiffness parameter α.

Other reasons may result in a high value α as well. However, independent on the particular reason, the previous predicting algorithm based on the equation (13) may not be ideal in this case of providing good precision of the drug delivery. The integral equation (11) is still valid even in this case. That is why in order to obtain the highest dosing precision, the processor should receive maximum information with as high frequency $f_0$ of measurements of signals S(t) as possible. In this case during the entire cycle the processor acquires more than one digital signal so that the actual integral dose may be represented by a discrete sum consisting of many members L(t)>1. White circles in the top view of FIG. 20 show multiple signals S(t) acquired in the case of an unstable process $\Delta P_{ind}$(t). With higher frequency of sampling, the more L(t) is obtained during the cycle, resulting in higher final precision based on the following integral equation:

$$D(t) = \frac{\alpha\beta}{R_2}\int_0^t dt\, S(t) \cong \frac{\alpha\beta}{f_0 R_2}\sum_{k=1}^{L(t)} S(t_k) = D(t_L) \qquad \text{(Eq. 14)}$$

This equation tells that the calculated sum $D(t_L)$ depends on the number L(t) of acquired signals as shown by black circles in the bottom view of FIG. 20. In order to determine the final moment $T_c$ one algorithm directs the processor to repeat the following cyclic real time operations starting from the number L=1: (i) the sum $D(t_L)$ is calculated first in accordance with the equation (14); (ii) then the difference $\Delta D(L) = D_0 - D(t_L)$ is calculated; (iii) if the $\Delta D(L)$ obtained at given L is positive then the processor adds 1 to the present L and returns back to the step (i) thus repeating the same cycle until $\Delta D(L) \leq 0$. The moment $T_c$ corresponds to such $t_L$ when the condition $\Delta D(L) \leq 0$ is fulfilled the first time. At this moment the third step of the method is complete and the processor begins to fulfill the last step terminating the cycle.

Comparison of equations (12) and (14) shows that in the case of simple devices the integral constituting the numerator of the ratio in Eq. 9 is proportional to the sum of all signals S(t) acquired while $T_c$ independent on whether factor α is low or high. In the first case an advantage of the equations (12) and (13) related to low α is that this sum may contain the only signal. However, the advantage of last algorithm, related to high α and comprising multiple measurements and summation of more than one signals S(t) acquired, is that at L>>1 applicability and high precision does not depend on the exact kinetic shape of the pressure difference $\Delta P_{ind}$(t). This means that in addition to spontaneous fluctuations of $P_0$, the shape of each pressure pulse is also allowed to be rather far from an ideal quasi-rectangular form. Moreover, in this case even the condition $T_{up} \ll T_c$ is not mandatory. Therefore, the system 14 forming pulses $\Delta P_{ind}$(t) may be made extremely simple and cheap. The present description of the simple algorithm of digital integration is provided as an example only. Anyone skilled in the art of mathematical treatment of digital signals knows how the precision of such algorithm can be further improved if one uses the first and highest derivatives calculated from the same sequence of measured signals S(t).

At the same time the major disadvantage of whole first group of simple devices of the invention is that the simple algorithms and their operation are not capable of self-control in regard to accidental or slow long-term changes of internal parameters of the whole delivery system. For example, the descriptions in both sections F-1 and F-2 assume that the exit hydraulic resistance $R_{exit}$ is stable in time and equal pre-set $R_2$. In order to control potential occlusion, such devices must be equipped with additional sensors. This problem is addressed by more advanced methods of operation applicable to more advanced and most advanced devices discussed below.

G. Methods for Drug Delivery with More Advanced Devices

Additional embodiments of the invention represent combinations of more advanced methods and devices of the invention wherein relationships of a few basic parameters, such as resistances $R_1$ and $R_2$, the stiffness factor α of the indicator, and the highest frequency $f_0$ of a sensor's signal acquisition satisfy one or more of a few additional requirements described below. One additional feature is that both resistances $R_1$ and $R_2$ can be represented by corresponding quantitative equations containing given ratio $\alpha/f_0$ as follows:

$$R_1 = n\alpha/f_0 \text{ and } R_2 = m\alpha/f_0 \qquad \text{(Eq. 15)}$$

where both n and m may be chosen positive numbers exceeding 1. The fulfilling of the first condition (15) is desirable in order to bring the rate $f_0$ of signal acquisition in accordance with an algorithm treating these signals. However, in order to obtain improved performance of devices of the second and the third groups, a second additional requirement provides desirable relationships of these numbers:

$$\frac{n}{m} \geq \frac{1}{m-1} \qquad \text{(Eq. 16)}$$

In simple words the condition of Eq. 16 tells that improved performance of devices of the invention requires that a ratio $R_1/R_2$ cannot be too low and must exceed certain predetermined level considered below.

In order to increase the range of operating parameters of more desirable embodiments, it may be desirable that $R_1$ is close to $R_2$ by an order of magnitude, and at least $R_1$ is not less than about 0.05 $R_2$ and not more than about 200 $R_2$ because at higher $R_1$ the increased pressure in the indicator 9 can be not enough for precise measurements. It may be desirable that the ratio $R_1/R_2$ is between about 0.25 and about 40. Alternatively, it may be even more desirable that the ratio $R_1/R_2$ is between about 1 and about 10. For example, in accordance with linear hydraulic characteristics of both resistors shown in FIG. 11, one can choose $R_1 = 24\alpha/f_0$ (line (b) with n=24) and $R_2 = 7\alpha/f_0$ (line (a) with m=7), thus providing the ratio $R_1/R_2$ close to about 3.5. It can be demonstrated that such particular choices, satisfying both conditions (15, 16), is in the range suitable for detection of a potential occlusion. However, other combinations of n and m are permitted by the conditions (15, 16) as well, and may be used in different embodiments.

Similar to simple devices described above, other embodiments allow different choices of mechanisms applying the force to the fluid in the compression section of the reservoir. However, in many of these cases it may be desirable that any particular mechanism be capable of: (a) providing a short time $T_{up}$ of the first pressure transition so that $T_{up}$ corresponds to the limitation of the following equation at least by an order of magnitude:

$$T_{up} \ll \frac{n}{f_0(1+n/m)} \qquad \text{(Eq. 17)}$$

For example, fast latch-type system 14 providing transition time $T_{up}$ less than or about 0.02 s has to be used in order to be compatible with high frequency signal acquisition $f_0=50$ Hz if the same numbers n=24 and m=7 are chosen as in previous paragraph; (b) providing after a transition $T_{up}$ such pressure plateau $P_0$ in the compression section, which is relatively stable during the period $T_c$ of any delivery cycle; and (c) providing the ability to fulfill from time-to-time a special command of the controlling processor 17 resulting in the creation of the negative pressure change in the compression section of the reservoir during the special self-calibration procedure ordered by the program of the operation. To fulfill conditions stated above in the present paragraph, it may be desirable that the hydraulic system of the replaceable cartridge is similar to the one shown in either FIG. 9a, comprising the syringe made of hard materials and the only resilient element 10 located in the indicator section 9, or FIG. 7, FIG. 9b, FIG. 12, and FIG. 13 wherein the walls of the compression section of the reservoir are made at least partially of a soft material either resilient or not. Because embodiments discussed in this section are designed to use cartridges having substantially increased parameter $R_1$ in comparison with simple devices of the first group, a factory pre-filled replaceable cartridges are more desirable because they can reduce or eliminate the possibility of internal or external contamination and thus prevent any change of factory pre-set very stable resistance $R_1$, saved in the processor's memory as an individual parameter of each particular cartridge. In this case only some changes of output resistance $R_{exit}$ can be expected if the occlusion occurs. In order to highlight main features of methods related to second group of more advanced devices, the initial consideration assumes that most simple hydraulic system does not comprise any passive valve as shown, for example, in FIG. 7. Additional advantages of devices comprising such valves will be considered separately.

In accordance with features listed in the preceding paragraphs the diagram of the pressure change in the compression section of more desirable embodiment is represented by a well formed quasi-rectangular pulse exemplified by the top curve (a) in FIG. 31, which is similar to diagrams of simplified devices in FIG. 19. Diagrams of pressure change in the indicator section of certain desirable embodiments can differ substantially from those of simple devices, because now the fluid flow arrives at indicator 9 through the resistor 5 having high resistance $R_1$ and goes out through the flow passage 12 having the output resistance $R_{exit}$. In contrast to simple devices of the invention, in more complex embodiments, the parameter $R_{exit}$ can be considered according to the equation (5) taking into account certain external processes changing this parameter unpredictably. The algorithm of more complex methods takes also into account that both incoming and outgoing flows in the indicator section of the reservoir depend on time differently as it follows from exact equations considered below.

In accordance with equation (1) the magnitude $F_1(t)$ of the first fluid flow, arriving into the indicator after a short transition time $T_{up}$, may be expressed with the use of the resistance $R_1$ and the difference of absolute fluid pressures in compression 8 and indicator 9 sections. Also nothing can change if one adds and immediately subtracts the external atmospheric pressure. These mathematical operations, taking also the equations (3) and (4) into account, result in following equation which is valid at any time $t > T_{up}$:

$$F_1(t) = \frac{P_{comp} - P_{atm} + P_{atm} - P_{ind}(t)}{R_1} = \frac{P_0 - \Delta P_{ind}(t)}{R_1} \quad \text{(Eq. 18)}$$

At the same time the magnitude of the second fluid flow leaving the indicator section 9 and passing through the flow passage 12 is described by the following equation:

$$F_2(t) = \frac{P_{ind}(t) - P_{atm}}{R_{exit}} = \frac{\Delta P_{ind}(t)}{R_2 + R_3} \quad \text{(Eq. 19)}$$

where the additional output resistance $R_3$ is close to zero in the very beginning of the device's operation but it can increase spontaneously during long-term operation of the device. The reason for that may be an accidental damage of the flow passage, caused by unskilled user, or its occlusion either partial or insurmountable one.

It can be appreciated that the speed of volume expansion of the indicator section 9 is equal the difference of intensities of entering and exiting fluid flows. Both equations (18) and (19) allow transforming this statement into explicit form of the following differential equation where the equation (4) is taken into account as well:

$$\frac{d}{dt}\Delta V_{ind}(t) = \frac{d}{\alpha dt}\Delta P_{ind}(t) = \frac{P_0}{R_1} - \Delta P_{ind}(t)\left(\frac{1}{R_1} + \frac{1}{R_2 + R_3}\right) \quad \text{(Eq. 20)}$$

The inventor has found a rigorous solution of equation (20), which is valid during time period $0 < t < T_c$, and is provided by the following equation:

$$\Delta P_{ind}(t) = \frac{P_0}{\left(1 + \frac{R_1}{R_2 + R_3}\right)}\left[1 - \exp\left\{\frac{\alpha t}{R_1}\left(1 + \frac{R_1}{R_2 + R_3}\right)\right\}\right] \quad \text{(Eq. 21)}$$

At the same time the equation (6) shows that output sensor's signals S(t), reflecting the kinetics of solution (21), obey simple exponential law as follows:

$$S(t) = S^{(0)}\left[1 - \exp\left\{-\frac{t}{\tau_{act}}\right\}\right] \quad \text{(Eq. 22)}$$

where the first independently measurable parameter of every cycle is the amplitude $S^{(0)}$ of the exponential kinetic curve which is correlated with both the amplitude of the pressure increase in the indicator $P^{(0)}_{ind}$ and corresponding maximum expansion of its volume $\Delta V^{(0)}_{ind}$ expressed as:

$$S^{(0)} = \frac{\Delta V^{(0)}_{ind}}{\beta} \quad \text{(Eq. 23)}$$

$$= \frac{P^{(0)}_{ind}}{\alpha\beta}$$

$$= \frac{P_0}{\alpha\beta\left(1 + \frac{R_1}{R_2 + R_3}\right)}$$

$$= \frac{P_0 \tau_{act}}{\beta R_1}$$

The second independently measurable parameter is the actual value of time-constant $\tau_{act}$, related to the same cycle and defining the actual exponential kinetics. This time-constant is correlated with other parameters of more complex devices:

$$\tau_{act} = \frac{R_1}{\alpha\left(1 + \frac{R_1}{R_2 + R_3}\right)} = \frac{\tau_{oc}}{\left(1 + \frac{R_1}{R_2 + R_3}\right)} \quad \text{(Eq. 24)}$$

where the parameter $\tau_{oc}$ is to be considered now as the device's constant related to the state of an insurmountable occlusion and discussed in more details herein below.

Examples of exponential kinetics of signals S(t) recorded in different cycles are shown as curves (b), (c), (d), and (e) in bottom part of FIG. 31. When conditions of equations (15) and (16) are fulfilled, the pressure in the indicator section changes more slowly than that in the compression section of the reservoir. It has been unexpectedly discovered that the value $\tau_{act}$ does not depend on the pressure amplitude $P_0$. That is a reason why, even if driving force system 14 is very simple and can potentially cause wide variations of $P_0$ in different cycles, the measurements of $\tau_{act}$ can provide very precise information about the actual values of hydraulic resistance $R_{exit}$ of the flow passage at the time of each cycle, especially because the value $R_1$ is known and can be stable enough, especially in the case of fully disposable cartridges used for limited time about few days. Because of the mechanical nature of the parameter α, which must be factory pre-calibrated for every particular cartridge, it can drift in time only slowly because of very slow aging of the elastic materials. The complex methods of the operation of other devices include procedures for periodic self-calibration, which decreases or eliminates uncertainty related to potential drifts. This means that the exact value of α can always be known and stored in the processor's memory.

It can be appreciated that to determine the parameters of exponential kinetics of the equation (22), namely the parameter $S^{(0)}$ and $\tau_{act}$, at least two signals S(t) must be acquired and treated by the processor during the initial part of the exponential pressure change in the indicator section. The analysis of exponential curves is quite standard mathematical procedure which does not need to be separately discussed further herein. It can be appreciated that this procedure can be incorporated into mathematical algorithms of more complex embodiments. It also may be apparent that the precision of the determination of parameters of exponential curves may be further increased if the processor acquires and treats more than two signals S(t) during the time $T_c$. Examples of desirable discrete signals transferred to the processor are shown by white circles placed on curves (b) and (c) in FIG. 31.

It can be desirable that every time when a new replaceable cartridge is connected with the actuating module, and before the assembled device is connected with patient's body, a patient uses either control means 18 or means 38 and orders the processor to perform self-calibration of all internal parameters of the device except the resistance $R_1$ which is factory pre-set parameter. The start of self-calibration procedure requires that the sterile cap 153 (see FIG. 10 for example) is on in order to lock the exit opening of the flow passage 12 so that artificial situation of insurmountable occlusion takes place. In this case the output resistance $R_{exit} \approx R_3$ becomes so high indefinitely that $R_3 \gg$ both $R_1, R_2$.

Self-calibration procedure can be easier explained and understood if hydraulic system of assembled device have syringe-like reservoir shown in FIG. 7. Self-calibration begins at t 0 when the driving force system 14 fulfills the special signal of the processor and moves driving camshaft 15b in left direction (accordingly to this particular FIG. 7) so that substantial expansion of the compression section causes absolute pressure in the reservoir to drop to about zero. That corresponds to negative value $P_0 = -P_{atm}$, which is known rather well. All necessary corrections in regard of the fluid's vapor pressure and the altitude of current geographic point above the sea level can be easily calculated by the processor. After t=0 the pressure in the indicator section reacts exponentially (see curve (b) in FIG. 31) with the actual time-constant $\tau_{act}$ equal $\tau_{oc}$, which is a characteristic parameter of a given occluded cartridge. Simultaneously with the slowed-down exponential change of the pressure inside the indicator section, the processor acquires and treats as many discrete signals S(t) as may be necessary to be sure that this pressure reaches a high and stable value. This occurs at $t \gg \tau_{oc}$ when the exponential term in both equations (21) and (22) drops to zero and the content of their square brackets becomes equal 1. Multiple acquisition of signals S(t) allow high precision measuring of characteristic value $\tau_{oc}$ which is further saved in processor's memory. It also follows from the equation (21) that due to intentionally created situation $R_3 \gg R_1, R_2$ the change of indicator's pressure obtained at that time is equal $P^{(0)}_{ind} = P_0 = -P_{atm}$, whereas the corresponding maximum signal $S^{(0)}$ measured by sensor system is equal to: $-S_{atm}$. Both these measured values must be also saved in processor's memory.

After completing of all these actions, the processor's memory contains the following values: $R_1$, $P_0 = P_{atm}$, $S^{(0)} = -S_{atm}$ and $\tau_{act} = \tau_{oc}$ related to special case $R_{exit} \approx R_3 \gg R_1, R_2$ The immediate result following from the equation (24) is the determining the parameter α reflecting the stiffness of the indicator section of given cartridge at current moment of the time:

$$\alpha = R_1/\tau_{oc} \quad \text{(Eq. 25)}$$

The equation (23) may be used next to determine the parameter β as follows:

$$\beta = \frac{P^{(0)}_{ind}}{\alpha S^{(0)}} = \frac{P_{atm}\tau_{oc}}{R_1 S_{atm}} \quad \text{(Eq. 26)}$$

After that all constants of the device become known to the processor, and it orders the system 14 to restore normal pressure in the reservoir in order to complete the calibration. The customer can be promptly supplied with the personal information that the locking cap 153 can be now removed and the device can be connected with patient's body for normal operation. In the course of long-term operation, the customer may order the processor to repeat the self-calibration procedure while every installation of new disposable cartridge or even more often in order to correct the values of device's constants if potential long-term changes take place in the device. In the case of any abnormal behavior of the device the direct knowledge of changes occurring with separate values α and β may be very useful to detect easy and rapidly what has happened to the device. However, for normally functioning devices the knowledge of only two primarily calibrated parameters $S_{atm}$ and $\tau_{oc}$ are needed.

Normal processes of the drug delivery begin after completing the self-calibration when the cap 153 is removed and the exit opening 13 is brought in the contact with patient's body. In this case the first and the last step of the general method remain the same as they have been described in the section F-1 related to simple devices having low parameter α. The third step developed to operate more complex embodiments can use different predictive algorithms that calculate the expected moment $T_c$ corresponding to termination of the cycle. There are two reasons for that. The first reason is that, according to equation (24), the time-constant $\tau_{act}$ measured in each cycle reflects both the actual state of the delivery process and actual output resistance $R_{exit}$. Normally, in the very beginning of the operation there is no occlusion at all. So, initial $R_3 \approx 0$ and $R_{exit} = R_2$ in accordance with the equation (5). This corresponds to the lowest $\tau_{act} = \tau_{norm}$ and the lowest amplitudes of both the pressure $P^{(0)}_{ind}$ in the indicator and corresponding signal $S^{(0)}_{norm}$ as shown by the exponential curve (c) in FIG. 31. If during long-term operation (typically few days with one replaceable cartridge), a partial occlusion takes place, the $R_3 \neq 0$ any more, and the output hydraulic resistance increases so that $R_{exit} = R_2 + R_3 > R_2$. Correspondingly to that all $\tau_{act}$, $S^{(0)}$ and $P^{(0)}_{ind}$ become higher as the curve (d) shows in FIG. 31. This increase of $R_{exit}$ causes the decrease of the magnitude of flow $F_2$ exiting the device. However, in order to keep the dose constant, this decrease can be automatically compensated by corresponding increase of $T_c$ until $\tau_{act}$ calculated by the processor's algorithm is in the allowed range $\tau_{norm} \leq \tau_{act} < \tau_{oc}$. So, in this range, the device is capable of self-recovering partial occlusions, and there is no need to disturb a patient even in the case of modestly high occlusion. The unlikely event of the insurmountable occlusion shown by the curve (e) in FIG. 31 corresponds to the equality $\tau_{act} = \tau_{oc}$, where the value $\tau_{oc}$ is already stored in the memory. When processor's algorithm detects such equality, then it must stop further operation and produce an alarm signal informing a patient promptly. This explains the first reason why the mathematic algorithm of the more complex embodiments can desirably be very different from simple equations (13, 14) disclosed herein above. The equations provided below show examples of how a self-recovering algorithm can work and the correct $T_c$ can be determined.

It has been already mentioned before that at least two signals $S(t)$ must be acquired at the period $0 < t < T_c$. It can be desirable that measurements are made in a limited time period $0 < t < \tau_{oc}$ related to the beginning of each cycle, in order to obtain two actual parameters $\tau_{act}$ and $S^{(0)}$ corresponding to the current cycle in accordance with the kinetics of equation (22). When these measurements are completed, the kinetics (22) of outgoing fluid flow $F_2(t)$ is fully determined in the entire time period $0 < t < T_c$ as follows:

$$F_2(t) = \frac{\Delta P_{ind}(t)}{R_{exit}} = \frac{P_{atm}S^{(0)}}{R_1 S_{atm}}\left(\frac{\tau_{oc}}{\tau_{act}} - 1\right)\left[1 - \exp\left\{-\frac{t}{\tau_{act}}\right\}\right] \quad \text{(Eq. 27)}$$

Because of high resistances $R_2$ and $R_1$, the flow $F_2(t)$ does not stop immediately after the pressure drop occurring at the moment $T_c$, in the compression section of the reservoir. This delay occurs because the elevated pressure in the indicator remains non-zero for some while after $T_c$, and the fluid is moving exactly as it is shown in the bottom view of FIG. 2. The inventor has discovered that in the framework of hydraulic scheme shown in FIG. 3 the flow $F_2(t)$ decays after $T_c$ exponentially with the same time-constant $\tau_{act}$, which has been already determined before $T_c$, namely as:

$$F_2(t) = \frac{P_{atm}S^{(0)}}{R_1 S_{atm}}\left(\frac{\tau_{oc}}{\tau_{act}} - 1\right)\left[1 - \exp\left\{-\frac{T_c}{\tau_{act}}\right\}\right]\exp\left\{\frac{T_c - t}{\tau_{act}}\right\} \quad \text{(Eq. 28)}$$

This slow decay occurs at $t > T_c$ (see curves (b, c, d, e) in FIG. 31), and can contribute a substantial part of the final dose delivered to the exit opening. In order to determine the dependence of the final dose on the duration $T_c$ of the cycle, one can substitute each of two equations (27) and (28) into the general integral equation (9), to calculate each integral separately, and then to summating both integral equations. After summating these two integrals found analytically one obtains the following result:

$$D(T_c) = \frac{P_{atm}S^{(0)}}{R_1 S_{atm}}\left(\frac{\tau_{oc}}{\tau_{act}} - 1\right)T_c \quad \text{(Eq. 29)}$$

The final equation (29) shows a natural result that the fluid dose actually delivered to the exit opening is proportional to the product of both the cycle duration $T_c$ and the maximum pressure $P^{(0)}_{ind}$ in the indicator, which is reflected by the amplitude $S^{(0)}$ of sensor's exponential kinetics while this cycle. The second consequence demonstrated by the equation (29) is that the non-zero fluid dose may be delivered in the finite time $T_c$ only if there is no insurmountable occlusion and $\tau_{act} < \tau_{oc}$. In accordance with the result (29) the predicted time $T_c$ is to be calculated by the processor as:

$$T_c = \frac{\tau_{act}D_0 R_1 S_{atm}}{(\tau_{oc} - \tau_{act})P_{atm}S^{(0)}} = t_{end} - t_{st} \quad \text{(Eq. 30)}$$

The resulting equation (30) is produced in accordance with general equation (9) wherein actual output resistance $R_{exit}$ is determined during the cycle and then is directly substituted into the denominator of the equation (9). The same actual $R_{exit}$ is indirectly substituted into an analytic expression of the integral constituting the numerator of the equation (9) because it follows from the comparison of equations (30) and (24). Because the dose $D_0$ is predetermined by the delivery instructions, and all other variables and parameters in the equation (30) have been either determined during calibration of the device or measured during the current cycle, the calculation of the predicted time $T_c$ related to this cycle is possible if $(\tau_{oc} - \tau_{act}) > 0$. The only non-analytic case excluding determining the $T_c$ is at least approximate equality $\tau_{oc} \approx \tau_{act}$ corresponding to an insurmountable occlusion, wherein actual $R_{exit}$ exceeds a certain predetermined level. If the algorithm detects this situation, the time $T_c$ cannot be calculated, and the processor generates an alarm signal. However, the system can self-recover fully even in cases of such high occlusion that the positive term $(\tau_{oc} - \tau_{act}) > 0$ becomes much smaller than $\tau_{act}$. In order to reach this aim, the processor calculates high $T_c$ in accordance with equation (30), then it waits until the real time coincides with determined moment $t_{end} = T_c + t_{st}$, and transmits the ending signal to the system 14 after corresponding delay. The result of such operation in time is that actually delivered dose is always kept either precisely equal or very close to desirable $D_0$.

To provide another example, consider the previous quantitative example where values of initial resistances were chosen as follows: $R_1 = 24\alpha/f_0$ and $R_2 = 7\alpha/f_0$. For simplicity consider that the initial contact resistance is as low as $R_3 = \alpha/f_0$ so that the initial ratio $R_1/(R_2 + R_3) = 3$. According to equation (24) $\tau_{oc} = 24/f_0$ and normal time constant corresponding to non-occluded state is $\tau_{act} = \tau_{norm} = 6/f_0$. Such a situation provides the sensor system with the ability to measure at least two and more desirable up to 10-12 signals $S(t)$ during the exponential kinetics after $t > 0$. Mathematical treatment of these signals shows that their amplitude $S^{(0)}$ corresponds to the maximum pressure in the indicator, which is now only $P_0/4$ in accordance with equation (23). In order to deal with real numbers let us think also that the normal non occluded delivery of desirable dose $D_0$ requires average time $T_c=10$ s.

Consider that after some time an occlusion of the exit opening occurs so that the resistance $R_3$ increase to 113 times and is now $R_3=113\alpha/f_0$. Because $R_1$ and $R_2$ remain the same as before, the new ratio is $R_1/(R_2+R_3)=0.2$ and the corresponding time-constant increases to $\tau_{act}=20/f_0$. The amplitude $S^{(0)}$ increases as well because in the occluded state the maximum pressure in the indicator becomes $P_0/1.2$. In accordance with these numbers the equation (30) predicts that the actual dose delivered will be the same $D_0$ as before if the algorithm of the occluded device changes the $T_c$ from normal 10 s to much longer time about 80 s.

The same equation (30) demonstrates also that it can take into account that a simple system 14, and especially the system comprising the syringe-like reservoir shown in FIG. 7, may be a potential source of rather substantial variations of the pressure amplitude $P_0$ in the compression section of the reservoir due to low mechanical precision of the system and substantial variations in displacement of syringe's piston in different cycles. For example, if in a certain cycle the actual $P_0$ exceeds its average value, ordered by the processor, for example, 5 times, the corresponding measurement of the signal $S^{(0)}$ increases the same 5 times and the device terminates this particular cycle in shorter time $T_c=2$ s instead of the average of 10 s, thus keeping a stable output dose. In the opposite case the termination of another cycle can be done with longer time $T_c=50$ s if the actual $P_0$ is 5 times less than ordered average value.

It can be appreciated that all the quantitative estimates provided in the three previous paragraphs are given as examples only, and any particular realization of the present invention may also posses quite different quantitative features. However, even these limited examples are enough to illustrate that devices of the present invention, being supplied with the only sensor and a simple driving force system, can perform better than previously known, more complicated devices of the prior art. It can be clear also that an advantage of the invention, namely its ability for self-correction in changing internal and external environments, depends on the precision and sensitivity of the sensor because only the sensor supplies the processor with the information. The more information comes to the processor, and the higher precision of this information, the "smarter" decisions can be made. For example, some estimates show that other embodiments supplied with a high precision sensor may, in principle, withstand successfully a level of occlusion which exceeds the resistance $R_2$ more than few hundred times, and may be even more than one thousand times. In addition it may be noted that abilities of more complex devices of the invention discussed above become possible if the ratio $R_1/R_2$ is not too low and is not too high as one can easily see from the analysis of the equation (24). That explains the purposes of conditions (15) and (16) restricting both upper and lower limits of this ratio.

At the same time there are few minor not critical disadvantages which are inherent for more advanced devices comprising only linear hydraulic resistors in a hydraulic system. The first one is that a patient needs to be directly involved in the calibration procedure, namely from time-to-time he or she must participate in this operation by putting the cap 153 on and off. The second is the necessity to rely upon the stability of factory pre-set resistance $R_1$ because the system itself has no means to control $R_1$. The last one is that potentially low level residual pressure $P_{res}$ may remain in the reservoir after the end of the cycle if the driving force system 14 has too low precision because of excessive simplicity as shown, for example, in FIG. 32, curve (a). If this is a case it may lead to very slow leak of the fluid between two cycles. Next section discusses the most advanced devices and desirable methods capable of reducing or eliminating disadvantages listed above.

H. Methods for the Drug Delivery with Most Advanced Devices

Figure 10:
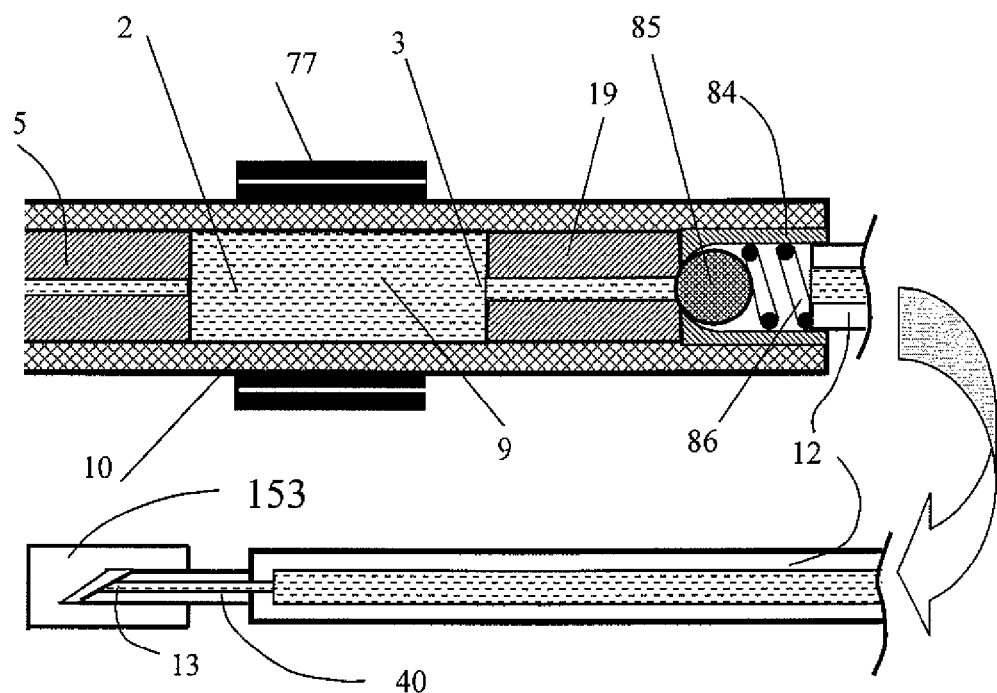
FIG. 10 depicts other parts of a replaceable cartridge of the embodiment shown in FIG. 9, including calibrated passive valve located between the reservoir and exit opening.

Additional embodiments of the invention are capable of either reducing or eliminating one or more of the minor disadvantages listed in the last paragraph of the previous section. For that they require such modification of the method which is applicable only to most advanced cartridges having slightly modified hydraulic systems shown in either FIG. 10, 12 or 13. Being compared with the device shown in FIG. 7, an additional feature of most advanced devices is that their flow passage comprises a passive non-linear hydraulic element 84 (the device shown in FIG. 21) or the element 87 (see also FIG. 12) incorporated into devices shown in FIGS. 23, 25, 26, 27 and 29. Each of said elements 84 and 87 is controlled only by its own pressure drop $\Delta\pi$ so that the element 84 is capable of switching hydraulic resistance at one predetermined pressure drop $\Delta\pi=P_{op}$ (non-linear curve (c) in FIG. 11) whereas hydraulic resistance of the element 87 drops sharply at predetermined pressure drop $\Delta\pi=P_{op}$, but the restoration of initial high resistance occurs at another pressure drop $\Delta\pi=P_{cl}<P_{op}$ (see non linear hydraulic characteristics in FIG. 14). One can see that in the case of the element 84 there is a coincidence $P_{cl}=P_{op}$. It may be desirable that these non-linear elements 84 and 87, comprising for example the locking ball 85 and calibrated spring 86 as shown in FIG. 10 and FIG. 12 correspondingly, are called hereinafter "the valve" for brevity. It may be appreciated by those skilled in the art that present description uses the ball valves for example only. Similar functionality can be also achieved in frameworks of valves having other design which doesn't contain the locking ball. For example, the other valve passively depending on pressure drop $\Delta\pi$ can be formed by two parallel sheets made of silicon rubber so that the fluid must flow between said sheets in order to reach the exit opening. In this case such other valve containing no ball is closed if $\Delta\pi$ is less than the pressure of calibrated spring compressing these sheets slightly. At certain $\Delta\pi$ exceeding spring's pressure the fluid pushes elastic sheets apart and opens up a gap providing low hydraulic resistance. This example shows that particular technical design of similar valves is not a matter of a critical importance if following points are satisfied: (i) the valve takes opened state at certain pressure drop $\Delta\pi$ equal fixed $P_{op}$ calibrated by the manufacturer and stored in processor's memory; (ii) at any $\Delta\pi>P_{op}$ the hydraulic resistance $R_{val}$ of the valve obeys at least the condition $R_{val}<R_2$, and preferably $R_{val}$ is low in comparison with $R_2$; (iii) at any $\Delta\pi<P_{cl}$ the valve is reliably closed so that $R_{val}>R_2$, desirably it is closed so that the resistance $R_{val}$ exceeds $R_2$ at least by the order of magnitude, and in other embodiments, $R_{val}$ exceeds both $R_1$ and $R_2$ more than two orders of magnitude; (iv) fixed $P_{op}$ and $P_{cl}$ are chosen to obey the relationships: $P^{(0)}_{ind})_{avr}>P_{op}$ and $P_{cl}>P_{res}>0$, where $(P^{(0)}_{ind})_{avr}$ is an average pressure in the indicator section while the cycle, and $P_{res}$ is the maximum residual pressure which may potentially remain in the reservoir operated by given driving force system 14 (see diagram (a) in FIG. 32 for example).

It can be appreciated that the condition (iv) stated in the previous paragraph excludes any possibility of non controllable fluid leakage, because after the end of the cycle the low excess pressure in the reservoir $\Delta P_{comp}=P_{res}<P_{cl}$ and the valve is fully closed in accordance with the condition (iii). Thus, this valve resolves immediately one problem of three mentioned above.

The explanation of how the modified method resolves two other problems takes a little bit longer time. It should be noted preliminary that both the first (starting) and the last (ending) steps of the general method remain the same as they have been described in previous sections. All differences of the modified method are concentrated only in the third general step which controls the duration of each cycle by determining the specific ending moment $T_c$ executed while the last step. The previous important requirements of the third step, related to short time intervals $T_{up}$ and $T_{down}$ and high stability pressure plateau $P_0$, remain in effect. That is why it is most preferable that most advanced devices of the invention: (i) are supplied with the latch-type driving force system providing both highly stable force applied to the fluid and shortest $T_{up}$ and $T_{down}$, and (ii) comprise cartridges supplied with particular hydraulic system shown in FIG. 12 or 13 which is fully compatible with said latch-type system 14. However, a modified method of the invention remains applicable to less preferable syringe-based cartridges and motor-driven systems 14, which can be used in most advanced devices as well. A modified method includes that after installation of new replaceable cartridge the processor's memory must be supplied with two very stable factory pre-set calibrated values, namely $P_{op}$ and $\alpha_{ini}$, where $\alpha_{ini}$ is the value of stiffness factor of the expandable indicator 9 in the very beginning of long-term operation. The first significant difference of the modified method is that the processor needs now to be supplied with much more information than before. That is a reason why the frequency $f_0$ should be chosen as high as possible, and the number of signals S(t) acquired for the cycle's duration is at least five, and for better precision it is more desirable that this number exceeds five significantly. It will be shown below that complex kinetics of signals S(t) produced by the modified devices consists of at least two different branches. Quantitatively good measurement of the first branch requires at least two signals acquired for initial time interval $0<t<t_1$, whereas good measurement of the second branch of said kinetics requires at least three signals, and more desirable significantly more than three signals, acquired in the time interval $T_c>t>t_1$. It may be desirable also that acquisition of a few additional signals is required after the end of the cycle. This last option will be discussed separately.

Also it may be noted that any real valve passively controlled by its own pressure drop is always characterized by a certain pressure drop interval in which the transition occurs from closed to opened states. Rather narrow drop interval can be reached with the design of the valve 87 shown in FIG. 12 or 13. However, in order to simplify the mathematical model of the modified method of most desirable embodiments, in the present description this transition interval may be thought to be about zero for both designs 87 and 84, because the general scope of the modified method does not depend significantly on the width of this interval. For brevity, the next analysis provided below is only an example taking into account the hydraulic properties of the valve 84 only. For simplicity, this analysis is also done in frameworks of the assumption that there is no short-term decompressing force after the end of the cycle. The presence of such decompressing force will be shortly discussed later. Those skilled in math art should appreciate that standard corrections of the math algorithm can be always made if one needs to use another type of the valve or to get better precision of the practical device by taking said width of actual transition interval into account.

In order to obtain the correct mathematical description of the fluid delivery processes provided by specific hydraulic system of FIG. 12 comprising the valve 87, first of all one needs to modify the expressions related to both fluid flows $F_1(t)$ and $F_2(t)$. Taking into account the finite hydraulic resistance $R_1$, related to communication between both the compression section 8 and the indicator section 9, one can transform the previous equation (18) so that arriving into indicator flow $F_1(t)$ is represented now in the following modified form which is valid at any time $t>0$:

$$F_1(t) = \frac{P_{comp} - P_{op} + P_{op} - P_{ind}(t)}{R_1} \qquad \text{(Eq. 31)}$$

$$= \frac{P_0 - P_{op}}{R_1} - \frac{\Delta P_{ind}(t) - P_{op}}{R_1}$$

In contrast to that the output flow $F_2(t)$ in the flow passage 12 is locked completely if the valve 84 is in its closed state:

$$F_2(t)=0 \text{ at } \Delta P_{ind}(t)<P_{op} \qquad \text{(Eq. 32)}$$

When the valve 84 is switched to the opened state, its pressure drop $P_{op}$ is practically constant (see the curve (c) in FIG. 11). This drop reduces the pressure difference applied to output resistance $R_{exit}$ related to remaining part of the flow passage. The result is that non zero output fluid flow $F_2(t)$ depends now on the effective pressure change $\Delta P_{eff}(t)=\Delta P_{ind}(t)-P_{op}$ as follows:

$$F_2(t) = \frac{\Delta P_{eff}(t)}{R_{exit}} = \frac{\Delta P_{ind}(t) - P_{op}}{R_2 + R_3} \text{ at } \Delta P_{ind}(t) > P_{op} \qquad \text{(Eq. 33)}$$

Correspondingly, the initial part of each cycle consists of two kinetic branches. The first branch is described by the equations (31) and (32). The equation (32) applicable to the first branch corresponds to the presence of an insurmountable occlusion. The exponential kinetics of any entirely occluded device has been already expressed by the equation (22) where $\tau_{act}=\tau_{oc}$ and $S^{(0)}=P_0/(\alpha \beta)$. In some embodiments the artificially occluded state takes place only for a certain initial interval $0<t<t_1$, because at the moment $t_1$, the pressure in the indicator 9 reaches the value $\Delta P_{ind}(t_1)=P_{op}$ and the valve 84 is switched to the open state. In FIG. 32 the solid line of diagram (b) shows only a real initial part of the occluded kinetics, whereas dash-dotted line shows its extrapolated continuation as if the valve 84 is never open. Actual switching of the valve 84 at the moment $t_1$ is demonstrated also by the diagram (e) in FIG. 32 where the non-zero output flow $F_2(t)$ begins only after the point $t=t_1$.

It is important to stress here that accordingly to Eq. 31 the exponential kinetics of the first branch at $0<t<t_1$ involves only one hydraulic resistor $R_1$ which defines potential changes of important parameter $\tau_{oc}$. That is why measurements made before $t_1$ take into account any change of capillary resistance $R_1$ caused, for example, by changes of a viscosity of the fluid which depends on current temperature of the device.

Another branch of the kinetics, represented by the curve (c) in FIG. 32, begins at the same $t_1$ immediately after the switching of valve 84. It can be appreciated that at the moment $t_1$ the sensor system 16 produces the following signal $S(t_1)=S_1$, which corresponds to the equality $\Delta P_{ind}(t_1)=P_{op}$. Because both $P_{op}$ and $\Delta_{ini}$ are calibrated constants of the device, the processor can use the equation (6) to calculate the following important parameter, which calibrates the readings of the sensor system in units of absolute pressure:

$$(\alpha_{ini}\beta) = \frac{P_{op}}{S_1} \qquad \text{(Eq. 34)}$$

It is useful to note that in some embodiments, quantitative self-calibration of the sensor system occurs in the beginning of every cycle. This eliminates potential effects of either slow drift caused by temperature changes or material aging, or fast accidental changes of the sensor's characteristics, which may happen during long-term operation, possibly due to mechanical shocks or other unpredictable reasons.

Because time $t_1$ in equation (32) is not valid under this circumstance, equation (33) can be used instead. The difference of two fluid flows, namely the difference of incoming $F_1(t)$ and outgoing $F_2(t)$, describes the speed of the volume expansion of the indicator 9 and leads finally to the following differential equation corresponding to the second branch of the delivery process:

$$\frac{d[\Delta P_{ind}(t) - P_{val}]}{\alpha dt} = \frac{P_0 - P_{val}}{R_1} - [\Delta P_{ind}(t) - P_{val}]\left(\frac{1}{R_1} + \frac{1}{R_2 + R_3}\right) \qquad \text{(Eq. 35)}$$

Because this equation starts at $t_1$ with initial conditions (i) $S(t_1)=S_1$, and (ii) $\Delta P_{ind}(t_1)=P_{op}$, the rigorous solution satisfying these conditions at all times $t_1<t<T_c$ may be finally expressed as:

$$S(t) = S_1\left\{1 + \frac{\tau_{act}}{\tau_{oc}}\left(\frac{P_0}{P_{val}} - 1\right)\left[1 - \exp\left\{-\frac{t-t_1}{\tau_{act}}\right\}\right]\right\} \qquad \text{(Eq. 36)}$$

The behavior of the second branch, namely equation (36), is represented by diagram (c) in FIG. 32 starting at $t_1$. One can note that the open valve 32 provides the exponential kinetics (c) of the second branch with the characteristic time constant $\tau_{act}\neq\tau_{oc}$, which makes the diagram (c) very different from the diagram (b) representing the case where $\tau_{act}=\tau_{oc}$. The sharp transition of the solution from the branch (b) to branch (c), having a different slope, allows the easy and very precise determination of both the exact moment $t_1$ and the specific signal $S_1$ corresponding to that $t_1$. One way to do this is if the processor extrapolates both the acquired branch (b) above $t_1$ as shown with dash-dotted line in FIG. 32 and the acquired branch (c) below $t_1$, and looks for the time-point where both extrapolations merge. Another way is to look for the time $t_1$ and to calculate the derivative of the entire sequence of all signals S(t) acquired after the moment t=0. The diagram (d) in FIG. 32 shows that the change in slope at the moment $t_1$ results in the sharp drop of the derivative dS(t)/dt. If the number of acquired discrete signals is high enough, any method of these two can give precise values for both $t_1$ and $S_1$. It follows from the above that the while at least about $2.5\,t_1$ is enough time to acquire a desirable number of signals and calculate both $t_1$ and $S_1$ when the frequency $f_0$ is chosen so high that $2.5\,t_1\,f_0\geq5$, and more desirably $2.5\,t_1\,f_0>>5$. At the same time it can be appreciated that the calculation time $2.5\,t_1\,f_0$ cannot exceed the shortest time $T_c$ which can be desirable in accordance with the lowest predetermined dose $D_0$.

The value of two calculated parameters $t_0$ and $S_1$ is that they reflect the specificity of each cycle and can desirably be directly used for further calculation of the time period $T_c$, which determines the moment $t_{end}$ for termination of this cycle. Thus, both parameters $t_1$ and $S_1$ may desirably be calculated in the beginning of each cycle and stored in processor's memory. After this is done, the next actions performed by the processor are: the analysis of the branch (b) in order to determine time-constant $\tau_{oc}$, and then the analysis of the branch (c) determining time-constant $\tau_{act}$ related to the current cycle. Because both branches represent exponential functions, the processor can perform this analysis with the use of standard mathematical methods. Then the processor extrapolates the recorded part of the branch (c) to higher times and calculates the maximum signal $S_{max}$ that could be reached if the cycle continues for an indefinitely long time. Quantitatively determined $S_{max}$ is further substituted into the left part of the equation (36) wherein the exponent in the right part is set to zero. After that one can do simple mathematical transformations leading to the following form of time-dependent effective pressure change $\Delta P_{\it eff}(t)$ where the calibrating factor (34) previously determined is also taken into account:

$$\Delta P_{\it eff}(t) = \alpha\beta(S(t) - S_1) \qquad \text{(Eq. 37)}$$
$$= P_{op}\left(\frac{S_{max}}{S_1} - 1\right)\left[1 - \exp\left\{-\frac{t-t_1}{\tau_{act}}\right\}\right]$$

The initial equation (33) describing the output fluid flow $F_2(t)$ of some embodiments in very general form, becomes fully determined by the equations (24) and (37) as a function of the running time wherein two device's constants $\alpha_{ini}$ and $P_{op}$ are known to the processor in advance, and other parameters that can vary from one cycle to another one, namely $t_1$, $S_1$, $S_{max}$, $\tau_{act}$, and $\tau_{oc}$, are determined in the process of each particular cycle. In the time interval $t_1<t<T_c$ this function can be expressed as follows:

$$F_2(t) = \frac{P_{op}}{\alpha_{ini}}\left(\frac{1}{\tau_{act}} - \frac{1}{\tau_{oc}}\right)\left(\frac{S_{max}}{S_1} - 1\right)\left[1 - \exp\left\{\frac{t_1-t}{\tau_{act}}\right\}\right] \qquad \text{(Eq. 38)}$$

One can note that all parameters of equation (38) are either calibrated values or values determined in the process of current cycle. It should be appreciated that quantitative measurement of current value $\tau_{oc}$ corresponds to determining of the resistance $R_1$ according to equation (25), and any accidental change of this resistance (including its dependence on the temperature, mechanical damage caused by improper usage, and so on) can be recorded by the processor. At the same time potential change of output resistance $R_{exit}$ reflected by the equation (5) can be easily found from the analysis according to the equation (24). Taking into account the calibration (34) discussed before one can see that the modified method of these embodiments can provide self-calibration of the whole device of the fluid delivery, and this complete calibration may be performed by the processor in the process of each cycle. It can be appreciated that such self-calibration can be automatic.

It can be appreciated that integration of the equation (38) over time period $t_1<t<T_c$ determines only part of the fluid dose delivered to the exit opening. At the time $T_c$ the pressure in the compression section 8 of the reservoir drops sharply but the fluid flow $F_2(t)$ decays relatively slow with the same time-constant $\tau_{act}$. The diagram (e) in FIG. 32 representing $F_2(t)$ shows that this exponential decay can continue only for the limited while $T_c<t<t_2$ because the decreasing pressure in the indicator 9 again crosses value $\Delta P_{ind}(t_2)=P_{op}$ at the moment $t_2$ (see also the diagram (c) in FIG. 32), and the valve 84 returns to the closed state. Therefore the last stage of the fluid flow $F_2(t)$ related to final interval $T_c<t<t_2$ is expressed as follows:

$$F_2(t) = \frac{P_{val}}{\alpha_{ini}}\left(\frac{1}{\tau_{act}} - \frac{1}{\tau_{oc}}\right)\left(\frac{S_{max}}{S_1} - 1\right)\left[1 - \exp\left\{\frac{t_1 - T_c}{\tau_{act}}\right\}\right]\exp\left\{\frac{T_c - t}{\tau_{act}}\right\} \quad \text{(Eq. 39)}$$

where the final point $t_2$ of outgoing flow $F_2(t)$ satisfies the following equation:

$$\exp\left\{\frac{T_c - t_2}{\tau_{act}}\right\} = \frac{S_1}{S_{max}} \quad \text{(Eq. 40)}$$

It follows from the above that according to a general approach of the integral equation (9) the predetermined dose $D_0$ must be equal the actual dose which is formed by the such sum of two integrals. The initial part of the actual dose corresponds to the flow $F_2(t)$ expressed as equation (38) which is integrated in the first time interval $t_1<t<T_c$. The final part of the actual dose corresponds to the flow $F_2(t)$ expressed as equation (39) which is integrated in the second time interval $T_c<t<t_2$. The sum of these two integrals representing the actual dose can be calculated. It becomes equal to $D_0$ if the expected moment $T_c$ is chosen in accordance with following transcendental equation:

$$T_c + \frac{\tau_{act}S_1}{S_{max}}\exp\left\{\frac{t_1 - T_c}{\tau_{act}}\right\} = t_1 + \frac{\tau_{act}S_1}{S_{max}} + \frac{\alpha_{ini}\tau_{act}D_0}{P_{val}\left(1 - \frac{\tau_{act}}{\tau_{oc}}\right)\left(\frac{S_{max}}{S_1} - 1\right)} \quad \text{(Eq. 41)}$$

Complicated analytical form of this equation does not create a problem because the algorithm of a digital processor can use standard numeric methods in order to determine $T_c$ corresponding to the solution of this transcendental equation (41). Because the time $2.5\, t_1 f_0$ required to complete the prediction is shorter than $T_c$, in the beginning of the last step of the modified method the processor is waiting for such real time moment $t_{end}=T_c+t_{st}$ which is appropriate to send the terminating signal to the system 14 so that the drop of the pressure in the compression section of the reservoir occurs exactly at the predicted moment $T_c$.

It should be appreciated that the final equation (41) has been developed by the inventor only as an example to demonstrate how mathematical algorithms of the invention can be developed. This particular example considers only simple exponential kinetics of the processes occurring in the expandable indicator section 9 when a quasi-rectangular pressure pulse is performed in the compression section. The algorithm developed on this basis is rather good for cases of devices wherein a low transition time $T_{up}$ can be neglected in comparison with $T_c$, and then relatively a stable pressure plateau $P_0$ is produced in the compression section 8 of the reservoir. However, it should be appreciated that the teaching of the present invention, based on represented by the equation (9) a general method of the integration of outgoing fluid flow, includes also all other cases where the smooth pressure plateau $P_0$ may have a certain slope during the time $T_c$, similar to that one shown in the top view of FIG. 20. There is no doubt that necessary corrections can be easily done with the use of very similar approach in the framework of the same scope of the invention. For example, it may be possible that in some embodiments sufficiently simple system 14 produces so long transition time $T_{up}$ that the pressure in the compression section reaches $P_0$ for finite time about $2T_{up}$ and cannot be neglected. In this case one can easily modify initial differential equations so that they are valid for whole period $0<t<T_c$. In this case shown below more complex rigorous solution (42) differs a little bit from simple solution (21). It has to be appreciated that at negligibly low $T_{up}$ the more complicated equation (42) coincides with relatively simple solution (21). Improved algorithm corresponding to the kinetics (42) can be further developed similar to a general approach disclosed above. Taking into account that real $T_{up}$ is never equal zero, more complex and simultaneously more precise solution in equation (42) looks as follows:

$$\Delta P_{ind}(t) = \frac{P_0}{(1+R_1/R_{exit})} \ast\ast \left[1 + \frac{\alpha T_{up}(1+R_1/R_{exit})\exp\{-2t/T_{up}\} - 2R_1\exp\{-t/\tau_{act}\}}{2R_1 - \alpha T_{up}(1+R_1/R_{exit})}\right] \quad \text{(Eq. 42)}$$

It provides an example of how a mathematical correction can be done if one needs to obtain more precise algorithm controlling the device.

In the case of very simple system 14, even low residual pressure remaining in the reservoir after the end of the current cycle may not be desirable. That is why the most advanced method of certain embodiments may comprise one more additional step aiming to remove the residual pressure completely before the beginning of the next cycle. The first approach relates to syringe-based replaceable cartridge coupled with motor-driven system 14. In this case the improved method comprises the acquiring of at least one, and most desirable more than one, signals S(t) after the end of previous cycle. The processor detects the presence of the low residual pressure and sends additional output signals to the motor of the system 14 after certain moment $t_3>t_2$. These additional signals cause fine adjustment of the force applied to the fluid until the pressure inside the reservoir becomes equal external pressure $P_{ext}$.

The second approach is simpler from technical viewpoint and can be applicable to embodiments wherein the latch-type system 14 is used in combination with the cartridges comprising more desirable hydraulic system depicted in FIG. 12. This type of the hydraulic system comprises the reservoir having additional section 32 made of flexible material similar to silicon rubber or alike which is always subjected to external atmospheric pressure. Static hydraulic resistor 33 connects this section 32 with the compression section 8 so that resistance $R_0$ of the element 33 significantly exceeds predetermined resistance $R_1$ when the fluid in the section 8 undergoes compressing force. It can be desirable that during this time interval $R_0$ exceeds $R_1$ at least one order of magnitude, and most desirable $R_0$ exceeds $R_1$ more than two orders of magnitude. If this condition is fulfilled the resistor 33 practically does not influence the process of fluid delivery while the cycle $T_c$ when compressing force is applied to the fluid in compression section 8 because at said time interval the flow from the section 8 to section 32 is very low. When the time $T_c$ calculated by the processor 17 is over the latch-type system 14 returns to its initial inactive state and quickly moves the piston 78 back a little bit from the section 8 as described before. In this case the elastic diaphragm 76 expands slightly and applies decompressing force to the fluid in the section 8. Correspondingly, the pressure in this section drops below external atmospheric pressure thus making temporarily $\Delta P_{comp}(t)$ slightly negative after $T_c$ (see diagram (a) in FIG. 33). That means that after $T_c$ the fluid begins to flow slowly from the section 32 subjected to $P_{atm}$ to the section 8 in which the pressure is made below $P_{atm}$. This flow refills the section 8 in order to prepare it for the next cycle. Refilling flow passes through resistor 33 and stops automatically when the pressure inside the section 8 becomes precisely equal external $P_{atm}$. Said refilling can be made even faster if the resistor 33 is made as a pressure-dependent static hydraulic resistor. For fast refilling it can be desirable that the resistance $R_0(\Delta\pi)$ switches so that $R_0$ does not exceeds $R_1$ when said decompressing force is applied to the fluid in the reservoir.

It can be appreciated that there is also rather simple method of direct determining of both $\tau_{oc}$ and $\tau_{act}$ which can be used at high frequency $f_0$. In this case the processor can acquire enough signals to calculate precisely both the first and the second derivatives related to the exponential kinetics S(t). It follows from equations provided above that a ratio of said first and second d derivatives reflects exact value of time constant of that exponent. The diagram (d) in FIG. 33 demonstrates that before opening of the valve 84 said ratio is a constant equal high value of $\tau_{oc}$. Immediately after the opening of the valve 84 the curve (d) drops to another constant equal $\tau_{act}$. At $t_1$ high transition peak appears on this curve if a difference $\tau_{oc}-\tau_{act}$ exceeds the noise of recording system. Therefore, until the processor can detect this peak the device is capable of self-compensating even very strong partial occlusion. Otherwise the processor decides that values $\tau_{oc}$ and $\tau_{act}$ coincide, and turns on alarm signal to inform a patient about emergency situation which requires his or her personal attention. FIG. 34 depicts a diagram of the algorithm of one cycle of fluid delivery applicable to advanced and most advanced embodiments which comprises said method to determine $\tau_{oc}$ and $\tau_{act}$. Rectangular boxes in FIG. 34 depict procedures, ellipsoid-like cells contain numeric values, and dashed arrows depict a transfer of said numeric values from one procedure to another one.

At this point it may be relevant to point out some advantages of the modified method applicable to most advanced devices of the invention. One can see that the right side of the final equation (41) contains predetermined dose $D_0$, two calibrated factory pre-set constants $P_{op}$ and $\alpha_{ini}$ known to the processor in advance, and also only a few variable parameters need be directly determined in the beginning of each cycle. It has been demonstrated that said determinations, carried out by processor's algorithm treating signals of the sensor system, provide self-calibration of the entire device before determining the end moment $t_{end}$ corresponding to each predicted $T_c$. That is why all variable parameters of the equation (41) reflect potential changes of either external or internal conditions, including (i) the variations of external pressure $P_{ext}$ and internal excessive pressure $P_0$; (ii) potentially possible, unpredictable changes of resistances $R_1$, $R_2$, and $R_3$ which may be sensitive to the temperature, external or internal occlusions whether partial or insurmountable ones, and/or accidental mechanical damages; and also (iii) the variations of the parameter ($\alpha$ $\beta$) calibrating the sensitivity which may be different for each particular cartridge and can depend on the particular position of the cartridge inside the device, voltage of batteries supplying electric power, mechanical shocks, and so on. Thus, the right side of the equation (41) is fully determined so that each prediction of $T_c$ takes into account everything what may happen to the device.

The methods and compact devices of the invention may be used for the delivery of any soluble drugs in as low doses as about 0.02 mm³ of the solution or better, with high resolution about 0.001 mm³ or better by the order of magnitude. However, there is no practical upper limit if desirable dose exceeds 0.02 mm³. This statement can be confirmed by the following quantitative example related to the delivering of the insulin in order to treat the diabetes. Consider that the average speed of delivery of insulin treatment is prescribed to be 12 mm³/hour if there is no medical emergency. The replaceable cartridge can comprise the capillary resistor 5 having the length 10 mm and the diameter 0.052 mm which correspond to the hydraulic resistance about $R_1$=500 Kgram·s/cm⁵ for the insulin dissolved in a water. At the same time the capillary resistor 19 is chosen to have the length 10 mm and the diameter 0.07 mm providing the hydraulic resistance $R_2$=165 Kgram·s/cm⁵ so that the ratio $R_1/R_{exit}=R_1/R_2=3$ corresponds to normal conditions with no occlusion. The stiffness factor of the indicator 9 having internal diameter 2 mm and the length 3 mm (see FIG. 10 for example) is about $\alpha$=50 Kgram/cm⁵, whereas the driving force system is designed so that the average $P_0$ is about 0.2 Kgram/cm² in the compression section 8, which corresponds to average $\Delta P_{ind}$ about 0.05 Kgram/cm² if there is no external occlusion and $R_3$=0. It is assumed that the valve 84 is calibrated to become open at the pressure drop $P_{op}$=0.015 Kgram/cm². At zero pressure the indicator 9 can be located so that the gap 101 of the capacitor sensor (see FIG. 16b) can be relatively high about 0.12 mm. The desirable frequency of signal acquisition can be chosen $f_0$=30 Hz, and the precision of signal's digitization can be at least 0.1% of full range.

It is easy to use the equations (21-41) and to see that under the normal conditions of a delivery cycle assumed in the previous paragraph, the state of the device is: $\tau_{oc}$=10 s, $\tau_{act}$=2.5 s, $t_1$=0.75 s, the change of the gap 101 about 0.045 mm (30% of full range) corresponds to the indicator's volume expansion $\Delta V$ about 1 mm³ (11% of $V_0$=9 mm³), the minimum $T_c$=1.15 s, the outgoing flow $F_2(t)$ reaches its maximum rate about 0.21 mm³/s if $T_c$ is about 5 s or longer. For initial 1.15 s of the cycle the processor acquires 35 signals which provide 22 points to measure $\tau_{oc}$ and 13 points to measure $\tau_{act}$. The amount of the insulin delivered to the exit opening for this 1.15 s initial period is equal only 0.017 mm³ which may be considered as the minimum dose inherent for this particular device. With the frequency $f_0$=30 Hz the precision of the device in the time is about 0.03 s, and corresponding precision of the dosage is close to 0.001 mm³. Taking into account the preprogrammed average speed of the insulin delivery 12 mm³/hour, it may be reasonable to choose the dose of one cycle $D_0$=1 mm³ which requires $T_c$=6.16 s in accordance with the equation (41) at normal conditions. The desirable average speed of the delivery is fulfilled if the device's program performs 12 cycles/hour or one cycle per 300 s. In the case of medical emergency the device having such parameters is capable of increasing the repetition rate up to 1 cycle per 10 s, thus increasing the average speed of the delivery about 30 times from the standard 12 mm³/hour to about 360 mm³/hour. This example is based on realistic numbers and demonstrates that the performance of devices of the invention can exceed that of prior art systems for insulin delivery by more than one order of magnitude in regard of the minimum dose, and more than two orders of magnitude in regard of the precision. The reliability and smart behavior of the invented devices is also demonstrated below in realistic numbers.

For example, due to the simplicity of the driving force system the pressure plateau $P_0$ achieved in different cycles can fluctuate by ±50% between 0.3 Kgram/cm² and 0.1 Kgram/cm². This results in a corresponding fluctuation of $S_{max}/S_1$ between 5 and 1.67, and in entire accordance with the solution of the equation (41) the processor keeps constant preprogrammed dose 1 mm³ of each cycle by corresponding changes of the predicted $T_c$ between about 4.03 s and 18.82 s. The other case is if at normal pressure $P_0$ a partial occlusion occurs so that $R_3=19\ R_2$. Then the processor detects the increase of $\tau_{act}$ from initial 2.5 s up to 8.69 s, followed by the pressure increase in the indicator section up to 0.176 Kgram/cm² instead of normal 0.05 Kgram/cm². It corresponds to a new ratios $S_{max}/S_1=11.7$ and $\tau_{act}/\tau_{oc}=0.87$. The processor uses new numbers to resolve the equation (41) and compensate this strong occlusion completely by changing $T_c$ from 6.16 s to 21.8 s so that this increase prevents any change of predetermined dose $D_0=1$ mm³. It should be appreciated that the quantitative examples considered above are provided for better illustration of the invention only, and should not create any limitation in the design of other devices of the same invention having rather different quantitative parameters and abilities.

Other advantages of embodiments of this invention include non-interrupted self-monitoring of internal parameters and using the processor's memory to store the history of changes detected. Analysis of that history, including periods between the cycles, can provide reliable self-diagnosis of the internal state of the device. For example, detection of a sharp drop of the measurable parameter $S_{max}$ below a predetermined level, repeated over a few cycles, may be evidence of incorrect operation or even a defect in the driving force system. Likewise, a relatively gradual decrease of the $S_{max}$ observed over several cycles may indicate that the reservoir is practically empty and the user should be advised to change the replaceable cartridge. Similarly, the history of the measurable parameter $\tau_{oc}$ which reflects the ratio $R_1/\alpha$ can be useful. The stiffness factor $\alpha$ is a mechanic characteristic and its potential change can be very gradual, because of slow aging of the elastic material. The use of fully disposable cartridges having short life-time reduces the likelihood that $\alpha$ would change significantly over time. That is why a rapid increase of $\tau_{oc}$ determined by the algorithm with a simultaneous change of the ratio $\tau_{oc}/\tau_{act}$ may only mean either the mechanical damage or accidental occlusion of the internal hydraulic resistor $R_1$, which can especially happen if an inexperienced user introduces mechanical contaminants while filling the cartridge before installation (it has been already mentioned that factory pre-filled cartridges are most desirable to exclude such accidents). The opposite case can occur if $\tau_{oc}$ remains constant and only the rapid change of $\tau_{act}$ is detected. This could be a sign of either mechanical damage of the hydraulic resistor $R_2$ or the occlusion in the exit opening of the flow passage.

When a change of a parameter is detected, an additional program of the processor first analyzes potential consequences of this change. If the predetermined dosage can be preserved by making a corresponding adjustment of the device's regime during the next cycle, there is no need to disturb the user. Conversely, if a malfunction is detected that cannot be self-compensated by the algorithm controlling the delivery cycles, the processor can inform the user promptly regarding what has happened to the device and what actions are advised to improve the situation. For example, the user can be advised to change a replaceable cartridge if the program detects too little fluid remaining in the reservoir. It may be desirable that ether visual or acoustic alarm signal is produced to attract the user's attention, and report the situation and provide instructions via an LCD screen of the control panel.

Simple design and very low technical requirements related to the driving force system considered above in section D allow obtaining of uniquely high reliability of whole device even in certain very rare emergency cases when processor detects critically strong malfunctioning of automatically controlled driving force system. Such malfunctioning may happen suddenly, for example, if the driving force system is accidentally damaged by any reason or by a patient (especially if he or she is an inaccurate child) or, for another example, if during patient's long-term flight the battery becomes so low that latch-type driving force system cannot work properly whereas there is no possibility to recharge the battery till the end of a flight. However, the device of the invention may keep quite reasonable level of its functionality for indefinitely long time with minimum participation of the patient thus saving his or her life even in such rare critical events. That is why the device of the invention having latch-type system 14 may be also supplied with additional emergency means 71 providing a patient with an ability of manual control of such system 14 in order to cause such changing of squeezing out force over time which is similar to the change while normal work of driving force system. The only what the patient has to do is to remove protecting lid of battery compartment 69 in order to reach the lever 71. To provide acceptable precision of drug delivery in manual mode (see in FIG. 30 how the lever 71 is to be used) the patient must act under supervision of the processor. It should be appreciated by anyone skilled in the art that in such emergency cases the processor receiving signals of the sensor system can automatically detect the moment $t_{st}$ when the patient manually initiates squeezing out force. After that the processor should use most appropriate algorithm among of few ones described above and define necessary duration of the cycle $T_c$ accordingly to actual pressure created by the patient manually. That is why the only real necessity is that the processor should be capable of initiating at least one either acoustic or visual signal at the moment $t_{end}$ corresponding to calculated $T_c$, said signal providing the patient with strict recommendation to terminate the squeezing out force as soon as possible. For example, the device may display such ending signal at the moment $t_{end}$ on LCD screen, or use flashing lamp, or use any other suitable information means. However, for better precision of manual dosing it is more desirable that the processor is also capable of initiating a preceding signal at the moment $t_{st}$ (it may be also called "first emergency signal") destined to prompt the patient to start immediate manual application of squeezing out force in accordance with programmatically predetermined moment. Correspondingly, the ending signal produced at the moment $t_{end}$ and destined to prompt the patient to terminate said manual application of the squeezing out force may be also called "second emergency signal". Cyclic manual operation based on the use of these two signals should be repeated until substantial technical help can be provided to the patient in order to restore normal automatic work of the device. Thus, even partially broken device of the invention may be used temporarily in order to overcome certain very serious dangers irresolvable by any known drug delivery devices.

It may be appreciated that a wide dynamic range of programmatically determined doses combined with high precision of liquid drug dosing, create one more advantage over prior art devices. It is well known that medical condition of an outpatient may depend on multiple factors, including personal physiological peculiarities, environmental factors, quantity and quality of food, and so on. These factors can change a personal medical condition unpredictably at different times and different places. In such cases embodiments of this invention can provide this person one or more specific bio-medical devices or sensors capable of prompt analysis of important physiological parameters to find adjusted dosing to meet the needs of the patient at a particular moment in time. For example, a sensor can analyze the concentration of a specific molecule in patient's blood, or electric activity of the brain, or something else what is reasonable in each particular case. The state of the patient can be improved if signals produced by such a bio-medical device or sensor are periodically transmitted to the control system to make prompt corrections of doses of the liquid drug delivered. That is why it may be appreciated that in order to improve a quality of medical treatment, the improved methods and devices of the invention comprise transmitting signals of at least one bio-medical device capable of detecting a physiological feature of a patient to the control system of the device, and the method further comprises correcting the dose delivered accordingly to the transmitted signal from the bio-medical device.

The descriptions of embodiments above demonstrates that the devices and methods of the invention are simple in their engineering design, inexpensive in mass fabrication, highly reliable in all respects, and posses the ability of "smart" behavior in practical use in unpredictably changing environments of the real life. Certain embodiments are so small that they can be deployed on patient's skin and fully hidden under clothes. It can be appreciated that the above descriptions and embodiments are illustrative of the invention, and numerous modifications of similar devices and methods may be developed and remain within the scope of the invention. All references cited herein are incorporated fully by reference.

INDUSTRIAL APPLICABILITY

Devices and methods of this invention can be used in the medical and veterinary fields for delivering doses of fluids to animals being treated for diseases or other conditions requiring such treatment. Devices and methods of this invention also find use in other fields in which precision deliver and control over release of fluids is desired.

What is claimed is:

1. A device for programmable delivery of a predetermined dose of a fluid, the device comprising:
   (a) a replaceable cartridge located in a first housing, wherein the replaceable cartridge comprises:
      a reservoir comprising at least one expandable element made of resilient material, said reservoir having at least two spatially separated sections connected so that hydraulic resistance between said two sections is not less than non-zero $R_1$ defined as a first time-independent ratio having a numerator being a first fluid pressure difference between said two sections and the denominator being the flow rate caused by said first fluid pressure difference; and
      a flow passage connecting an internal volume of said reservoir with an input and at least one exit opening so that under conditions of fluid flow, hydraulic resistance to flow of said flow passage is not less than predetermined non-zero $R_2$ defined as a second time-independent ratio having a numerator being a second fluid pressure difference between the input and exit of said flow passage and the denominator being the flow rate caused by said second fluid pressure difference;
   (b) an actuating module located in a second housing, said module comprising:
      a driving force system capable of both creating a propelling force and transferring said propelling force to the fluid in the reservoir of said replaceable cartridge when both first and second housings are connected to each other; and
      at least part of a sensor system, wherein said part of the sensor system is capable of producing an output associated with at least one geometric parameter of said expandable element;
   (c) a connector to provide a temporary connection of said replaceable cartridge and said actuating module; and
   (d) a programmable processor with fluid delivery instructions stored therein, said processor capable of acquiring said output of the sensor system and capable of producing an other output, said other output controlling the driving force system; whereas
   when both housings are connected to each other, the driving force system is capable of applying a force changing over time to the fluid in the reservoir.

2. The device of claim 1, wherein at least part of said processor is located in a third housing comprising:
   a display; and
   a system providing a exchange of data between said actuating module and said third housing.

3. The device of claim 1, wherein the driving force system comprises at least one a mediatory element which, when said first and second housings are connected, said mediatory element operably transmits said force changing over time to a force receiving element of said reservoir in said replaceable cartridge.

4. The device of claim 3, wherein both said mediatory element and said force receiving element are at least partially made of a ferromagnetic material.

5. The device of claim 3, wherein both said mediatory element and said force receiving element each comprises a permanent magnet.

6. The device of claim 5, wherein said magnets have an orientation such that the mediatory element applies said driving force remotely to said force receiving element.

7. The device of claim 1, wherein said driving force system comprises a latch capable of switching between two stable states;
   whereas in a first stable state the driving force applied to a force receiving element is a continuous compressive force applied to the fluid in said reservoir to urge said fluid out of said reservoir; and
   whereas in a second stable state the driving force is a decompressive force applied to said fluid in the reservoir.

8. The device of claim 7, wherein said latch comprises:
   a permanently stressed spring to create said continuous compressive force;
   at least one permanent magnet;
   at least one electromagnet; and
   a mechanism capable of switching a distance between two said magnets so that one stable state occurs at greater distance between said magnets, and
   whereas said second stable state occurs at shorter distance between said magnets.

9. The device of claim 7, wherein the actuating module further comprises a manual switch between said two stable states of said latch; and wherein said processor is programmed to initiate at least one signal to a patient.

10. The device of claim 9, wherein said signal is at least one of visual, mechanical, and auditory.

11. The device of claim 1, wherein said reservoir further comprises an additional section connected to said other two sections of said reservoir by a hydraulic element providing a resistance $R_0$ so that $R_0$ exceeds $R_1$ when a compressive force is applied to a fluid in said reservoir, and more preferably $R_0$ exceeds $R_1$ at least one order of magnitude, and most preferably more than two orders of magnitude.

12. The device of claim 11, wherein said hydraulic element is a pressure-dependent static hydraulic resistor capable of switching its resistance $R_0$ so that $R_0$ does not exceed $R_1$ when a decompressive force is applied to the fluid.

13. The device of claim 1, wherein said reservoir comprises an additional element made of resilient material, said element separating a movable piston from the internal volume of said reservoir, wherein said movable piston is adapted to transmit said driving force to said fluid.

14. The device of claim 13, wherein said additional element is capable of expanding into a cavity made in said movable piston when fluid in said reservoir is subjected to an internal pressure exceeding external pressure.

15. The device of claim 14, wherein said additional element is adapted to eliminate direct correspondence between displacement of said movable piston and a dose of the fluid delivered to said exit opening.

16. The device of claim 1, wherein a ratio of $R_1/R_2$ is greater than 0.05 and less than 200.

17. The device of claim 1, wherein said flow passage connecting said internal volume of said reservoir with at least one exit opening further comprises a pressure-dependent valve capable of switching to an open state under conditions of fluid flow so that hydraulic resistance of said open valve is less than $R_2$ at least by one order of magnitude when a pressure drop applied to said valve is equal or exceeds a predetermined value $P_{open}$ ("$P_{op}$"), and wherein said pressure dependent valve is capable of switching into a closed state when said pressure drop is below a predetermined value $P_{closed}$ ("$P_{cl}$"), which is either equal or less than said $P_{op}$, whereas the hydraulic resistance of said closed valve exceeds $R_2$ by at least one order of magnitude, and most desirable it exceeds $R_2$ by more than two orders of magnitude.

18. The device of claim 1, wherein at least one element of said sensor system comprises a piezoelectric sensor, and when said first and said second housings are connected, the device further comprises a direct or an indirect mechanical connection of said piezoelectric sensor with an external surface of said reservoir.

19. The device of claim 1, wherein when said first and said second housings are connected together, the sensor system comprises at least one such electrically conducting area which is capable of forming a non-contact capacitor sensor so that said electrically conducting area is located in proximity to at least one other electrically conducting area which is attached to said reservoir and capable of relocating in response to deformation of said expandable element.

20. The device of claim 1, wherein said sensor system comprises a magnetic detector adapted to form a non-contact magnetic sensor when said first and said second housings are connected, so that said magnetic detector is located in proximity to either a magnetic substance or a magnetized substance attached to said reservoir and capable of relocating in response to deformation of said expandable element.

21. The device of claim 1, wherein at least one element of said sensor system is housed in said actuating module, said one element of said sensor system comprising a non-contact optical sensor comprising:
   a light emitter directed onto said replaceable cartridge when said first and said second housings are connected together, and
   at least one detector adapted to receive light emitted by said light emitter, either reflected by said replaceable cartridge or transmitted through said reservoir.

22. The device of claim 1, where the replaceable cartridge comprises:
   at least a portion of a connector to at least temporarily operably connect said cartridge with a housing containing an actuator; wherein said connector provides that relative locations of said reservoir and said housing containing said actuator to permit transfer a force from said actuator to internal surface of a second section of said two sections of said reservoir.

23. The device of claim 22, wherein under flow conditions, the ratio $R_1/R_2$ exceeds 0.05 and is less than 200, more desirably said ratio is in between 0.25 and 40, and most desirably said ratio is in between 1 and 10.

24. The device of claim 22,
   wherein when said actuator and said replaceable cartridge are connected to each other, said driving force system is capable of applying a force changing over time to a fluid in the reservoir.

25. The device of claim 24, wherein said sensor system comprises at least one such electrically conducting area which is capable of forming a non-contact capacitor sensor when said actuator and a replaceable cartridge comprising a reservoir having an expandable element made of resilient material are connected, so that said electrically conducting area is located in proximity to at least one other electrically conducting area which is attached to said reservoir and capable of relocating in response to deformation of said expandable element.

26. The device of claim 24, wherein said sensor system comprises a magnetic detector adapted to form a non-contact magnetic sensor when said actuator and a replaceable cartridge comprising a reservoir having an expandable element made of resilient material are connected, so that said magnetic detector is located in proximity to either a magnetic substance or a magnetized substance attached to said reservoir and capable of relocating in response to deformation of said expandable element.

27. The device of claim 24, wherein at least one element of said sensor system is housed in said actuating module, said one element of said sensor system comprising a non-contact optical sensor comprising:
   a light emitter directed onto said replaceable cartridge when said actuator and said replaceable cartridge are connected together, and
   at least one detector, wherein said detector is adapted to receive light emitted by said light emitter, either reflected by said replaceable cartridge or transmitted through said reservoir.

28. A method for a delivering of a dose of a fluid, comprising the steps:
   (a) providing a device of claim 1;
   (b) introducing said fluid into said reservoir;
   (c) initiating a non-zero force urging said fluid out of the reservoir;
   (d) acquiring at least one output from said sensor system associated with at least one geometric parameter of said resilient element;
   (e) calculating a time to stop ("$t_{end}$") providing said force urging said fluid out of the reservoir comprising treating said acquired output by a processor executing commands based upon instructions stored in said processor; and
   (f) terminating said force at $t_{end}$.

29. The method of claim 28, further comprising the steps:
(i) before step (c) subjecting said fluid in the reservoir to a sufficiently low pressure to prevent said fluid from flowing out of said exit opening, said pressure in the reservoir close to an external pressure $P_{ext}$;
(ii) the step (c) further comprising producing at least one starting electric output at a predetermined moment $t_{st}$, said starting output resulting in producing:
said force urging said fluid out of said reservoir; and
subjecting said expandable element to a pressure $P_{ind}(t)$ within the range defined by the expression:
$P_{max}+P_{ext}>P_{ind}(t)>P_{min}+P_{ext}$, wherein $P_{max}$ and $P_{min}$ are correspondingly a maximum and a minimum pressure increase caused in the reservoir by the driving force system which obey condition $25>P_{max}/P_{min}>1$;
(iii) treating said output of said sensor, comprising determining a pressure difference $P_{ind}(t)-P_{ext}$, and further comprising determining a period $T_c$ satisfying the condition $T_c=t_{end}-t_{st}$, wherein $T_c$ is of such duration of said force urging said fluid out of said reservoir to provide an equality of said predetermined dose and an actual dose delivered, said actual dose being an integral found by integrating over time from time $t_{st}$ of a ratio having a numerator being said pressure difference, and a denominator being a parameter expressing hydraulic resistance $R_{exit}$ of said flow passage connecting the reservoir with said exit opening;
(iv) the step (f) comprises producing at least one ending electric output at $t_{end}=T_c+t_{st}$, wherein said ending output results in either decreasing the force or changing a direction of the force or both so that the pressure of the fluid in said first section can relax in time up to about its initial value before step (c).

30. The method of claim 29, wherein under flow conditions, hydraulic communication between said two spatially separated sections of the reservoir has a resistance $R_1 \geq 0.05 R_2$;
wherein step (d) comprises acquiring at least two outputs from said sensor system;
wherein said step (e) further comprises:
determining an actual hydraulic resistance $R_{exit}$ of said flow passage connecting the reservoir with said exit opening;
setting said denominator equal to said actual $R_{exit}$;
producing an alarm signal if said actual $R_{exit}$ exceeds a predetermined level; or
substituting said actual $R_{exit}$ into an analytic expression of said integral if said actual $R_{exit}$ does not exceed said predetermined level.

31. The method of claim 28, wherein said flow passage connecting the reservoir with said exit opening is further supplied with an element switching hydraulic resistance at a predetermined pressure drop $P_{op}$;
wherein step (d) comprises acquiring at least five outputs and desirably more than five outputs from said sensor system;
said treating of step (e) further comprising:
calibrating said device delivering the fluid;
checking current performance of components of said device;
determining the amount of the fluid remaining in the reservoir; and
producing one or more of a report and an alarm signal to inform a user if said amount of remaining fluid is below a predetermined amount or a malfunction is detected that cannot be self-compensated by said steps determining of the time $t_{end}$.

32. The method of claim 28, wherein step (c) further comprises creating a first emergency signal if after said starting electric output said force urging the fluid out of said reservoir is not produced, said first emergency signal resulting in the at least one of:
(i) prompting a patient to initiate a manual application of said force to said reservoir;
(ii) determining an actual starting time $t_{st}$, when an appearance of manually created non-zero force urging the fluid out of said reservoir is detected by said sensor system;
(iii) said ending electric output of step (e) results in creating such second emergency signal at the moment $t_{end}$ which recommends the patient to terminate manually said application of said force, whereas both said first and second emergency signals are visual, mechanical or acoustic signals.

33. The method of claim 29, wherein said predetermined $R_2$ is substituted into said denominator in order to fulfill the role of said parameter expressing said $R_{exit}$, and said integral is proportional to a sum of all said outputs of said sensor system acquired since the time $t_{st}$.

34. The method of claim 28, further comprising:
transmitting at least one output of at least one bio-medical device analyzing a physiological feature of a patient to a control system, and
correcting the predetermined dose delivered by said device according to said transmitted output of said bio-medical device.

35. A method for a delivery of a predetermined dose of a fluid, comprising the steps:
(a) providing a device of claim 1;
(b) switching said module into a stable state which results in producing of a continuous compressive force applied to the fluid in said reservoir;
(c) acquiring at least one output from a sensor system associated with at least one geometric parameter of said resilient element;
(d) calculating a time $t_{end}$, comprising treating said acquired output by a processor capable of executing commands stored in said processor; and
(e) switching said module into said other stable state at $t_{end}$.

* * * * *